US012070572B2

(12) United States Patent
Kamen et al.

(10) Patent No.: US 12,070,572 B2
(45) Date of Patent: *Aug. 27, 2024

(54) SYSTEM, METHOD, AND APPARATUS FOR ELECTRONIC PATIENT CARE

(71) Applicant: DEKA Products Limited Partnership, Manchester, NH (US)

(72) Inventors: Dean Kamen, Bedford, NH (US); John J. Biasi, Lancaster, MA (US); Jacob W. Scarpaci, Manchester, NH (US); John M. Kerwin, Manchester, NH (US); James G. Turner, Manchester, NH (US); Todd A. Ballantyne, Amherst, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/078,312

(22) Filed: Dec. 9, 2022

(65) Prior Publication Data

US 2023/0102396 A1   Mar. 30, 2023

Related U.S. Application Data

(63) Continuation of application No. 16/654,391, filed on Oct. 16, 2019, now Pat. No. 11,524,107, which is a
(Continued)

(51) Int. Cl.
*A61M 5/14* (2006.01)
*A61B 5/00* (2006.01)
(Continued)

(52) U.S. Cl.
CPC ......... *A61M 5/1413* (2013.01); *A61B 5/0024* (2013.01); *A61M 5/1415* (2013.01);
(Continued)

(58) Field of Classification Search
CPC ............. A61M 5/1413; A61M 5/1415; A61M 5/1417; A61M 5/142; A61M 5/16827;
(Continued)

(56) References Cited

U.S. PATENT DOCUMENTS

| 3,658,445 A | 4/1972 | Pulman et al. |
| 4,470,758 A | 9/1984 | Pazemenas et al. |

(Continued)

FOREIGN PATENT DOCUMENTS

| CN | 101681455 A | 3/2010 |
| CN | 102113034 A | 6/2011 |

(Continued)

*Primary Examiner* — Eliza A Lam
(74) *Attorney, Agent, or Firm* — William A. Bonk, III

(57) ABSTRACT

A system for electronic patient care includes a hub. The hub is configured to monitor a patient-care device. The sandbox may be configured to control access to at least one of a hardware resource and a software resource. The hub is further configured to identify the patient-care device and execute an application to monitor the patient-care device. The hub executes the application within the sandbox component such that the application accesses the at least one of the hardware resource and the software resource through the sandbox component. The hub may be further configured to control the patient-care device. The hub may be further configured to receive an identification from the patient-care device and download the application from a server associated with the identification. The hub may be further configured to receive an identification from the patient-care device and update the application from a server associated with the identification.

32 Claims, 128 Drawing Sheets

Related U.S. Application Data continuation of application No. 13/333,574, filed on Dec. 21, 2011, now Pat. No. 10,453,157, which is a continuation-in-part of application No. 13/011,543, filed on Jan. 21, 2011, now abandoned.

(60) Provisional application No. 61/297,544, filed on Jan. 22, 2010.

(51) Int. Cl.
| | |
|---|---|
| *A61M 5/142* | (2006.01) |
| *A61M 5/168* | (2006.01) |
| *G03B 15/05* | (2021.01) |
| *G08B 21/02* | (2006.01) |
| *G16H 20/17* | (2018.01) |
| *G16H 40/40* | (2018.01) |
| *G16H 40/63* | (2018.01) |
| *G16H 40/67* | (2018.01) |

(52) U.S. Cl.
CPC .......... *A61M 5/1417* (2013.01); *A61M 5/142* (2013.01); *A61M 5/16827* (2013.01); *G03B 15/05* (2013.01); *G08B 21/02* (2013.01); *G16H 20/17* (2018.01); *G16H 40/40* (2018.01); *G16H 40/63* (2018.01); *G16H 40/67* (2018.01); *A61M 2205/3553* (2013.01); *A61M 2205/3561* (2013.01); *A61M 2205/3569* (2013.01); *A61M 2205/3584* (2013.01); *A61M 2205/6009* (2013.01); *G03B 2215/0521* (2013.01); *G03B 2215/056* (2013.01)

(58) Field of Classification Search
CPC .. A61M 2205/3553; A61M 2205/3561; A61M 2205/3569; A61M 2205/3584; A61M 2205/6009; A61B 5/0024; G03B 15/05; G03B 2215/0521; G03B 2215/056; G08B 21/02; G16H 20/17; G16H 40/40; G16H 40/63; G16H 40/67
See application file for complete search history.

(56) References Cited

U.S. PATENT DOCUMENTS

| | | |
|---|---|---|
| 4,696,671 A | 9/1987 | Epstein et al. |
| 4,877,034 A | 10/1989 | Atkins et al. |
| 4,939,689 A | 7/1990 | Davis et al. |
| 5,041,086 A | 8/1991 | Koenig et al. |
| 5,153,827 A | 10/1992 | Coutre et al. |
| 5,207,642 A | 5/1993 | Orkin et al. |
| 5,317,506 A | 5/1994 | Coutre et al. |
| D348,101 S | 6/1994 | Poli et al. |
| 5,331,549 A | 7/1994 | Crawford, Jr. |
| 5,368,562 A | 11/1994 | Blomquist et al. |
| 5,482,446 A | 1/1996 | Williamson et al. |
| 5,485,408 A | 1/1996 | Blomquist |
| 5,527,289 A | 6/1996 | Foster et al. |
| 5,537,618 A | 7/1996 | Boulton et al. |
| 5,681,285 A | 10/1997 | Ford et al. |
| 5,713,856 A | 2/1998 | Eggers et al. |
| 5,719,761 A | 2/1998 | Gatti et al. |
| 5,781,442 A | 7/1998 | Engleson et al. |
| 5,836,910 A | 11/1998 | Duffy et al. |
| 5,937,353 A | 8/1999 | Fapojuwo |
| 5,941,846 A | 8/1999 | Duffy et al. |
| 5,961,487 A | 10/1999 | Davis |
| 6,021,392 A | 2/2000 | Lester et al. |
| 6,024,539 A | 2/2000 | Blomquist |
| 6,139,495 A | 10/2000 | De La Huerga |
| 6,255,951 B1 | 7/2001 | De La Huerga |
| 6,267,559 B1 | 7/2001 | Mossman et al. |
| 6,269,340 B1 | 7/2001 | Ford et al. |
| 6,308,171 B1 | 10/2001 | De La Huerga |
| 6,314,384 B1 | 11/2001 | Goetz |
| 6,315,720 B1 | 11/2001 | Williams et al. |
| 6,317,719 B1 | 11/2001 | Schrier et al. |
| 6,319,200 B1 | 11/2001 | Lai et al. |
| 6,327,570 B1 | 12/2001 | Stevens |
| 6,346,886 B1 | 2/2002 | De La Huerga |
| 6,348,777 B1 | 2/2002 | Brown et al. |
| 6,398,727 B1 | 6/2002 | Bui et al. |
| 6,408,330 B1 | 6/2002 | DeLaHuerga |
| 6,421,650 B1 | 7/2002 | Goetz et al. |
| 6,427,088 B1 | 7/2002 | Bowman, IV et al. |
| 6,519,569 B1 | 2/2003 | White et al. |
| 6,554,798 B1 | 4/2003 | Mann et al. |
| 6,579,242 B2 | 6/2003 | Bui et al. |
| 6,668,196 B1 | 12/2003 | Villegas et al. |
| 6,671,563 B1 | 12/2003 | Engleson et al. |
| 6,694,334 B2 | 2/2004 | Dulong et al. |
| 6,745,764 B2 | 6/2004 | Hickle |
| 6,775,577 B2 | 8/2004 | Crnkovich et al. |
| 6,776,152 B2 | 8/2004 | Lee |
| 6,790,198 B1 | 9/2004 | White et al. |
| 6,880,034 B2 | 4/2005 | Manke et al. |
| 6,976,349 B2 | 12/2005 | Baldwin et al. |
| 6,985,870 B2 | 1/2006 | Martucci et al. |
| 6,993,402 B2 | 1/2006 | Klass et al. |
| 7,039,878 B2 | 5/2006 | Auer et al. |
| 7,096,072 B2 | 8/2006 | Engleson et al. |
| 7,103,419 B2 | 9/2006 | Engleson et al. |
| 7,107,106 B2 | 9/2006 | Engleson et al. |
| 7,117,041 B2 | 10/2006 | Engleson et al. |
| 7,161,484 B2 | 1/2007 | Tsoukalis |
| 7,165,221 B2 | 1/2007 | Monteleone et al. |
| 7,171,277 B2 | 1/2007 | Engleson et al. |
| 7,216,802 B1 | 5/2007 | De La Huerga |
| 7,236,936 B2 | 6/2007 | White et al. |
| 7,300,418 B2 | 11/2007 | Zaleski |
| 7,302,266 B1 | 11/2007 | Sill et al. |
| 7,303,549 B2 | 12/2007 | Flaherty et al. |
| 7,366,934 B1 | 4/2008 | Narayan et al. |
| 7,379,885 B1 | 5/2008 | Zakim |
| 7,384,410 B2 | 6/2008 | Eggers et al. |
| 7,433,853 B2 | 10/2008 | Brockway et al. |
| 7,452,190 B2 | 11/2008 | Bouton et al. |
| 7,471,994 B2 | 12/2008 | Ford et al. |
| 7,539,593 B2 | 5/2009 | Machacek |
| 7,565,301 B2 | 7/2009 | Moubayed et al. |
| 7,569,030 B2 | 8/2009 | Lebel et al. |
| 7,590,551 B2 | 9/2009 | Auer |
| 7,612,679 B1 | 11/2009 | Fackler et al. |
| 7,636,718 B1 | 12/2009 | Steen et al. |
| 7,645,258 B2 | 1/2010 | White et al. |
| 7,647,237 B2 | 1/2010 | Malave et al. |
| 7,664,660 B2 | 2/2010 | Korpman et al. |
| 7,678,071 B2 | 3/2010 | Lebel et al. |
| 7,685,003 B2 | 3/2010 | Hasan et al. |
| 7,689,394 B2 | 3/2010 | Furem et al. |
| 7,693,730 B2 | 4/2010 | Hasan et al. |
| 7,699,806 B2 | 4/2010 | Ware et al. |
| 7,703,042 B2 | 4/2010 | Brummel et al. |
| 7,707,047 B2 | 4/2010 | Hasan et al. |
| 7,715,277 B2 | 5/2010 | De la Huerga |
| 7,743,975 B2 | 6/2010 | Miller |
| 7,771,385 B2 | 8/2010 | Eggers et al. |
| 7,771,386 B2 | 8/2010 | Eggers et al. |
| 7,788,369 B2 | 8/2010 | McAllen et al. |
| 7,805,377 B2 | 9/2010 | Felsher |
| 7,813,879 B2 | 10/2010 | Bush et al. |
| 7,815,602 B2 | 10/2010 | Mann et al. |
| 7,818,184 B2 | 10/2010 | Penny et al. |
| 7,819,843 B2 | 10/2010 | Mann et al. |
| 7,831,446 B2 | 11/2010 | Korpman et al. |
| 7,835,927 B2 | 11/2010 | Schlotterbeck et al. |
| 7,839,266 B2 | 11/2010 | Hoglund et al. |
| 7,850,641 B2 | 12/2010 | Lebel et al. |
| 7,859,401 B2 | 12/2010 | Falck et al. |
| 7,860,583 B2 | 12/2010 | Condurso et al. |
| 7,871,394 B2 | 1/2011 | Halbert et al. |
| 7,873,489 B2 | 1/2011 | Dolgos et al. |
| 7,886,231 B2 | 2/2011 | Hopermann et al. |

(56) References Cited

U.S. PATENT DOCUMENTS

| | | | |
|---|---|---|---|
| 7,893,876 B2 | 2/2011 | Brown et al. |
| 7,896,842 B2 | 3/2011 | Palmroos et al. |
| 7,901,394 B2 | 3/2011 | Ireland et al. |
| 7,911,353 B2 | 3/2011 | Bedingfield |
| D636,779 S | 4/2011 | Boush et al. |
| D636,780 S | 4/2011 | Musleh |
| 7,933,780 B2 | 4/2011 | De La Huerga |
| 7,935,076 B2 | 5/2011 | Estes et al. |
| 7,938,796 B2 | 5/2011 | Moubayed et al. |
| 7,941,534 B2 | 5/2011 | De La Huerga |
| 7,942,844 B2 | 5/2011 | Moberg et al. |
| 7,946,985 B2 | 5/2011 | Mastrototaro et al. |
| 7,955,289 B2 | 6/2011 | O'Mahony et al. |
| 7,976,508 B2 | 7/2011 | Hoag |
| 7,978,564 B2 | 7/2011 | De La Huerga |
| 8,025,634 B1 | 9/2011 | Moubayed et al. |
| 8,032,226 B2 | 10/2011 | Miller et al. |
| 8,038,593 B2 | 10/2011 | Friedman et al. |
| 8,041,542 B2 | 10/2011 | Pearson |
| 8,060,381 B2 | 11/2011 | Dyer et al. |
| 8,065,161 B2 | 11/2011 | Howard et al. |
| 8,073,710 B2 | 12/2011 | Hasan et al. |
| 8,095,390 B2 | 1/2012 | Bluemler et al. |
| 8,099,301 B2 | 1/2012 | Keresman, III et al. |
| 8,126,728 B2 | 2/2012 | Dicks et al. |
| 8,126,729 B2 | 2/2012 | Dicks et al. |
| 8,131,565 B2 | 3/2012 | Dicks et al. |
| 8,131,566 B2 | 3/2012 | Dicks et al. |
| 8,134,459 B2 | 3/2012 | Smith et al. |
| 8,149,131 B2 | 4/2012 | Blomquist |
| 8,152,486 B2 | 4/2012 | Fathallah et al. |
| 8,178,040 B2 | 5/2012 | Brauer |
| 8,192,394 B2 | 6/2012 | Estes et al. |
| 8,214,227 B2 | 7/2012 | Patterson et al. |
| 8,214,234 B2 | 7/2012 | Hasan et al. |
| 8,217,946 B2 | 7/2012 | Halpern et al. |
| 8,219,413 B2 | 7/2012 | Martinez et al. |
| 8,219,982 B2 | 7/2012 | Harkanyi et al. |
| 8,222,768 B2 | 7/2012 | Cassidy |
| 8,225,015 B2 | 7/2012 | Gao-Saari et al. |
| 8,229,760 B2 | 7/2012 | Hasan et al. |
| D665,401 S | 8/2012 | Rai et al. |
| 8,235,938 B2 | 8/2012 | Eggers et al. |
| 8,239,780 B2 | 8/2012 | Manetta et al. |
| 8,244,555 B2 | 8/2012 | Masson et al. |
| 8,255,585 B2 | 8/2012 | Levin |
| 8,260,635 B2 | 9/2012 | Hasan et al. |
| 8,271,106 B2 | 9/2012 | Wehba et al. |
| 8,273,018 B1 | 9/2012 | Fackler et al. |
| 8,275,576 B2 | 9/2012 | Furem et al. |
| 8,275,633 B2 | 9/2012 | Baker |
| 8,291,337 B2 | 10/2012 | Gannin et al. |
| 8,306,797 B2 | 11/2012 | Furem et al. |
| 8,308,680 B1 | 11/2012 | Chawla |
| 8,312,877 B2 | 11/2012 | Elaz et al. |
| 8,317,752 B2 | 11/2012 | Cozmi et al. |
| D672,785 S | 12/2012 | Rai et al. |
| 8,340,792 B2 | 12/2012 | Condurso et al. |
| 8,352,290 B2 | 1/2013 | Bartz et al. |
| 8,359,338 B2 | 1/2013 | Butterfield et al. |
| 8,373,557 B2 | 2/2013 | Smith et al. |
| 8,380,126 B1 | 2/2013 | Ma et al. |
| 8,380,536 B2 | 2/2013 | Howard et al. |
| 8,414,523 B2 | 4/2013 | Blomquist et al. |
| D682,861 S | 5/2013 | Rounding et al. |
| 8,444,595 B2 | 5/2013 | Brukalo et al. |
| 8,451,230 B2 | 5/2013 | Celentano et al. |
| D694,774 S | 12/2013 | Schuller et al. |
| D701,526 S | 3/2014 | Poston et al. |
| 8,663,201 B2 | 3/2014 | Hill et al. |
| D705,242 S | 5/2014 | Bohmfalk et al. |
| D709,905 S | 7/2014 | Bohmfalk et al. |
| D714,339 S | 9/2014 | Hendrickson et al. |
| 8,938,684 B2 | 1/2015 | Guertler et al. |
| 8,954,336 B2 | 2/2015 | Blomquist |
| D726,752 S | 4/2015 | Angelides |
| D728,601 S | 5/2015 | Angelides |
| D728,779 S | 5/2015 | Sabin et al. |
| D733,724 S | 7/2015 | Kim |
| D735,319 S | 7/2015 | Sabin et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg, Jr. |
| 9,724,465 B2 | 8/2017 | Peret et al. |
| 9,724,466 B2 | 8/2017 | Peret et al. |
| 9,724,467 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| 9,789,247 B2 | 10/2017 | Kamen et al. |
| 9,801,519 B2 | 10/2017 | Reed, Jr. et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |
| D805,183 S | 12/2017 | Sabin et al. |
| 9,856,990 B2 | 1/2018 | Peret et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,032,002 B2 * | 7/2018 | Kiani ............... G16H 40/63 |
| 10,044,791 B2 | 8/2018 | Kamen et al. |
| 10,082,241 B2 | 9/2018 | Janway et al. |
| 10,088,346 B2 | 10/2018 | Kane et al. |
| 10,108,785 B2 | 10/2018 | Kamen et al. |
| 10,113,660 B2 | 10/2018 | Peret et al. |
| 10,126,267 B2 | 11/2018 | Blumberg, Jr. |
| 10,185,812 B2 | 1/2019 | Kamen et al. |
| 10,202,970 B2 | 2/2019 | Kamen et al. |
| 10,202,971 B2 | 2/2019 | Kamen et al. |
| 10,220,135 B2 | 3/2019 | Kamen et al. |

(56) References Cited

U.S. PATENT DOCUMENTS

| | | |
|---|---|---|
| 10,228,683 B2 | 3/2019 | Peret et al. |
| 10,242,159 B2 | 3/2019 | Kamen et al. |
| 10,245,374 B2 | 4/2019 | Kamen et al. |
| 10,265,463 B2 | 4/2019 | Biasi et al. |
| 10,288,057 B2 | 5/2019 | Kamen et al. |
| 10,316,834 B2 | 6/2019 | Kamen et al. |
| D854,145 S | 7/2019 | Collins |
| 10,380,321 B2 | 8/2019 | Kamen et al. |
| 10,391,241 B2 | 8/2019 | Desch et al. |
| D860,437 S | 9/2019 | Collins |
| 10,426,517 B2 | 10/2019 | Langenfeld et al. |
| 10,436,342 B2 | 10/2019 | Peret et al. |
| 10,453,157 B2 | 10/2019 | Kamen et al. |
| 10,468,132 B2 | 11/2019 | Kamen et al. |
| 10,471,402 B2 | 11/2019 | Demers et al. |
| 10,478,261 B2 | 11/2019 | Demers et al. |
| 10,488,848 B2 | 11/2019 | Peret et al. |
| 10,561,787 B2 | 2/2020 | Kamen et al. |
| 10,563,681 B2 | 2/2020 | Kamen et al. |
| 10,571,070 B2 | 2/2020 | Gray et al. |
| 10,655,779 B2 | 5/2020 | Janway et al. |
| 10,670,182 B2 | 6/2020 | Janway et al. |
| 10,718,445 B2 | 7/2020 | Yoo |
| 10,722,645 B2 | 7/2020 | Kamen et al. |
| 10,739,759 B2 | 8/2020 | Peret et al. |
| 10,753,353 B2 | 8/2020 | Kamen et al. |
| 10,761,061 B2 | 9/2020 | Wilt et al. |
| 10,839,953 B2 | 11/2020 | Kamen et al. |
| 10,844,970 B2 | 11/2020 | Peret et al. |
| D905,848 S | 12/2020 | Sloss et al. |
| 10,857,293 B2 | 12/2020 | Kamen et al. |
| 10,872,685 B2 | 12/2020 | Blumberg, Jr. et al. |
| 10,876,868 B2 | 12/2020 | Kane et al. |
| 10,894,638 B2 | 1/2021 | Peret et al. |
| 10,911,515 B2 | 2/2021 | Biasi et al. |
| D917,045 S | 4/2021 | Gray |
| 10,969,766 B2 * | 4/2021 | Wang ............... G05B 19/414 |
| 10,994,074 B2 | 5/2021 | Blumberg, Jr. et al. |
| 11,024,409 B2 | 6/2021 | Kamen et al. |
| 11,024,419 B2 | 6/2021 | Kamen et al. |
| 2001/0031944 A1 | 10/2001 | Peterson et al. |
| 2001/0044731 A1 | 11/2001 | Coffman et al. |
| 2001/0051787 A1 | 12/2001 | Haller et al. |
| 2002/0013538 A1 | 1/2002 | Teller |
| 2002/0016568 A1 | 2/2002 | Lebel et al. |
| 2002/0032583 A1 | 3/2002 | Joao |
| 2002/0044059 A1 | 4/2002 | Reeder et al. |
| 2002/0072934 A1 | 6/2002 | Ross et al. |
| 2002/0077852 A1 | 6/2002 | Ford et al. |
| 2002/0084904 A1 | 7/2002 | De La Huerga |
| 2002/0169636 A1 | 11/2002 | Eggers et al. |
| 2002/0178126 A1 | 11/2002 | Beck et al. |
| 2002/0184589 A1 | 12/2002 | Eatough et al. |
| 2002/0188465 A1 | 12/2002 | Gogolak et al. |
| 2003/0036683 A1 | 2/2003 | Kehr et al. |
| 2003/0036744 A1 | 2/2003 | Struys et al. |
| 2003/0046110 A1 | 3/2003 | Gogolak |
| 2003/0061073 A1 | 3/2003 | Seow et al. |
| 2003/0106553 A1 | 6/2003 | Vanderveen |
| 2003/0114751 A1 | 6/2003 | Pedain et al. |
| 2003/0117296 A1 | 6/2003 | Seely |
| 2003/0135087 A1 | 7/2003 | Hickle et al. |
| 2003/0135388 A1 | 7/2003 | Martucci et al. |
| 2003/0140928 A1 | 7/2003 | Bui et al. |
| 2003/0165128 A1 | 9/2003 | Sisodia et al. |
| 2003/0167030 A1 | 9/2003 | Weitzel et al. |
| 2004/0010425 A1 | 1/2004 | Wilkes et al. |
| 2004/0015132 A1 | 1/2004 | Brown |
| 2004/0085186 A1 | 5/2004 | Eveland et al. |
| 2004/0138724 A1 | 7/2004 | Sieracki et al. |
| 2004/0147818 A1 | 7/2004 | Levy et al. |
| 2004/0158193 A1 | 8/2004 | Bui et al. |
| 2004/0172283 A1 | 9/2004 | Vanderveen et al. |
| 2004/0193325 A1 | 9/2004 | Bonderud et al. |
| 2004/0193453 A1 | 9/2004 | Butterfield et al. |
| 2005/0021622 A1 | 1/2005 | Cullen |
| 2005/0022184 A1 | 1/2005 | Birkestrand et al. |
| 2005/0055242 A1 | 3/2005 | Bello et al. |
| 2005/0060202 A1 | 3/2005 | Taylor et al. |
| 2005/0070227 A1 | 3/2005 | Shen et al. |
| 2005/0070767 A1 | 3/2005 | Maschke |
| 2005/0086288 A1 | 4/2005 | Datta et al. |
| 2005/0099624 A1 | 5/2005 | Staehr et al. |
| 2005/0133027 A1 | 6/2005 | Elaz et al. |
| 2005/0143632 A1 | 6/2005 | Elaz et al. |
| 2005/0144043 A1 | 6/2005 | Holland et al. |
| 2005/0171815 A1 | 8/2005 | Vanderveen |
| 2005/0177096 A1 | 8/2005 | Bollish et al. |
| 2005/0192844 A1 | 9/2005 | Esler et al. |
| 2005/0224083 A1 | 10/2005 | Crass et al. |
| 2005/0288571 A1 | 12/2005 | Perkins et al. |
| 2006/0047538 A1 | 3/2006 | Condurso et al. |
| 2006/0080140 A1 | 4/2006 | Buttner et al. |
| 2006/0089592 A1 | 4/2006 | Kadhiresan et al. |
| 2006/0095300 A1 | 5/2006 | Schrier et al. |
| 2006/0149140 A1 | 7/2006 | Eldridge |
| 2006/0149591 A1 | 7/2006 | Hanf et al. |
| 2006/0161214 A1 | 7/2006 | Patel |
| 2006/0168043 A1 | 7/2006 | Eisenberger et al. |
| 2006/0184123 A1 | 8/2006 | Gillespie, Jr. et al. |
| 2006/0229557 A1 | 10/2006 | Fathallah et al. |
| 2006/0253301 A1 | 11/2006 | Simms et al. |
| 2006/0258985 A1 | 11/2006 | Russell |
| 2006/0265246 A1 | 11/2006 | Hoag |
| 2006/0294230 A1 | 12/2006 | Takasu |
| 2007/0052683 A1 | 3/2007 | Knott et al. |
| 2007/0061393 A1 | 3/2007 | Moore |
| 2007/0078445 A1 | 4/2007 | Malloy |
| 2007/0088574 A1 | 4/2007 | Byer et al. |
| 2007/0093786 A1 * | 4/2007 | Goldsmith ......... A61B 5/14532 604/890.1 |
| 2007/0109325 A1 | 5/2007 | Eveleigh |
| 2007/0136090 A1 | 6/2007 | Loutzenhiser et al. |
| 2007/0191817 A1 | 8/2007 | Martin |
| 2007/0219823 A1 | 9/2007 | Warner |
| 2007/0249286 A1 | 10/2007 | Ma et al. |
| 2007/0250927 A1 | 10/2007 | Naik et al. |
| 2007/0255114 A1 | 11/2007 | Ackermann et al. |
| 2007/0255250 A1 | 11/2007 | Moberg et al. |
| 2007/0255348 A1 | 11/2007 | Holtzclaw |
| 2008/0033361 A1 | 2/2008 | Evans et al. |
| 2008/0039744 A1 | 2/2008 | Hamilton |
| 2008/0086086 A1 | 4/2008 | Field et al. |
| 2008/0091175 A1 | 4/2008 | Frikart et al. |
| 2008/0097913 A1 | 4/2008 | Dicks et al. |
| 2008/0129496 A1 | 6/2008 | Koblasz |
| 2008/0133265 A1 | 6/2008 | Silkaitis et al. |
| 2008/0140157 A1 | 6/2008 | Goetz et al. |
| 2008/0160492 A1 | 7/2008 | Campbell et al. |
| 2008/0183910 A1 | 7/2008 | Natoli et al. |
| 2008/0235765 A1 | 9/2008 | Shimizu |
| 2008/0243055 A1 | 10/2008 | Fathallah et al. |
| 2008/0255438 A1 | 10/2008 | Saidara et al. |
| 2008/0262441 A1 | 10/2008 | Walborn et al. |
| 2008/0281259 A1 | 11/2008 | Owens et al. |
| 2008/0300572 A1 | 12/2008 | Rankers et al. |
| 2009/0006640 A1 | 1/2009 | Brouwer et al. |
| 2009/0063187 A1 | 3/2009 | Johnson et al. |
| 2009/0069642 A1 | 3/2009 | Gao et al. |
| 2009/0069743 A1 | 3/2009 | Krishnamoorthy et al. |
| 2009/0099866 A1 | 4/2009 | Newman |
| 2009/0099867 A1 | 4/2009 | Newman |
| 2009/0119330 A1 | 5/2009 | Sampath et al. |
| 2009/0150818 A1 | 6/2009 | Bakhreiba et al. |
| 2009/0153058 A1 | 6/2009 | Feng et al. |
| 2009/0153463 A1 | 6/2009 | Arrizza et al. |
| 2009/0153595 A1 | 6/2009 | Cozmi et al. |
| 2009/0157432 A1 | 6/2009 | Palmroos et al. |
| 2009/0163855 A1 | 6/2009 | Shin et al. |
| 2009/0183147 A1 | 7/2009 | Davis et al. |
| 2009/0184842 A1 | 7/2009 | Baldus et al. |
| 2009/0203329 A1 | 8/2009 | White et al. |
| 2009/0210152 A1 | 8/2009 | Kawa |
| 2009/0216562 A1 | 8/2009 | Faulkner et al. |

(56) References Cited

U.S. PATENT DOCUMENTS

| | | |
|---|---|---|
| 2009/0217194 A1 | 8/2009 | Martin et al. |
| 2009/0234672 A1 | 9/2009 | Dicks et al. |
| 2009/0240526 A1 | 9/2009 | Vesto et al. |
| 2009/0270810 A1 | 10/2009 | Debelser et al. |
| 2009/0270833 A1 | 10/2009 | Debelser et al. |
| 2009/0275808 A1 | 11/2009 | Dimaio et al. |
| 2010/0019910 A1 | 1/2010 | Hassing et al. |
| 2010/0094653 A1 | 4/2010 | Tribble et al. |
| 2010/0106224 A1 | 4/2010 | Von Arx et al. |
| 2010/0114027 A1 | 5/2010 | Jacobson et al. |
| 2010/0130933 A1 | 5/2010 | Holland et al. |
| 2010/0145506 A1 | 6/2010 | Waugh et al. |
| 2010/0150176 A1 | 6/2010 | Yakashiro |
| 2010/0160628 A1 | 6/2010 | Peglion et al. |
| 2010/0176166 A1 | 7/2010 | Siagri et al. |
| 2010/0229096 A1 | 9/2010 | Maiocco et al. |
| 2010/0234718 A1 | 9/2010 | Sampath et al. |
| 2010/0257189 A1 | 10/2010 | Campbell et al. |
| 2010/0268157 A1 | 10/2010 | Wehba et al. |
| 2010/0280486 A1 | 11/2010 | Khair et al. |
| 2010/0287006 A1 | 11/2010 | Cannon et al. |
| 2010/0292544 A1 | 11/2010 | Sherman et al. |
| 2010/0292556 A1 | 11/2010 | Golden |
| 2010/0298662 A1 | 11/2010 | Yu et al. |
| 2011/0004186 A1 | 1/2011 | Butterfield |
| 2011/0006876 A1 | 1/2011 | Moberg et al. |
| 2011/0071420 A1 | 3/2011 | Shawn et al. |
| 2011/0074342 A1 | 3/2011 | MacLaughlin |
| 2011/0105979 A1 | 5/2011 | Schlaeper et al. |
| 2011/0112418 A1 | 5/2011 | Feild et al. |
| 2011/0119612 A1 | 5/2011 | Gannon et al. |
| 2011/0152629 A1 | 6/2011 | Eaton et al. |
| 2011/0153343 A1 | 6/2011 | Tremblay et al. |
| 2011/0167250 A1 | 7/2011 | Dicks et al. |
| 2011/0173704 A1 | 7/2011 | Hanov et al. |
| 2011/0179083 A1 | 7/2011 | Galloway et al. |
| 2011/0179405 A1 | 7/2011 | Dicks et al. |
| 2011/0184379 A1 | 7/2011 | Van Antwerp et al. |
| 2011/0191767 A1 | 8/2011 | Pinsky et al. |
| 2011/0196306 A1 | 8/2011 | De La Huerga |
| 2011/0205965 A1 | 8/2011 | Sprigg et al. |
| 2011/0218406 A1 | 9/2011 | Hussain |
| 2011/0224646 A1 | 9/2011 | Yodfat et al. |
| 2011/0231203 A1 | 9/2011 | Rosow et al. |
| 2011/0231204 A1 | 9/2011 | De La Huerga |
| 2011/0241878 A1 | 10/2011 | Hoag |
| 2011/0254794 A1 | 10/2011 | Knott et al. |
| 2011/0276605 A1 | 11/2011 | Masson et al. |
| 2011/0282168 A1 | 11/2011 | Weiss et al. |
| 2011/0282688 A1 | 11/2011 | Raggousis |
| 2011/0282691 A1 | 11/2011 | Coffman et al. |
| 2011/0313789 A1 | 12/2011 | Kamen et al. |
| 2011/0320049 A1 | 12/2011 | Chossat et al. |
| 2012/0011253 A1 | 1/2012 | Friedman et al. |
| 2012/0016215 A1 | 1/2012 | Condurso et al. |
| 2012/0016295 A1 | 1/2012 | Tsoukalis |
| 2012/0016305 A1 | 1/2012 | Jollota et al. |
| 2012/0029300 A1 | 2/2012 | Paquet |
| 2012/0029303 A1 | 2/2012 | Shaya |
| 2012/0029307 A1 | 2/2012 | Paquet et al. |
| 2012/0029308 A1 | 2/2012 | Paquet |
| 2012/0029309 A1 | 2/2012 | Paquet et al. |
| 2012/0029310 A1 | 2/2012 | Paquet et al. |
| 2012/0029311 A1 | 2/2012 | Raptis et al. |
| 2012/0029312 A1 | 2/2012 | Beaudry et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0029941 A1 | 2/2012 | Malave et al. |
| 2012/0030547 A1 | 2/2012 | Raptis et al. |
| 2012/0047289 A1 | 2/2012 | Krzystofczyk et al. |
| 2012/0053533 A1 | 3/2012 | Butterfield et al. |
| 2012/0062387 A1 | 3/2012 | Vik et al. |
| 2012/0065990 A1 | 3/2012 | Howard et al. |
| 2012/0066609 A1 | 3/2012 | Howard et al. |
| 2012/0075061 A1 | 3/2012 | Barnes |
| 2012/0078218 A1 | 3/2012 | Barnes |
| 2012/0084303 A1 | 4/2012 | Ledford et al. |
| 2012/0092157 A1 | 4/2012 | Tran |
| 2012/0116796 A1 | 5/2012 | Bellon et al. |
| 2012/0116800 A1 | 5/2012 | McCallie et al. |
| 2012/0123229 A1 | 5/2012 | Butterfield et al. |
| 2012/0124174 A1 | 5/2012 | Nudelman et al. |
| 2012/0130308 A1 | 5/2012 | Silkaitis et al. |
| 2012/0157920 A1 | 6/2012 | Flachbart et al. |
| 2012/0172802 A1 | 7/2012 | Blomquist |
| 2012/0176394 A1 | 7/2012 | Vik et al. |
| 2012/0179093 A1 | 7/2012 | Rinehart et al. |
| 2012/0179136 A1 | 7/2012 | Rinehart et al. |
| 2012/0181795 A1 | 7/2012 | Lobsiger |
| 2012/0185267 A1 | 7/2012 | Kamen et al. |
| 2012/0239824 A1 | 9/2012 | Nguyen et al. |
| 2012/0260012 A1 | 10/2012 | Gao-Saari et al. |
| 2012/0302991 A1 | 11/2012 | Blomquist et al. |
| 2012/0303388 A1 | 11/2012 | Venkata et al. |
| 2012/0310205 A1 | 12/2012 | Lee et al. |
| 2012/0323212 A1 | 12/2012 | Murphy et al. |
| 2013/0006651 A1 | 1/2013 | Saus et al. |
| 2013/0006666 A1 | 1/2013 | Schneider et al. |
| 2013/0012880 A1 | 1/2013 | Blomquist |
| 2013/0030830 A1 | 1/2013 | Schmoll et al. |
| 2013/0041257 A1 | 2/2013 | Nemoto |
| 2013/0042194 A1 | 2/2013 | Gannon et al. |
| 2013/0045764 A1 | 2/2013 | Vik et al. |
| 2013/0046871 A1 | 2/2013 | Vik et al. |
| 2013/0091191 A1 | 4/2013 | Levin et al. |
| 2013/0104120 A1 | 4/2013 | Arrizza et al. |
| 2013/0132465 A1 | 5/2013 | Brown |
| 2013/0133036 A1 | 5/2013 | Wang et al. |
| 2013/0141329 A1 | 6/2013 | Halbert et al. |
| 2013/0177455 A1 | 7/2013 | Kamen et al. |
| 2013/0182381 A1 | 7/2013 | Gray et al. |
| 2013/0184676 A1 | 7/2013 | Kamen et al. |
| 2013/0188040 A1 | 7/2013 | Kamen et al. |
| 2013/0191513 A1 | 7/2013 | Kamen et al. |
| 2013/0197693 A1 | 8/2013 | Kamen et al. |
| 2013/0204188 A1 | 8/2013 | Kamen et al. |
| 2013/0227462 A1 | 8/2013 | Hsu |
| 2013/0272773 A1 | 10/2013 | Kamen et al. |
| 2013/0281965 A1 | 10/2013 | Kamen et al. |
| 2013/0297330 A1 | 11/2013 | Kamen et al. |
| 2013/0310990 A1 | 11/2013 | David et al. |
| 2013/0317753 A1 | 11/2013 | Kamen et al. |
| 2013/0317837 A1 | 11/2013 | Ballantyne et al. |
| 2013/0336814 A1 | 12/2013 | Kamen et al. |
| 2013/0339049 A1 | 12/2013 | Blumberg, Jr. et al. |
| 2013/0346108 A1 | 12/2013 | Kamen et al. |
| 2014/0165703 A1 | 6/2014 | Wilt et al. |
| 2014/0180711 A1 | 6/2014 | Kamen et al. |
| 2014/0188076 A1 | 7/2014 | Kamen et al. |
| 2014/0188516 A1 | 7/2014 | Kamen et al. |
| 2014/0195639 A1 | 7/2014 | Kamen et al. |
| 2014/0227021 A1 | 8/2014 | Kamen et al. |
| 2014/0278458 A1 | 9/2014 | Borges et al. |
| 2014/0318639 A1 | 10/2014 | Peret et al. |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |

(56) References Cited

U.S. PATENT DOCUMENTS

| | | |
|---|---|---|
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2018/0224012 A1 | 8/2018 | Peret et al. |
| 2018/0228964 A1 | 8/2018 | Blumberg, Jr. et al. |
| 2018/0252359 A1 | 9/2018 | Janway et al. |
| 2018/0278676 A1 | 9/2018 | Kamen et al. |
| 2019/0009018 A1 | 1/2019 | Kamen et al. |
| 2019/0033104 A1 | 1/2019 | Kane et al. |
| 2019/0041362 A1 | 2/2019 | Blumberg, Jr. |
| 2019/0049029 A1 | 2/2019 | Peret et al. |
| 2019/0134298 A1 | 5/2019 | Kamen et al. |
| 2019/0139640 A1 | 5/2019 | Kamen et al. |
| 2019/0154026 A1 | 5/2019 | Kamen et al. |
| 2019/0170134 A1 | 6/2019 | Kamen et al. |
| 2019/0175821 A1 | 6/2019 | Kamen et al. |
| 2019/0179289 A1 | 6/2019 | Peret et al. |
| 2019/0189272 A1 | 6/2019 | Kamen et al. |
| 2019/0219047 A1 | 7/2019 | Kamen et al. |
| 2019/0249657 A1 | 8/2019 | Kamen et al. |
| 2019/0298913 A1 | 10/2019 | Biasi et al. |
| 2019/0316948 A1 | 10/2019 | Karol et al. |
| 2019/0328964 A1 | 10/2019 | Desch et al. |
| 2019/0341146 A1 | 11/2019 | Kamen et al. |
| 2019/0365421 A1 | 12/2019 | Langenfeld et al. |
| 2020/0025305 A1 | 1/2020 | Peret et al. |
| 2020/0051190 A1 | 2/2020 | Kamen et al. |
| 2020/0054823 A1 | 2/2020 | Baier et al. |
| 2020/0066388 A1 | 2/2020 | Kamen et al. |
| 2020/0070113 A1 | 3/2020 | Demers et al. |
| 2020/0078127 A1 | 3/2020 | Demers et al. |
| 2020/0171241 A1 | 6/2020 | Kamen et al. |
| 2020/0173469 A1 | 6/2020 | Kamen et al. |
| 2020/0182400 A1 | 6/2020 | Gray et al. |
| 2020/0278078 A1 | 9/2020 | Janway et al. |
| 2020/0292127 A1 | 9/2020 | Janway et al. |
| 2020/0347949 A1 | 11/2020 | Yoo |
| 2020/0371497 A1 | 11/2020 | Peret et al. |
| 2020/0386220 A1 | 12/2020 | Kamen et al. |
| 2020/0393414 A1 | 12/2020 | Wilt et al. |
| 2021/0023296 A1 | 1/2021 | Langenfeld et al. |
| 2021/0062929 A1 | 3/2021 | Peret et al. |
| 2021/0065867 A1 | 3/2021 | Kamen et al. |
| 2021/0085858 A1 | 3/2021 | Kamen et al. |
| 2021/0098102 A1 | 4/2021 | Blumberg, Jr. et al. |
| 2021/0125719 A1 | 4/2021 | Peret et al. |

FOREIGN PATENT DOCUMENTS

| | | |
|---|---|---|
| EP | 2216913 A1 | 8/2010 |
| EP | 2701131 A2 | 2/2014 |
| JP | 2006-163891 A2 | 6/2006 |
| JP | 2006-520037 A2 | 8/2006 |
| JP | 2009-059040 A2 | 3/2009 |
| JP | 2009-531146 A2 | 9/2009 |
| JP | 2010-050460 A2 | 3/2010 |
| JP | 2010-130193 A2 | 6/2010 |
| JP | 4488735 B2 | 6/2010 |
| JP | 2010-524050 A2 | 7/2010 |
| JP | 2010-538696 A2 | 12/2010 |
| JP | 4867980 B2 | 2/2012 |
| JP | 5555162 B2 | 7/2014 |
| JP | 5559810 B2 | 7/2014 |
| WO | WO03038566 A2 | 5/2003 |
| WO | WO2004070562 A2 | 8/2004 |
| WO | WO2005008947 A1 | 1/2005 |
| WO | WO2006050206 A1 | 5/2006 |
| WO | WO2010053703 A1 | 5/2010 |
| WO | WO2010135340 A2 | 11/2010 |
| WO | WO2012073166 A1 | 6/2012 |

* cited by examiner

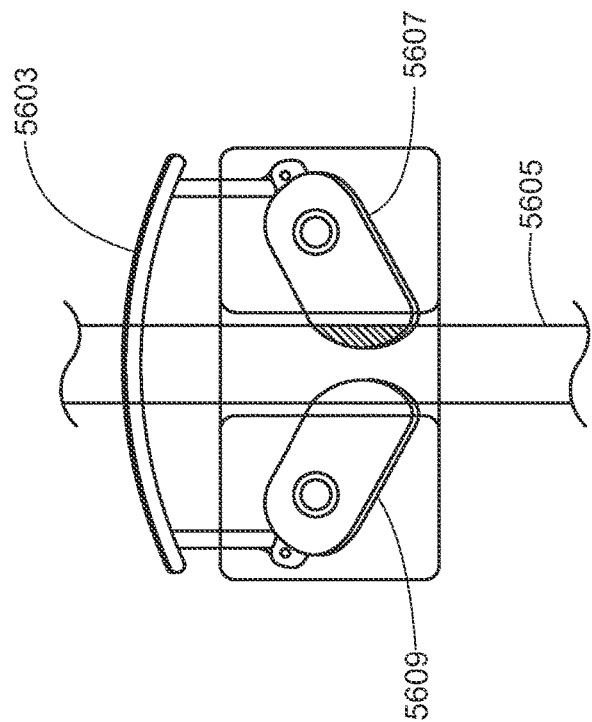
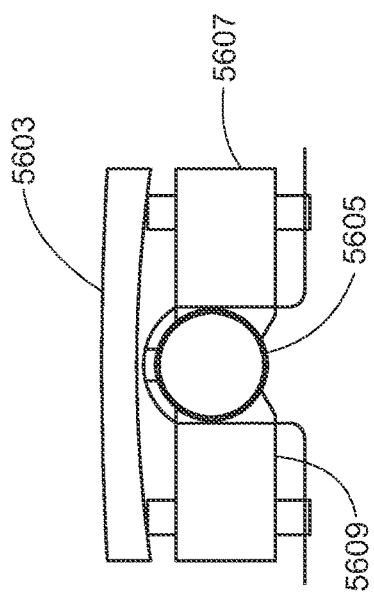
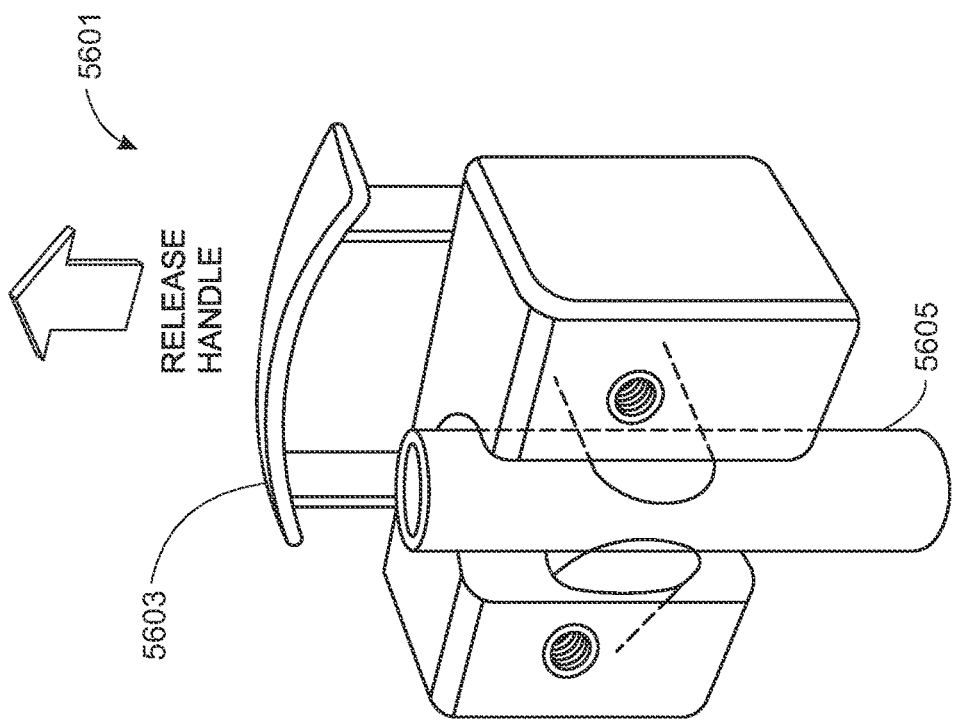
FIG. 57
FIG. 58
FIG. 56

Note 1: The supply voltage (Vs) to the Devices could be programmed or a constant

PT List    IV List

McKnight, James    01-Apr-1960
MRN: 23478654    M    2 days
2 East/2145    75 kg ▶ Pump Pod 1
Channel A    ⊙    Channel B    ⊙
Nitroglycerin    Abciximab
5 mcg/kg/min    0.125 mcg/kg/min
3mL/hour    5.25 mL/hour ▶ Pump Pod 2    ⊙
Channel A
Clarithromycin
500 mg
IVSS Q12H ● Micro Pump 1    ⊙
Insulin
U100
5 units/hour PT Dash | PT Info | Worklist | IV List

Occlusion Checklist
☐ Inspect infusion site
☐ Inspect the catheter
☐ Inspect the entire IV line for kinks or other obstructions
☐ Inspect for any visible obstructions in the IV tubing Check for occlusion?

[Silence] [Home] [Yes]

5 R's Confirmed
☐ Right Patient
☐ Right Route
☐ Right Dose
☐ Right Time
☐ Right Medicine

[Cancel] [Next]

SYSTEM, METHOD, AND APPARATUS FOR ELECTRONIC PATIENT CARE

CROSS-REFERENCE TO RELATED APPLICATIONS

The present application is a Continuation of U.S. patent application Ser. No. 16/654,391, filed Oct. 16, 2019 and entitled System, Method, and Apparatus for Electronic Patient Care, which will be U.S. Pat. No. 11,524,107, issuing Dec. 13, 2022, which is a Continuation of U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, which is a Continuation-in-Part of U.S. patent application Ser. No. 13/011,543, filed Jan. 21, 2011 and entitled Electronic Patient Monitoring System, which claims priority to U.S. Provisional Patent Application No. 61/297,544, filed Jan. 22, 2010 and entitled Electronic Order Intermediation System for a Medical Facility, all of which are hereby incorporated herein by reference in their entireties.

BACKGROUND

Field of Disclosure

The present disclosure relates to patient care. More particularly, the present disclosure relates to a system, method, and apparatus for electronic patient care.

Description of Related Art

Providing patient care in a hospital generally necessitates the interaction of numerous professionals and caregivers (e.g., doctors, nurses, pharmacists, technicians, nurse practitioners, etc.) and any number of medical devices/systems needed for treatment of a given patient. Despite the existence of systems intended to facilitate the care process, such as those incorporating electronic medical records ("EMR") and computerized provider order entry ("CPOE"), the process of providing comprehensive care to patients including ordering and delivering medical treatments, such as medications, is associated with a number of non-trivial issues.

SUMMARY

In an exemplary embodiment involving the ordering and administration of medications, the electronic patient care system may comprise a first data-gathering module (e.g., a monitoring client) and a second order-input module (e.g., a fixed or portable monitoring client) having a user interface for transmitting an order or receiving patient-related information. The first module may be configured to receive and store measured parameters pertaining to a patient's current condition (i.e., patient-condition parameters), such as blood pressure, heart rate, heart rhythm, temperature, oxygenation, respiratory rate, or ventilation, for example. The first module may also be configured to receive information about pre-existing parameters related to the patient from a first database (e.g., an EHR database containing information about the patient), for example, including patient-condition parameters such as medication allergies or sensitivities, other currently administered medications presently in the patient's tissue, age, weight, height, kidney, or liver function. The first module may also be configured to obtain medication information about the ordered medication and/or pre-existing medications from a second database (e.g., a drug information database), such as known medication interactions, effects of the medication or pre-existing medications on blood pressure, pulse, heart rhythm, or respirations, for example. The first module can be configured to compare the patient's currently-measured, patient-condition parameters and received, pre-existing, patient-condition parameters with known normal ranges, and create a table of patient-condition parameters found to be outside the normal ranges. The first module may then compare the table of patient-condition parameters with a table of corresponding parameters obtained from the drug information database. If a match is found to exist between the table of patient-condition parameters and the table of corresponding parameters, the first module may then retrieve one or more pre-entered and stored messages for transmission to the second (order input) module. These messages may include, for example, warnings to a user of the second module that are appropriate for the particular medication ordered, the patient's pre-existing medications, and the patient's current and pre-existing medical condition. Optionally, further repetitions of warnings may be avoided once a warning has been received by the second module, and the warning has been acknowledged by the user of the second module through an input signal from the user interface.

In other embodiments, the electronic patient-care system may provide the user with editable default values derived from standard dosing and administration guidelines obtained from the drug information database, and can alert the user to modifications that may be indicated based on the patient's current and pre-existing medical condition, allergies, existing medications, or other patient-condition parameters. The electronic patient-care system preferably minimizes the amount of typed input from a user.

In other embodiments, the first module or other modules of the electronic patient-care system may also be used to identify ordered medications to be delivered to the patient's bedside (through the use of, for example, bar codes and readers, or RFID tags and scanners), and verify that the appropriate medication and dosage are being prepared and delivered to the patient. In an embodiment, the first module may also interact through a wired or wireless communications link with a patient-care device that administers treatment, such as an infusion pump or pill dispenser. In the case of an infusion pump, the first module or another connected module may provide the infusion pump with patient-treatment parameters, such as infusion settings including an infusion rate or infusion pressure, and receive from it various operating parameters, such for example, the presence of air in the infusion line, the amount of solution remaining in an IV bag to which it is connected, or the pressure of fluid in the infusion line. If the operating parameters are found to be abnormal, the first module may be configured to respond by signaling the infusion pump to halt infusion, respond by signaling a mechanical occlude to occlude the IV line, alter the infusion rate, and/or alert a health care provider or others of the abnormality, either directly through an alarm incorporated in the first module, or by transmission of an alarm to the second module. In a further embodiment, the first module may also be configured to communicate with various patient-care devices used to monitor a patient's condition and determine patient-condition parameters, such as, for example, blood pressure monitors, ECG monitors, pulse oximetry monitors, temperature monitors, and the like. The various parameters monitored by be monitored and/or logged by a mobile device and/or within an EMR. In some cases, the first module can be programmed to emit an alert to the patient or other persons if the monitored patient-condition parameters fall outside a predetermined range. In some embodiments, the first module can transmit a signal to a monitoring client to conduct an unscheduled measurement by the patient-care device to obtain another patient-condition parameter. The first module may communicate with various health care providers at various locations, and in an embodiment may be able to notify the patient to whom it is assigned of an abnormality, and recommend corrective action through, for example an audible alert or recorded message.

In one embodiment, a system for preparing a microinfusion pump includes a monitoring client, a pharmacy computer, a compounding robot, a microinfusion pump, and a data download device. The monitoring client is configured to communicate a prescription order via a user interface. The pharmacy computer in is operative communication with the monitoring client to receive the prescription order. The compounding robot is configured to prepare the prescription into at least one liquid corresponding to the prescription order. The microinfusion pump is configured to receive the at least one liquid corresponding to the prescription order. The data download device is configured to download the prescription order into a memory of the microinfusion pump.

In some embodiments, the compounding robot fills the microinfusion pump with the at least one liquid. The compounding robot may be in operative communication with the data download device, and the compounding robot may instruct the data download device to download the prescription order into the memory of the microinfusion pump. The data download device may receive the prescription order from the compounding robot and/or the pharmacy computer. In some embodiments, the compounding robot receives the prescription order from the pharmacy computer.

In one embodiment of the present disclosure, a system includes a hub. The hub is configured to monitor a patient-care device. The hub includes an operating system (which may be embodied as a processor executing software) and a sandbox component (which may be embodied as a processor executing software). The operating system component is configured to access at least one of a hardware resource of the hub and a software resource of the hub.

The sandbox component is configured to control the access to the at least one of the hardware resource and the software resource. The hub is further configured to identify the patient-care device and execute an application to monitor the patient-care device. The hub may execute the application within the sandbox component such that the application accesses the at least one of the hardware resource and the software resource through the sandbox component.

The hub may be further configured to control the patient-care device. The patient-care device may be one or more of an infusion pump, a pill dispenser, a microinfusion pump, an ECG monitor, a blood pressure monitor, a pulse oximeter, a CO2 capometer, an intravenous bag, and/or a drip-flow meter.

The hub may be configured to receive an identification (e.g., a serial number, code (encrypted or unencrypted), or other identifying value) from the patient-care device and download the application from a server associated with the identification. The hub may also be configured to receive an identification from the patient-care device and update the application from a server associated with the identification.

The hardware resource may be a disk drive, memory, a buzzard, a microphone, a speaker and a camera. The software resource may be of a variable, a secure data object, a secure variable, a secured API, an API, and a software representation of a hardware component.

In yet another embodiment, a system for electronic patient care includes a hub. The hub is configured to monitor a patient-care device. The sandbox may be configured to control access to at least one of a hardware resource and a software resource. The hub is further configured to identify the patient-care device and execute an application to monitor the patient-care device. The hub executes the application within the sandbox component such that the application accesses the at least one of the hardware resource and the software resource through the sandbox component. The hub may be further configured to control the patient-care device. The hub may be further configured to receive an identification from the patient-care device and download the application from a server associated with the identification. The hub may be further configured to receive an identification from the patient-care device and update the application from a server associated with the identification.

The hardware resource may be a disk drive, memory, a buzzard, a microphone, a speaker and a camera. The software resource may be of a variable, a secure data object, a secure variable, a secured API, an API, and a software representation of a hardware component.

In yet another embodiment, a system for electronic patient care includes a monitoring client. The monitoring client is configured to monitor a patient-care device. The monitoring client includes an operating system component configured to access at least one of a hardware resource of the monitoring client and a software resource of the monitoring client. The sandbox component is configured to control the access to the at least one of a hardware resource and the software resource. The monitoring client may be further configured to identify the patient-care device and execute an application to monitor the patient-care device. The monitoring client executes the application within the sandbox component such that the application accesses the at least one of the hardware resource and the software resource through the sandbox component. The monitoring client is further configured to control the patient-care device.

The patient-care device may be an infusion pump, a pill dispenser, a microinfusion pump, an ECG monitor, a blood pressure monitor, a pulse oximeter, and/or a CO2 capometer, an intravenous bag, and a drip-flow meter.

The monitoring client may be further configured to receive an identification from the patient-care device and download the application from a server associated with the identification. The monitoring client may be further configured to receive an identification from the patient-care device and update the application from a server associated with the identification.

The hardware resource may be a disk drive, memory, a buzzard, a microphone, a speaker and a camera. The software resource may be of a variable, a secure data object, a secure variable, a secured API, an API, and a software representation of a hardware component.

In yet another embodiment, a system for electronic patient care includes a monitoring client configured to monitor a patient-care device. The monitoring client includes a sandbox component configured to control access to at least one of a hardware resource and a software resource. The monitoring client may be is further configured to identify the patient-care device and execute an application to monitor the patient-care device. The monitoring client executes the application within the sandbox component such that the application accesses the at least one of the hardware resource and the software resource through the sandbox component. The monitoring client may be further configured to control the patient-care device.

The patient-care device may be an infusion pump, a pill dispenser, a microinfusion pump, an ECG monitor, a blood pressure monitor, a pulse oximeter, and/or a CO2 capometer, an intravenous bag, and a drip-flow meter.

The monitoring client may be further configured to receive an identification from the patient-care device and download the application from a server associated with the identification. The monitoring client may be further configured to receive an identification from the patient-care device and update the application from a server associated with the identification.

The hardware resource may be a disk drive, memory, a buzzard, a microphone, a speaker and a camera. The software resource may be of a variable, a secure data object, a secure variable, a secured API, an API, and a software representation of a hardware component.

In another embodiment, a system for electronic patient care includes a hub configured to communicate with electronic medical records, and a patient-care device. The hub is configured to identify a patient and the patient-care device (e.g., an infusion pump). The hub is also configured to download at least one treatment parameter (e.g., an infusion drug, and/or an infusion rate or rate profile, etc.) from the electronic medical records and program the patient-care device with the at least one treatment parameter. The hub identifies the patient in accordance with at least one of reading an RFID tag using an RFID interrogator, a voice using voice recognition software coupled using a microphone, a face using face-recognition software coupled to a camera, a biometric parameter of biometric read, an identification, a barcode read by a barcode reader. In one specific embodiment, the hub may download the at least one treatment parameter using one or more of the identification techniques described herein.

In another embodiment, a system for electronic patient care includes a monitoring client configured to communicate with electronic medical records, and a patient-care device. The monitoring client is configured to identify a patient and the patient-care device (e.g., an infusion pump). The monitoring client is also configured to download at least one treatment parameter (e.g., an infusion drug, and/or an infusion rate or rate profile, etc.) from the electronic medical records and program the patient-care device with the at least one treatment parameter. The monitoring client identifies the patient in accordance with at least one of reading an RFID tag using an RFID interrogator, a voice using voice recognition software coupled using a microphone, a face using face-recognition software coupled to a camera, a biometric parameter of biometric read, an identification, a barcode read by a barcode reader. In one specific embodiment, the monitoring client may download the at least one treatment parameter using one or more of the identification techniques described herein.

In yet another embodiment, a system for electronic patient care comprises a monitoring client, a monitoring-client dock, a patient-care device, and a device dock. The monitoring client is configured to communicate at least one patient-care parameter. The monitoring-client dock is configured to receive the monitoring client for docking the monitoring client thereto. The patient-care device is configured to communicate the at least one patient-care parameter. The device dock is configured to receive the patient-care device for docking the patient-care device thereto.

In an embodiment, the monitoring-client dock and the device dock are configured to communicate one of wirelessly, and through a cable operatively coupled to the monitoring-client dock and the device dock.

In another embodiment, the monitoring client is configured to wirelessly communicate the at least one patient-care parameter.

In another embodiment, the monitoring-client dock is configured to wirelessly communicate with the monitoring client, and wherein the monitoring client operatively communicates with the patient-care device by communicating the at least one patient-care parameter wirelessly with the monitoring-client dock, through the cable to the dock, and to the docked patient-care device.

In another embodiment, the monitoring client operatively communicates the at least one patient-care parameter utilizing wireless communications to the monitoring-client dock when the monitoring client determines at least one of: communication through the cable is unavailable; and the monitoring client is undocked from the monitoring-client dock.

In another embodiment, the device dock is configured to wirelessly communicate with the monitoring client, and wherein the monitoring client operatively communicates with the patient-care device by communicating the at least one patient-care parameter wirelessly with the device dock to the docked patient-care device.

In another embodiment, the monitoring client operatively communicates the at least one patient-care parameter utilizing wireless communications with the device dock when the monitoring client determines at least one of: communication through the cable is unavailable; communication between the monitoring client and the monitoring-client dock is unavailable; and the monitoring client is undocked from the monitoring-client dock.

In another embodiment, the patient care device is configured to wirelessly communicate with the monitoring client, and wherein the monitoring client wirelessly communicates the at least one patient-care parameter with the patient-care device.

In another embodiment, the monitoring client operatively communicates the at least one patient-care parameter wirelessly with the patient-care device when the monitoring client determines at least one of: communication through the cable is unavailable; communication between the monitoring client and the monitoring-client dock is unavailable; communication between the device dock and the patient-care device is unavailable; the monitoring client is undocked from the monitoring-client dock.

In another embodiment, the monitoring-client dock and the dock are configured to communicate the at least one patient parameter wirelessly. The system may further comprise a cable operatively coupled to the monitoring-client dock and the device dock; and wherein the monitoring-client dock and the dock are configured to communicate wirelessly when at least one of the device dock, the monitoring-client dock, and the monitoring client determines the cable is unavailable as a communications link.

In another embodiment, the monitoring client is configured to communicate with the patient-care device via a plurality of communication links, and wherein the monitoring client communicates via an operative one of the plurality of communications links.

In another embodiment, the patient-care device is one of an infusion pump, a pill dispenser, a microinfusion pump, an ECG monitor, a blood pressure monitor, a pulse oximeter, and a CO2 capometer, an intravenous bag, and a drip-flow meter.

In another embodiment, the patient-care parameter is at least one of a intravenous pump flow parameter, an ECG parameter, a blood pressure parameter, a pulse oximeter parameter, a CO2 capometer parameter, an intravenous bag parameter, and a drip-flow meter value. The patient-care parameter may be a patient-condition parameter and/or a patient-treatment parameter.

In another embodiment, the patient-care device is configured to wirelessly communicate as a node of a mesh network.

In another embodiment, a cable operatively coupled to the monitoring-client dock and the device dock; wherein the monitoring client is configured to communicate the at least one patient-care parameter with the patient-care device through the cable when the patient-care device is docked to the device dock and the monitoring client is docked to the monitoring-client dock.

In yet another embodiment, a system for electronic patient care comprises a monitoring client, a patient-care device, and a device dock. The monitoring client is configured to communicate at least one patient-care parameter. The patient-care device is configured to communicate the at least one patient-care parameter. The device dock is configured to receive the patient-care device for docking the patient-care device thereto and to receive the monitoring client for docking the monitoring client thereto.

In yet another embodiment, a system for electronic patient care comprises: a patient-care device configured to communicate the at least one patient-care parameter; a monitoring client configured to communicate at least one patient-care parameter; and a device dock configured to receive the patient-care device for docking the patient-care device thereto. The device dock and the monitoring client are integrated together.

In yet another embodiment, a system for electronic patient care comprises: a stackable monitoring client configured to communicate at least one patient-care parameter; and a stackable patient-care device configured to communicate the at least one patient-care parameter. The stackable monitoring client and the stackable patient-care device may communicate the at least one patient-care parameter via a daisy-chained communications link and/or using a backplane.

In yet another embodiment, a system for electronic patient care comprises: a patient-care device configured to communicate the at least one patient-care parameter; a hub client configured to communicate at least one patient-care parameter; and a device dock configured to receive the patient-care device for docking the patient-care device thereto. The hub may plug into the device dock to establish a communications link therebetween. The system may further comprise a monitoring client in operative communication with the hub to receive the at least one patient-care parameter. The patient-treatment parameter may be operatively communicated to the hub and the hub communicates the patient-treatment parameter to the patient care device.

In a specific embodiment, the hub may include a user interface, and the hub may require user verification prior to sending the patient-treatment parameter to the patient-care device.

In a specific embodiment, the monitoring client may include a user interface, and the monitoring client may require user verification prior to sending the patient-treatment parameter to the patient-care device through the hub.

In a specific embodiment, the patient-care device may include a user interface, and the patient-care device may require user verification of the patient-treatment parameter prior to treating a patient.

The hub may be configured to monitor a patient-care device. In a specific embodiment, the hub may include a sandbox component configured to control access to at least one of a hardware resource and a software resource.

The hub may be further configured to identify the patient-care device and execute an application to monitor the patient-care device. The hub may execute the application within the sandbox component such that the application accesses the at least one of the hardware resource and the software resource through the sandbox component.

In another embodiment, a system for electronic patient care comprises: at least one patient monitor adapted to monitor at least one patient parameter; a monitoring client in operative communication with the at least one patient monitor to receive the at least one patient parameter therefrom; and a monitoring server in operative communication with the monitoring client for receiving the at least one patient parameter from the monitoring client.

In another embodiment, the system may further comprise a remote communicator in operative communication with the at least one patient monitor to receive the at least one patient parameter.

The at least one patient monitor may includes at least one of an electrocardiography monitor, a blood pressure monitor, a pulse oximeter monitor, and a CO2 capnometer. The monitoring client may be configured to download patient information in accordance with a designated unique patient identifier. The unique patient identifier may be encoded in a bar code disposed on a wrist band. The unique patient identifier may be encoded on an RFID tag coupled to a wrist band. (e.g., an RFID interrogator). The patient information includes a patient condition or a patient care parameter. The unique patient identifier may be operatively sent to the monitoring server to obtain electronic permission to communicate patient-specific data. A subset of the patient-specific data may be stored within a memory of the monitoring client. The monitoring client may be adapted to determine if a new order meets predetermined criteria based upon the subset of the patient-specific data stored within the memory.

In another embodiment, the system further comprises a portable monitoring client adapted to submit the new order to the monitoring client. At least one of the monitoring client and/or the remote communicator may be adapted to communicate the new order to the monitoring server, and wherein the monitoring server may be adapted to determine if the new order meets another predetermined criteria.

In another embodiment, the new order may be an order for medication and the monitoring server may be adapted to determine if the new order meets the another predetermined criteria by determining if the order for medication is contraindicated by a currently prescribed medication. The monitoring server may communicate with a database to determine if the new order meets the another predetermined criteria. The monitoring server may be configured to send an alert to the monitoring client when the new order does not meet the another predetermined criteria.

In another embodiment, the system may comprise a remote communication adapted for operative communication with at least one of the monitoring client and the monitoring server.

In another embodiment, the monitoring client may be one of a desk-based device, a portable device, a hand-held controller, a notebook PC, a netbook PC, a tablet PC, and a smart phone. The monitoring client includes a touchscreen.

In another embodiment, the system may further include an infusion pump, and the monitoring client is in operative communication with the infusion pump. The infusion pump may be attachable to the monitoring client. The infusion pump may be detachable to the monitoring client.

In another embodiment, the system further comprises a dock configured to dock the monitoring client to the infusion pump.

In another embodiment, the monitoring client is in operative communication with the infusion pump via a wireless link.

In another embodiment, the monitoring server is configured to communicate with a plurality of databases, and wherein at least one of the plurality of databases includes a data formatting or a communications protocol different from another database of the plurality of databases.

In another embodiment, the monitoring server is adapted to format data from the plurality of databases to download the data into the monitoring client. Optionally, and in some specific embodiment, the monitoring client may communicate the at least one patient parameter to the monitoring server. In a specific embodiment, the patient parameter may be one or more of and/or comprise at least one of treatment progress of an infusion pump, an electrocardiographic signal, a blood pressure signal, a pulse oximeter signal, a $CO_2$ capnometer signal, and/or a temperature signal.

In another embodiment, the monitoring server may be configured to download operational instructions to an infusion pump via the monitoring client.

The monitoring client may receive a user request to read the patient parameter and may interrogate the monitoring device to receive the patient parameter.

In another embodiment, the system may further comprise a portable monitoring client. The portable monitoring client may be in operative communication with the monitoring client for directly communicating patient information thereby bypassing the monitoring server. The portable monitoring client may be configured to change at least one parameter of an infusion pump and communicate the changed at least one parameter to the monitoring server.

A change in a patient order submitted via the portable monitoring client may be transmitted to another portable monitoring client.

In another embodiment, the monitoring client is configured to periodically upload information to the monitoring server for storage in a patient-specific database.

The system may further comprise another monitoring client adapted to receive the information from the patient-specific database.

The information may include at least one of a patient order, a patient medication, a progress note, monitoring data from the patient monitor, and treatment data from an attached device.

The monitoring server may be configured to interrogate an electronic health records database to receive patient information therefrom. The monitoring server may be further configured to populate the monitoring client with a predefined set of information in accordance with the patient information.

The predefined set of information may include at least one of a patient age, a height, a weight, a diagnosis, a current medication, a medication category, a medication allergies, and a sensitivity.

In another embodiment, the remote portable monitoring client is adapted to communicate with the monitoring client via the monitoring server. The remote portable monitoring client may be one of a tablet PC, a netbook, and a PC. The remote portable monitoring client may include a touchscreen.

In another embodiment, a method for electronic patient care comprises: displaying a plurality of patients on a display; displaying at least one patient parameter on the display associated with a patient of the plurality of patients; displaying at least one alert associated with the patient on the display; and selecting the patient from the plurality of patients.

The method, in some specific embodiments, may further comprise sending the alert to a portable remote communicator device having the display from a monitoring client.

In yet another embodiment, an electronic patient-care system comprises: a monitoring client configured to communicate at least one patient-care parameter; a patient-care device configured to communicate the at least one patient-care parameter; and a communication interface configured to facilitate communication between the monitoring client and the at least one patient care device, by discovering the presence of the at least one patient-care device and translating communication signals from that device into a communication protocol associated with the monitoring client.

In a specific embodiment, the communication interface is further configured to discover the presence of additional other patient-care devices that are different from one another, and to translate communication signals from those devices into the communication protocol associated with the monitoring client.

In another specific embodiment, the communication interface is further configured to provision power suitable for each of the devices. In yet another specific embodiment, the system further comprises one or more databases accessible by the monitoring client that allow for at least one of central storage of patient info and/or downloading information that can be used in treating of a patient associated with the monitoring client.

In yet another specific embodiment, the communication interface is further configured to perform fault checking to at least one of assess data integrity of communications with the patient-care device, assess whether the monitoring the client is functioning properly, assess whether the patient-care device is functioning properly, and/or assess whether the communication interface is functioning properly.

In yet another embodiment, an electronic patient-care system comprises: a hub client configured to communicate at least one patient-care parameter; a patient-care device configured to communicate the at least one patient-care parameter; and a communication interface configured to facilitate communication between the hub and the at least one patient care device, by discovering the presence of the at least one patient-care device and translating communication signals from that device into a communication protocol associated with the hub.

In a specific embodiment, the communication interface is further configured to discover the presence of additional other patient-care devices that are different from one another, and to translate communication signals from those devices into the communication protocol associated with the hub.

In another specific embodiment, the communication interface is further configured to provision power suitable for each of the devices. In yet another specific embodiment, the system further comprises one or more databases accessible by the hub that allow for at least one of central storage of patient info and/or downloading information that can be used in treating of a patient associated with the hub.

In yet another specific embodiment, the communication interface is further configured to perform fault checking to at least one of assess data integrity of communications with the patient-care device, assess whether the monitoring the client is functioning properly, assess whether the patient-care device is functioning properly, and/or assess whether the communication interface is functioning properly.

In yet another embodiment, an electronic patient-care system comprises: a dock configured to communicate at least one patient-care parameter; a patient-care device configured to communicate the at least one patient-care parameter; and a communication interface configured to facilitate communication between the dock and the at least one patient care device, by discovering the presence of the at least one patient-care device and translating communication signals from that device into a communication protocol associated with the dock.

In a specific embodiment, the communication interface is further configured to discover the presence of additional other patient-care devices that are different from one another, and to translate communication signals from those devices into the communication protocol associated with the dock.

In another specific embodiment, the communication interface is further configured to provision power suitable for each of the devices. In yet another specific embodiment, the system further comprises one or more databases accessible by the dock that allow for at least one of central storage of patient info and/or downloading information that can be used in treating of a patient associated with the dock.

In yet another specific embodiment, the communication interface is further configured to perform fault checking to at least one of assess data integrity of communications with the patient-care device, assess whether the monitoring the client is functioning properly, assess whether the patient-care device is functioning properly, and/or assess whether the communication interface is functioning properly.

In an embodiment, a patient-care device comprises: a body; a raceway within the body configured to receive a pole; and two friction members coupled to the body and configured to frictionally lock the body to a pole within the raceway.

In an embodiment, a hub comprises: a patient-care device interface; a power supply coupled to the patient-care device interface and configured to supply power to a patient-care device; a processor; a transceiver coupled to the patient-care device interface configured to provide communications between the processor and the patient-care device. The processor may be configured, in some specific embodiments, to disable the patient-care device when in an alarm state.

In an embodiment, a dock comprises: a patient-care device interface; a power supply coupled to the patient-care device interface and configured to supply power to a patient-care device; a processor; a transceiver coupled to the patient-care device interface configured to provide communications between the processor and the patient-care device. The processor may be configured, in some specific embodiments, to disable the patient-care device when in an alarm state.

In an embodiment, a communication module comprises: a patient-care device interface; a power supply coupled to the patient-care device interface and configured to supply power to a patient-care device; a processor; a transceiver coupled to the patient-care device interface configured to provide communications for patient-care device and another device. The processor may be configured, in some specific embodiments, to disable the patient-care device when in an alarm state.

In another embodiment, a patient-care system comprises: a dock; a plurality of modular patient-care device configured to dock with the dock; and a retracting display of a monitoring client. The modular patient-care devices may interface with the dock along a horizontal plane, in a staggered fashion, or via a connector.

In yet another embodiment, an electronic patient care system comprises: a first module configured to receive and store information pertaining to a patient, said information including data related to a first parameter of the patient measured by a device connected to the patient, and data related to a second parameter of the patient received from a first database containing information about the patient; and a second module configured to receive a medication order from a user via a user interface associated with the second module, said second module being further configured to transmit said treatment order to the first module, wherein said first module is further configured to: a) obtain medication information about said medication or other drugs from a second database, the medication information including data providing limitations under which such medication is generally administered; b) determine whether the medication order must (in this specific embodiment) be confirmed by the second module based on the medication information, the value of the first parameter and the value of the second parameter; and c) transmit a pre-established message from the first module to the second module for display on the user interface, said message confirming or warning about the acceptability of said medication order.

The medication information may include drug interactions information, drug allergies information, blood pressure effects information, heart rate effects information, heart rhythm effects information, or respiration effects information, and wherein the first parameter or the second parameter include data about the patient's currently administered drugs, known drug allergies, current blood pressure, current pulse rate, current heart rhythm, current respiratory rate or current ventilation.

The pre-established message may include a warning about the potential effects of the ordered medication, said warning including measured data about the first parameter, received data about the second parameter, or medication information obtained by the first module.

The first module may be configured to generate a signal that the medication order or a modified medication order is to be processed after the pre-established message has been transmitted and upon receipt of a confirmation signal from the second module, the confirmation signal being triggered by an input signal from the user interface.

In another embodiment, a patient-care device comprises a first communications link and a second communications link; and a dock includes a first communications link and a second communications link. When the patient-care device is within a predetermined range with the dock, the patient-care device and the dock are paired using the first communications link and remain in communication using the second communications link after the pairing. The pairing that occurs using the first communications link may be to pair the patient-care device and the dock for the second communications link. The first communications link may be near-field communications and the second communications link may be Bluetooth, Bluetooth Low Energy, WiFi, or other communications link.

In another embodiment, a patient-care device comprises a first communications link and a second communications link; and a monitoring client includes a first communications link and a second communications link. When the patient-care device is within a predetermined range with the monitoring client, the patient-care device and the monitoring client are paired using the first communications link and remain in communication using the second communications link after the pairing. The pairing that occurs using the first communications link may be to pair the patient-care device and the monitoring client for the second communications link. The first communications link may be near-field communications and the second communications link may be Bluetooth, Bluetooth Low Energy, WiFi, or other communications link.

In some embodiments, a patient-care device comprises memory having a user interface template stored therein. The user interface template may be communicated to a dock, a hub, and or a monitoring client for displaying on a user interface of the dock, the hub, and/or the monitoring client. The user interface template may be configured to display one or more patient-care parameters received from the patient-care device (e.g., in real-time).

In yet another embodiment, an infusion pump includes an attachable electronic component. The attachable electronics component includes at least one processor, a power regulator, and a control system.

In an embodiment, a communication module includes at least one processor, and one or more of a transceiver, a battery, and a power supply to provide at least one of communications capability and power to a patient-care device.

In yet another embodiment, a wearable system monitor includes a watchdog component and a transceiver. The wearable system monitor may include a processor coupled to the watchdog component and the transceiver to perform a watchdog function for at least one paired device. The paired device may be at least one of a dock, a hub, a monitoring client, and/or a patient-care device.

In yet another embodiment, a method includes one or more of: establish a communications link between a patient-care device and a monitoring server; communicate a patient-care parameter to the monitoring server; de-identify the patient-care parameter; and/or store the de-identified patient-care parameter in the monitoring server.

In yet another embodiment, a method includes one or more of: establish communications links between a monitoring server and a plurality of patient-care devices associated with a plurality of patients; communicate a plurality of patient-care parameters from the plurality of patient-care device to the monitoring server; de-identify the patient-care parameters; store the patient-care parameters in the monitoring server; treat a plurality of patients with a treatment; and analyze a subset of the plurality of patient-care parameters associated with the plurality of patients to determine the efficacy of the treatment.

In yet another embodiment, a patient-care device (e.g., an infusion pump) is hot-swappable in at least one of a dock, a hub, and/or a monitoring client connection.

In yet another embodiment, a method for having a hot-swappable patient-care device, e.g., an infusion pump, includes one or more of: receiving one or more patient-care parameters associated with a patient-care device; storing the one or more patient-care parameters in a non-volatile memory of the patient-care device; loading the one or more patient-care parameters into the working memory; and resuming operation of the patient-care device. The method may include, in an additional embodiment determining that operation of the patient-care device can resume.

In yet another embodiment, a method for having a hot-swappable patient-care device, e.g., an infusion pump, includes one or more of: calculating one or more operating parameters associated with a patient-care device; storing the one or more operating parameters in a non-volatile memory of the patient-care device; loading the one or more operating parameters into the working memory; and resuming operation of the patient-care device. The method may include, in an additional embodiment determining that operation of the patient-care device can resume.

In yet another embodiment, a method for pairing includes: positioning a monitoring client and/or a hub having a user interface within an operational distance of a patient-care device (e.g., an infusion pump); displaying the identity of the patient-care device on the user interface; selecting the patient-care device for pairing using the user interface; pairing the patient-care device to the monitoring client and/or the hub; and/or communicating patient-care parameters to the monitoring client and/or the hub. In yet another embodiment, and optionally, the method may include operatively communicating additional patient-care parameters with another patient-care device through the patient-care device, e.g., to the monitoring client and/or the hub.

In yet another embodiment, a method includes: docking a patient-care device into a dock; identifying the patient-care device; querying a server for an application to control the patient-care device; downloading the application into a dock, a hub, and/or a monitoring client; executing the application using the dock, the hub, and/or the monitoring client; and controlling the patient-care device using the application.

In yet another embodiment, a method includes: placing a patient-care device into in operative communication with a hub; the hub may identify the patient-care device; the hub may query a server for an application to control the patient-care device; the hub may download the application into a hub; the hub may execute the application; and the hub may control the patient-care device using the application.

In yet another embodiment, a method includes: placing a patient-care device into in operative communication with a dock; the dock may identify the patient-care device; the dock may query a server for an application to control the patient-care device; the dock may download the application into a dock; the dock may execute the application; and the dock may control the patient-care device using the application.

In yet another embodiment, a method includes: placing a patient-care device into in operative communication with a monitoring client; the monitoring client may identify the patient-care device; the monitoring client may query a server for an application to control the patient-care device; the monitoring client may download the application into a monitoring client; the monitoring client may execute the application; and the monitoring client may control the patient-care device using the application.

In yet another embodiment, a method may include: submit a request on a user interface of a communications device; confirm the request; and send the request; receive the request with a check value; and confirm that the check value is in accordance with the request prior to sending.

In yet another embodiment, a hub includes a dock to receive a patient-care device, and at least one connector coupled to an opening door configured to receive another patient-care device.

In yet another embodiment, a hub is in operative communication with at least one of electronic medical records, DERS, CPOE, and/or and the internet to control and/or monitor a patient-care device.

In another embodiment, a hub is adapted to connect to a cradle to control one or more patient-care devices coupled to the cradle.

In yet another embodiment, a battery pack includes a patient-care device interface, a battery, and a regulated power supply configured to supply power to a patient-care device using the battery. The battery may, in some embodiment, be recharged using a DC power source.

In an embodiment, a patient-care device includes a screen and an accelerometer. The patient-care device is configured to display the screen in an upright position as determined using the accelerometer.

In yet another embodiment, an electronic patient-care system includes: a monitoring client and a dock configured to couple to a pole. An adapter may be coupled to the dock. The adapter may include at least one electronic coupler to place a patient-care device in operative communication with the monitoring client. The patient-care device may slide into the adapter.

In yet another embodiment, an electronic patient-care system includes a monitoring client, a patient-care device, and a communication module. The patient-care device and/or the communication module are fault-tolerant of the monitoring client. For example, the monitoring client cannot direct the patient-care device to perform an unsafe operation.

BRIEF DESCRIPTION OF THE DRAWINGS

These and other aspects will become more apparent from the following detailed description of the various embodiments of the present disclosure with reference to the drawings wherein:

FIG. 56 shows a perspective-view of a clutch system having a release handle for frictionally gripping to a pole in accordance with another embodiment of the present disclosure;

FIG. 57 shows a back-view of the clutch system of FIG. 56 showing a transparent back in accordance with another embodiment of the present disclosure;

FIG. 58 shows a top, cross-sectional view of the clutch system of FIG. 56 in accordance with another embodiment of the present disclosure;

FIG. 132 shows a 5 R's checklist that may be displayed on a monitoring client in accordance with an embodiment of the present disclosure;

FIG. 133 shows an occlusion checklist that may be displayed on a monitoring client in accordance with an embodiment of the present disclosure;

FIG. 134 shows a display of a monitoring client in operative communication with several infusion pumps in accordance with an embodiment of the present disclosure;

Figures 137, 138:
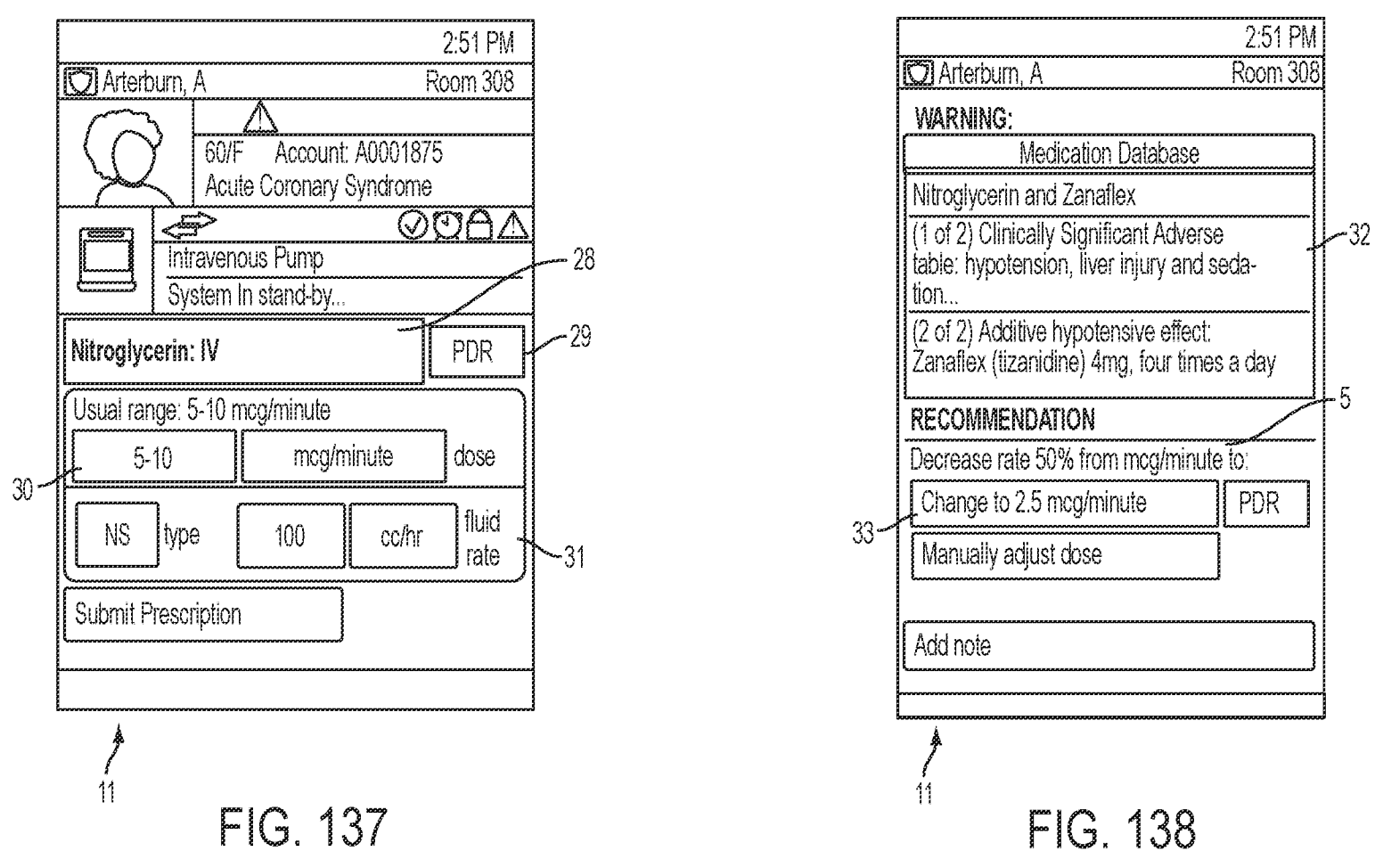

FIG. 137 is an illustration of a display on a health care provider's portable monitoring client, showing data entry fields for a prescription for a medication for use with an intravenous infusion pump in accordance with an embodiment of the present disclosure;

FIG. 138 is an illustration of a display on a health care provider's portable monitoring client, showing a risk profile associated with an ordered medication, and a suggested course of action, as generated by the monitoring client in accordance with an embodiment of the present disclosure;

DETAILED DESCRIPTION

Figure 1:
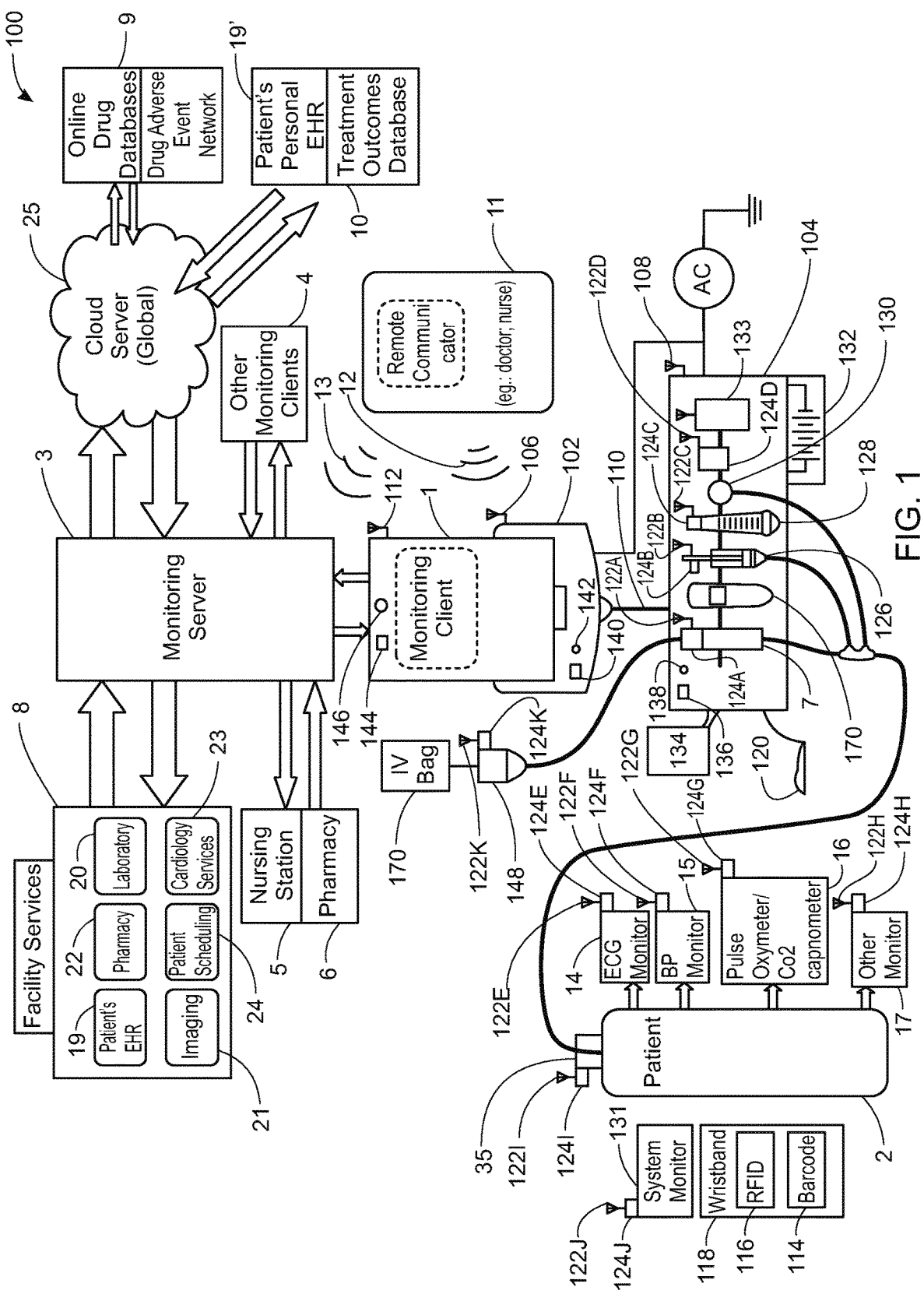
FIG. 1 is a block diagram of an electronic patient-care system having two docks in accordance with an embodiment of the present disclosure.

Techniques for facilitating patient care are disclosed. The techniques can be implemented, for example, in a system having one or more patient-care devices that are communicatively coupled to a monitoring client, in accordance with one exemplary embodiment. The patient-care devices may include any number of diverse functionalities and/or may be produced by different manufacturers. In one such case, a communication interface between the client monitoring station and the various diverse patient-care devices allows for discovery and protocol translation, as well as various other functionalities such as power provisioning, regulatory compliance, and user interface to name a few. A patient-care device may be an infusion pump, a microinfusion pump, an insulin pump, a syringe pump, a pill dispenser, a dialysis machine, a ventilator, a sonogram, a ECG monitor, a blood pressure monitor, a pulse oxymeter, a CO2 capnometer, a drip counter, a flow-rate meter, an optical Doppler device, a heart rate monitor, an IV bag, a hemodialysis machine, a peritoneal dialysis machine, intestinal dialysis machine, a patient thermometer, and/or other bedside patient-care device. U.S. patent application Ser. No. 11/704,899, filed Feb. 9, 2007 and entitled Fluid Delivery Systems and Methods, now U.S. Publication No. US-2007-0228071-A1 published Oct. 4, 2007, U.S. patent application Ser. No. 11/704,896, filed Feb. 9, 2007 and entitled Pumping Fluid Delivery Systems and Methods Using Force Application Assembly, now U.S. Publication No. US-2007-0219496, published Sep. 20, 2007, U.S. patent application Ser. No. 11/704,886, filed Feb. 9, 2007 and entitled Patch-Sized Fluid Delivery Systems and Methods, now U.S. Publication No. US-2007-0219481, published Sep. 20, 2007 and entitled Adhesive and Peripheral Systems and Methods for Medical Devices, now U.S. U.S. patent application Ser. No. 12/347,985, filed Dec. 31, 2008, and entitled Infusion Pump Assembly, now U.S. Publication No. US-2009-0299277 published Dec. 3, 2009, U.S. patent application Ser. No. 12/347,982, filed Dec. 31, 2008 and entitled Wearable Pump Assembly, now U.S. Publication No. US-2009-0281497, published Nov. 12, 2009, U.S. patent application Ser. No. 12/347,981, filed Dec. 31, 2008 and entitled Infusion Pump Assembly, now U.S. Publication No. US-2009-0275896, published Nov. 5, 2009, U.S. patent application Ser. No. 12/347,984 filed Dec. 31, 2008 and entitled Pump Assembly With Switch, now U.S. Publication No. US-2009-0299289, published Dec. 3, 2009, U.S. patent application Ser. No. 12/249,882, filed Oct. 10, 2008 and entitled Infusion Pump Assembly, now U.S. Publication No. US-2010-0094222, published Apr. 15, 2010, U.S. patent application Ser. No. 12/249,636, filed Oct. 10, 2008 and entitled System and Method for Administering an Infusible Fluid, now U.S. Publication No. US-2010-0094261, published Apr. 15, 2010, U.S. patent application Ser. No. 12/249,621, filed Oct. 10, 2008 and entitled Occlusion Detection System and Method, now U.S. Publication No. US-2010-0090843, published Apr. 15, 2010, U.S. patent application Ser. No. 12/249,600, filed Oct. 10, 2008 and entitled Multi-Language/Multi-Processor Infusion Pump Assembly, now U.S. Publication No. US-2010-0094221, published Apr. 15, 2010, U.S. Pat. No. 8,066,672, issued Nov. 29, 2011 and entitled An Infusion Pump Assembly with a Backup Power Supply, U.S. Pat. No. 8,016,789, issued Sep. 13, 2011 and entitled Pump Assembly with a Removable Cover Assembly, U.S. Pat. No. 7,306,578, issued Dec. 11, 2007 and entitled Loading Mechanism for Infusion Pump, all which are hereby incorporated herein by reference in their entireties. The techniques can be used to allow for seamless communication and failsafe operation. Numerous other features, functionalities, and applications will be apparent in light of this disclosure.

General Overview

As previously described the process of providing comprehensive care to patients, such as ordering and delivering of medical treatments, is associated with a number of non-trivial issues. For instance, there is great potential for critical information to be miscommunicated, treatment decisions to be made without ready access to complete information, and/or delay in implementation of prescriptions due to unnecessarily redundant and inefficient procedures.

In more detail, medication errors may be responsible for hundreds of deaths and may injure thousands or even millions of people each year in the United States alone. Hospitals under financial stress may experience an increased incidence of medication errors. Medications associated with the most dangerous errors include insulin, narcotics, heparin, and chemotherapy. Sources of medication errors include administering the wrong medication, administering the wrong concentration of medication, delivering the medication at the wrong rate, or delivering the medication through the wrong route (medications can be administered orally, intravenously, intramuscularly, subcutaneously, rectally, topically to the skin, eye or ear, intrathecally, intraperitoneally, or even intravesically). Even with proper ordering and proper labeling, medications may still be administered improperly because of illegible handwriting, miscommunication of prescriptions for medications, and mispronunciation of medications having similar names. The trend of using electronic medical records ("EMR") and bar coding systems for medications has been shown to reduce the incidence of medication errors. EMR systems, for example, can facilitate computerized provider order entry ("CPOE") and flag prescriptions that do not match a patient's diagnosis, allergies, weight, and/or age. However, these systems have not been widely adopted and their implementation can result in significant delays and inefficiencies in ordering, preparing, and administering medications.

In addition, medication infusion devices, e.g., infusion pumps, are involved in a substantial number (e.g., up to one third) of all medication errors that result in significant harm. The wrong medication may be hung, incorrect parameters (e.g., medication concentration or infusion rate) may be entered, or existing infusion parameters may be improperly changed. Of the deaths related to infusion pumps, nearly half may be due to user error and most of these errors may be due to errors in programming the infusion pump.

An effective monitoring system may monitor and intercede at any phase of the medication ordering and administration process to help minimize any of a number of adverse events that could result from the treatment. The medication treatment process may be conceptually separated into three phases: a prescription phase, a medication preparation phase, and a medication administration phase. Errors can occur when a prescription for a medication is written or entered, when the medication is retrieved for use or mixed in a solution, or when the medication is administered to the patient.

Thus, in accordance with an embodiment of the present disclosure, an electronic patient-care system is disclosed that includes a monitoring client configured to communicate at least one patient-care parameter, a patient-care device configured to communicate the at least one patient-care parameter, and a communication interface configured to facilitate communication between the monitoring client and the at least one patient care device, by discovering the presence of the at least one patient-care device and translating communication signals from that device into a communication protocol associated with the monitoring client. In some embodiments, the monitoring client passively monitors the operation of a patient-care device. The communication interface may be implemented by a communication module described below. The communication interface may be further configured to discover the presence of additional other patient-care devices that are different from one another (e.g., diverse manufacturers, functions, and/or communication protocols, etc), and to translate communication signals from those devices into the communication protocol associated with the monitoring client or a hub. Thus, the communication interface allows the monitoring client, such as a tablet computer, to effectively be used as common generic user interface that healthcare providers can use when providing treatment to a patient associated with the monitoring client.

One or more databases accessible by the monitoring client allow for central storage of patient info (in any format and database structure, as desired by the healthcare facility or database maintainer), as well as for downloading information that can be used by the healthcare providers in treatment of the patient associated with the monitoring client. The communication interface can be implemented in a number of ways, using wired and/or wireless technologies, and allows for seamless communication and failsafe operation of multiple patient-care devices. Some patient-care devices, hubs, docks, and/or monitoring clients may communicate simultaneously over two or more communications links and/or simultaneously over two frequency channels (in some embodiments, the data may be redundant). In some embodiments, the communication module may allow a patient-care device to be portability used, e.g., by including a battery and sufficient circuitry for mobile operation of the patient-care device, such as an infusion pump. Additionally or alternatively, a patient wristband may include batteries that can plug into the communication module to power the patient-care device (or in some embodiments, it may be plugged directly into the patient-care device). The communication module may be wirelessly charged.

In some embodiments, data such as patient-care parameters (e.g., real-time parameters, in some embodiments) may be transmitted to a cloud server for storage and may be de-identified.

System Architecture

As shown in FIG. 1, an electronic patient care system 100 includes one or more monitoring clients 1,4, each of which may be assigned and in physical proximity to an individual patient 2, and a remote monitoring server 3 for the uploading of information from a number of the various monitoring clients 1,4, and for downloading information and instructions from various sources to the monitoring clients 1,4. When in the patient's room, a health care provider can interact directly with a monitoring client 1 to obtain information about the patient 2 or to enter orders pertaining to the patient 2. Multiple monitoring clients 1 may interact with a single monitoring server 3. The monitoring server 3 may include middleware (e.g., middleware on the monitoring server 3 of FIG. 1). Additionally or alternatively, providers at remote locations (e.g., doctor's office, nursing station 5, hospital pharmacy 6) may interact with an individual monitoring client 1 through a communications link with the monitoring server 3 or directly via a hospital local area network having each of the monitoring clients 1,4 as a node.

A remote communicator 11, other monitoring clients 4, a nursing station 5, or a doctor's office may enter in prescriptions which are sent to update the Patient's Personal EHR 19 or are sent to the pharmacy 6 for filling. The prescription may be a prescription for pills, for infusing a fluid, or other treatment. The prescription may be a prescription for infusing a fluid using the infusion pump 7, the syringe pump 126 or the microinfusion pump 130, or for dispensing pills using the pill dispenser 128.

The pharmacy 6 may include one or more computers connected to a network, e.g., the internet, to receive the prescription and queue the prescription within the one or more computers. The pharmacy may use the prescription: (1) to compound the drug (e.g., using an automated compounding device that can compound a fluid or create a pill that is coupled to the one or more computers, or manually by a pharmacists viewing the queue of the one or more computers); (2) to pre-fill a fluid reservoir of a syringe pump 126; (3) to program the syringe pump 126 (e.g., a treatment regime is programmed into the syringe pump 126); (4) to pre-fill the microinfusion pump 130; (5) to program the microinfusion pump 130; (6) to pre-fill the IV bag 170; (7) to program the infusion pump 7; (8) to pre-fill the pill dispenser 128; (9) or to program the pill dispenser 128 at the pharmacy in accordance with the prescription. The automated compounding device may automatically fill the fluid within one or more of the syringe pump 126, the IV bag 170 or the microinfusion pump 130, and/or may automatically fill the pill dispenser 128 with pills. The automated compounding device may generate a barcode, an RFID tag and/or data. The information within the barcode, RFID tag, and/or data may include the treatment regime, prescription, and/or patient information.

The automated compounding device may: (1) attach the barcode to the infusion pump 7, the syringe pump 126, the microinfusion pump 130, the pill dispenser 128, or the IV bag 170; (2) attach the RFID tag to the infusion pump 7, the syringe pump 126, the microinfusion pump 130, the pill dispenser 128, or the IV bag 170; and/or (3) program the RFID tag or memory within the infusion pump 7, the syringe pump 126, the microinfusion pump 130, the pill dispenser 128, or the IV bag 170 with the information or data. The data or information may be sent to a database (e.g., the patient's EHR 19 or the patient's personal EHR 19') that associates the prescription with the infusion pump 7, the syringe pump 126, the microinfusion pump 130, the pill dispenser 128, or the IV bag 170, e.g., using a serial number or other identifying information within the barcode, RFID tag, or memory.

The infusion pump 7, the syringe pump 126, the microinfusion pump 130, or the pill dispenser 128 may have a scanner (e.g., an RFID interrogator or barcode scanner) that determines: (1) if the syringe pump 126 or the IV bag 170 has the correct fluid; (2) if the microinfusion pump 130 has the correct fluid; (3) if the pill dispenser 128 has the correct pills; (4) if the treatment programmed into the infusion pump 7, the syringe pump 126, the microinfusion pump 130, or the IV bag 170 corresponds to the fluid within the syringe pump 126, the microinfusion pump 130 or IV bag 170; (5) if the treatment programmed into the pill dispenser 128 corresponds to the pills within the pill dispenser 128; and/or (6) if the treatment programmed into the infusion pump 7, the syringe pump 126, the microinfusion pump 130, or the pill dispenser 128 is correct for the particular patient (e.g., as determined from a patient's barcode, RFID, or other patient identification). That is, in some specific embodiments, the infusion pump 7, the syringe pump 126, the microinfusion pump 130 and/or the pill dispenser 128 may read one or more serial numbers off of an RFID tag or barcode and ensure that the value matches a value as found in internal memory (e.g., downloaded via the automated compounding device, for example) or that the value matches a value as found in electronic medical records of a patient (e.g., via a patient's serial number as determined by a scan of an RFID tag of a patient or a scan of a barcode by the patient as stored in the patient's EHR 19 or the patient's personal EHR 19').

For example, the scanner of the infusion pump 7, the syringe pump 126, the microinfusion pump 130, or the pill dispenser 128 may scan a barcode of another patient-care device to obtain a serial number of the patient care device and a patient's barcode to determine a serial number of the patient, and may query the electronic medical records data to determine if the serial number of the patient-care device corresponds to the serial number of the patient as stored within the electronic medical records (e.g., which may have been updated by the pharmacy 22 or the automated compounding device of the pharmacy).

Additionally or alternatively, the monitoring client 6 may scan the infusion pump 7, the syringe pump 126, the pill dispenser 128, the microinfusion pump 130, or the IV bag 170 to determine: (1) if the syringe pump 126 or the IV bag 170 has the correct fluid; (2) if the microinfusion pump 130 has the correct fluid; (3) if the pill dispenser 128 has the correct pills; (4) if the treatment programmed into the infusion pump 7, the syringe pump 126, the microinfusion pump 130, or the IV bag 170 corresponds to the fluid within the syringe pump 126, the microinfusion pump 130 or IV bag 170; (5) if the treatment programmed into the pill dispenser 128 corresponds to the pills within the pill dispenser 128; and/or (6) if the treatment programmed into the infusion pump 7, the syringe pump 126, the microinfusion pump 130, or the pill dispenser 128 is correct for the particular patient (e.g., as determined from a patient's barcode, RFID, or other patient identification). Additionally or alternatively, the monitoring client 1, the infusion pump 7, the syringe pump 126, the microinfusion pump 130, or the pill dispenser 128 may interrogate the electronic medical records database 19 or 19' and/or the pharmacy 22 to verify the prescription or download the prescription, e.g., using a barcode serial number on the infusion pump 7, the syringe pump 126, the microinfusion pump 130, the pill dispenser 128, or the IV bag 170.

Optionally, the monitoring client 1, the other monitoring client 4, and/or the remote communicator 11 may be used to send commands or requests to the patient-care devices 7, 14, 15, 16, 17, 35, 126, 128, 130, 148 such as for example, a bolus amount, an infusion flow rate, a total fluid for delivery, a start time for drug delivery, a stop time for drug delivery or a flow-delivery-rate profile to the infusion pump 7, the syringe pump 126 and/or the microinfusion pump 130. In some embodiments, one or more of the monitoring clients 1, 4, 11 may be used to send commands or requests to the pill dispenser 7, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata); however, the medication may not be safe if taken in excess and the max pill-dispensing criteria may prevent the medication from being taken at unsafe levels by the patient, e.g., a predetermined amount during a predetermined interval of time.

Optionally, the patient-care devices 7, 14, 15, 16, 17, 35, 126, 128, 130, 148 may also communicate data back to the monitoring client 1, the other monitoring client 4 and/or the remote communicator 11 for: determining if an alarm or alert should be issued or sent; determining if the treatment or condition is safe for the patient; determining if the system 100 is operating properly or within predetermined bounds; and/or for displaying the data on a display of the monitoring client 1, the other monitoring client 4 and/or the remote communicator 11. For example, optionally, the infusion pump 7, the syringe pump 126, and/or the microinfusion pump 130 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the monitoring client 1, the other monitoring client 4 and/or the remote communicator 11. In another embodiment, the pill dispenser 128 may optionally communicate data back to the monitoring client 1, the other monitoring client 4, and/or the remote communicator 11, such as, for example, an actual pill dispensed, an actual pill-type dispensed, an actual pill dispensing schedule as dispensed, or whether or not a max pill-dispensing criteria was exceeded.

The data received from the patient-care devices 7, 14, 15, 16, 17, 35, 126, 128, 130, 148 may be analyzed for any predefined conditions to issue an alarm and/or an alert. For example, one or more of the monitoring clients 1, 4, 11 may use an increase in pressure downstream of the infusion pump 7, the syringe pump 126 and/or the microinfusion pump 130 to be an indication of one of: excessive clotting, infiltration, occlusion or kinking of the tubing to the patient; or occlusion caused downstream by material, e.g., such as contamination found within the IV bag 170. In response to the sudden increase in downstream pressure, one or more of the monitoring clients 1, 4, 11 may visually or audibly alarm or alert a user. These alarms and/or alerts may also inform a nurse to take other appropriate actions, e.g., a suggestion to change a needle in response to an occlusion (e.g., one caused by clotting) when the pressure downstream to the patient rises above a predetermined threshold, or a suggestion to check for a kink in the line when the pressure downstream to the patient rises above a predetermined threshold Additionally or alternatively, a sudden decrease in pressure downstream to the patient 2 may be an indication that the tubing has become detached from the needle and/or the needle is now out of the patient; and, in response, one or more of the monitoring clients 1, 4, 11 may visually or audibly alarm or alert a user to reattach the tubing to the needle or insert a new needle for continued infusion. The alarm may also indicate that action needs to be taken quickly, e.g., because the patient may be bleeding such as when the tubing becomes detached from the needle and the patient is bleeding through the unattached needle coupler.

In some embodiments, additionally or alternatively, the pressure upstream to one or more infusion pumps 7 may be monitored for any upstream occlusions. For example, contamination with the IV bag 170 may clog the tubing upstream of the infusion pump 7. During each time the infusion pump 7 attempts to pump fluid from the IV bag 170, the pressure upstream to the infusion pump 7 may drop lower than would occur when there is no occlusion upstream. Therefore, one or more of the monitoring clients 1, 4, 11 may issue an alarm or alert when the upstream pressure drops below a predetermined threshold and suggest or require a caregiver to alleviate the occlusion, e.g., by changing tubing or a IV bag 170.

One or more of the monitoring clients 1, 4, 11 may, optionally, send a command to one or more of the infusion pump 7, the syringe pump 126, and/or the microinfusion pump 130 to stop delivery of fluid in response to the sudden increase and/or decrease of pressure downstream to the patient 2.

As shown in FIG. 1, and as in some embodiments, the system 100 includes a monitoring-client dock 102 and a device dock 104. The monitoring-client dock 102 is configured to receive the monitoring client 1, and the device dock 104 is configured to receive one or more patient-care devices to facilitate bedside patient care (described in more detail below). Although the device dock 104 is shows as being capable of receiving several patient-care devices, in other embodiments, the device dock 104 can receive one patient-care device, a plurality of patient-care devices, or any arbitrary number of patient-care devices. Additionally, although the monitoring-client dock 102 is shown as being capable of receiving one monitoring client 1, in other embodiments, the monitoring-client dock 102 can receive two monitoring clients 1, more than two monitoring clients 1, or any arbitrary number of monitoring clients 1.

In this example embodiment, a cable 110 is coupled to both of the docks 102, 104 to provide a communications link therebetween. The cable 110 may be permanently attached to or is attachable to one or both of the docks 102, 104. Additionally or alternatively, the cable 110 may include one or more connectors (not explicitly shown) for plugging the cable into one or both of the docks 102, 104.

In some embodiments, the docks 102, 104 can communicate with each other using one or more wires and/or waveguides within the cable 110. For example, in an embodiment of the present disclosure, the cable 110 includes a fiber-optic waveguide to provide an optical communications link between the docks 102, 104. In other embodiments, and as will be appreciated in light of this disclosure, cable 110 can be replaced with one or more wireless communication links (e.g., Bluetooth, etc), if so desired. Still other embodiments may employ a combination of wired and wireless communication channels between docks 102, 104. Any number of suitable wired connection types can be used in various embodiments.

In some embodiments, the communications link between the docks 102, 104 may use any know communications links, such as serial communications, parallel communications, synchronous communications, asynchronous communications, packet-based communications, virtual-circuit based communications, and the like. Additionally or alternatively, in some embodiments, the communications link established between the docks 102, 104 may utilize a wireless connection, a wired connection, a connectionless protocol, e.g., User Datagram Protocol ("UDP"), or a connection-based protocol, e.g., Transmission Control Protocol ("TCP"). For example, the communications between the docks 102, 104 may be based upon one or more of a Universal Serial Bus standard, SATA, eSATA, firewire, an Ethernet standard, Fibre Channel, Bluetooth, Bluetooth Low Energy, WiFi, any physical layer technology, any OSI-layer technology, and the like.

When the monitoring client 1 is docked to the monitoring-client dock 102, the monitoring client 1 has access to the communications between the docks 102, 104. For example, in some embodiments of the present disclosure, the monitoring client 1 can communicate with electronic circuitry within the device dock 104, e.g., a memory, via the communications link provided by the cable 110. Additionally or alternatively, the monitoring client 1 can communicate with any device docked to the device dock 104 through the communications link provided by the cable 110 and/or one or more wireless communication links (described in more detail below).

With further reference to the example embodiment shown in FIG. 1, the device dock 104 may include a variety of accessories, each of which is optional, such as an attachable display 134, a camera 136, and a microphone 138. Likewise, the monitoring-client dock 102 may include a variety of accessories, each of which is optional, such as a camera 140 and a microphone 142. The monitoring client 1 may include a variety of accessories, each of which is optional, such as a camera 144 and a microphone 146. The cameras 136, 140, 144 may be used, for example, by facial-recognition software to authenticate or identify the presence of a provider (e.g., a nurse, nurse practitioner, doctor, etc.) and/or a patient. Additionally or alternatively, the microphones 138, 142, and 146 may be used, for instance, by voice-recognition software to authenticate or identify the presence of the provider and/or a patient. As will be appreciated in light of this disclosure, the cameras 136, 140, 144 and microphones 138, 142, and 146 can also be used, for example, to allow a patient to communicate with a remote care provider and/or to confirm the identity of a patient (e.g., using voice and/or facial recognition techniques, retinal scans, etc) prior to commencing a treatment, so as to ensure the right patient receives the right treatment.

As shown in FIG. 1, in some embodiments, the monitoring client 1, the monitoring-client dock 102, and the device dock 104, each have a respective antenna 112, 106, and 108 for wireless communications (each of the antennas 112, 106, and/or 108 is optional). If the cable 110 is unplugged or the communications between the docks 102, 104 via the cable 110 is otherwise interrupted or impaired, the monitoring-client dock 102 and the device dock 104 can continue to communicate with each other using a wireless communications link established through the antennas 106, 108. Additionally, when the monitoring client 1 is removed from the monitoring-client dock 102, the monitoring client 1 can communicate, for example, directly to the device dock 104 and/or the monitoring client 1 can communicate with the device dock 104 by wirelessly communicating with the monitoring-client dock 102, which relays the communications via the cable 110 or via a wireless communications link between the docks 102, 104. As previously mentioned, communications between the monitoring client 1 and the device dock 104 may be utilized by the monitoring client 1 to communicate with the various devices docked to the device dock 104.

In some embodiments, the monitoring client 1 may electrically determine if one or more electrical contacts of one or more connectors are in electrical engagement with the monitoring-client dock 102 to determine if the cable 110 is available as a communications link, e.g., by measuring a voltage or an impedance between two electrical contacts of a connector of the monitoring client 1 used for docking to the monitoring-client dock 102 and for providing electrical communication between the monitoring-client dock 102 and the monitoring client 1. Also, the monitoring client 1 may determine the cable 110 is unavailable if the monitoring client 1 determines it is not electrically coupled to the cable 110. Additionally or alternatively, in some embodiments, a magnet in the dock 102 engages a Hall-Effect sensor in the monitoring client 1, which the monitoring client 1 uses, in turn, to determine if it is docked such that the monitoring client 1 assumes the cable 110 is unavailable as a communications link when the monitoring client 1 is undocked. Additionally or alternatively, circuitry within the monitoring-client dock 102 may signal the monitoring client 1 when the cable is unavailable as a communications link. In some embodiments, the monitoring client 1 may periodically "ping" the device dock 104 via the cable 110; if the monitoring client does not receive a response from the device dock 104 within a predetermined amount of time, the monitoring client 1 will assume the cable 110 is unavailable as a communications link.

In the event the monitoring client 1 determines the cable 110 is unavailable as a communications link, the monitoring client 1 may issue an alarm or alert using a speaker and/or a vibration motor, an alarm or alert signal may be sent to the remote communicator 11 to alarm or alert the remote communicator using a speaker and/or a vibration motor, and/or the monitoring client 1 may attempt to communicate with the patient-care devices via other communications links. The term "alert" as used herein is intended to include "soft" alerts, such as, for example, an alert that is not brought to a person's attention until after a predetermined amount of time has passed and the cause of the alert remains.

In some embodiments of the present disclosure, the monitoring-client dock 102 includes one or more wires or waveguides from the monitoring client 1 to the cable 110 using minimal or no circuitry. For example, in some embodiments of the present disclosure, the monitoring-client dock 102 is a cradle which provides direct electrical coupling from the monitoring client 1 to the cable 110. Additionally or alternatively, in some embodiments of the present disclosure, the device dock 104 includes one or more wires or waveguides to facilitate communications among various docked devices and/or the monitoring client 1 via the monitoring-client dock 102 using minimal or no circuitry. The device dock 104, in some embodiments, may be a cradle.

In an embodiment of the present disclosure, each monitoring client 1 is assigned to a specific patient 2 and may be a desk-based, portable, or hand-held and may have a display and user input capability. The monitoring client 1 may be portable and can facilitate efficient data viewing and data entry; the monitoring client 1 may be a notebook PC, a netbook PC, a tablet PC, a "smart-phone," with or without a touchscreen. Additionally or alternatively, in some embodiments, the monitoring client 1 and/or the remote communicator 11 may be docked or coupled to a cable that is connected to a much larger display thereby turning the much larger display (e.g., a 24-inch display) into the display of the monitoring client 1 and/or the remote communicator 11; the much larger display may having input capabilities, such as touchscreen capabilities, stylus-input capabilities, keyboard input capabilities, remote-control input capabilities, and the like that are communicated to the monitoring client 1 and/or the remote communicator 11. For example, the viewing of X-ray or patient imaging files may be facilitated by docking the monitoring client 1 and/or the remote communicator 11 to a viewing-dock coupled to a larger display such that the care giver can see the patient imaging file using the larger display. The viewing-dock may also charge the monitoring client and/or remote communicator 11.

The monitoring client 1 may run a Linux-based operating system, an Android-based operating system, a Blackberry-based operating system, a tablet-based operating system, iOS, an iPad OS, an iPhone OS, and the like. The designation of a particular monitoring client 1 to a particular patient 2 may be made using any of a number of methods, including (but not limited to) a unique patient identifier encoded on a bar code 114 or an RFID tag 116 embedded in a wrist band 118, for example. The device dock 104 includes a scanner 120 to determine the unique patient identifier of the bar code 114 or RFID tag 116. The scanner 120 may be a laser barcode scanner, a CCD-based barcode scanner, a near field communicator or interrogator, an RFID reader, and the like. In other embodiments, note that the unique patient identifier can be based on biometric data of the patient. In one such example case, biometric capability (e.g., facial and/or voice recognition, retina scan, blood type monitor, finger print scan, etc) can be embedded in or otherwise associated with the monitoring client 1. The device dock 104 can communicate the unique patient identifier to the monitoring-client dock 102, the monitoring client 1, the monitoring server 3, the remote communicator 11, other monitoring clients 4, another server, or an electronic computing apparatus to facilitate the treatment of the patient 2.

The monitoring client 1 may include one or more of microprocessors, microcontrollers, logic devices, digital circuitry, analog circuitry, and the like to communicate (e.g., send or receive) information relevant to the patient's 9 care, condition, disease, or treatment. For example, the monitoring client 1 may send or receive patient-care parameters, such as patient-condition parameters and/or patient-treatment parameters. Some exemplary patient-condition parameters are measurements of blood pressure, body temperature, heart rate, a pulse oxymeter, CO2 levels, blood oxygen levels, patient alertness, patient consciousness, patient responsiveness, and the like. Some exemplarily patient-treatment parameters include a drug to be administrator, a flow rate of a drug or liquid, a drug administration schedule, or other bedside treatment parameter.

In some embodiments, for example, the monitoring client 1 may be physically associated with, permanently attached to, is attachable to, is detachable from, or is attachably detachable from the infusion pump 7. This can be accomplished by a docking interface between the two devices, e.g., the monitoring-client dock 102 and the device dock 104. In one such embodiment, the monitoring client 1 communicates with the pump 7 (or other patient-care device) in a number of ways, including, for example, through electrical contacts in the docks 102, 104, by means of an electrical connector, or wirelessly by means of transceivers on each device using a respective antenna 112, 122A. Additionally or alternatively, the infusion pump may include preprogrammed treatment data indicating a particular treatment for a particular patient that is uploaded to the monitoring client 1 when the infusion pump 7 becomes in operative communication with the monitoring client 1.

The monitoring client 1 may also communicate with one or more databases in the facility 8, with databases external to the facility 9, 10, and/or with health care providers using portable communicators 11 (including, for example, physicians, nurses, and pharmacists). This can be accomplished by a wired connection to a facility server 8 through a connector in the patient's room (such as, for example, a Category 5 local area network connector, USB, wired Ethernet, and the like), or wirelessly 12 (such as, for example, WiFi, 3G, 4G, EVDO, WiMax, and the like). In one embodiment, access to intra- and extra-facility databases is mediated 13 through the monitoring server 3 (e.g., using middleware), which can then centralize the software and application programming interfaces to communicate with databases having disparate organization, formatting, and communications protocols. Thus, in an embodiment of the present disclosure, any software updates may be largely limited to the monitoring server 3, reducing the maintenance requirements on the individual monitoring clients 1, 4, 11. Optionally, a monitoring client 1 can communicate with patient-treatment devices, such as an infusion pump 7, to receive information about the progress of treatment (such as operating parameters) and to provide operational instructions to the patient-treatment device. In another embodiment, the monitoring client 1 may also communicate with patient-care devices for diagnostic or monitoring purposes to receive patient-condition parameters (such as, for example, an electrocardiographic ("ECG") monitor 14, a blood pressure ("BP") monitor 15, a pulse oximeter or CO2 capnometer 16, or other devices such as temperature monitors, etc.) to receive readout information from the devices and potentially to instruct the devices 14, 15, 16, 17 to take a reading when desired by a provider or by an algorithm.

In an embodiment of the present disclosure, the facility services 8 and/or the drug adverse event network 9 may also include a Drug Error Reduction System ("DERS"). The DERS system may include a first set of predetermined criteria to trigger soft alarms and/or a second set of predetermined criteria to trigger hard alarms. Soft alarms may be overridden (e.g., turned off) by a caregiver using a user interface of an infusion pump 7 and/or a monitoring client 1 (and may be only an audible and/or vibratory alarm) while hard alarms cause the treatment to cease until the source of the hard alarm is removed.

In yet an additional embodiment of the present disclosure, the DERS system may include a first set of predetermined criteria defining soft limits and/or a second set of predetermined criteria defining hard limits. The hard and soft limits define treatment limits, such as drug dosage limits based upon size, weight, age, other patient parameters, or other criteria. Soft limits may be overridden by a caregiver using a user interface of the infusion pump 7 and/or the monitoring client 1 to start treatment despite that the treatment is outside of the first set of predetermined criteria while the hard limits prevent the treatment from starting until the settings are changed to confirm to the second set of predetermined criteria defining the hard limits.

As can further be seen in the example embodiments of FIG. 1, system 100 also includes communication modules 124A-124K, each having a respective antenna of the antennas 122A-122K. In some embodiments, each of the communication modules 124A-124K is optional and/or each device may have integrated communications capability. Each of the communication modules 124A-124K includes a connector for coupling to a respective device. In other embodiments, each of the communication modules 124A-124K is permanently integrated with the device it is shown as being attached to in FIG. 1.

Each of the communication modules 124A-124K optionally includes one or more transceivers for optionally communicating over one or more wireless links to each other, to the device dock 104, to the monitoring-client dock 102, to the monitoring client 1, to the remote communicator 11, to the monitoring server 3, over the local area network and/or wide area network (e.g., the Internet), to a hub 802 (see FIG. 8) and/or otherwise to communicate with any other device having sufficient wireless communications capability. In some specific embodiments, the communication modules 124A-124K may operate, for example, as a wireless mesh network, e.g., using IEEE 802.14.4, Zigbee, XBee, Wibree, IEEE 802.11, and the like. In a more general sense, communication between modules 124A-124K and other components of system 100 (e.g., docks 102 and 104, monitoring clients 1,4,11, etc.) can be implemented using any wireless communication protocol that, for example, allows for device discovery, handshaking, and/or inter-device communication as described herein, whether in a static, dynamic, or ad hoc topology (to accommodate mobility of, for example, monitoring clients 1, 4, 11 and/or the various medical devices associated with the dock 104).

In other embodiments, each patient-care device may include no modules or more than two modules (e.g., communication modules). For example, each module may have a specific function, e.g., WiFi, and a user can select a plurality of modules each having a specific function and couple them together. The group of modules may then be applied to the patient-care device, e.g., an infusion pump. Consider yet another example: each module may have a primary processor, a backup processor, and functional circuitry, all in operative communication with each other. The functional circuitry may be a wireless transceiver, a battery, an interface to a touchscreen or display (the display may be attached to the housing), a wire connection, Bluetooth, Bluetooth Low Energy, WiFi, 3G, 4G, a co-processor, a control system (e.g., to control an infusion pump), a medication with fluid measurement circuitry, and the like. The selected modules may be connected together, e.g., in a daisy chain, and thereafter connected to an infusion pump. The selected modules, in this example, may be in operative communication with each other to coordinate their action and/or function, e.g., via a CAN bus, wired connection, wirelessly, and/or the like.

The modules may each include a speaker and a microphone. When several modules are connected to together, the modules may coordinate their operation such that one module audibly signals a speaker while another module uses a microphone to determine if the speaker is functioning properly. Several modules may each use their speaker on a different frequency such that any one of the modules may sense the sound via its microphone and demodulate the different frequencies to test several of the speakers simultaneously. The test may be requested by a first module to a second module, and the second module may send the results from the test to the first module.

Continuing to refer to FIG. 1, one or more of the communication modules 124A-124K may also optionally include one or more batteries to provide power to the device coupled thereto. For example, the communication module 124A may be coupled to the infusion pump 7 to provide power thereto. Other structure and functionality of the communication modules 124A-124K may be included, depending on the purpose and functionality of the device with which it is associated. For instance, in some embodiments, control of infusion takes place at the infusion pump and inputs regarding desired delivery take place on the infusion pump; therefore, in some embodiments of the present disclosure, the communication module 124A implements a control algorithm, e.g., a proportional-integral-derivative ("PID") control loop, to control the infusion pump 7. In such cases, the monitoring client 1 may communicate, for instance, a fluid-flow rate signal to the communication module 124A (e.g., via a wireless link), which then applies a signal corresponding to the fluid-flow rate signal through electrical contacts coupled to the motor (not explicitly shown) of the infusion pump 7 to achieve the desired flow rate. In some embodiments, the infusion pump 7 provides one or more feedback signals from a flow-rate meter provided within the infusion pump 7 to the communication module 124A so the communication module 124A can control the operation of the infusion pump 7 (e.g., some aspects of the operation, such as a PID control system, etc.). The results may be delivered to the monitoring client 1 for being displayed to a user using a GUI, such as a QT-based GUI (in some embodiments, the monitoring client 1 is a tablet). Additionally or alternatively, in some embodiments, a drip flow meter 148 can be used to wirelessly communicate the flow rate to the communication module 124A via the communication module 124K and antenna 122K associated with the drip flow meter 148.

As will be appreciated in light of this disclosure, the communication modules 124A-124K can be operatively coupled to a variety of patient-care devices 7, 14, 15, 16, 17, 35, 126, 128, 148. For example and with further reference to FIG. 1, the communication module 124B is operatively coupled to a syringe pump 126, and the communication module 124C is operatively coupled to a pill dispenser 128. Additionally or alternatively, the communication module 124E is operatively coupled to the ECG monitor 12, the communication module 124F is operatively coupled to the blood pressure monitor 15, the communication module 124G is operatively coupled to the pulse oximeter/CO2 capnometer 16, the communication module 124H is operatively coupled to the other monitor 17, the communication module 124I is operatively coupled to the patient's IV access 35, and the communication module 124K is operatively coupled to the drip flow meter 148. Each respective communication module 124A-124K can provide, for instance, an appropriate control system, control algorithm, battery power, or other functionality for its respective patient-care device 7, 14, 15, 16, 17, 35, 126, 128, or 148 coupled thereto.

Additionally or alternatively, in some embodiments, the communication module 124D is docked in the device dock 104 and is operatively coupled to the device dock 104 via, for example, a bus or backplane for communicating with any device attached to the device dock 104, as well as for communicating with electronic circuitry within the device dock 104, electronic circuitry within the monitoring-client dock 102, and/or the monitoring client 1. Optionally, the communication module 124D can provide communications for and/or power to any device docked within the device dock 104, e.g., the infusion pump 7, the syringe pump 126, the pill dispenser 128, or a microinfusion pump 130. Note the functionality of communication module 124D can also be integrated into the circuitry of the device dock 104 itself.

Additionally or alternatively, in some embodiments, it is optional for the communication modules 124 to each be configured to provide a sufficient power supply for their respective device 7, 14, 15, 16, 17, 35, 126, 128, 148 which may be supplemented by one or more wired power sources, for example, a power source accessible through the bus or backplane within the device dock 104. As previously mentioned, in some embodiments of the present disclosure, the communication module 124D provides sufficient power to the devices 7, 126, 128, 130, and 133.

As previously mentioned, in some embodiments, the communication modules 124 are each configured with power circuitry (e.g., a voltage converter, regulator circuitry, rectification and filtering circuitry, a buck circuit, a boost circuit, a buck-boost circuit, a switched-mode power supply, etc.) that provides sufficient power to the corresponding devices 7, 126, 128, and 130. In some such cases, this power circuitry may be configurable so as to allow for provisioning of various power supply characteristics (e.g., voltage level, maximum load/current requirements, and A/C frequency) associated with the different and diverse patient-care devices 7, 14, 15, 16, 17, 35, 126, 128, 148. Any number of power provisioning and management schemes will be apparent in light of this disclosure.

Optionally, in other embodiments of the present disclosure, a power module 132 having one or more battery cells, e.g., lithium-ion battery cells, is attached to the device dock 104 to provide sufficient power to the devices 7, 126, 128, 130, 133 for the full treatment duration. Additionally or alternatively, the power module 132 may be plugged into an outlet in the patient's room (generally depicted in FIG. 1 as an AC source), when available. In such cases, the outlet power can be used, where available, to power the devices in dock 104 and to charge batteries included in the power module 132 (this may occur simultaneously); when outlet power is lost or is otherwise unavailable, the power module 132 and/or batteries within the communication modules 124A, 124B, 124C can provide power to the docked devices.

The example system 100 may optionally include a dongle 133. The dongle 133 is docked in the device dock 104 in FIG. 1 or, in other embodiments, may be remote to the device dock 104 and/or the monitoring client 1. The dongle 133 can provide a communications link or protocol for wireless devices not otherwise available. For example, as new wireless protocols, technologies, standards, and techniques become available with the passage of time, the dongle 133 can be used to provide a bridge, router, or repeater between the new communications protocol and translate the information transmitted under one protocol to the other protocol so that the new protocol device can communicate with the patient-care devices 7, 14, 15, 17, 35, 126, 128, 130, the device dock 104, the communication module 124D, the monitoring-client dock 102, the monitoring client 1, a hub 802 of FIG. 8, and/or other devices. The dongle 133 may retransmit the data received from the new communications link using a wireless protocol, technology, standard, or technique used by any one or more of the patient-care devices 7, 14, 15, 17, 35, 126, 128, 130, the device dock 104, the communication module 124D, the monitoring-client dock 102, the monitoring client 1, the hub 802 of FIG. 8, and/or other devices in a format known or used by another one, such as, for example, the monitoring server 3 or the monitoring client 1. The dongle 133 may also provide a communications bridge to cellular-based communications links, such as EVDO- or CDMA-based cellular systems.

Figure 8:
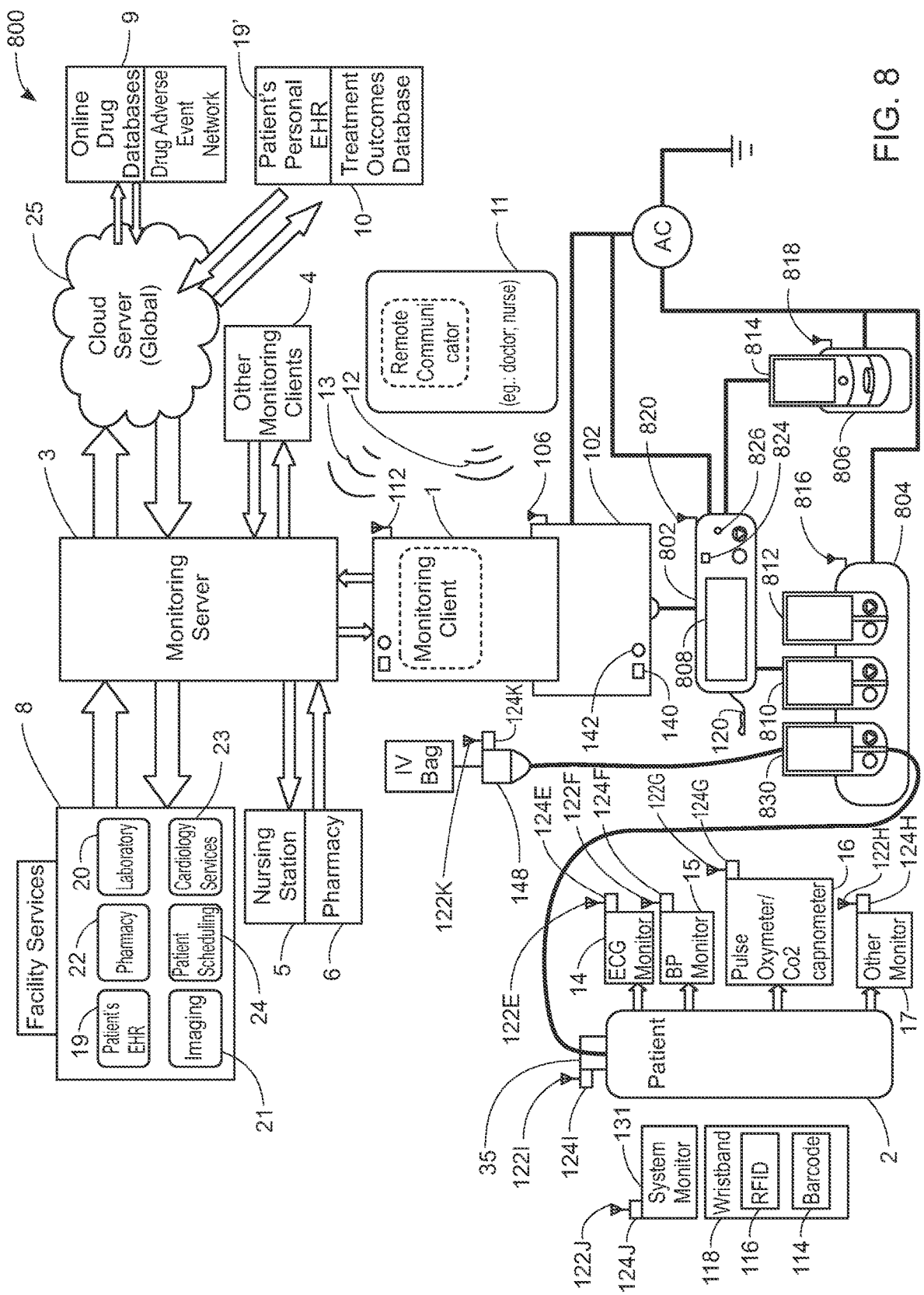
FIG. 8 is a block diagram of an electronic patient-care system having a hub in accordance with yet another embodiment of the present disclosure.

In some embodiments, the dongle 133 may communicate patient-care parameters, e.g., patient-treatment parameters or patient-condition parameters, from one or more patient-care devices and retransmit them to the monitoring client 1, the hub 802 of FIG. 8, and/or the monitoring server 3, and vice versa. Optionally, in some embodiments, the dongle 133 may include a wired attachment connector, e.g., a RS-232 connector, and is connectable to a legacy device to provide communications from the legacy device to one or more other patient-care devices, the monitoring client 1, the hub 802 of FIG. 8, and/or the monitoring server 3, and the like. The legacy device may be, for example, a legacy patient-care device, a legacy computing device, other device using a legacy wired communications protocol, or the like.

Optionally, the system 100 may also include a wearable system monitor 131 for monitoring the operation of various devices, docks, monitoring clients, and/or servers. A monitoring client 1, a remote communicator 11, and/or a hub 802 of FIG. 8 may be used to program, interact with, and/or pair with the wearable system monitor 131. The wearable system monitor 131 may be worn by the patient 2 or by providers, and multiple wearable system monitors 131 may be used. The wearable system monitor 131 can interrogate various devices to ensure their proper operation. For example, in one example embodiment, the wearable system monitor 131 communicates with the patient-care devices 14, 15, 16, 17, 35, 126, 128, 130, the monitoring client 1, the monitoring-client dock 102, the device dock 104, and/or the hub 802 of FIG. 8 to determine if any faults, errors, irregularities, data corruption, communication degradation, incomplete operation, slow operation, or other issues exists.

The communications from the wearable system monitor 131 may include one or more interrogation signals to determine if the device being interrogated is functioning properly, is functioning within predetermined operating parameters, and/or is otherwise in a condition or state that is undesirable. The system monitor 131 can communicate the detected condition or error to one or more devices, such as to the monitoring server 3, the monitoring client 1 or the hub 802 of FIG. 8, to alert a provider, to initiate a shut-down procedure, and/or to initiate other suitable remedial action directed to the malfunctioning device. For example, the system monitor 131 can use the transceiver of the communication module 124J for communicating with the monitoring client 1, the monitoring server 3 via a WiFi-router coupled to the network and/or the internet, other monitoring clients 4, other devices configured with a communication module 124, or with the remote communicator 11 to signal an alert and/or alarm resulting from an abnormal or absent interrogation response. The alert and/or alarm may cause the device to audibly sound or visually indicate an alert and/or an alarm. In some embodiments of the present disclosure, the system monitor 131 includes a call button (not explicitly shown) for allowing the patient 2 to request a care provider, e.g., the request is routed to the monitoring client 1 or the remote communicator 11 for visually and/or audibly indicating the request to the user in possession of the device.

The system monitor 131 can implement its functionality in various ways, including, for example: (1) anticipating a response to an interrogation within a predetermined amount of time; (2) incrementing a counter within the device being interrogated, and requesting the value of the counter from the device after being incremented; (3) a challenge-response interrogation; and/or (4) other system monitoring technique or method.

As previously mentioned, in some embodiments, the system monitor 131 anticipates a response to an interrogation within a predetermined amount of time after interrogating a patient-care device paired to the system monitor 131. For example, the system monitor 131 may send a text-string message to the infusion pump 7 of "system monitor interrogation." In this example, the infusion pump 7 receives the message from the system monitor 131 labeled "system monitor interrogation," and processes the message using one or more processors therein. When the infusion pump 7 processes the message, a software routine therein executes code that sends a response message back to the system monitor 131; for example, the response message may be a text-string message of "system monitor response" that is sent to the system monitor 131. In this example, the system monitor 131 may expect to receive the response message within a predetermined amount of time, such as 2 seconds, which if the system monitor 131 does not receive the response message within 2 seconds, the system monitor 131 alarms and/or sends an alert to other devices (e.g., the system monitor 131 may broadcast an alert or error message, or may cause can alarm or alert, audibly or visually, to be provided to the possessor via the remote communicator 11).

As previously mentioned, in some embodiments, the system monitor 131 causes a counter within the device being interrogated to increment and requests the value of the counter from the device after being incremented. For example, the system monitor 131 may send a request to a patient-care device, e.g., infusion pump 7, by sending it a message, such as "increment counter," to the device. The device's processor receives the "increment counter" message and reads a value from a memory location of the device, increments the value found in the memory location, and stores the new value in the same memory location by overwriting the previous value. Thereafter, in this example, the processor reads the new value from the memory location and sends that new value to the system monitor 131, e.g., via a wireless transceiver on the device being interrogated. The system monitor 131, in this example, will expect a certain value from the device being interrogated (this expected value may be stored in a memory of the system monitor, such as, for example, in a table). For example, the system monitor 131 may have stored within its memory that a value of 48 that was previously received from the device, and after requesting the value be updated within the interrogated device, expects to receive a value of 49 from the device.

Also as previously mentioned, a challenge-response interrogation may be used by the system monitor 131. For example, the system monitor 131 may send an encrypted message to a patient-care device. The patient-care device is then tasked to decrypt the message, e.g., using an encryption key, and send the message back to the system monitor 131. The system monitor 131 may expect the unencrypted message to return within a predetermined amount of time. In this example, if the system monitor 131 does not receive the response message within the predetermined amount of time, the system monitor 131 alarms and/or sends an alert to other devices (e.g., the system monitor 131 may broadcast an alert or alarm message and/or transmit them to the monitoring client 1, the monitoring server 3, to the hub 802 of FIG. 8 or to the remote communicator 11, which in turn displays or audibly indicates the alert or alarm).

In an embodiment of the present disclosure, the monitoring client 1 has the ability to communicate and interact directly with a health care provider using a hand-held or portable remote communicator 11 (which can be, for example, a smartphone, a tablet computer, a PDA, a laptop, or other portable computing device). This may be accomplished wirelessly 12, so that communications can be maintained regardless of the patient's location in the facility, or the provider's location either within or outside the facility. In one aspect, information specific to the patient 2 can be stored locally in the monitoring client 1, so that the patient's health care provider can access the information directly without having to access the monitoring server 3.

In some embodiments, optionally, by incorporating appropriate safety and security clearances, changes to the settings or flow parameters of a connected infusion pump 7 or patient-monitoring device 14-17, 35, 126, 128, 130, 148 can be accomplished directly between a provider's monitoring client 11 and the monitoring client 1 (via wired or wireless communications), with selected changes also being communicated to the monitoring server 3, and thence optionally to other appropriate locations, such as the nursing station 5 and/or the pharmacy 6. Furthermore, any new order pertaining to the patient 2 may be entered in the ordering provider's remote communicator 11 (e.g., smartphone) and transmitted to the monitoring client 1, which in turn can then notify the care giver (e.g. a nurse, nurse practitioner, doctor, physician, or other health-care professional) via the care giver's own portable communicator 11. Additionally or alternatively, in some embodiments, the new order may also be communicated to the infusion pump 7 or patient-monitoring device 14-17, 35, 126, 128, 130, 148 such that the control system therein or coupled thereto can change its operation, e.g., setpoint, in response to the new order. In some embodiments, any information acquired and stored in the monitoring client 1 is periodically uploaded to the monitoring server 3 and stored in a patient-specific database. Thus, if a patient's monitoring client 1 is taken out of service, a new device can be assigned to the patient 2 and quickly re-populated with the patient's current information from the monitoring server 3. Orders, medications, progress notes, monitoring data, treatment data, patient-treatment parameters, patient-monitoring parameters, and/or operating parameters from the patient's attached devices may also be uploaded from the monitoring client 1 to the patient's EHRs 19, any applicable remote communicators 11, the hub 802 of FIG. 8 and/or the monitoring server 3 for permanent, temporary or ephemeral storage, and/or for analysis to confirm it is in accordance with predetermined criteria, e.g., ranges, threshold values, and the like.

In some embodiments, the monitoring server 3 may comprise a computer that can communicate with and provide some elements of control for a number of monitoring clients 1, 4, 11 in the facility 8. The monitoring server 3 may provide the monitoring clients 1, 4, 11 with data extracted from a number of databases both within 8 and outside 9 of the facility. In an embodiment of the present disclosure, the monitoring server 3 can interrogate the facility's EHR system 19 for targeted information pertaining to a patient 2, and then populate that patient's monitoring client 1 with a pre-defined set of information (such as, for example, the patient's age, height, weight, categories of diagnoses, current medications and medication categories, medication allergies and sensitivities, etc.). In accordance with one such example, the monitoring server 3 may establish a communication link to the EHR 19, laboratory 20, radiology 21, pharmacy 22, and/or other systems (such as, e.g., cardiology 23 or scheduling database 24) in the facility when, for example, a monitoring client 1 has been assigned to a patient 2. With a unique patient identifier, the monitoring server 3 can obtain electronic access (permission) to receive and send patient-specific data from and to these systems. A predetermined (but selectable) subset of the data may be downloadable into the monitoring client 1's memory (not explicitly shown in FIG. 1).

The information thus acquired can then serve as a key database against which new orders can be analyzed. Orders entered into a monitoring client 1 can be checked for compatibility with the patient-specific information obtained by the monitoring server 3. Optionally, for safety redundancy, orders entered remotely from a communicator 11 can be intercepted by the monitoring server 3 and similarly can be checked. The monitoring server 3 may also obtain information from medication databases residing in the facility's pharmacy 22 or externally 9 to determine whether a new patient order may generate an incompatibility with a patient's existing medications, for example. In an embodiment of the present disclosure, the monitoring server 3 may be programmed to access publicly available internet sites 25 to determine whether new information pertaining to the patient's ordered medication should be downloaded and transmitted 13 in an alert or alarm to the patient's health care provider(s). The monitoring server 3 may also route information between remote portable communicators 11 and a patient's monitoring client 1.

In an embodiment of the present disclosure, the patient's physician, nurse or pharmacist may have access to the patient's monitoring client 1 to relay or receive new orders (such as medication orders, for example) pertaining to the patient 2. The monitoring client 1 or server 3 may then log the new order and relay the request to the pharmacist 6, and the patient's nurse via the nurse's portable communicator 11 and/or via a fixed terminal at the nursing station 5. A 'smart phone' having a customized communications application with the monitoring client 1 (such as, e.g., a Google's Nexus One phone, Apple's iPhone, or RIM's Blackberry OS, among others) may serve as a convenient portable communicator 11 for providers who are not at a fixed location (such as at an office or remote nursing station). A tablet PC, netbook, or laptop computer may also serve as a convenient portable communicator 11 for both portable and fixed locations. A PC may act as a convenient communication device 11 for fixed or desktop locations. If a provider is located in the patient's room, he or she may enter or receive information pertaining to the patient 2 using a direct input through a keyboard or touchscreen on the monitoring client 1.

A monitoring client 1 can receive, process, and transmit information about a specific patient 2 to which it has been assigned or designated. The monitoring client 1 can most conveniently be attachable or dockable to the monitoring-client dock 102 to communicate with the infusion pump 7, or any other device to which the patient 2 may be connected or associated. The monitoring client 1 can be a hand-held device about the size of a wireless phone or tablet-style netbook, for example. Conveniently, it may have a touchscreen interface for use by the patient's provider. It may also be capable of providing output to a larger stationary display in the patient's room or at a nursing station 5 or other convenient location, either through a wired or wireless connection. Each monitoring client 1 may communicate with a central monitoring server 3, through which it can access patient data from the facility's EHR database 19, a laboratory database 20, a radiology database 21, a pharmacy database 22, or other databases in various other facility departments. In some cases, the monitoring client 1 can upload information it receives from patient monitoring devices 14-17 or from provider inputs to the patient's EHR 19 via the Monitoring Server 3. Monitoring clients 1,4 may also receive information from databases outside of the facility through a monitoring server 3 having an internet connection 25. Various external databases 9 may thus be accessible, including various drug information databases and alert networks dealing with adverse medication-related events.

The monitoring server 3 could be arranged, for example, to manage various levels of external database information helpful in keeping the monitoring client 1 contents as up-to-date as possible. This can be accomplished, for example, by comparing safety and drug information related to the patient as it becomes available, and prioritizing for updates/downloads on a data transfer schedule. The monitoring clients 1,4 may also communicate either directly or through the monitoring server 3 with portable communicators 11 used by health care providers such as nurses, physicians and pharmacists. In some cases, these devices can have wired connections to the monitoring server 3 (if used, for example, in fixed locations such as hospital pharmacies or nursing stations). In other cases, a portable communicator 11 may communicate with the monitoring server 3 through secure internet connections (e.g., a VPN-based internet connections, UPN, Https, a private key mechanism, etc.) using a computer and a wired or wireless (e.g., Bluetooth or WiFi 802.11) connection 13 with the device 11. Alternatively, a hand-held remote communicator 11 (such as a smart-phone or tablet netbook) may communicate directly 12 with the facility's monitoring client 1 via a cellular telephone network and/or the facility may include a private cell network that may include a WiFi network (e.g., 2.4 GHz to 2.4835 GHz unlicensed ISM band, for example).

In some embodiments, the communication link between the monitoring clients 1,4 and the monitoring server 3 may exist via an Ethernet network if widely available in the facility, or via wireless transmission using one of a number of standards, linking all the patient-specific monitoring clients 1,4 with the central monitoring server 3. The server 3 may then serve as a relay for communications with other facility servers 8, with the web-based servers 25, and with inside and outside portable communicators 11 carried by medical care providers. In some embodiments, a wireless network provides the additional functionality of being able to communicate with the monitoring server 3 no matter where in the facility the patient 2 may be.

One method of blanketing an entire facility with wireless coverage involves having the facility obtain a license for a private cell-phone network. It may obtain or lease one or more micro-cellular frequencies to provide for a local communications network throughout the facility. This arrangement can preserve communications when patients and their monitoring clients 1,4 are moved from one location to another within the facility, maintaining communications with a monitoring server 3, various in-hospital and out-of-hospital databases 8, 25, and users at fixed stations (e.g., in some embodiments, the nursing station 5 and the pharmacy 6) or with a monitoring client 11 (e.g., mobile smart-phone, laptop or tablet-type devices) either inside or outside the hospital. In some embodiments, this type of system provides additional security via a licensed cellular communications infrastructure. In addition, in some embodiments, an active wireless system can monitor the intensity of use in an area and direct additional channel frequencies to that area. However, in some embodiments, the bandwidth capacity of the network may not allow for efficient transmission of large data files, such as those containing radiology images, for example. Such bandwidth-heavy data files can be communicated more efficiently via wired connections.

Alternatively or additionally, a hospital may implement an internet- or intranet-based communications system, in which an 802.11 WiFi-type protocol is used for wireless communications between individual monitoring clients 1,4 and the monitoring server 3. To ensure adequate signal reception throughout the facility, a broadband antenna may be mounted on the roof of the building to collect cell phone signals from local wireless phone companies. A fiber-optic or cable network may then distribute the signals throughout the facility. Additionally or alternatively, the monitoring server 3 may use the private cell-phone network mentioned above. Such systems typically allow for provisioning of secure communications, and are capable of efficiently communicating large files, such as, for example, radiology images stored in the radiology database 21. Home or office-based users may be able to connect to the hospital server through, for example, VPN or other secure access using wired or fiber-optic cable, or a DSL phone line. Data encryption may be used to provide patient data security. In some applications it may be advantageous to implement an asymmetric bandwidth communications network in order to optimize infrastructure capabilities. An example of this would be using licensed cellular frequencies in the "upstream" direction from the monitoring client 1 to the monitoring server 3 and the unlicensed 802.11 WiFi frequencies in the "downstream" direction from the monitoring server 3 to the monitoring client 1. In this example, the upstream bandwidth and data rate requirements are relatively small compared to the downstream requirements. In low priority upstream transmissions, the monitoring client 1 may allow data to be sent over a more distributed and cost-efficient network, such as, for example, a ZigBee network, a Bluetooth network, a mesh network, or the like.

As previously mentioned, communications between various monitoring devices, such as patient-care devices 14, 15, 16, 17, 35, and the monitoring client 1 may be achieved in a cost effective manner using, for example, a ZigBee wireless mesh network and/or a Bluetooth network. Exemplary monitoring devices include ECG monitors 14, blood pressure monitors 15, pulse oximeters/capnometers 16, thermometers, and weight scales, among others. A common characteristic of most of these devices is that they provide periodic readouts of a single or small number of parameters. An intra-hospital device communications system such as the wireless mesh network provides for low-power digital radio connectivity among devices, and may employ a widely available, license-free frequency band (e.g., 2.4 GHz in some jurisdictions). High-level communications protocols may be employed to ensure data fidelity and security, such as, for example, TCP, UDP, and the like. For example, symmetrical encryption keys may be used to secure communications between the monitoring client and patient-care devices, such as those generated for the encryption algorithms of Twofish, Serpent, AES (Rijndael), Blowfish, CASTS, RC4, 3DES, IDEA, and the like. Additionally or alternatively, various data integrity techniques may be used, for example, CRC, odd parity-bit checking, or even parity-bit checking, and the like.

Mesh networks are highly scalable, allowing many devices to be used on a single self-forming, self-healing mesh network. Devices connected to the network may communicate with one another and serve as repeaters to transfer data. Mesh network may be relatively low cost, scalable and mobile for the patient being monitored. In some embodiments, the wireless range for devices linked to the wireless mesh network can approach 70 meters from each node of the system inside a facility. A similar network may be used in providing a wireless link within the facility between portable communicators 11 carried by health care providers and their assigned patients through the patients' monitoring clients 1,4.

In many cases, the information being transmitted to the monitoring client 1 may include a single parameter value (such as, for example, blood pressure) and a time stamp. The monitoring client 1 can be programmed to determine whether the value is outside a predetermined range, record the value in the patient's EHR 19, and notify the appropriate provider via their monitoring client 11. Furthermore, the network may enable bidirectional communications, and may allow the monitoring client 1 to query the patient-monitoring device (e.g., BP monitor 15), instructing it to take an unscheduled reading. This can be useful, for example, when an abnormal reading is received, and its authenticity needs to be verified. The monitoring client 1 may be programmed to request a repeat reading to verify the abnormal reading. In a further embodiment, the monitoring client 1 may be programmed to interrupt or adjust the infusion pump 7 flow rate, operating parameter, and/or treatment parameter depending on the value of the reading received from a monitoring device 14-17. For example, if the BP monitor 15 indicates a blood pressure below a predetermined acceptable range, the monitoring client 1 may be programmed to instruct the infusion pump 7 to stop the infusion, and it can transmit an urgent notification 12 to the health care provider (s)' monitoring clients 11. In another embodiment, if the infusion pump 7 is capable of determining the volume of fluid being delivered to the patient 2 (e.g., the flow rate or the cumulative amount of fluid pumped during an interval), a processor in the monitoring client 1 may track the cumulative volume delivered and estimate the amount of fluid remaining in the medication bag 170. (Alternatively, a processor in the monitoring client 1 or infusion pump 7 may calculate the volume delivered from the infusion rate and elapsed time of infusion).

Once the estimated residual volume reaches a predetermined amount, the monitoring client 1 may signal the infusion pump 7 to reduce its flow rate to keep the patient's IV access 35 from running dry. For example, the monitoring client 1 may determine that a nurse is scheduled to return at a specific time to change the bag, and rather than alarming and/or sending an alarm that the IV fluid will run out prior to the nurse's scheduled return, the monitoring client 1 may signal the infusion pump 7 to slow the infusion rate such that the IV bag will run out when the nurse arrives or after a predetermined amount of time from the nurse's scheduled return time. It may also send a notification to the nurse's monitoring client 11, recommending replenishment of the IV bag 17.

In some embodiments, the operation of a patient-care device progresses is indicated by an outer border on a display of the monitoring client 1 to show the status and/or progress of the patient-care device. For example, an outer border will be display on the monitoring client 1 such that a percentage of the border that lights up (e.g., starts to form a fully filled outer periphery as the border fills in) to indicate the progress of a treatment being performed by a patient-care device, such as the infusion pump 7. The border may be transmitted in image format (e.g., JPEG, BMP, etc.) to the monitoring 1 from the infusion pump 7 and/or as a percentage completed to the monitoring client 1, in which case the monitoring client 1 generates the border.

In some embodiments, a GPS and/or a ranging module (e.g., ultrasonic ranging module using time-of-flight estimations) may be installed on the infusion pump 7, the monitoring client 1, a caregiver, and/or a patient. Predetermined settings may require that a predetermined group of the infusion pump 7, the monitoring client 1, the hub 802 of FIG. 8, the caregiver, and/or the patient must, in this specific embodiment, be in a predetermined distance relative to each other prior to starting treatment and/or prior to configuring one of the infusion pump 7 and/or the monitoring client 1.

In some embodiments, a patient-care device 7, 170, 126, 128, 130, 14, 15, 16, 17, 124, or 148, a dock 102 or 104, a monitoring client 1, the hub 802 of FIG. 8 may send a soft alarm, hard alarm, and/or non-critical alarms to the remote communicator 11 without alarming on the device that issues the alarm and/or on the monitoring client 1 until after a predetermined amount of times has passed (to allow a caregiver to find a solution to remove the cause of the alarm without disturbing a patient, for example). If the cause of the alarm is removed prior to the predetermined amount of time, the device that issues the alarm and/or on the monitoring client 1 may not alarm thereby avoiding an additional disturbance of the patient.

In some embodiments, the AC cable of FIG. 1 includes clips such that IV tubes can be clipped thereto.

In some embodiments, the infusion pump 7 includes status LED lights indicating one or more of: safety-checks have passed; the pump is flowing; there is an occlusion; and/or the pump is being disconnected). A user can use the monitoring client 1 to read a bar code on the IV bag 170 (e.g., using the camera 144 or the camera 136, and/or the scanner 120) at which time an LED over a plug may flash to indicate to the user that the tube connected to the IV bag 170 should be inserted therein.

In some embodiments, each item, component, device, patient-care device, dock, and computing device, numbered or unnumbered, as shown in FIG. 1 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 7, 14, 15, 16, 17, 35, 126, 128, 130, 148 is optional. Likewise, each of the system monitor 131, the wrist band 118, the RFID 116, the barcode 114, the scanner 120, the display 134, and/or AC power, is optional in some embodiments of the present disclosure.

Additionally, in some embodiments, although some items, components, devices, patient-care devices, docks, and computing devices, numbered or unnumbered, as shown in FIG. 1 or described therewith are shown as being the sole item, component, device, patient-care device, dock or computing device, multiple items, components, devices, patient-care devices, docks and computing devices, are contemplated; for example, although a single infusion pump 7 is shown in FIG. 1, in some embodiments, two infusion pumps 7 may be used, multiple infusion pumps 7 may be used, or any arbitrary number of infusion pumps 7 may be used. Additionally or alternatively, in some embodiments, multiple device docks 104 and/or multiple monitoring-client docks 102 may be used.

Additionally or alternatively, although particular patient-care devices 7, 14, 15, 16, 17, 126, 128, 130, 148 are shown, other combinations, subsets, multiple ones of a particular patient-care device, or combinations thereof may be used. For example, in some embodiments, only an infusion pump 7 is used of the patient-care devices, and, in this specific example, the other patient-care devices 14, 15, 16, 17, 126, 128, 130, 148 may be disabled, may not be present or available for system use, may be turned off, or may not be part of system 100 of FIG. 1. Additionally or alternatively, in some specific embodiments, only the patient-care devices used are dockable to the device dock 104; for example, in this specific embodiment, the infusion pump 7 is the only device docked into the device dock 102 and the device dock 102 only receives one device, e.g., the infusion pump 7. Additionally, alternatively, or optionally, in some specific embodiments, the patient-care devices 7, 14, 15, 16, 17, 35, 126, 128, 130, 148, are dockable, may operate undocked, and/or may not be dockable and can operate as a stand-alone patient-care device.

In some embodiments, the patient-care devices 7, 14, 15, 16, 17, 35, 126, 128, 130, and/or 148, the monitoring client 1, the remote communicator 11, and docks 102 and/or 104 may include a secure data class, e.g., via an API.

Any function described with reference to FIG. 1, may be performed by the hub 802 of FIG. 8, in some embodiments.

Figure 2:
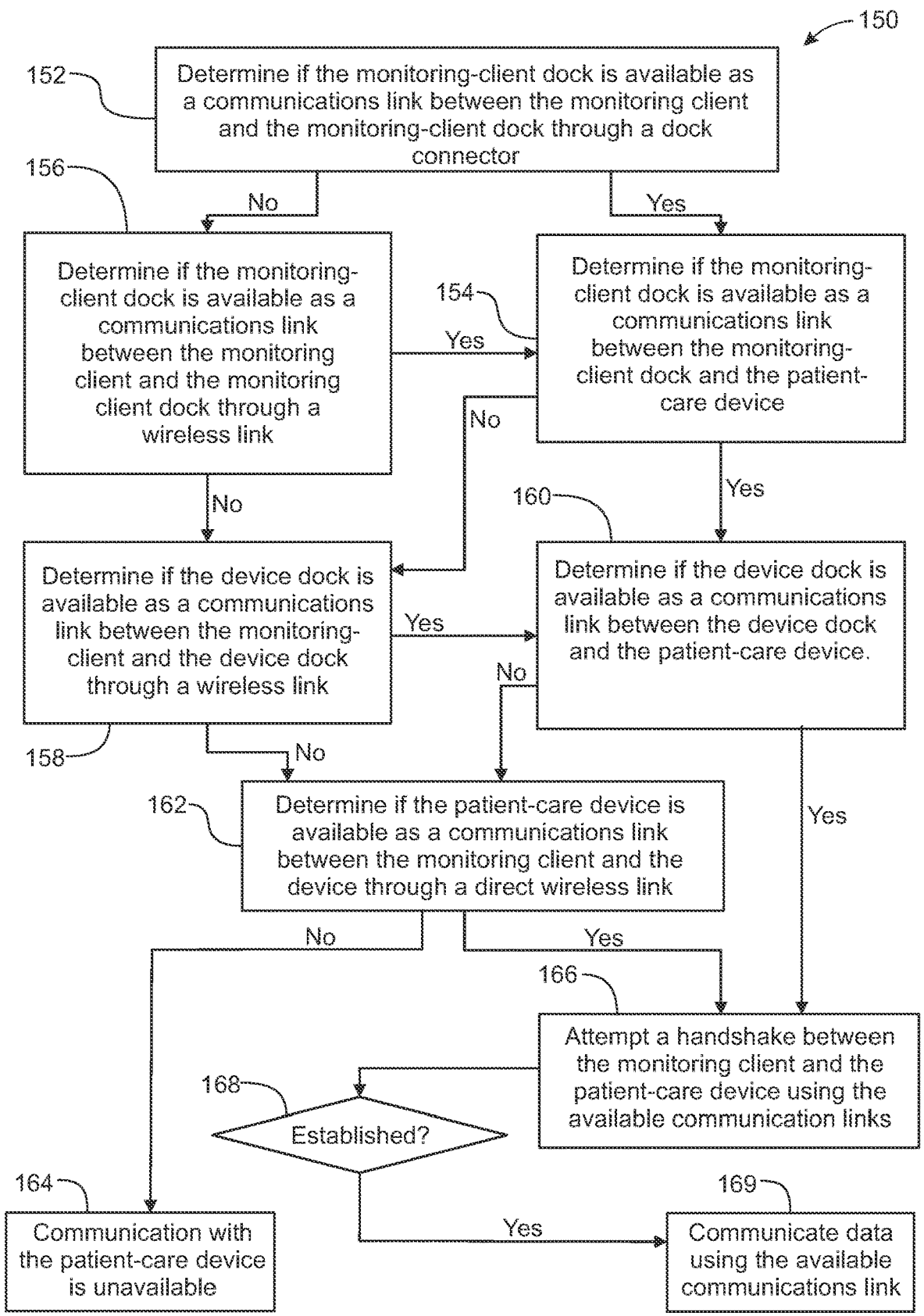
FIG. 2 is a flow chart diagram illustrating a method for maintaining communications between the monitoring client and a patient-care device of FIG. 1 in accordance with an embodiment of the present disclosure.

FIG. 2 shows a flow chart diagram illustrating a method 150 for maintaining communications between a monitoring client, e.g., the monitoring client 1 of FIG. 1, and one or more of patient-care devices, e.g., one or more of the patient-care devices 7, 14, 15, 16, 17, 35 126, 128, 130, 148 of FIG. 1, in accordance with an embodiment of the present disclosure. The method 150 of this example includes acts 152-169. The monitoring client 1 may display an icon indicating when communications are established to the paired and/or designated patient-care devices. The monitoring client 1 may check to determine that communications with the paired and/or designated patient-care devices is available at predetermined intervals, and if communications to a paired or designated patient-care device is unavailable for a predetermined amount of time, the monitoring client 1 may sound an alarm or alert.

Act 152 determines if the monitoring-client dock is available as a communications link between the monitoring client and the monitoring-client dock through a dock connector. If the communications link of act 152 is available, the method 150 continues to act 154, otherwise the method 150 continues to act 156.

Act 156 determines if the monitoring-client dock is available as a communications link between the monitoring-client and the monitoring-client dock through a wireless link. If the link of act 156 is available, the method 150 continues to act 154, otherwise, the method 150 continues to act 158.

Act 154 determines if the monitoring-client dock is available as a communications link between the monitoring-client dock and a device dock using a cable. If the communications link of act 154 is available, the method 150 continues to act 160, otherwise, the method 150 continues to the act 158. The act 160 determines if the device dock is available as a communications link between the device dock and the patient-care device, e.g., through a wireless or wired communications link. If the communications link of act 160 is available, the method 150 continues to the act 166, otherwise, the method 150 continues to the act 162. The act 162 determines if the patient-care device is available as a communications link between the monitoring-client and a patient-care device dock through a direct wireless link. If the communications link of act 162 is available, the method continues to act 166, otherwise, the method 150 continues to act 164.

Act 158 determines if the device dock is available as a communications link between the monitoring client and the device dock through a wireless link. If the communications link of act 158 is not available, the method 150 continues to act 162, otherwise, the method 150 continues to act 160.

Act 166 attempts a handshake between the monitoring client and the patient-care device using the available communications link. In alternative embodiments, no handshaking is used; for example, not all protocols use handshaking between communication endpoints. Decision act 168 determines if the handshake of act 166 was successful. If the decision act 168 determines the handshake of act 166 was unsuccessful, then act 164 determines that communication with the patient device is unavailable and/or method 150 attempts to establish communications using other links (not explicitly shown). Otherwise, if decision act 168 determines the handshake of act 166 was successful, act 169 communicates data using a sufficient number of communications links determined to be available by method 150.

Method 150 is an exemplary embodiment of the present disclosure describing a method of maintaining communications between a monitoring client and one or more patient-care devices. In some embodiments, although method 150 includes a schedule of communications links, other schedules may be used, broadcasting, anycast, multicast or unicast may be used, routing algorithms may be used, a distance-vector routing protocol may be used, a link-state routing protocol may be used, an optimized link state routing protocol may be used, a path-vector protocol may be used, static routing with predefined alternative communications paths may be used, and/or adaptive networking may be used. For example, in some embodiments of the present disclosure, weights may be assigned to each communications path and Dijkstra's Algorithm may be used to communicate between the monitoring client 1 and one or more patient-care devices; the weights may be determined in any know way, including as a function of bandwidth, signal quality, bit-error rate, may be linear to the available data throughput or latency, and/or the like.

Figure 3:
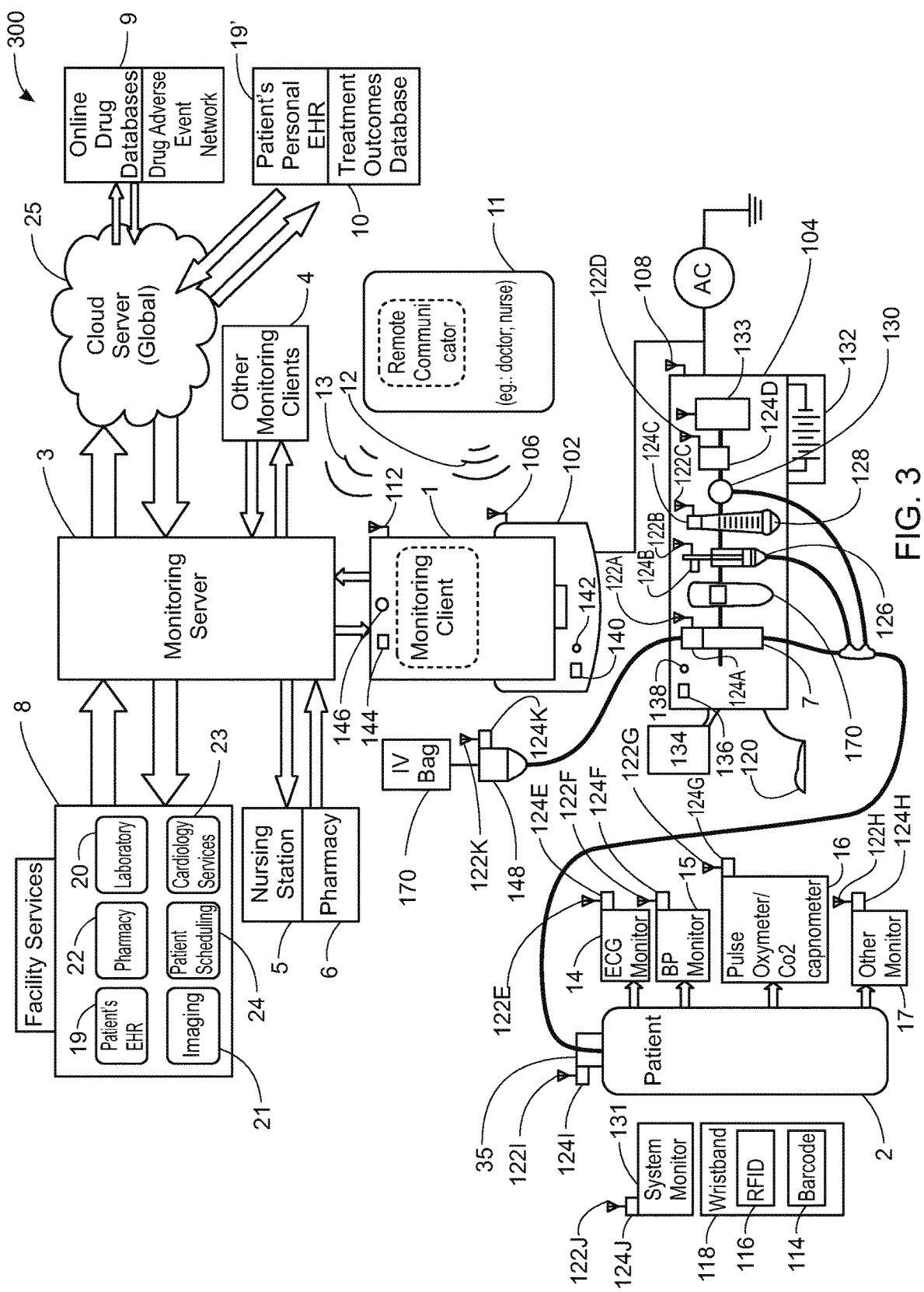
FIG. 3 is a block diagram of an electronic patient-care system having two docks for wireless communications therebetween in accordance with another embodiment of the present disclosure.

Referring to the drawings, FIG. 3 shows a block diagram of an electronic patient-care system 300 having two docks 102, 104 for wireless communications therebetween in accordance with another embodiment of the present disclosure. The system 300 is similar to the system 100 of FIG. 1;

however, the communications between the monitoring-client dock 102 and the device dock 104 are through a wireless link. For example, in some embodiments, system 300 of FIG. 3 may be system 100 of FIG. 1 with the cable 110 of FIG. 1 absent or non-operative; additionally or alternatively, system 300 of FIG. 3 may have docks 102 and 104 that are not connectable together using a cable.

Optionally, the monitoring client 1, other monitoring client 4, and/or the remote communicator 11 may be used to send commands or requests to patient-care devices 7, 14, 15, 16, 17, 35, 126, 128, 130, 148 such as for example, a bolus amount, an infusion flow rate, a total fluid for delivery, a start time for drug delivery, a stop time for drug delivery or a flow-delivery-rate profile to the infusion pump 7, the syringe pump 126 and/or the microinfusion pump 130. In some embodiments, one or more of the monitoring clients 1, 4, 11 may be used to send commands or requests to the pill dispenser 128, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata), however, the medication may not be safe if taken in excess and the max pill-dispensing criteria may prevent the medication from being taken at unsafe levels by the patient, e.g., a predetermined amount during a predetermined interval of time.

In some embodiments, the remote communicator 11 may be used to initiate two-way audio/visual communications between the remote communicator 11 and the monitoring client 1 (e.g., a video call). Additionally or alternatively, the monitoring client 1 may be used to initiate two-way audio/visual communications between the monitoring client 1 and the monitoring client remote communicator 11.

Optionally, the patient-care devices 7, 14, 15, 16, 17, 35, 126, 128, 130, 148 may also communicate data back to the monitoring client 1, the other monitoring client 4 and/or the remote communicator 11 for: determining if an alarm or alert should be issued or sent; determining if the treatment or condition is safe for the patient; determining if the system 300 is operating properly or within predetermined bounds; and/or for displaying the data on a display of the monitoring client 1, the other monitoring client 4 and/or the remote communicator 11. For example, optionally, the infusion pump 7, the syringe pump 126, and/or the microinfusion pump 130 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the monitoring client 1, the other monitoring client 4 and/or the remote communicator 11. In another embodiment, the pill dispenser 128 may optionally communicate data back to the monitoring client 1, the other monitoring client 4, and/or the remote communicator 11, such as for example, an actual pill dispensed, an actual pill-type dispensed, an actual pill dispensing schedule as dispensed, or whether or not a max pill-dispensing criteria was exceeded.

The data received from the patient-care devices 7, 14, 15, 16, 17, 35, 126, 128, 130, 148 may be analyzed for any predefined conditions to issue an alarm and/or an alert. For example, one or more of the monitoring clients 1, 4, 11 may use an increase in pressure downstream of the infusion pump 7, the syringe pump 126 and/or the microinfusion pump 130 to be an indication of one of: excessive clotting, infiltration, occlusion or kinking of the tubing to the patient; or occlusion by other material within the IV bag 170. In response to the sudden increase in downstream pressure, one or more of the monitoring clients 1, 4, 11 may visually or audibly alarm or alert a user. Additionally or alternatively, a sudden decrease in pressure downstream to the patient 2 may be an indication that the tubing has become detached from the needle and/or the needle is now out of the patient; and, in response, one or more of the monitoring clients 1, 4, 11 may visually or audibly alarm or alert a user. One or more of the monitoring clients 1, 4, 11 may, optionally, send a command to one or more of the infusion pump 7, the syringe pump 126, and/or the microinfusion pump 130 to stop delivery of fluid in response to the sudden increase and/or decrease of pressure downstream to the patient 2.

In some embodiments, each item, component, device, patient-care device, dock, and computing device, numbered or unnumbered, as shown in FIG. 3 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 7, 14, 15, 16, 17, 35, 126, 128, 130, 148 is optional. Likewise, each of the system monitor 131, the wrist band 118, the RFID 116, the barcode 114, the scanner 120, the display 134, and/or AC power, is optional in some embodiments of the present disclosure.

Additionally, in some embodiments, although some items, components, devices, patient-care devices, docks, and computing devices, numbered or unnumbered, as shown in FIG. 3 or described therewith are shown as being the sole item, component, device, patient-care device, dock or computing device, multiple items, components, devices, patient-care devices, docks and computing devices, are contemplated; for example, although a single infusion pump 7 is shown in FIG. 3, in some embodiments, two infusion pumps 7 may be used, multiple infusion pumps 7 may be used, or any arbitrary number of infusion pumps 7 may be used. Additionally or alternatively, in some embodiments, multiple device docks 104 and/or multiple monitoring-client docks 102 may be used.

Additionally or alternatively, although particular patient-care devices 7, 14, 15, 16, 17, 126, 128, 130, 148 are shown, other combinations, subsets, multiple ones of a particular patient-care device, or combinations thereof may be used. For example, in some embodiments, only an infusion pump 7 is used of the patient-care devices, and, in this specific example, the other patient-care devices 14, 15, 16, 17, 126, 128, 130, 148 may be disabled, may not be present or available for system use, may be turned off, or may not be part of system 300 of FIG. 3. Additionally or alternatively, in some specific embodiments, only the patient-care devices used are dockable to the device dock 104; for example, in one specific embodiment, the infusion pump 7 is the only device docked into the device dock 102 and the device dock 102 only receives one device, e.g., the infusion pump 7. Additionally, alternatively, or optionally, in some specific embodiments, the patient-care devices 7, 14, 15, 16, 17, 35, 126, 128, 130, 148, are dockable, may operate undocked, and/or may not be dockable and can operate as a stand-alone patient-care device.

In FIG. 3, although the device dock 104 is shows as being capable of receiving several patient-care devices, in other embodiments, the device dock 104 can receive one patient-care device, a plurality of patient-care devices, or any arbitrary number of patient-care devices. Also, bays of a dock may be unused, for example, as shown in FIG. 3, empty bay 170 is shown in device dock 104. Additionally, although the monitoring-client dock 102 is shown as be capable of receiving one monitoring client 1, in other embodiments, the monitoring-client dock 102 can receive two monitoring clients 1, more than two monitoring clients 1, or any arbitrary number of monitoring clients 1.

Figure 4:
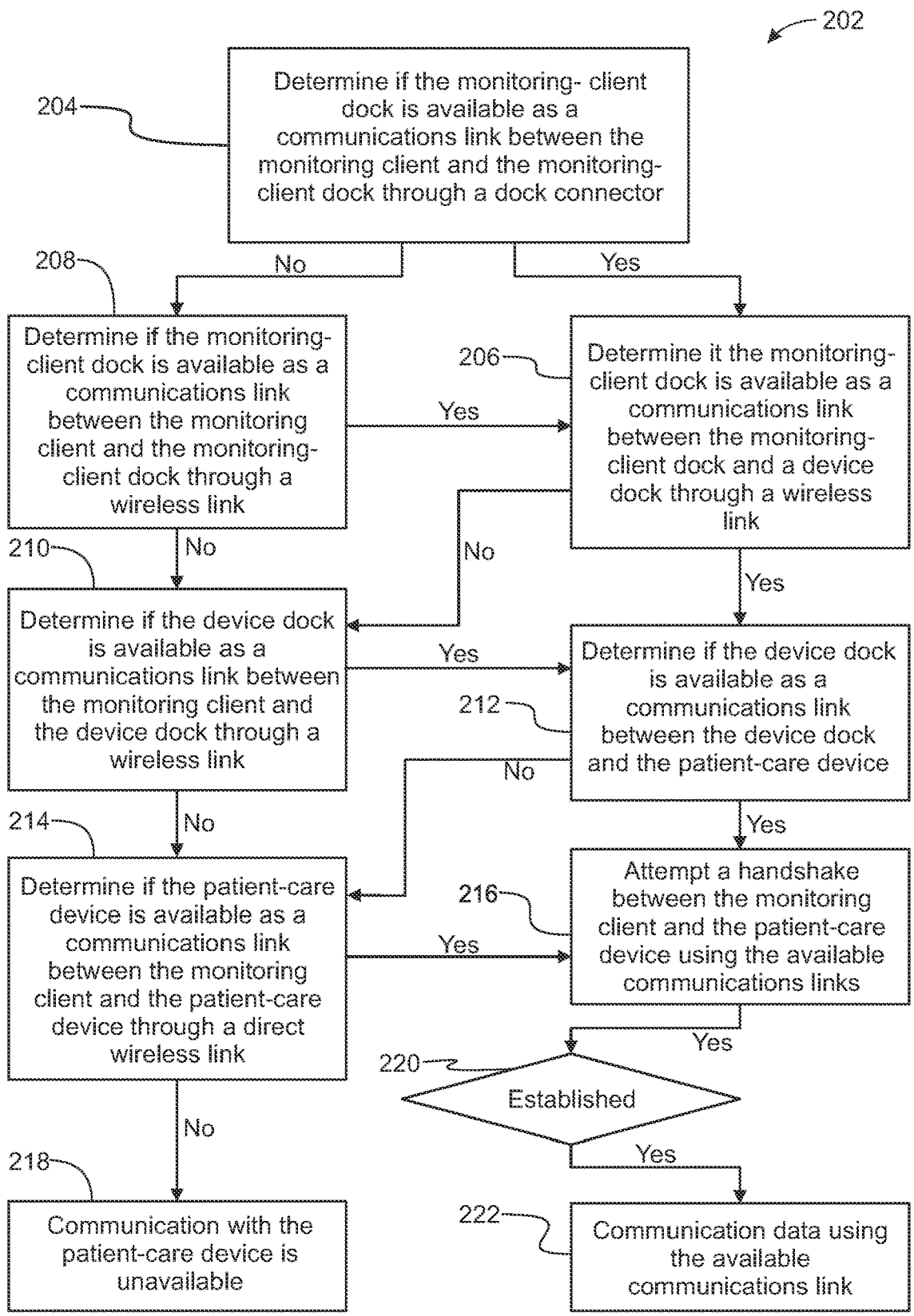
FIG. 4 is a flow chart diagram illustrating a method for maintaining communications between the monitoring client and a patient-care device of FIG. 3 in accordance with an embodiment of the present disclosure.

FIG. 4 shows a flow chart diagram illustrating a method 202 for maintaining communications between a monitoring client, e.g., the monitoring client 1, and one or more of devices, e.g., the patient-care devices 7, 14, 15, 16, 17, 35 126, 128, 130, 148 of FIG. 3 in accordance with an embodiment of the present disclosure.

Act 204 determines if the monitoring-client dock is available as a communications link between the monitoring client and the monitoring-client dock through a dock connector. If the communications link of act 204 is available, the method 202 continues to act 206, otherwise the method 202 continues to act 208. Act 208 determines if the monitoring-client dock is available as a communications link between the monitoring client and the monitoring-client dock through a wireless link. If the communications link of act 208 is available, the method 202 continues to act 206, otherwise, the method 202 continues to act 210.

Act 206 determines if the monitoring-client dock is available as a communications link between the monitoring-client dock and a device dock through a wireless link. If the communications link of act 206 is available, the method 202 continues to act 212, otherwise, the method 202 continues to act 210.

Act 210 determines if the device dock is available as a communications link between the monitoring client and the device dock through a wireless link. If the communications link of act 210 is available, the method 202 continues to act 212, otherwise, the method 202 continues to act 214.

Act 212 determines if the device dock is available as a communications link between the device dock and the patient-care device. If the communications link of act 212 is available, then method 202 continues to act 216, otherwise, the method 202 continues to act 214.

Act 214 determines if the patient-care device is available as a communications link between the monitoring client and the patient-care device through a direct wireless link. If the communications link of act 214 is available, the method 202 continues to act 216, otherwise, act 218 determines that communication with the patient-care device is unavailable.

Act 216 attempts a handshake between the monitoring client and the patient-care device using the available communications link(s). In alternative embodiments, no handshake is attempted; for example, some communication protocols do not utilize handshaking. Decision act 220 determines if the handshake was successful and communications between the monitoring client and the device have been established. If act 220 determines a communications link has been established, the method 202 communicates data between the monitoring client and the device during act 222 using the available communications link(s). If decision act 220 determines the handshake was not successful, either method 202 determines that communication with the device is unavailable in act 218 or method 202 attempts communications between the monitoring client through untried communication links (not explicitly shown).

Method 202 is an exemplary embodiment of the present disclosure describing a method of maintaining communications between a monitoring client and one or more patient-care devices. In some embodiments, although method 202 includes a schedule of communications links, other schedules may be used, broadcasting, anycast, multicast or unicast may be used, routing algorithms may be used, a distance-vector routing protocol may be used, a link-state routing protocol may be used, an optimized link state routing protocol may be used, a path-vector protocol may be used, static routing with predefined alternative communications paths may be used, and/or adaptive networking may be used. For example, in some embodiments of the present disclosure, weights may be assigned to each communications path and Dijkstra's Algorithm may be used to communicate between the monitoring client 1 and one or more patient-care devices; the weights may be determined in any know way, including as a function of bandwidth, signal quality, bit-error rate, may be linear to the available data throughput or latency, and/or the like.

Figure 5:
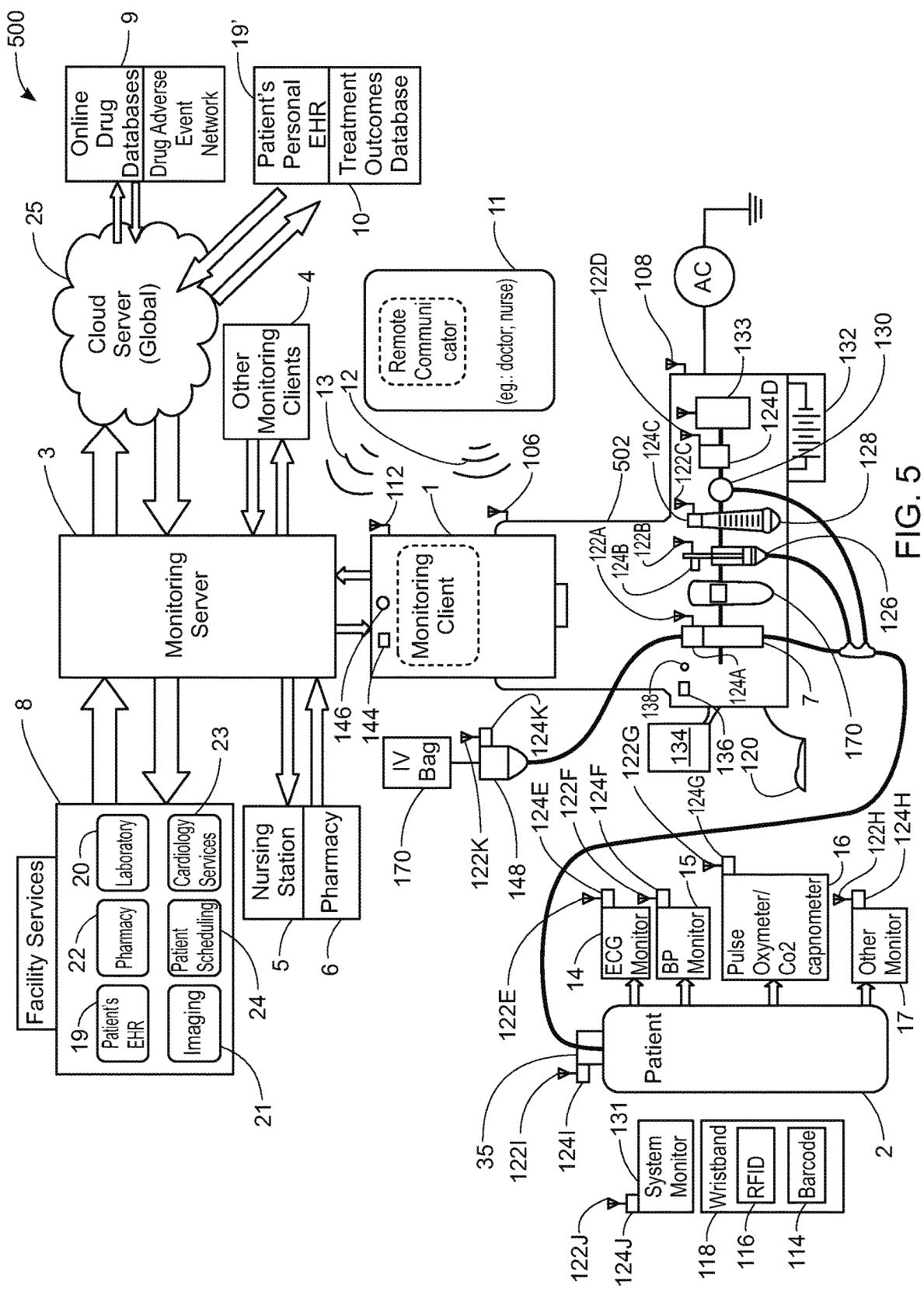
FIG. 5 is a block diagram of an electronic patient-care system having a dock for docking together a monitoring client and patient-care devices in accordance with yet another embodiment of the present disclosure.

Referring now the FIG. 5, an electronic patient-care system 500 in block diagram form is shown having a dock 502 for docking together a monitoring client 1 and various patient-care devices (e.g., patient-care devices 7, 126, 128, or 130), a communication module 124D, and a dongle 133 in accordance with yet another embodiment of the present disclosure. The electronic patient-care system 500 of FIG. 5 is similar to the electronic patient-care system 100 of FIG. 1; however, each of the monitoring client 1, the patient-care devices 7, 126, 128, 130, a communication module 124D, and a dongle 133 are all dockable to a dock 502. As will be appreciated in light of this disclosure, the dock 502 may include one or more buses, backplanes, communications paths, electronic circuitry, and the like to facilitate communications.

Optionally, the monitoring client 1, other monitoring client 4, and/or the remote communicator 11 may be used to send commands or requests to patient-care devices 7, 14, 15, 16, 17, 35, 126, 128, 130, 148 such as for example, a bolus amount, an infusion flow rate, a total fluid for delivery, a start time for drug delivery, a stop time for drug delivery or a flow-delivery-rate profile to the infusion pump 7, the syringe pump 126 and/or the microinfusion pump 130. In some embodiments, one or more of the monitoring clients 1, 4, 11 may be used to send commands or requests to the pill dispenser 128, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata), however, the medication may not be safe if taken in excess and the max pill-dispensing criteria may prevent the medication from being taken at unsafe levels by the patient, e.g., a predetermined amount during a predetermined interval of time.

Optionally, the patient-care devices 7, 14, 15, 16, 17, 35, 126, 128, 130, 148 may also communicate data back to the monitoring client 1, the other monitoring client 4 and/or the remote communicator 11 for: determining if an alarm or alert should be issued or sent; determining if the treatment or condition is safe for the patient; determining if the system 500 is operating properly or within predetermined bounds; and/or for displaying the data on a display of the monitoring client 1, the other monitoring client 4 and/or the remote communicator 11. For example, optionally, the infusion pump 7, the syringe pump 126, and/or the microinfusion pump 130 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the monitoring client 1, the other monitoring client 4 and/or the remote communicator 11. In another embodiment, the pill dispenser 128 may optionally communicate data back to the monitoring client 1, the other monitoring client 4, and/or the remote communicator 11, such as for example, an actual pill dispensed, an actual pill-type dispensed, an actual pill dispensing schedule as dispensed, or whether or not a max pill-dispensing criteria was exceeded.

The data received from the patient-care devices 7, 14, 15, 16, 17, 35, 126, 128, 130, 148 may be analyzed for any predefined conditions to issue an alarm and/or an alert. For example, one or more of the monitoring clients 1, 4, 11 may use an increase in pressure downstream of the infusion pump 7, the syringe pump 126 and/or the microinfusion pump 130 to be an indication of one of: excessive clotting, infiltration, occlusion or kinking of the tubing to the patient; or occlusion by other material within the IV bag 170. In response to the sudden increase in downstream pressure, one or more of the monitoring clients 1, 4, 11 may visually or audibly alarm or alert a user. Additionally or alternatively, a sudden decrease in pressure downstream to the patient 2 may be an indication that the tubing has become detached from the needle and/or the needle is now out of the patient; and, in response, one or more of the monitoring clients 1, 4, 11 may visually or audibly alarm or alert a user. One or more of the monitoring clients 1, 4, 11 may, optionally, send a command to one or more of the infusion pump 7, the syringe pump 126, and/or the microinfusion pump 130 to stop delivery of fluid in response to the sudden increase and/or decrease of pressure downstream to the patient 2.

In some embodiments, each item, component, device, patient-care device, dock, and computing device, numbered or unnumbered, as shown in FIG. 5 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 7, 14, 15, 16, 17, 35, 126, 128, 130, 148 is optional. Likewise, each of the system monitor 131, the wrist band 118, the RFID 116, the barcode 114, the scanner 120, the display 134, and/or AC power, is optional in some embodiments of the present disclosure.

Additionally, in some embodiments, although some items, components, devices, patient-care devices, docks, and computing devices, numbered or unnumbered, as shown in FIG. 5 or described therewith are shown as being the sole item, component, device, patient-care device, dock or computing device, multiple items, components, devices, patient-care devices, docks and computing devices, are contemplated; for example, although a single infusion pump 7 is shown in FIG. 5, in some embodiments, two infusion pumps 7 may be used, multiple infusion pumps 7 may be used, or any arbitrary number of infusion pumps 7 may be used. Additionally or alternatively, in some embodiments, multiple docks 502 may be used.

Additionally or alternatively, although particular patient-care devices 7, 14, 15, 16, 17, 126, 128, 130, 148 are shown, other combinations, subsets, multiple ones of a particular patient-care device, or combinations thereof may be used. For example, in some embodiments, only an infusion pump 7 is used of the patient-care devices, and, in this specific example, the other patient-care devices 14, 15, 16, 17, 126, 128, 130, 148 may be disabled, may not be present or available for system use, may be turned off, or may not be part of system 500 of FIG. 5. Additionally or alternatively, in some specific embodiments, only the patient-care devices used are dockable to the dock 502; for example, in one specific embodiment, the infusion pump 7 is the only device docked into the device dock 102 and the device dock 102 only receives one device, e.g., the infusion pump 7. Additionally, alternatively, or optionally, in some specific embodiments, the patient-care devices 7, 14, 15, 16, 17, 35, 126, 128, 130, 148, are dockable, may operate undocked, and/or may not be dockable and can operate as a stand-alone patient-care device.

In FIG. 5, although the dock 502 is shows as being capable of receiving several patient-care devices, in other embodiments, the dock 502 can receive one patient-care device, a plurality of patient-care devices, or any arbitrary number of patient-care devices. Also, bays of a dock may be unused, for example, as shown in FIG. 5, empty bay 170 is shown in dock 502. Additionally, although the dock 502 is shown as be capable of receiving one monitoring client 1, in other embodiments, the dock 502 can receive two monitoring clients 1, more than two monitoring clients 1, or any arbitrary number of monitoring clients 1.

Figure 6:
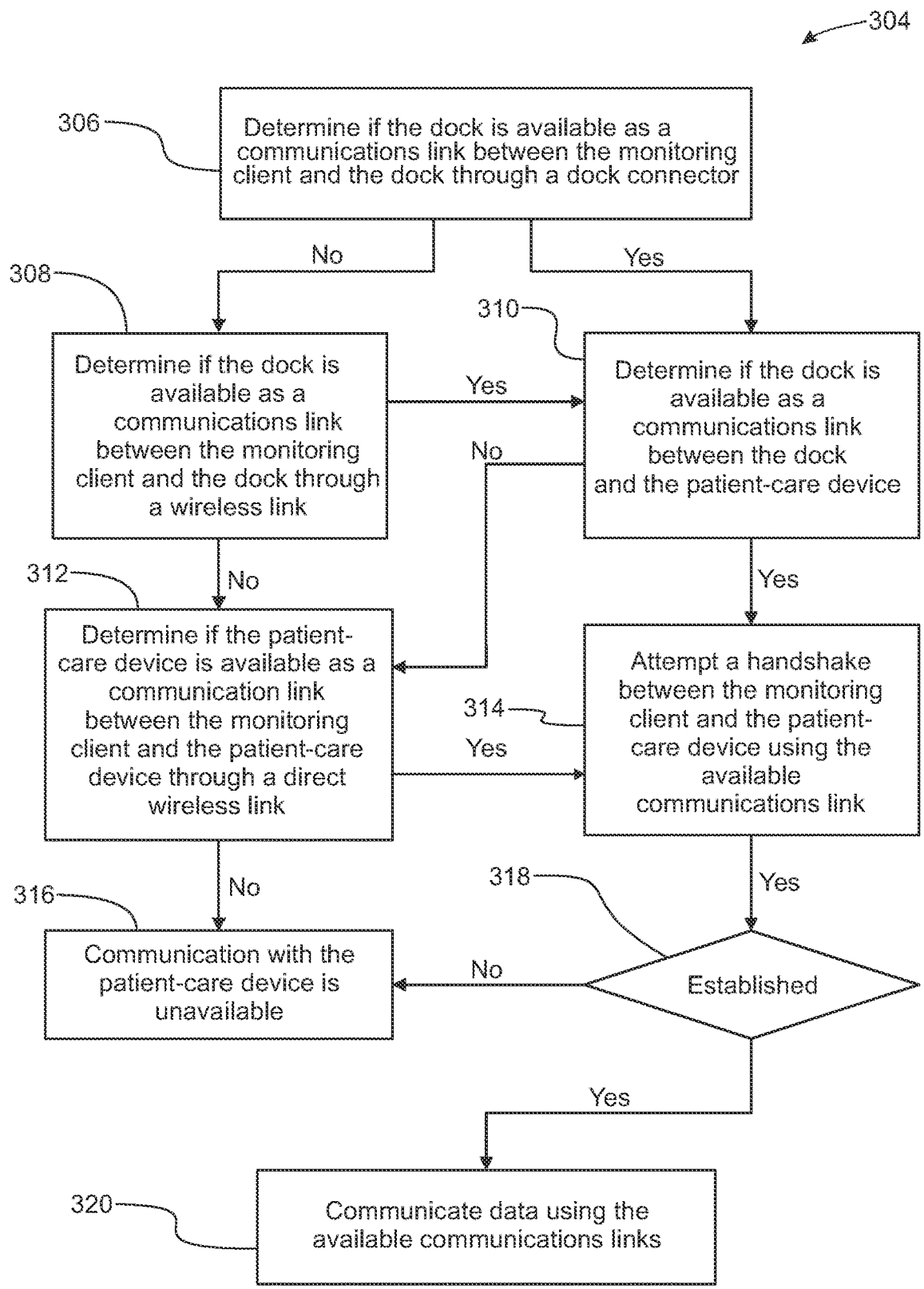
FIG. 6 is a flow chart diagram illustrating a method for maintaining communications between the monitoring client and a patient-care device of FIG. 5 in accordance with an embodiment of the present disclosure.

FIG. 6 is a flow chart diagram illustrating a method 304 for maintaining communications between a monitoring client, e.g., the monitoring client 1 of FIG. 5, and one more patient-care devices, e.g., patient care devices 7, 14, 15, 16, 17, 35 126, 128, 130, 148 of FIG. 5 in accordance with an embodiment of the present disclosure.

The method determines if the dock is available as a communications link between the monitoring client and the dock through a dock connector during act 306. If the communications link of act 306 is not available, method 304 continues to act 308, otherwise, the method 304 continues to act 310. Act 310 determines if the dock is available as a communications link between the dock and the patient-care device. If the communications link of act 310 is not available, the method 304 continues to act 312, otherwise, the method 304 continues to act 314.

Act 308 determines if the dock is available as a communications link between the monitoring client and the dock through a wireless link. If the communications link of act 308 is available, the method 304 continues to act 310, otherwise, the method 304 continues to act 312.

Act 312 determines if the patient-care device is available as a communications link between the monitoring client and the patient-care device through a direct wireless link. If the communications link of act 312 is unavailable, act 316 determines that communication between the monitoring client and the patient-care device is unavailable.

Act 314 attempts a handshake between the monitoring client and the device using the available communications link(s). In alternative embodiments, no handshaking is utilized; for example, some protocols do not employ handshaking. Decision act 318 determines if the handshake was successful, and if it was successful, method 304 continues to act 320 to communicate data using the available communications link(s). If the decision act 318 determines the handshake was unsuccessful in act 314, act 316 determines that communication with the device is unavailable. In other embodiments, if decision act 318 determines the handshake was unsuccessful in act 314, method 304 attempts to communicate with the patient-care device via untried communications links (not explicitly shown).

Method 304 is an exemplary embodiment of the present disclosure describing a method of maintaining communications between a monitoring client and one or more patient-care devices. In some embodiments, although method 304 includes a schedule of communications links, other schedules may be used, broadcasting, anycast, multicast or unicast may be used, routing algorithms may be used, a distance-vector routing protocol may be used, a link-state routing protocol may be used, an optimized link state routing protocol may be used, a path-vector protocol may be used, static routing with predefined alternative communications paths may be used, and/or adaptive networking may be used. For example, in some embodiments of the present disclosure, weights may be assigned to each communications path and Dijkstra's Algorithm may be used to communicate between the monitoring client 1 and one or more patient-care devices; the weights may be determined in any know way, including as a function of bandwidth, signal quality, bit-error rate, may be linear to the available data throughput or latency, and/or the like.

Figure 7:
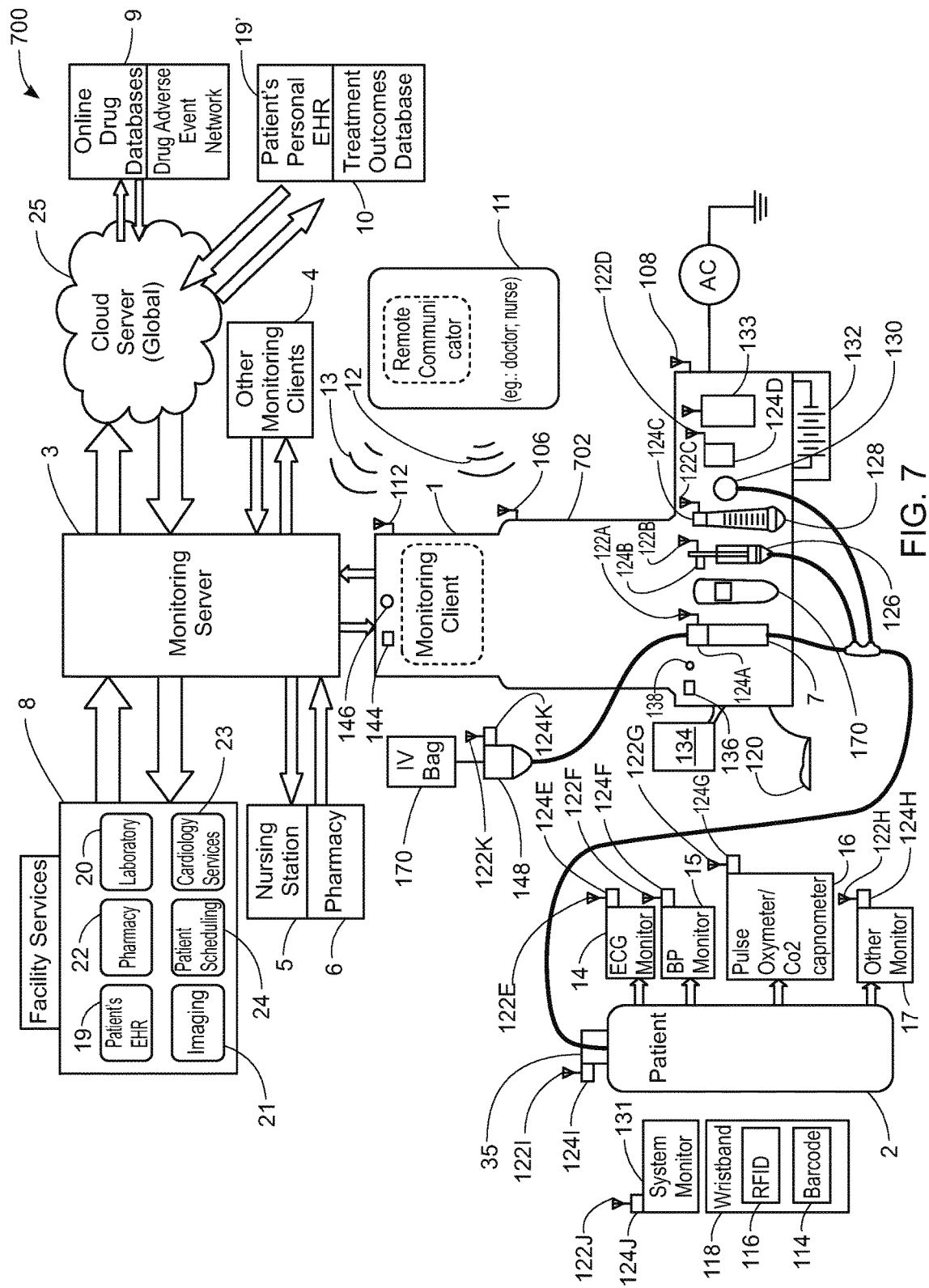
FIG. 7 is a block diagram of an electronic patient-care system having a monitoring client with an integrated dock for docking patient-care devices thereto in accordance with yet another embodiment of the present disclosure.

Turning now to FIG. 7, a block diagram is shown of an electronic patient-care system 700 having a monitoring client 1 with an integrated dock 702 for docking patient-care devices 7, 126, 128, 130 thereto in accordance with yet another embodiment of the present disclosure. Additionally in some embodiments, a communication module 124D, and a dongle 133 are all dockable to the dock 702. The patient-care system 700 of FIG. 7 is similar to the patient-care system 100 of FIG. 1; however, the patient-care system 700 includes the integrated dock 702. In some embodiments, the monitoring client 1 communicates with a patient-care devices when it is docked via the dock; however, if the monitoring client 1 cannot communicate with a patient-care device, e.g., patient-care devices 7, 14, 15, 16, 17, 35, 126, 128, 130, 148, the monitoring client 1 can communicate with it wirelessly, e.g., using the antenna 112 of the monitoring client 1.

Optionally, the monitoring client 1, other monitoring client 4, and/or the remote communicator 11 may be used to send commands or requests to patient-care devices 7, 14, 15, 16, 17, 35, 126, 128, 130, 148 such as for example, a bolus amount, an infusion flow rate, a total fluid for delivery, a start time for drug delivery, a stop time for drug delivery or a flow-delivery-rate profile to the infusion pump 7, the syringe pump 126 and/or the microinfusion pump 130. In some embodiments, one or more of the monitoring clients 1, 4, 11 may be used to send commands or requests to the pill dispenser 128, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata), however, the medication may not be safe if taken in excess and the max pill-dispensing criteria may prevent the medication from being taken at unsafe levels by the patient, e.g., a predetermined amount during a predetermined interval of time.

Optionally, the patient-care devices 7, 14, 15, 16, 17, 35, 126, 128, 130, 148 may also communicate data back to the monitoring client 1, the other monitoring client 4 and/or the remote communicator 11 for: determining if an alarm or alert should be issued or sent; determining if the treatment or condition is safe for the patient; determining if the system 700 is operating properly or within predetermined bounds; and/or for displaying the data on a display of the monitoring client 1, the other monitoring client 4 and/or the remote communicator 11. For example, optionally, the infusion pump 7, the syringe pump 126, and/or the microinfusion pump 130 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the monitoring client 1, the other monitoring client 4 and/or the remote communicator 11. In another embodiment, the pill dispenser 128 may optionally communicate data back to the monitoring client 1, the other monitoring client 4, and/or the remote communicator 11, such as for example, an actual pill dispensed, an actual pill-type dispensed, an actual pill dispensing schedule as dispensed, or whether or not a max pill-dispensing criteria was exceeded.

The data received from the patient-care devices 7, 14, 15, 16, 17, 35, 126, 128, 130, 148 may be analyzed for any predefined conditions to issue an alarm and/or an alert. For example, one or more of the monitoring clients 1, 4, 11 may use an increase in pressure downstream of the infusion pump 7, the syringe pump 126 and/or the microinfusion pump 130 to be an indication of one of: excessive clotting, infiltration, occlusion or kinking of the tubing to the patient; or occlusion by other material within the IV bag 170. In response to the sudden increase in downstream pressure, one or more of the monitoring clients 1, 4, 11 may visually or audibly alarm or alert a user. Additionally or alternatively, a sudden decrease in pressure downstream to the patient 2 may be an indication that the tubing has become detached from the needle and/or the needle is now out of the patient; and, in response, one or more of the monitoring clients 1, 4, 11 may visually or audibly alarm or alert a user. One or more of the monitoring clients 1, 4, 11 may, optionally, send a command to one or more of the infusion pump 7, the syringe pump 126, and/or the microinfusion pump 130 to stop delivery of fluid in response to the sudden increase and/or decrease of pressure downstream to the patient 2.

In some embodiments, each item, component, device, patient-care device, dock, and computing device, numbered or unnumbered, as shown in FIG. 7 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 7, 14, 15, 16, 17, 35, 126, 128, 130, 148 is optional. Likewise, each of the system monitor 131, the wrist band 118, the RFID 116, the barcode 114, the scanner 120, the display 134, and/or AC power, is optional in some embodiments of the present disclosure.

Additionally, in some embodiments, although some items, components, devices, patient-care devices, docks, and computing devices, numbered or unnumbered, as shown in FIG. 7 or described therewith are shown as being the sole item, component, device, patient-care device, dock or computing device, multiple items, components, devices, patient-care devices, docks and computing devices, are contemplated; for example, although a single infusion pump 7 is shown in FIG. 7, in some embodiments, two infusion pumps 7 may be used, multiple infusion pumps 7 may be used, or any arbitrary number of infusion pumps 7 may be used. Additionally or alternatively, in some embodiments, integrated docks 702 may be used.

Additionally or alternatively, although particular patient-care devices 7, 14, 15, 16, 17, 126, 128, 130, 148 are shown, other combinations, subsets, multiple ones of a particular patient-care device, or combinations thereof may be used. For example, in some embodiments, only an infusion pump 7 is used of the patient-care devices, and, in this specific example, the other patient-care devices 14, 15, 16, 17, 126, 128, 130, 148 may be disabled, may not be present or available for system use, may be turned off, or may not be part of system 700 of FIG. 7. Additionally or alternatively, in some specific embodiments, only the patient-care devices used are dockable to the integrated dock 702; for example, in one specific embodiment, the infusion pump 7 is the only device docked into the integrated dock 702 and the integrated dock 702 only receives one device, e.g., the infusion pump 7. Additionally, alternatively, or optionally, in some specific embodiments, the patient-care devices 7, 14, 15, 16, 17, 35, 126, 128, 130, 148, are dockable, may operate undocked, and/or may not be dockable and can operate as a stand-alone patient-care device.

In FIG. 7, although the integrated dock 702 is shows as being capable of receiving several patient-care devices, in other embodiments, the integrated dock 702 can receive one patient-care device, a plurality of patient-care devices, or any arbitrary number of patient-care devices. Also, bays of a dock may be unused, for example, as shown in FIG. 7, empty bay 170 is shown in integrated dock 702. Additionally, although the integrated dock 702 is shown as having one integrated monitoring client 1, in other embodiments, the integrated dock 702 has two integrated monitoring clients 1, more than two integrated monitoring clients 1, or any arbitrary number of integrated monitoring clients 1.

FIG. 8 is a block diagram of an electronic patient-care system 800 having a hub 802 in accordance with yet another embodiment of the present disclosure. Optionally, in some embodiments, the hub 802 provides a communications interface between the monitoring-client dock 102 and device docks 804, 806. In yet additional embodiments, the hub 802 controls the patient-care devices without a monitoring client 1, other monitoring client 4, and/or a remote communicator 11. For example, the hub 802 may communicate with the monitoring server 3, the facility services 8, the nursing station 5, the pharmacy 6, the cloud server 25, the online drug databases or drug adverse event network 9, a patient's personal EHR 19', and/or the treatment outcomes database 10. The hub 802 may provide a clock such that all devices connected thereto use the hub's 802 clock (e.g., patient-care devices, monitoring clients, remote communicators, etc.), real-time devices use the hub's 802 clock, or time-critical devices use the hub's 802 clock.

In some embodiments, a GPS and/or a ranging module (e.g., ultrasonic ranging module) may be installed on the infusion pump 830, the monitoring client 1, the hub 802, a caregiver, and/or a patient. Predetermined settings may require that a predetermined group of the infusion pump 830, the monitoring client 1, the hub 802, the caregiver, and/or the patient must, in this specific embodiment, be in a predetermined distance relative to each other prior to starting treatment and/or prior to configuring one of the infusion pump 830, the hub 802, and/or the monitoring client 1.

In some embodiments, the hub 802 includes an Application Programming Interface (API) to display GUIs, windows, data, etc. on the monitoring client 1 and/or the remote communicator 11. The API may include a secure data class. In yet additional embodiments, the docks 102, 804 and/or 806 include an API to display GUIs, windows, data, etc. on the monitoring client 1 or remote communicator 11. In yet an additional embodiment, the docks 102, 804, or 806, or the hub 802 includes an API to display GUIs, windows, data, etc. on a patient-care device 830, 810, and/or 814.

In some embodiments, the hub 802 and/or the docks 102, 804 and/or 806 may identify the type of patient-care device associated therewith and load configuration data based upon the type of the associated patient-care device (a device paired thereto, a device plugged in or docked to the hub 802 and/or the docks 102, 804, and/or 806).

In some embodiments, the hub 802 and/or the docks 102, 804 and/or 806 may identify the type of patient-care device associated therewith and configure a UI using html, CSS, JavaScript, Etc. In some embodiments, the hub 802 and/or the docks 102, 804 and/or 806 may have a distributed UI system.

The user interface described herein may utilize a request-action framework.

Optionally, in some specific embodiments, the hub 802 includes all of the safety-critical circuitry and software for communicating with the monitoring client 1; for example, in this specific embodiment, the hub 802 receives treatment parameters from the monitoring client 1, and the hub 802 ensures the treatment parameter is safe for the patient 2 independent of the any safety check performed elsewhere, for example, on the monitoring client 1. In yet an additional specific embodiment, system 800 is, optionally, wholly fault-tolerant of the monitoring client 1, and may ignore commands, requests, or parameters from the monitoring client 1 when, for example, independent safety checks performed therein does not satisfy predetermined criteria, for example, predetermined safe ranges of drug delivery of an infusion pump 7.

Optionally, in yet additional specific embodiments, a barcode attached to the IV bag 170 may be scanned by the scanner 120, which downloads a predetermined prescription (e.g., from the patient's personal EHR19') and/or an infusion pump 830 includes a predetermined prescription that is uploaded into the hub 802 when it is docked to the dock 804; thereafter, in this specific embodiment and optionally, the hub 802 initiates infusion of the IV bag 170 into the patient 2 and monitors the progress of the treatment to ensure the patient's 2 safety. Additionally, alternatively, or optionally, in this specific embodiment, a caregiver may interact with system 800 as shown in FIG. 8 exclusively via the hub 802. Optionally, in some embodiments, the hub 802 uploads treatment, status, or patient information to the monitoring client 1; for example, the hub 802 may upload treatment information it receives from the infusion pump 830 or treatment information it receives from the patient's personal EHR 19' corresponding to a scanned barcode on the IV bag 170, to the monitoring client 1 for display to a user, for confirmation of the information by the user, for storage within the monitoring client 1, and the like.

In some embodiments, the device dock 804 receives infusion pumps 830, 810, and 812. In some embodiments, the device dock 804 receives, one, more than one, or a plurality of patient-care devices. Device dock 806 receives a pill dispenser 814. In some embodiments, the device dock 806 receives, one, more than one, or a plurality of patient-care devices, such as pill dispensers 806. The device dock 804 includes an antenna 816 for wireless communications, and the device dock 806 includes an antenna 818 for wireless communications. Likewise, the hub 802 includes an antenna 820 for wireless communications. Additionally or alternatively, the device dock 804, the hub 802, and/or the monitoring client 1 communicate with each other using wired connections. Each of the hub 802, and the docks 804 and 806 may communicate with each other using, for example, a USB cable, an Ethernet cable, and/or via a wireless link. Optionally, the hub 802 may include additional accessories, such as a display 822, a camera 824, a microphone 826, a scanner 120, an attachable/detachable display (not shown), and the like. As previously mentioned, the hub 802 may provide all patient safety-critical functions and may operate independently of the monitoring client 1 and/or the monitoring-client dock 102.

Optionally, the monitoring client 1, other monitoring client 4, and/or the remote communicator 11 may be used to send commands or requests to patient-care devices 14, 15, 16, 17, 35, 830, 810, 812, 814, 830 148 such as for example, a bolus amount, an infusion flow rate, a total fluid for delivery, a start time for drug delivery, a stop time for drug delivery or a flow-delivery-rate profile to one or more of the infusion pumps 830, 810, 812. In some embodiments, one or more of the monitoring clients 1, 4, 11 may be used to send commands or requests to the pill dispenser 814, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata), however, the medication may not be safe if taken in excess and the max pill-dispensing criteria may prevent the medication from being taken at unsafe levels by the patient, e.g., a predetermined amount during a predetermined interval of time.

Optionally, the patient-care devices 14, 15, 16, 17, 35, 830, 810, 812, 814, 830, 148 may also communicate data back to the monitoring client 1, the other monitoring client 4 and/or the remote communicator 11 for: determining if an alarm or alert should be issued or sent; determining if the treatment or condition is safe for the patient; determining if the system 800 is operating properly or within predetermined bounds; and/or for displaying the data on a display of the monitoring client 1, the other monitoring client 4 and/or the remote communicator 11. For example, optionally, one or more of the infusion pumps 830, 810, 812 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the monitoring client 1, the other monitoring client 4 and/or the remote communicator 11. In another embodiment, the pill dispenser 814 may optionally communicate data back to the monitoring client 1, the other monitoring client 4, and/or the remote communicator 11, such as for example, an actual pill dispensed, an actual pill-type dispensed, an actual pill dispensing schedule as dispensed, or whether or not a max pill-dispensing criteria was exceeded.

The data received from the patient-care devices 14, 15, 16, 17, 35, 830, 810, 812, 814, 830, 148 may be analyzed for any predefined conditions to issue an alarm and/or an alert. For example, one or more of the monitoring clients 1, 4, 11 may use an increase in pressure downstream of one or more of the infusion pumps 830, 810, 812 to be an indication of one of: excessive clotting, infiltration, occlusion or kinking of the tubing to the patient; or occlusion by other material within the IV bag 170. In response to the sudden increase in downstream pressure, one or more of the monitoring clients 1, 4, 11 may visually or audibly alarm or alert a user. Additionally or alternatively, a sudden decrease in pressure downstream to the patient 2 may be an indication that the tubing has become detached from the needle and/or the needle is now out of the patient; and, in response, one or more of the monitoring clients 1, 4, 11 may visually or audibly alarm or alert a user. One or more of the monitoring clients 1, 4, 11 may, optionally, send a command to one or more of the infusion pumps 830, 810, 812 to stop delivery of fluid in response to the sudden increase and/or decrease of pressure downstream to the patient 2.

In some embodiments, each item, component, device, patient-care device, dock, and computing device, numbered or unnumbered, as shown in FIG. 8 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 830, 810, 812 is optional. Likewise, each of the system monitor 131, the wrist band 118, the RFID 116, the barcode 114, the scanner 120, the display 808, and/or AC power, is optional in some embodiments of the present disclosure.

Additionally, in some embodiments, although some items, components, devices, patient-care devices, docks, and computing devices, numbered or unnumbered, as shown in FIG. 8 or described therewith are shown as being the sole item, component, device, patient-care device, dock or computing device, multiple items, components, devices, patient-care devices, docks and computing devices, are contemplated; for example, although a single pill dispenser 814 is shown in FIG. 8, in some embodiments, two pill dispensers 814 may be used, multiple pill dispensers 814 may be used, or any arbitrary number of pill dispensers 814 may be used. Additionally or alternatively, in some embodiments, multiple docks 804 or 806 and/or multiple monitoring-client docks 102 may be used.

Additionally or alternatively, although particular patient-care devices 830, 810, 812 are shown, other combinations, subsets, multiple ones of a particular patient-care device, or combinations thereof may be used. For example, in some embodiments, only an infusion pump 830 is used of the patient-care devices, and, in this specific example, the other patient-care devices 810, 812, 814 may be disabled, may not be present or available for system use, may be turned off, or may not be part of system 800 of FIG. 8. Additionally or alternatively, in some specific embodiments, only the patient-care devices used are dockable to dock 804 or 806; for example, in one specific embodiment, the infusion pump 830 is the only device docked into the dock 804 and the dock 804 only receives one device, e.g., the infusion pump 830.

In FIG. 8, although the dock 804 is shows as being capable of receiving several patient-care devices, in other embodiments, the device dock 804 can receive one patient-care device, a plurality of patient-care devices, or any arbitrary number of patient-care devices. Also, bays of a dock may be unused (not shown in FIG. 8). Additionally, although the monitoring-client dock 102 is shown as be capable of receiving one monitoring client 1, in other embodiments, the monitoring-client dock 102 can receive two monitoring clients 1, more than two monitoring clients 1, or any arbitrary number of monitoring clients 1. Additionally, alternatively, or optionally, in some specific embodiments, the patient-care devices 14, 15, 16, 17, 35, 830, 810, 812, 814 are dockable, may operate undocked, and/or may not be dockable and can operate as a stand-alone patient-care device.

System 800 of FIG. 8 may use any known communications method to maintain communications therewithin. For example, in some embodiments, any schedule of communications may be used, broadcasting, anycast, multicast or unicast may be used, routing algorithms may be used, a distance-vector routing protocol may be used, a link-state routing protocol may be used, an optimized link state routing protocol may be used, a path-vector protocol may be used, static routing with predefined alternative communications paths may be used, and/or adaptive networking may be used. For example, in some embodiments of the present disclosure, weights may be assigned to each communications path and Dijkstra's Algorithm may be used to communicate between the monitoring client 1 or the hub 802 and one or more patient-care devices (e.g., patient-care devices 830, 810, 812, and 814); the weights may be determined in any know way, including as a function of bandwidth, signal quality, bit-error rate, may be linear to the available data throughput or latency, and/or the like.

In an embodiment of the present disclosure, the facility services 8 and/or the drug adverse event network 9 may also include a Drug Error Reduction System ("DERS"). The DERS system may include a first set of predetermined criteria to trigger soft alarms and/or a second set of predetermined criteria to trigger hard alarms. Soft alarms may be overridden (e.g., turned off) by a caregiver using a user interface of the infusion pump 830, the user interface 808 of the hub 802, and/or the user interface of the monitoring client 1 (and may be only an audible and/or vibratory alarm) while hard alarms cause the treatment to cease until the source of the hard alarm is removed.

In yet an additional embodiment of the present disclosure, the DERS system may include a first set of predetermined criteria defining soft limits and/or a second set of predetermined criteria defining hard limits. The hard and soft limits define treatment limits, such as drug dosage limits based upon size, weight, age, other patient parameters, or other criteria. Soft limits may be overridden by a caregiver using a user interface of the infusion pump 830, the user interface of the monitoring client 1, and/or the user interface 808 of the hub 802 to start treatment despite that the treatment is outside of the first set of predetermined criteria while the hard limits prevent the treatment from starting until the settings are changed to confirm to the second set of predetermined criteria defining the hard limits.

In some embodiments, the patient-care devices 830, 810, 812, 814, 14, 15, 16, 17, 35 and/or 148, the monitoring client 1, the remote communicator 11, and docks 102 and/or 804, and/or the hub 802 may include a secure data class, e.g., via an API.

Figure 9:
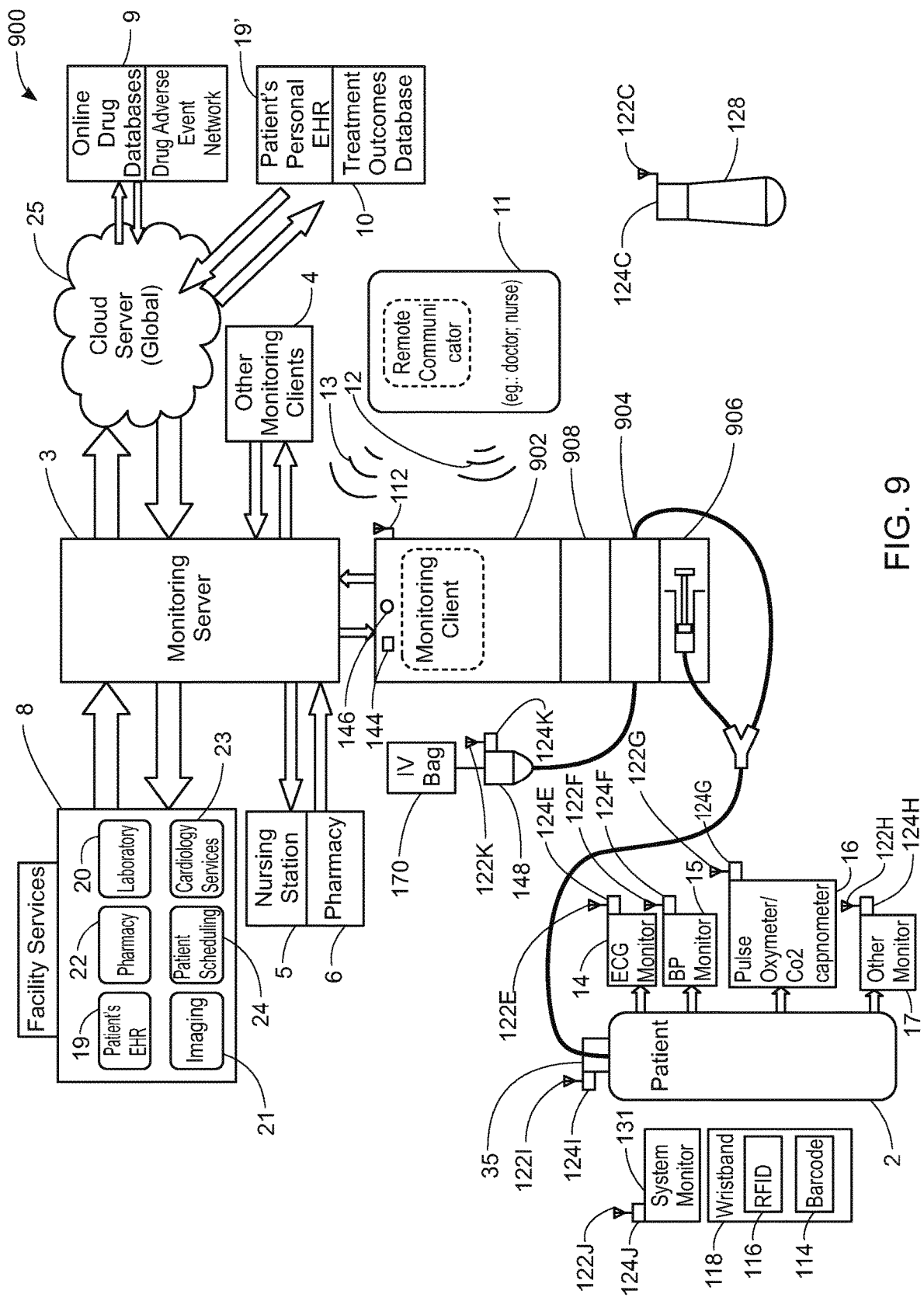
FIG. 9 is a block diagram of an electronic patient-care system having a stackable monitoring client and stackable patient-care devices in accordance with yet another embodiment of the present disclosure.

Referring again to the drawings, FIG. 9 shows a block diagram of an electronic patient-care system 900 having a stackable monitoring client 902, a stackable infusion pump 904, a stackable syringe pump 906, and another stackable patient-care device 908 in accordance with yet another embodiment of the present disclosure. The stackable devices 902-908 may communicate using a backplane and/or a bus (in some embodiments, the stackable devices 902-908 communicate via communication modules).

Optionally, the monitoring client 902, other monitoring client 4, and/or the remote communicator 11 may be used to send commands or requests to patient-care devices 14, 15, 16, 17, 35, 128, 904, 906, 908, 148 such as for example, a bolus amount, an infusion flow rate, a total fluid for delivery, a start time for drug delivery, a stop time for drug delivery or a flow-delivery-rate profile to the stackable infusion pump 904, the stackable syringe pump 906 and/or the other stackable patient-care device 908. In some embodiments, one or more of the monitoring clients 902, 4, 11 may be used to send commands or requests to the pill dispenser 128, such as, for example, a pill dispense command to dispense a pill, a pill-type, a pill dispensing schedule, and/or a max pill-dispensing criteria. The max pill-dispensing criteria may be a maximum amount of a medication that may be delivered within a predetermined interval of time; for example, certain medications are taken as needed (i.e., pro re nata), however, the medication may not be safe if taken in excess and the max pill-dispensing criteria may prevent the medication from being taken at unsafe levels by the patient, e.g., a predetermined amount during a predetermined interval of time.

Optionally, the patient-care devices 14, 15, 16, 17, 35, 128, 904, 906, 908, 148 may also communicate data back to the monitoring client 902, the other monitoring client 4 and/or the remote communicator 11 for: determining if an alarm or alert should be issued or sent; determining if the treatment or condition is safe for the patient; determining if the system 900 is operating properly or within predetermined bounds; and/or for displaying the data on a display of the monitoring client 902, the other monitoring client 4 and/or the remote communicator 11. For example, optionally, the stackable infusion pump 904, the stackable syringe pump 906, and/or the other stackable patient-care device 908 may communicate (where applicable): upstream pressure; changes in upstream pressure; pressure downstream to the patient 2; changes in pressure downstream to the patient 2; the presence or absence of air within an infusion line; an actual bolus amount delivered; an actual infusion flow rate; an actual total fluid delivered; an actual start time for drug delivery; an actual stop time for drug delivery; or an actual flow-delivery-rate profile to one or more of the stackable monitoring client 902, the other monitoring client 4 and/or the remote communicator 11. In another embodiment, the pill dispenser 128 may optionally communicate data back to the stackable monitoring client 902, the other monitoring client 4, and/or the remote communicator 11, such as for example, an actual pill dispensed, an actual pill-type dispensed, an actual pill dispensing schedule as dispensed, or whether or not a max pill-dispensing criteria was exceeded.

The data received from the patient-care devices 14, 15, 16, 17, 35, 128, 904, 906, 908, 148 may be analyzed for any predefined conditions to issue an alarm and/or an alert. For example, one or more of the monitoring clients 902, 4, 11 may use an increase in pressure downstream of the stackable infusion pump 904 and/or the stackable syringe pump 906 to be an indication of one of: excessive clotting, infiltration, occlusion or kinking of the tubing to the patient; or occlusion by other material within the IV bag 170. In response to the sudden increase in downstream pressure, one or more of the monitoring clients 902, 4, 11 may visually or audibly alarm or alert a user. Additionally or alternatively, a sudden decrease in pressure downstream to the patient 2 may be an indication that the tubing has become detached from the needle and/or the needle is now out of the patient; and, in response, one or more of the monitoring clients 902, 4, 11 may visually or audibly alarm or alert a user. One or more of the monitoring clients 902, 4, 11 may, optionally, send a command to one or more of the stackable infusion pump 902 and/or the stackable syringe pump 906 to stop delivery of fluid in response to the sudden increase and/or decrease of pressure downstream to the patient 2.

The stackable monitoring client 902, the stackable device 908, the stackable infusion pump 904, and the stackable syringe pump 906 may be daisy-chained together via connectors coupled to the top and bottom of each device. For example, the stackable syringe pump 906 may instead be stacked on top of the monitoring client 902 such that a bottom connector of the stackable syringe pump 906 electrically coupled to connectors on top of the monitoring client 902.

The daisy chain can be created, for example, through electrical conductors within each of stackable monitoring client 902, the stackable patient-care device 908, the stackable infusion pump 904, and the stackable syringe pump 906 such that a continuous electrical contact is maintained between each of these devices.

Additionally or alternatively, the stackable devices 902, 908, 904, 906 may optionally maintain wireless communications with each other. For example, the stackable monitoring client 902 may detect that daisy-chain conductors are electrically unresponsive because of an internal short within a stackable device of the stackable devices 902, 908, 904, 906, and the stackable monitoring client 902 can interrogate each of the stackable devices 908, 904, 906 to determine which device is faulted; after a determination is made, the stackable monitoring client 902 can wirelessly communicate with an isolated disconnect circuit within the faulted device of the stackable devices 902, 908, 904, 906 to electrically disengage the faulted device from the daisy-chained conductors. Additionally or alternatively, one or more of the stackable devices 902, 908, 904, 906 can alarm, send an alert, and/or display a message that one of the stackable devices 902, 908, 904, 906 is faulted and/or that one of the stackable devices 902, 908, 904, 906 is communicating wirelessly rather than via the daisy-chained, wired communications link.

Additionally or alternatively, each of stackable monitoring client 902, the stackable device 908, the stackable infusion pump 904, and the stackable syringe pump 906 may relay or retransmit information to a respective device below or above itself within the daisy chain. For example, the stackable infusion pump 904 may communicate all data received from the stackable syringe pump 906 by buffering the data within an internal memory and communicating the information when a signal is received from the stackable patient-care device 908 indicating the stackable patient-care device 908 is ready to receive additional data. In some embodiments, each item, component, device, patient-care device, dock, and computing device, numbered or unnumbered, as shown in FIG. 8 or described therewith is optional. For example, in some embodiments, the monitoring client 1 is optional, the monitoring server 3 is optional, the facility services 8 is optional, each of the services 19, 20, 21, 22, 23, 24 is optional, the cloud server 25 is optional, each of the other monitoring clients 4 is optional, the online drug databases 9 is optional, the drug adverse event network is optional, the patient's personal EHR 19' is optional, and/or the treatment outcomes database 10 is optional. Additionally or alternatively, in some embodiments, each of the patient-care devices 830, 810, 812 is optional. Likewise, each of the system monitor 131, the wrist band 118, the RFID 116, the barcode 114, the scanner 120, the display 808, and/or AC power, is optional in some embodiments of the present disclosure.

Additionally, in some embodiments, although some items, components, devices, patient-care devices, and computing devices, numbered or unnumbered, as shown in FIG. 9 or described therewith are shown as being the sole item, component, device, patient-care device, or computing device, multiple items, components, devices, patient-care devices, and computing devices, are contemplated; for example, although a single pill dispenser 128 is shown in FIG. 9, in some embodiments, two pill dispensers 128 may be used, multiple pill dispensers 128 may be used, or any arbitrary number of pill dispensers 128 may be used.

Additionally or alternatively, although particular patient-care devices 904, 906, 908 are shown, other combinations, subsets, multiple ones of a particular patient-care device, or combinations thereof may be used. For example, in some embodiments, only a stackable infusion pump 904 is used of the patient-care devices, and, in this specific example, the other patient-care devices 906, 908 may be disabled, may not be present or available for system use, may be turned off, or may not be part of system 900 of FIG. 9. Additionally or alternatively, in some specific embodiments, only the patient-care devices used are stacked; for example, in one specific embodiment, the infusion pump 904 is the only device stacked. Additionally or alternatively, unstacked patient-care devices, e.g., patient-care devices 904, 906, and/or 908, may continue to operate when it is operating as a stand-alone device. Additionally, alternatively, or optionally, in some specific embodiments, the patient-care devices 14, 15, 16, 17, 35, 904, 906, 908, 128, 148 are dockable, may operate undocked, and/or may not be dockable and can operate as a stand-alone patient-care device.

In FIG. 9, although the stack is shows as being capable of stacking several patient-care devices, in other embodiments, the stack can receive one patient-care device, a plurality of patient-care devices, or any arbitrary number of patient-care devices. Additionally, although the stack is shown as be capable of receiving one monitoring client 902, in other embodiments, the two stackable monitoring clients 902, more than two stackable monitoring clients 902, or any arbitrary number of stackable monitoring clients 902 are stacked together in system 900.

System 900 of FIG. 9 may use any known communications method to maintain communications therewithin. For example, in some embodiments, any schedule of communications may be used, broadcasting, anycast, multicast or unicast may be used, routing algorithms may be used, a distance-vector routing protocol may be used, a link-state routing protocol may be used, an optimized link state routing protocol may be used, a path-vector protocol may be used, static routing with predefined alternative communications paths may be used, and/or adaptive networking may be used. For example, in some embodiments of the present disclosure, weights may be assigned to each communications path and Dijkstra's Algorithm may be used to communicate between the monitoring client 902 and one or more patient-care devices (e.g., patient-care devices 904, 906, 908); the weights may be determined in any know way, including as a function of bandwidth, signal quality, bit-error rate, may be linear to the available data throughput or latency, and/or the like.

Referring to FIGS. 1, 3, 5, 7, 8, and 9, various updating technologies and/or techniques may be employed to update a hub, a dock, a device, an insulin pump, an infusion pump, and/or a patient-care device. For example, a patient-care device may be coupled to a computing device (which, in some embodiments, may be a personal computer or any device that may be used in a similar fashion as a personal computer, for example, but not limited to, a tablet) by way of bus translator, which converts, for example, and in some embodiments, RS232 formatted data to e.g., I2C formatted data. A processor within a hub, a dock, a device, an insulin pump, an infusion pump, and/or a patient-care device, may, in some embodiments, execute an update program to control and orchestrate the downloading a software into flash memory by a supervisor processor and/or a command processor, for example. In some embodiments, the computing device may orchestrate the downloading of software into the flash memory of the hub, a dock, a device, an insulin pump, an infusion pump, and/or a patient-care device. Software updates obtained by computing device may be flashed into flash memory (not shown) accessible by the supervisor processor and/or the command processor. The above-described software updates may be, in some embodiments, a command line program that may be automatically invoked by a script process.

In some embodiments, a hub, a dock, a device, an insulin pump, an infusion pump, and/or a patient-care device may be, or have the ability of, a web connected remote interface which may include, but is not limited to, capability to download applications, download software updates, upload information and/or send information to various machines, including, but not limited to, through a web based secure portal and/or through electronic mail and/or by way of a wireless communications protocol. Thus, in various embodiments, the remote interface application may run on any capable device and is not limited to a so-called proprietary device. Further, in some embodiments, the remote interface may be Bluetooth enabled, or otherwise enabled, to communicate, for example, using radio frequency ("RF") communication, with one or more devices which may include, but are not limited to, one or more of the following: hub, a dock, a device, an insulin pump, an infusion pump, a patient-care device, a Bluetooth or other communication device, a patient-care device, and/or any other device.

In some embodiments, a charging station may include a charging area for a hub, a dock, a device, an insulin pump, an infusion pump, and/or a patient-care device for the remote interface which may include a USB plug. In some embodiments, the charging station may include a USB port, and in some embodiments, may include a mini-USB port, allowing for the charging station to receive power, in some embodiments, for charging the hub, the dock, the device, the insulin pump, the infusion pump, the patient-care device, and/or the remote interface through a USB. Additionally and/or alternatively, the USB port may be configured for data transfer to/from a remote interface and/or the hub, the dock, the device, the insulin pump, the infusion pump, and/or the patient-care device by connection to a computer or other device and/or other computer-type apparatus. In embodiments including a USB port, whilst the remote interface is being charged, the system may call to a personal computer and/or web portal to check for updated software and if there is updated software available, may download software updates, e.g., via the USB connection. These updates may then be transferred to the hub, the dock, the device, the insulin pump, the infusion pump, and/or the patient-care device upon pairing.

Thus, the user may connect the remote interface of a hub, a dock, a device, an insulin pump, an infusion pump, and/or a patient-care device to a personal computer and/or, in some embodiments, upload data from the remote interface to a web portal or other. In some embodiments, this may be accomplished during "recharging" of the remote interface which, in some embodiments, may be done using a USB connection to the personal computer, which, in additional to charging/recharging the remote interface may synchronize and/or upload/download data from the personal computer, 1908 and/or web portal. At this time, the system may determine software updates for one or more of the devices and or for the remote interface are available. The user may select "download updates" and these may be downloaded to the remote interface of the a hub, a dock, a device, an insulin pump, an infusion pump, and/or a patient-care device, again, at the time of charging and/or at any time the remote interface is either connected, directly or indirectly, to the personal computer and/or to a web portal designed specifically for the system. As discussed above, the remote interface is capable of communication with the various devices. Thus, software updates may be communicated to any one or more device by the remote interface. This has many advantages, including, but not limited to, only having to connect the remote interface to the personal computer/web portal to both upload data/information from all of the devices and/or download updates and/or applications from the personal computer and/or from the internet/web portal to any of the devices. This may be desirable for many reasons, including but not limited to, the ability to efficiently and easily update all devices from one connection and/or the ability to view all of the data from all the devices on one location and/or the ability to download information and/or settings from the personal computer/web portal to any of the devices through the remote interface.

Thus, in some embodiments, as the personal computer/web portal contains all the information from all the devices, including, but not limited to, the remote interface, at any time, a new "remote interface" may be introduced to the system. This may be accomplished by connecting the new remote interface to the personal computer/web portal and downloading all the information regarding the system to the remote interface. In some embodiments, this may first require that the old remote interface be removed from "approved devices", however, in other embodiments; the system may "allow" additional remote interfaces by permission from the user. Thus, the system includes the ability to download all the information and applications to any internet connected and/or remote interface capable of communicating to the devices and/or capable of connecting the personal computer and/or web portal.

This also allows the remote interface to download any application from the internet to any device in the system. Thus, in various embodiments of the system, a user can turn any apparatus (including some parameters such as ability to wirelessly communicate and connect to the personal computer and/or web portal) into a device that could control the various device, for example, the infusion pump and/or receive data from and/or control a CGM sensor/transmitter, and/or other analyte sensors, and/or other devices, such as a hub, a dock, a device, an insulin pump, an infusion pump, and/or a patient-care device. In some embodiments, the remote interface and/or the one or more applications on the remote interface may be password or other protected and is paired with the one or more devices, for example, paired with an infusion pump and/or CGM sensor and or one or more other devices.

In some embodiments, the information on the remote interface may be uploaded and/or synchronized with another device and/or a computer and/or machine, including, but not limited to, uploading the data to an internet site that may be password protected (web portal). Thus, a user may access the information from any device and or may download the information to any device including any device specific applications and therefore the user information may be downloaded to any device including, but not limited to, history, preferred settings, etc., information.

Figure 10:
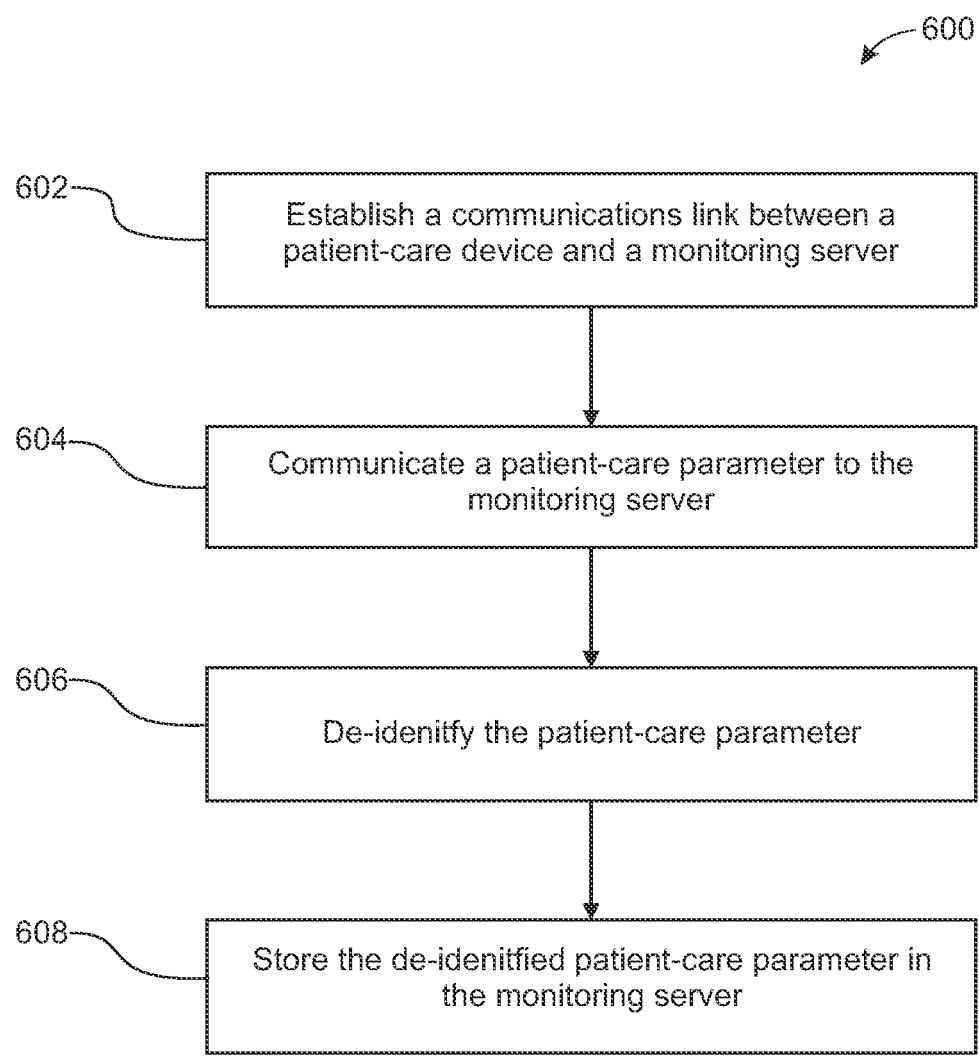
FIG. 10 is flow chart diagram of a method for communicating a patient-care parameter of a patient-care device to a monitoring server in accordance with an embodiment of the present disclosure.

FIG. 10 is flow chart diagram of a method 600 for communicating a patient-care parameter of a patient-care device to a monitoring server in accordance with an embodiment of the present disclosure. Method 600 includes acts 602-608. The patient-care device of method 600 may optionally be any patient-care device disclosed herein, e.g., patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein.

Act 602 establishes a communications link between a patient-care device and a monitoring server. Act 604 communicates the patient-care parameter to the monitoring server, e.g., over the local area network and/or the internet, through WiFi, through a monitoring client, one or more hubs, or a dock, etc. Act 606 de-identifies the patient-care parameter. Act 606 may be performed automatically and electronically, e.g., within the monitoring server 3 of FIGS. 1, 3, 5, 7, 8 and/or 9. For example, the name of the patient may be removed and replaced by a random serial number or other indicator that cannot be used to determine the identity of the patient in the monitoring server. Act 608 stores the de-identified, patient-care parameter in the monitoring server, e.g., within a database, such as a SQL database, a relational database, an associative database, a cloud server, and the like.

Figure 11:
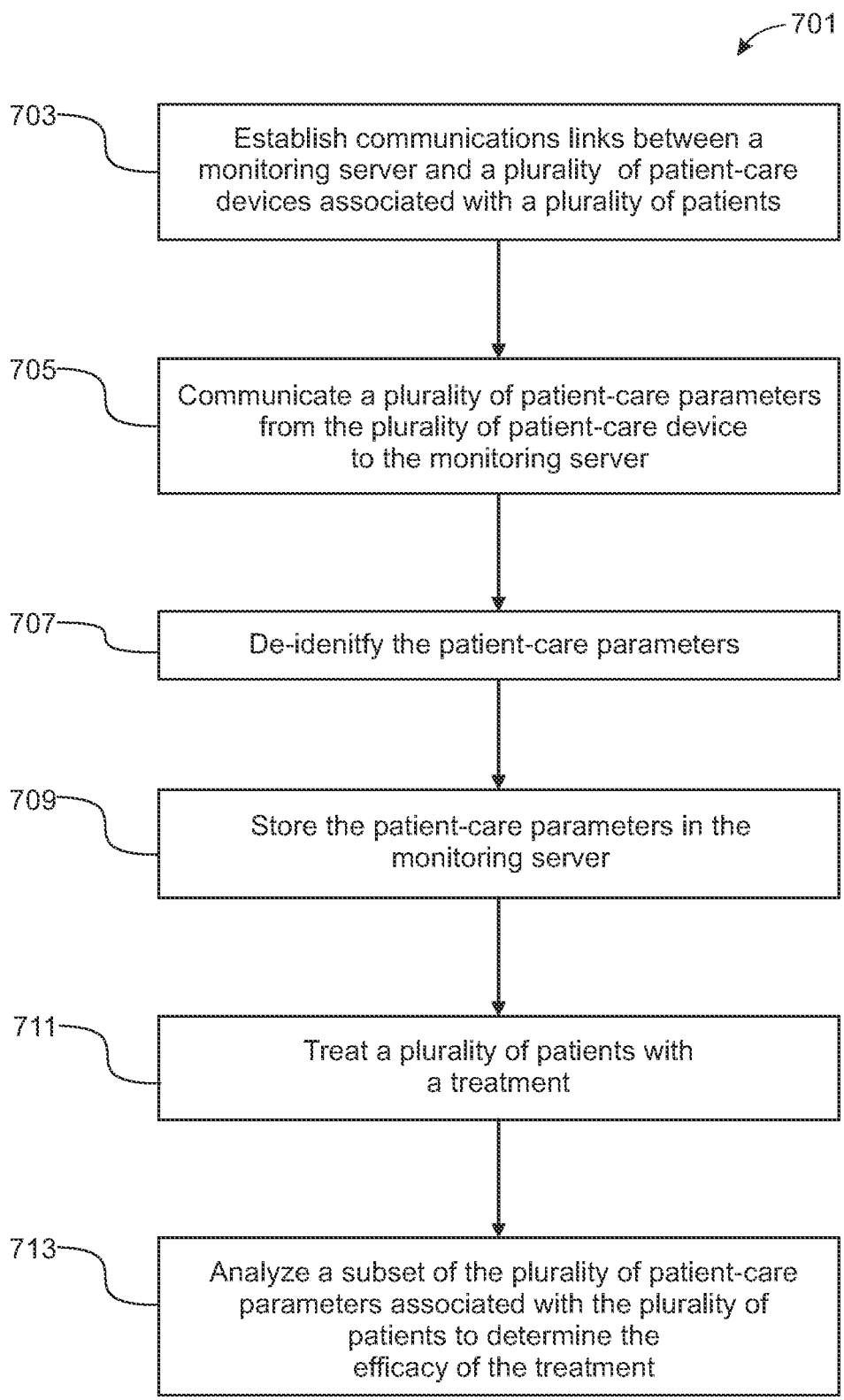
FIG. 11 is flow chart diagram of a method for aggregating patient-care parameters of multiple patients in a monitoring server in accordance with an embodiment of the present disclosure.

FIG. 11 is flow chart diagram of a method 701 for aggregating patient-care parameters from multiple patients as determined from patient-care devices in a monitoring server in accordance with an embodiment of the present disclosure. Method 701 includes acts 703-713. In some embodiments, all of the acts 703-713 are optional. The patient-care device may be any patient-care device disclosed herein, e.g., patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein.

Act 703 establishes communications links between a monitoring server, e.g., monitoring server 3 of FIG. 1, 3, 5, 7, 8, or 9, and a plurality of patient-care devices associated with a plurality of patients. Optionally, multiple patient-care devices may be associated with a single patient, and/or multiple patient-care devices may be associated with a different and respective patient.

Act 705 communicates a plurality of patient-care parameters from the plurality of patient-care devices to the monitoring server. Act 707 de-identifies the patient-care parameters, and act 709 stores the patient-care parameters in the monitoring server, e.g., within a database, such as an SQL database, a relational database, an associative database, and the like. Act 707 may be performed automatically and/or electronically. Act 711 treats a subset of patients of the plurality of patients with a treatment. For example, patients with high blood pressure may be treated with a medication designed to lower blood pressure. Act 713 analyzes a subset of the plurality of patients-care parameters associated with the plurality of patients to determine the efficacy of the treatment. For example, all patients that received the blood pressure medication of act 711 can have their blood pressure compared to a blood pressure reading after a predetermined amount of time, e.g., 6 months, to determine if the treatment was effective for one or more patients.

Figure 12:
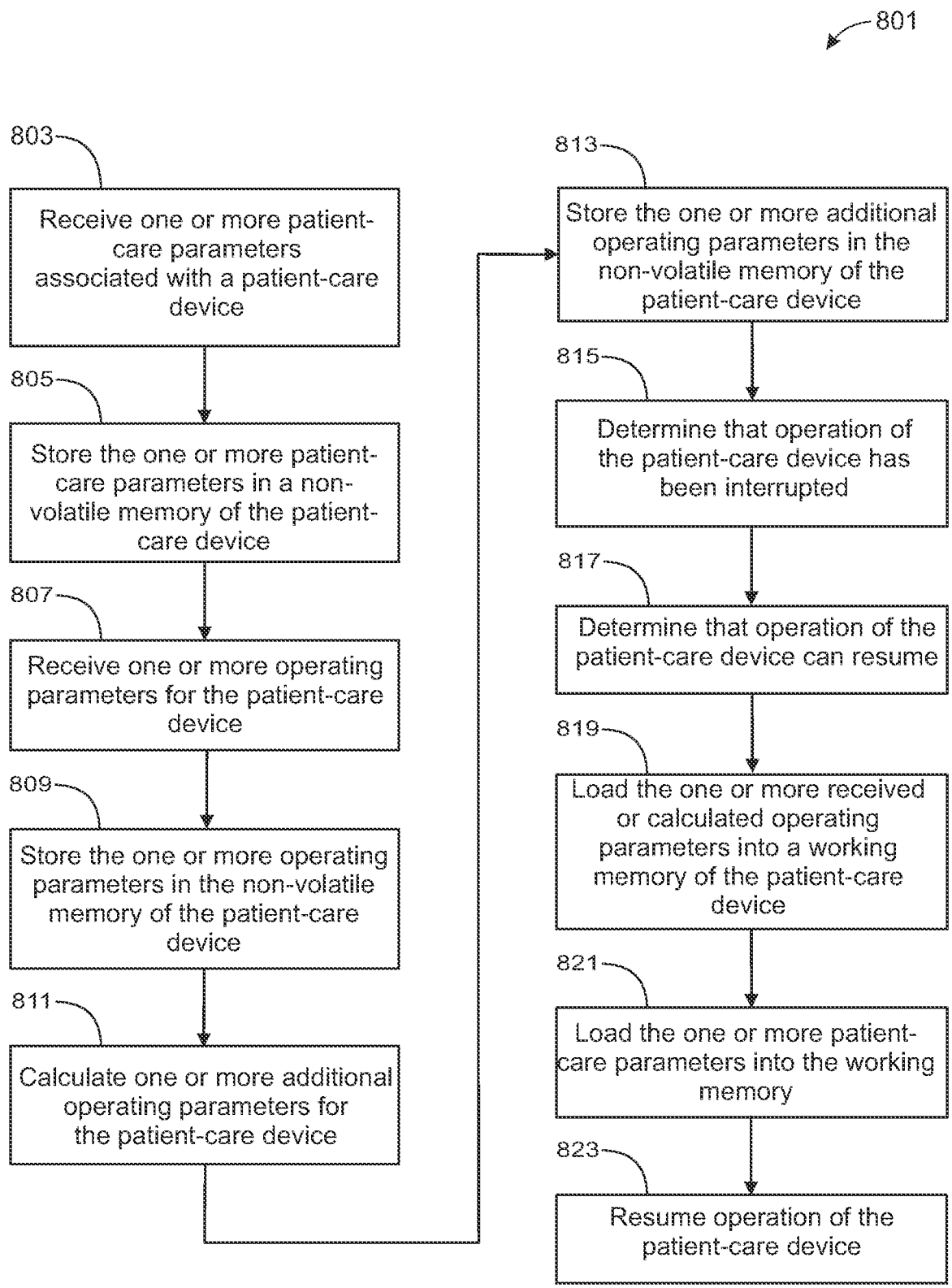
FIG. 12 is a flow chart diagram of a method of recovery for a patient-care device when the operation of the patient-care device is interrupted in accordance with an embodiment of the present disclosure.

FIG. 12 is a flow chart diagram of a method 801 of recovery for a patient-care device when the patient-care device's operation is interrupted in accordance with an embodiment of the present disclosure. For example, a patient-care device may be unplugged from a dock, the power may be interrupted, a hardware or software fault may temporarily disable one or more processors or other circuitry within the patient-care device, and the like. Additionally or alternatively, the one or more processors on a patient-care device may implement the method 801 so that the patient-care device is hot swappable.

Method 801 includes acts 803-823. Each of the acts 803-823, in some embodiments, is optional. Act 803 receives one or more patient-care parameters associated with a patient-care device. The patient-care device of method 801 may be any patient-care device disclosed herein, for example, it may be one or more of patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, or patient-care devices 14, 15, 16, 17 904, 906, 908 of FIG. 9.

Act 805 stores the one or more patient-care parameters in a non-volatile memory of the patient-care device. The patient-care parameters may be any values associated with patient care including patient-treatment parameters or patient-condition parameters, for example, an infusion rate for an infusion pump is a patient-treatment parameter.

Act 807 receives one or more operating parameters for the patient-care device. An operating parameter may be anything related to the operation of the device. For example, an operating parameter may be a limit on the speed of a motor of an infusion pump, an infusion pump speed, a wattage limitation on wireless communications, a battery discharge rate or rate limit, an update frequency, and the like. Act 809 stores the one or more operating parameters in the non-volatile memory of the patient-care device.

Act 811 calculates one or more additional operating parameters for the patient-care device. The calculated operating parameters are any parameters calculated for operating the patient-care device, for example, a gain coefficient of a proportional-integral-derivative ("PID") control loop that has adaptive gain coefficients used in automatic gain control. Act 813 stores the one or more additional operating parameters in the non-volatile memory of the patient-care device.

Act 815 determines that operation of the patient-care device has been interrupted, for example, power has been lost to the patient-care device, a fault has occurred in the patient-care device, a brown-out CPU reset has occurred, and the like. Act 817 determines that operation of the patient-care device can resume.

Act 819 loads the one or more received or calculated operating parameters into a working memory of the patient-care device; and, act 821 loads the one or more patient-care parameters into the working memory of the patient-care device. Act 823 resumes operation of the patient-care device.

Figure 13:
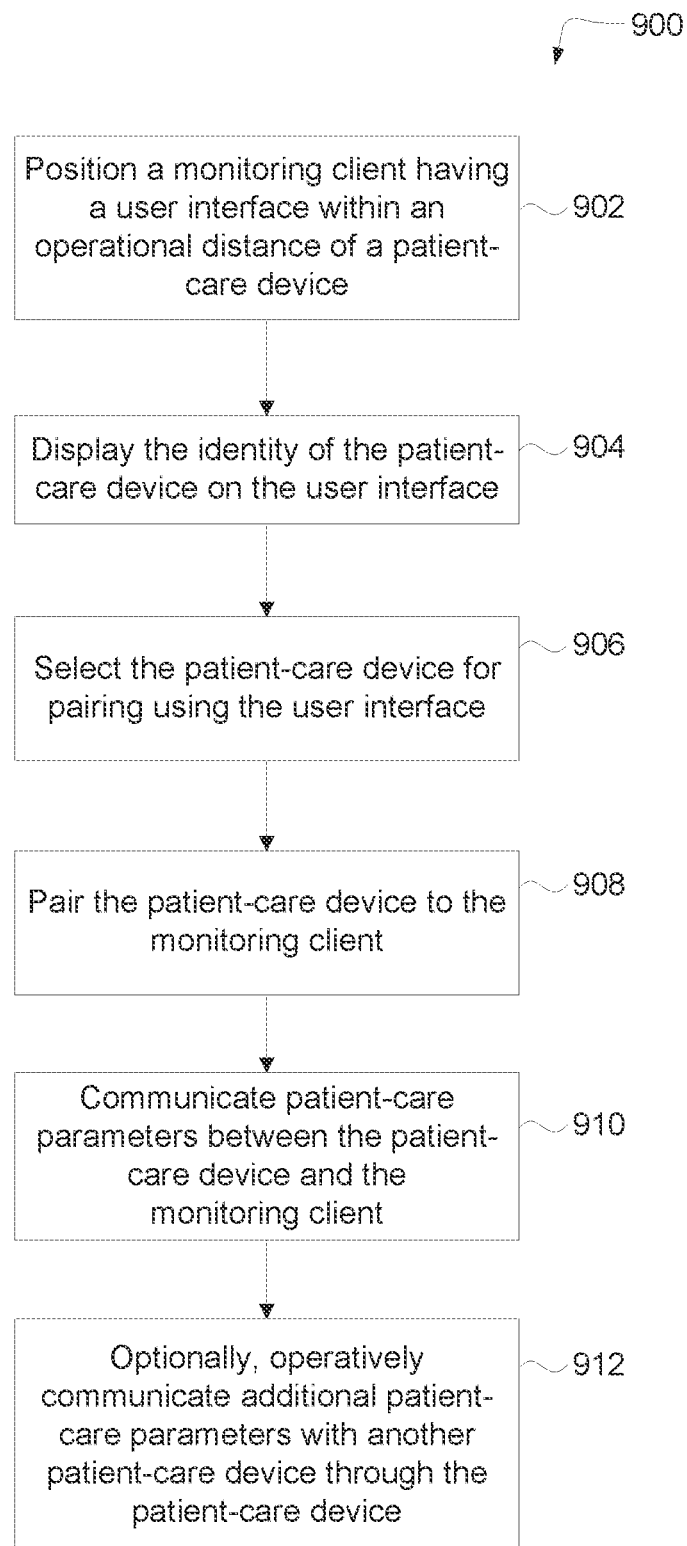
FIG. 13 is a flow chart diagram of a method for pairing a monitoring client with a patient-care device in accordance with an embodiment of the present disclosure.

Turning now to FIG. 13, a flow chart diagram of a method 900 is shown for pairing a monitoring client having a user interface with a patient-care device in accordance with an embodiment of the present disclosure. Method 900 includes acts 902-912. The monitoring client of method 900 may be a monitoring client 1, or remote communicator 11 of FIG. 1, 3, 5, 7, or 8, monitoring client 902 of FIG. 9, a remote communicator 11 of FIG. 1, 3, 5, 7, 8, or 9, a cell phone, a handled computer, a tablet computer, a laptop computer, a personal computer, a personal digital assistant, and the like. Although Method 900 described pairing between a monitoring client and a patient-care device, in some embodiments, the method 900 may be used to pair a hub (e.g., hub 802 of FIG. 8) with a patient-care device (e.g., patient-care device 830, 810, 812, and 814), to pair a first patient-care device (e.g., patient-care device 830 of FIG. 8) with a second patient-care device (e.g., patient-care device 814 of FIG. 8) such that the user interface of the first patient-care device can be used to control the second patient-care device, and/or to a pair the system monitor (e.g., system monitoring 131 of FIG. 1, 3, 5, 7, 8 or 9) with a patient-care device (e.g., patient-care devices 7, 170, 126, 128, 148, 14, 15, 16, 17 or 170 as shown in FIGS. 1, 3, 5 and 7, or the patient-care devices 830, 810, 812, 814, 14, 15, 16, 17 or 148 of FIG. 8, and/or the patient-care devices 904, 906, 908, 14, 15, 16, 17 or 148 of FIG. 9).

Act 902 positions a monitoring client having a user interface (e.g., a display, touchscreen, a display, buttons, accelerometer for user input, and the like) within an operational distance of a patient-care device. Act 904 displays the identity of the patient-care device on the user interface. The patient-care device may be identified by, for instance, a serial number, a device type, or a visual display on the user input of the patient-care device using standard or custom discovery protocols. Act 906 selects the patient-care device for pairing using the user interface. For example, a user in act 906 may touch a touchscreen of the monitoring client to indicate selection of the patient-care device.

Act 908 pairs the patient-care device to the monitoring client. For example, the paring of the patient-care device to the monitoring client may utilize Bluetooth, Bluetooth Low Energy (I.E.E.E. 802.15.1), WiFi, infrared communications, near field communication (NFC ISO 13157), IR communication, or optically. A custom pairing protocol may be used as well, as will be apparent in light of this disclosure, which may or may not employ the use of handshaking sequence. Act 910 communicates patient-care parameters between the patient-care device and the monitoring client, e.g., so that the patient-care device may be controlled or monitored by the monitoring client.

Act 912, optionally, operatively communicates additional patient-care parameters with another patient-care device through the patient-care device. In act 912, if the patient-care device is operatively coupled to or is in operative communication with another patient-care device, the patient-care device can act as a relay or router so that the monitoring client can communicate with the another patient-care device. Additionally or alternatively, the patient-care device may use information from another patient-care device for its operation, for example, an infusion pump may use a flow rate as determined by a flow rate meter or temperature from a temperature probe, and/or the infusion pump may relay information from the flow rate meter to a monitoring client. Additionally, the monitoring client can optionally communicate with multiple patient-care devices coupled to the paired patient-care device, either in parallel or in serial. Additionally or alternatively, in some embodiments of the present disclosure, in method 900 the monitoring client communicates with the patient-care device using an intravenous tube. The communications may occur via an electrical conductor embedded into or attached to the intravenous tube, via electrical communication using the fluid within the intravenous tube as a conductive medium, using sounds waves traveling through the intravenous tube, or optically by using the fluid within the tube as an optical waveguide. The communication via the intravenous tube may be used to set-up pairing (e.g., between a monitoring client, a hub, a dock, a patient care device and/or a system monitor with one or more of a monitoring client, a hub, a dock, a patient care device and/or a system monitor) using another communications link, e.g., Bluetooth, Bluetooth Low Energy, WiFi, etc.

In yet additional embodiments of the present disclosure, the pairing from a first device (e.g., a monitoring client, hub, patient-care device, or system monitor) with a second device (e.g., a monitoring client, hub, patient-care device, or system monitor) may be configured and/or initialized using a first communications link such that the devices are paired using a second communications link; for example, near-field communications or IR communications may set up pairing between the devices using Bluetooth, Bluetooth Low Energy, or WiFi, for example. The pairing setup (e.g., via near-field communications or IR communications) may prompt a request on a monitoring client, hub, patient-care device, and/or system monitoring requesting user confirmation of the device pairing, e.g., pairing via Bluetooth, for example. In some embodiments, when a patient-care device is paired to a hub, monitoring client, and/or dock, the ID and software version number is sent to the hub, monitoring client, and/or dock, which checks with a server, e.g., the monitoring server 3, middleware, the cloud server, or other server to determine if the software on the patient-care device is up-to-date; if the software is not up-to-date, the hub, monitoring client, dock, or the patient-care devices itself (e.g., directly) downloads updated software to program the patient-care device. The patient-care device may notify the user if the software is up to date and/or may give the user the option on the touch screen to optionally update the patient-care device if the software is not up to date. The communications link that sets up the pairing (e.g., NFC) and/or the communications link that uses the pairing (e.g., Bluetooth or Bluetooth Low Energy) may communicate the updated software, the ID, the software version number, provide the notification, etc. One pairing that may be used, e.g., with a pump patient-care device or insulin pump, may be found in: (1) the patent application entitled "INFUSION PUMP METHODS AND SYSTEMS" to Mandro et al., filed Mar. 25, 2010, and having the Ser. No. 12/731,843, (2) the patent application entitled "METHODS AND SYSTEMS FOR CONTROLLING AN INFUSION PUMP" to Bryant et al., filed Apr. 4, 2009, and having the Ser. No. 12/416,662, and/or (3) the patent application entitled G75, and having the Ser. No. 12/347,985, the entire contents of all three of which are hereby incorporated by reference in their entirety.

Figure 14:
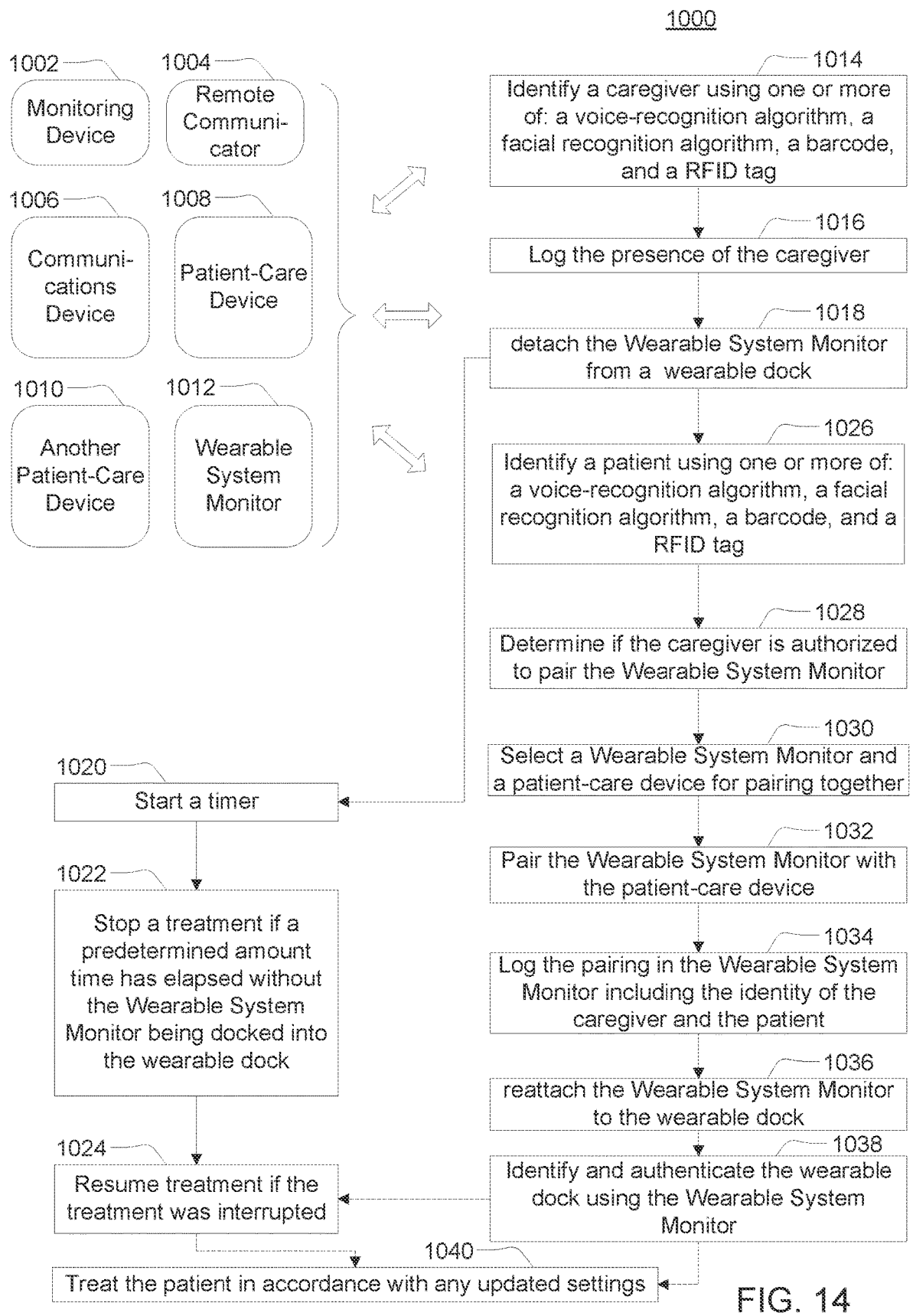
FIG. 14 is a flow chart diagram of a method for monitoring operation of a patient-care device using a wearable system monitor paired to the patient-care device in accordance with an embodiment of the present disclosure.

FIG. 14 is a flow chart diagram of a method 10000 for monitoring operation of a patient-care device using a wearable system monitor paired to the patient-care device in accordance with an embodiment of the present disclosure. Method 1000 includes acts 1014-1040 and can utilize various devices 1002, 1004, 1006, 1008, 1100, 1112 to facilitate the pairing of the wearable system monitor of method 1000 with a patient-care device. In some embodiments, each of the acts 1014-1040 is optional.

The wearable system monitor of method 10000 may be the wearable system monitor 131 of FIGS. 1, 3, 5, 7, 8, and 9. The pairing of the system monitor of method 1000 for monitoring one or more patient-care devices may be done using any one or more of the devices 1002-1012, or using any sufficient devices disclosed herein. For example, a user interface of the monitoring device 1002, a user interface of a remote communicator 1004, a user interface of a communications device 1006, a user interface of a patient-care device 1008, a user interface of another patient-care device 1010, or the user interface of the wearable system monitor 1012 may be used to pair the wearable system monitor of method 1000 with a patient-care device.

The patient-care device of method 1000 may be any patient-care device disclosed herein, such as patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein.

The system monitor of method 1000 may be used with system 100 of FIG. 1, system 300 of FIG. 3, system 500 of FIG. 5, system 700 of FIG. 7, system 800 of FIG. 8, system 900 of FIG. 9, may be used with a stand-alone system, and/or with any other sufficient system or group of devices disclosed herein.

Act 1014 identifies a caregiver (i.e., provider) using one or more of: a voice-recognition algorithm, a facial-recognition algorithm, a barcode, an RFID tag, near-field communications, simple login, secure signatures, and the like. For example, the identification of the caregiver in act 1040 may be done by a monitoring client, a monitoring-client docking station, a device docking station, by a communications module, other dock, or hub using an onboard camera and/or a microphone. Also, as a safety check, a monitoring client, a hub, dock, or patient-care device may request that a user enter in font as displayed to guard against font corruption errors. Additionally or alternatively, in some embodiments, if after one or more failed logins or verifications, the device may take a picture and store the picture; the picture may be transmitted for storage in a middleware server. Act 1016 logs the presence of the caregiver in one or more of the devices 1002-1012. The log entry may be stored on the any one of the devices 1002-1012, a patient-care device described herein, a monitoring client described herein, a wearable system monitor described herein, a remote communicator described herein, and/or a hub described herein. The log of act 1016 can be for caregiver compliance, diagnostic purposes, and the like. For example, if a caregiver is scheduled to appear and does not, the act of 1016 may log the non-appearance of the caregiver at the scheduled time.

The facial-recognition algorithm of act 1014 may relay on any facial features of the caregiver such as analyzing the relative size, shape, a position of the eyes, nose, jaw, cheekbones, or other facial features. The facial-recognition algorithm of act 1014 may use three-dimensional face recognition, skin texture analysis, or other facial-recognition algorithm. Additionally or alternatively, in some embodiments, the voice-recognition algorithm of act 1014 may use hidden Markov models, dynamic-time-warping based speech recognition, or other voice-recognition algorithm(s).

Act 1018 detaches the wearable system monitor from a wearable dock. For example, the system monitor 131 of FIG. 1 may be worn on the patient's wrist such that it is attached to the patient with a wristband similar to a watch wristband; a portion of the wearable system monitor may be detachable from a dock which includes the wristband and a snap-fit base member that the wearable system monitor snaps into (also referred to herein as a "wearable dock"). When the wearable system monitor is detached from its dock, act 1020 starts a timer. The timer and related acts are each optional in method 1000 of FIG. 14.

The timer of act 1020 keeps track of the amount of time the wearable system monitor is out of its dock. Act 1022 stops a treatment if a predetermined amount of time has elapsed after the wearable system monitor has been undocked from the wearable dock. For example, the wearable system monitor of method 1000 may signal an infusion pump to stop pumping. When the wearable system monitor is docked again, act 1024 resumes the treatment if the treatment was interrupted, e.g., from undocking the wearable system monitor from its wearable dock after the predetermined amount of time has elapsed.

As previously mentioned, act 1018 detaches the wearable system monitor from the wearable dock. Act 1026 identifies a patient using, for example, one or more of: a voice-recognition algorithm, a facial-recognition algorithm, a barcode, an RFID tag, near-filed communications, simple login, caregiver entry, and the like. Act 1026 may be similar to act 1014, may utilize the same software as utilized in act 1014, and/or may utilize one of the devices 1002-1020. In some embodiments, however, note that the identification procedure for a patient can include more than the identification of the caregiver by using, for example, biometrics or other identifying patient-specific information. Such patient identification standards may be used to ensure a particular treatment is being given to the correct patient and/or to provide compliance with given regulations. Act 1014 and/or 1026 may be performed using a passkey device on the patient and/or caregiver.

Act 1028 determines if the caregiver is authorized to pair the wearable system monitor, e.g., pair the wearable system monitor with a patient-care device. If the caregiver is not authorized, then the method 1000 prevents additional pairing (or editing of the pairing settings) of the wearable system monitor. If the caregiver is authorized to pair the wearable system monitor, act 1030 allows the caregiver to select one or more patient-care devices for pairing with the wearable system monitor. Caregiver authorization can be used, for instance, to ensure a particular treatment is being given to the correct patient and/or to provide compliance with given regulations.

The caregiver may be provided a list of patient-care devices that are available for pairing on one or more user interfaces of the devices 1002-1012. During act 1030, the caregiver selects a wearable system monitor (e.g., the patient-wearable system monitor of act 1018) and a patient-care device for pairing together. Act 1032 pairs the wearable system monitor with the patient-care device, and act 1034 logs the pairing of act 1032 in the wearable system monitor including the identity of the caregiver and the patient. In an additional specific embodiment, the pairing of the wearable system monitor with the patient-care device may be used with parallel or serial pairing of the patient-care device with another device (e.g., a monitoring client, a hub, another patient-care device etc.) As will be appreciated in light of this disclosure, any suitable pairing protocol (e.g., Bluetooth or IEEE 802.11) can be used. Additionally or alternatively, act 1034 can log the pairing into one or more of the devices 1002-1012.

Act 1036 reattaches the wearable system monitor to the wearable dock. Act 1038 identifies and authenticates the wearable docking using the wearable system monitor, e.g., to determine if the wearable system monitor and the wearable dock are authorized for docking together. For example, act 1038 may ensure that the wearable system monitor is docked to a wearable dock of the correct patient. If, for example, the wearable system monitor was docked to a wearable dock of the wrong patient, the wearable system monitor can recognize the error, preclude the associated treatment from proceeding by signaling the patient-care device associated with the patient-care device to stop operating (in some embodiments), and send an alert to a monitoring client, e.g., the monitoring client 1, 4, or 11 of FIGS. 1, 3, 5, 7, 8, monitoring client 9, 4, or 11 of FIG. 9, or other monitoring client disclosed herein. Act 1024 can resume treatment if the treatment was interrupted, or act 1040 can treat the patient in accordance with any updated settings 1040.

In some specific embodiments, when a caregiver is identified in act 1016 and/or the patient is identified in act 1026, the caregiver may update treatment settings, e.g., on a monitoring client, a hub, a remote communication or on the patient-care device.

Figure 15:
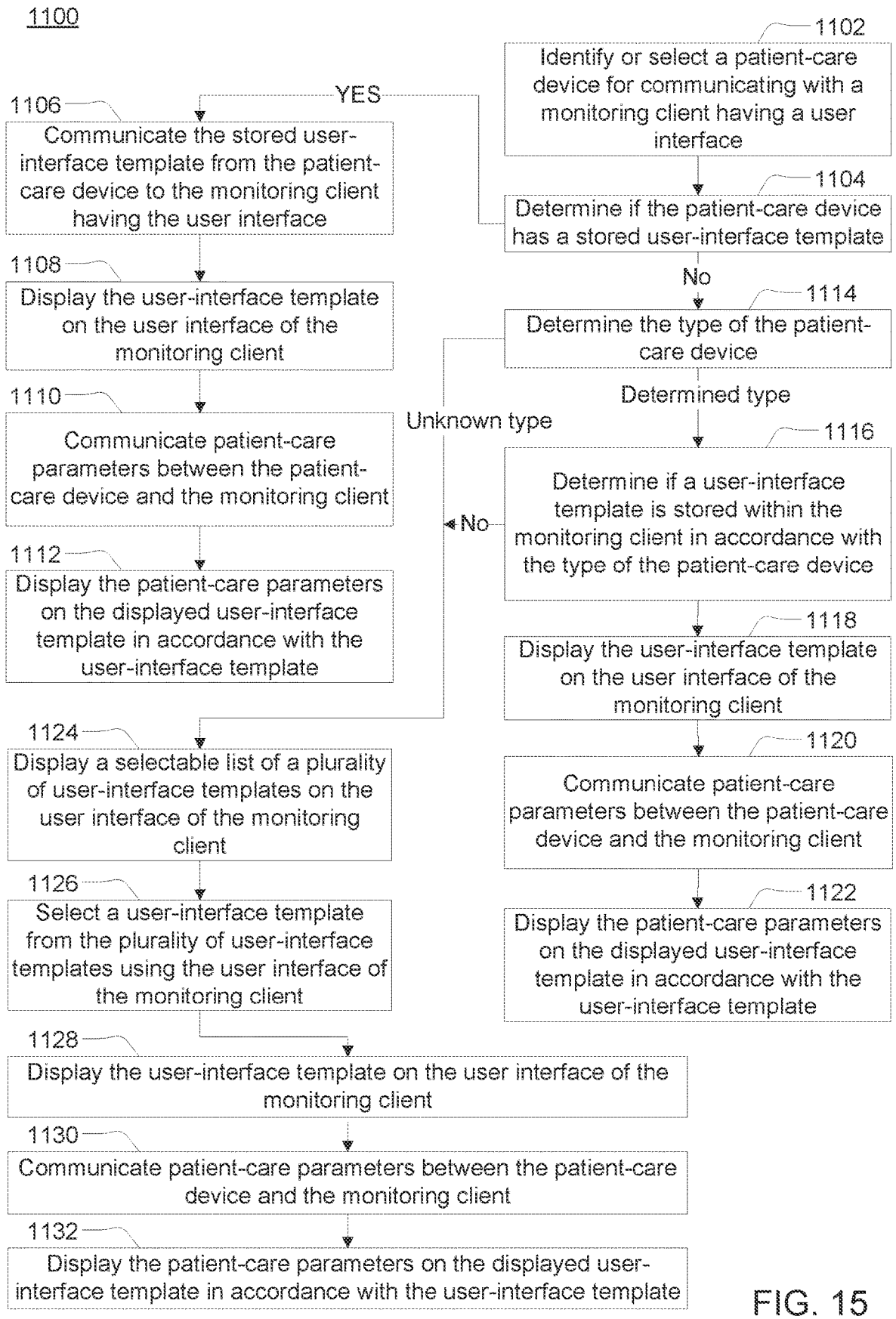
FIG. 15 is a flow chart diagram of a method for displaying a user interface using an user-interface template in accordance with an embodiment of the present disclosure.

FIG. 15 is a flow chart diagram of a method 1100 for displaying a user interface using a user-interface template in accordance with an embodiment of the present disclosure. Method 1100 includes act 1102-1132. In some embodiments, each of the acts 1102-1132 is optional.

The monitoring client of method 1100 may be one or more of monitoring clients 1, 4, or 11 of FIGS. 1, 3, 5, 7, 8, monitoring clients 9, 4, or 11 of FIG. 9, or other monitoring client disclosed herein. The patient-care device of method 1100 may be one or more of patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein.

Although method 1100 describes using a user-interface template with a monitoring client, the monitoring client may be substituted by a hub, a communications module, another patient-care device, or other sufficient device having a user interface. The user-interface template of the user interface of method 1100 provides a predefined display with specific fields for displaying patient-care parameters. For example, a user-interface template for an infusion pump may define certain fields for displaying on a GUI, such as the present fluid-flow rate. The user-interface template may also define an area on a display of the monitoring client for displaying the present fluid-flow rate as received from the infusion pump. The user-interface template may include layout information, such as: instructions how to display information; a description of various widgets; various widgets; graphs; labels for the graph axes; labels for the display; buttons; and/or labels to provide the user with control or visual information of one or more patient-care devices. The user-interface template may be a template describing a QT-based template, and/or may use HTML or CSS.

Act 1102 identifies or selects a patient-care device for communication with a monitoring client having a user interface. For example, in act 1102, the monitoring client may automatically identify a predetermined infusion pump that has been previously designated by a provider for treatment of a patient. Additionally or alternatively, in act 1102 a provider may be given a list of patient-care devices to select from for displaying on the user interface of the monitoring client information concerning operation of the selected patient-care device(s).

Act 1104 determines if the patient-care device has a stored user-interface template. For example, an infusion pump may include flash memory with a user-interface template stored therein. If the patient-care device has a stored user-interface template, act 1106 communicates the stored user-interface template from the patient-care device to the monitoring client having the user interface. Act 1108 displays the user-interface template on the user interface of the monitoring client. Act 1110 communicates patient-care parameters between the patient-care device and the monitoring client. Act 1112 displays the patient-care parameters on the displayed user-interface template in accordance with the user-interface template. For example, a user-interface template for an infusion pump may include a space for the present infusion rate; act 1112 displays, in this example, the present infusion rate (a patient-care parameter) on the display using the user-interface template.

If act 1104 determines that no patient-care device has a stored user-interface template, the method 1100 will determine if the monitoring client has a user-interface template for use for displaying the patient-care parameters of the patient-care device; additionally or alternatively, act 11004 may issue an alarm via the monitoring client and/or the patient-care device. Act 1114 determines the type of the patient-care device. If the type is determined, act 1116 determines if a user-interface template is stored within the monitoring client in accordance with the type of the patient-care device. If there is a user-interface template, act 1118 displays the user-interface template on the user interface of the monitoring client. Act 1120 communicates patient-care parameters between the patient-care device and the monitoring client. Act 1122 displays the patient-care parameters on the displayed user-interface template in accordance with the user-interface template. For example, patient-care parameters, such as an infusion rate, may be displayed in predefined areas of the user interface as designated by the user-interface template.

If the type is not determined in act 1114, or a user-interface template is not located within the monitoring client based upon the determined type, then act 1124 displays a selectable list of a plurality of user-interface templates on the user interface of the monitoring client; additionally or alternatively, act 1114 may issue an alarm or alert via the monitoring client and/or the patient-care device. Act 1126 allows a user to select a user-interface template from the plurality of user-interface templates using the user interface of the monitoring client. Act 1128 displays the user-interface template on the user interface of the monitoring client. Act 1130 communicates patient-care parameters between the patient-care device and the monitoring client. Act 1132 displays the patient-care parameters on the displayed user-interface template in accordance with the user-interface template.

In some embodiments of the present disclosure, the patient-care device of method 1100 may also store one or more fonts for display on the monitoring client, e.g., using the user-interface template described above. The fonts may be stored in any format, such as JPEGs, BMPs, image formats, pre-stored fonts, and the like and may be transmitted for use within the field to provide an indication of the operating parameter, (e.g., rather than transmitting a value, an image is transmitted showing a number or value which is then displayed on the monitoring client). In some embodiments, fonts stored within the monitoring client may be used such that a value of the operating parameter is sent to the monitoring client for display within the template using the fonts stored in the monitoring client.

Figure 16:
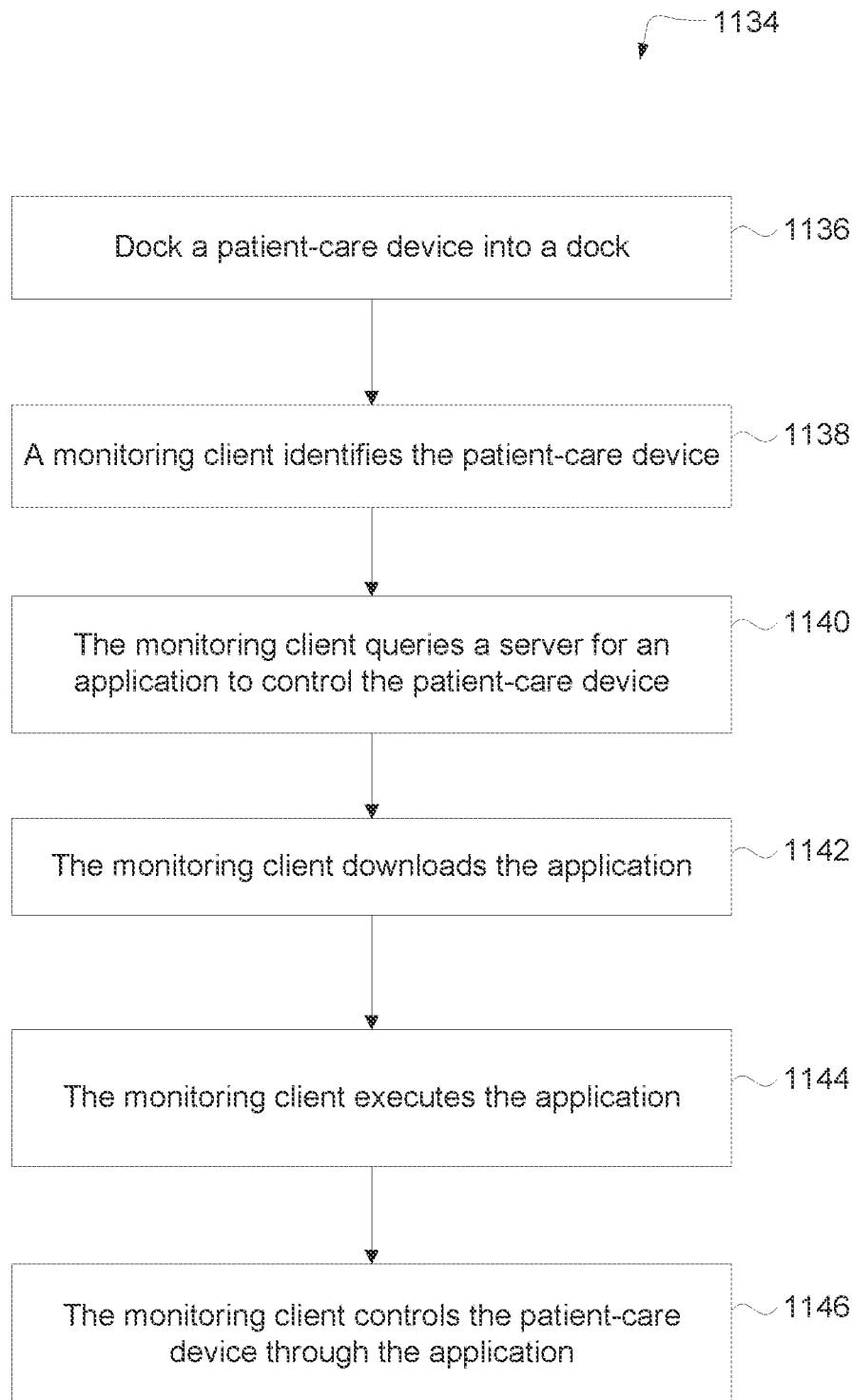
FIG. 16 is a flow chart diagram of a method for downloading an application for controlling a patient-care device in accordance with an embodiment of the present disclosure.

FIG. 16 is a flow chart diagram of a method 1134 for downloading an application for controlling a patient-care device in accordance with an embodiment of the present disclosure. In method 1134 of FIG. 16, although a monitoring device is described therewith as an exemplary device for controlling a patient-care device, the monitoring device may be substituted and/or supplemented by a dock, hub, communications module, remote communicator, communications device, and the like.

Method 1134 includes acts 1136-1146. In some embodiments, each of the acts 1136-1146 is optional. The monitoring client of method 1134 may optionally be one of the monitoring clients 1, 4, or 11 of FIGS. 1, 3, 5, 7, 8, the monitoring clients 9, 4, or 11 of FIG. 9, or other monitoring client disclosed herein. The patient-care device of method 1134 may optionally be one of patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein. The server of method 1134 may optionally be one of the monitoring servers 3 of FIG. 1, 3, 5, 7, 8, or 9.

Act 1136 docks a patient-care device into a dock. For example, an infusion device 7 of FIG. 1, 3, 5, or 7, infusion devices 830, 810, or 812 of FIG. 8, or an infusion device 904 of FIG. 9 may be docked into a respective dock. In act 1138, a monitoring client identifies the patient-care device. For example, the patient-care device may communicate, for instance, an ID number, a serial number, a description, a prescription, a treatment regime, a patient-treatment parameter, or the like, to the monitoring client, e.g., by way of a discovery protocol. The docked patient-care device may have stored therein treatment information (for example, a medication amount, infusion rate, total fluid amount, or other patient-treatment parameter), each of which may be associated with or correspond to a patient.

In act 1140, the monitoring client queries a server for an application to control the patient-care device (e.g, to set an infusion rate). The monitoring client downloads the application in act 1142. The communications between the monitoring client and the server may be encrypted. For example, the server may encrypt the application prior to sending to the monitoring client, and the monitoring client can decrypt the application using a sufficient encryption key. Additionally or alternatively, all communications may be encrypted. The monitoring client executes the application during act 1144. In act 1146, the monitoring client is communicatively and operatively coupled with the patient-care device through the application by executing the application on one or more processors. The monitoring client may place the application in a sandbox (as described below). In one such embodiment, the application includes an operative set of processor executable instruction configured for execution by one or more processors on the monitoring client. The application may include instructions to display a user interface on a display of the monitoring client, e.g., using the user interface template of method 1100 of FIG. 15. Additionally or alternatively, in some embodiments, the application may be used to control the patient-care device by optionally sending parameters or values to the patient-care device, e.g., a bolus amount, an infusion flow rate, a total fluid for delivery, a start time for drug delivery, a stop time for drug delivery, a flow-delivery-rate profile, a pill dispense command to dispense a pill, a pill-type, a pill dispensing schedule, and/or a max pill-dispensing criteria.

Figure 17:
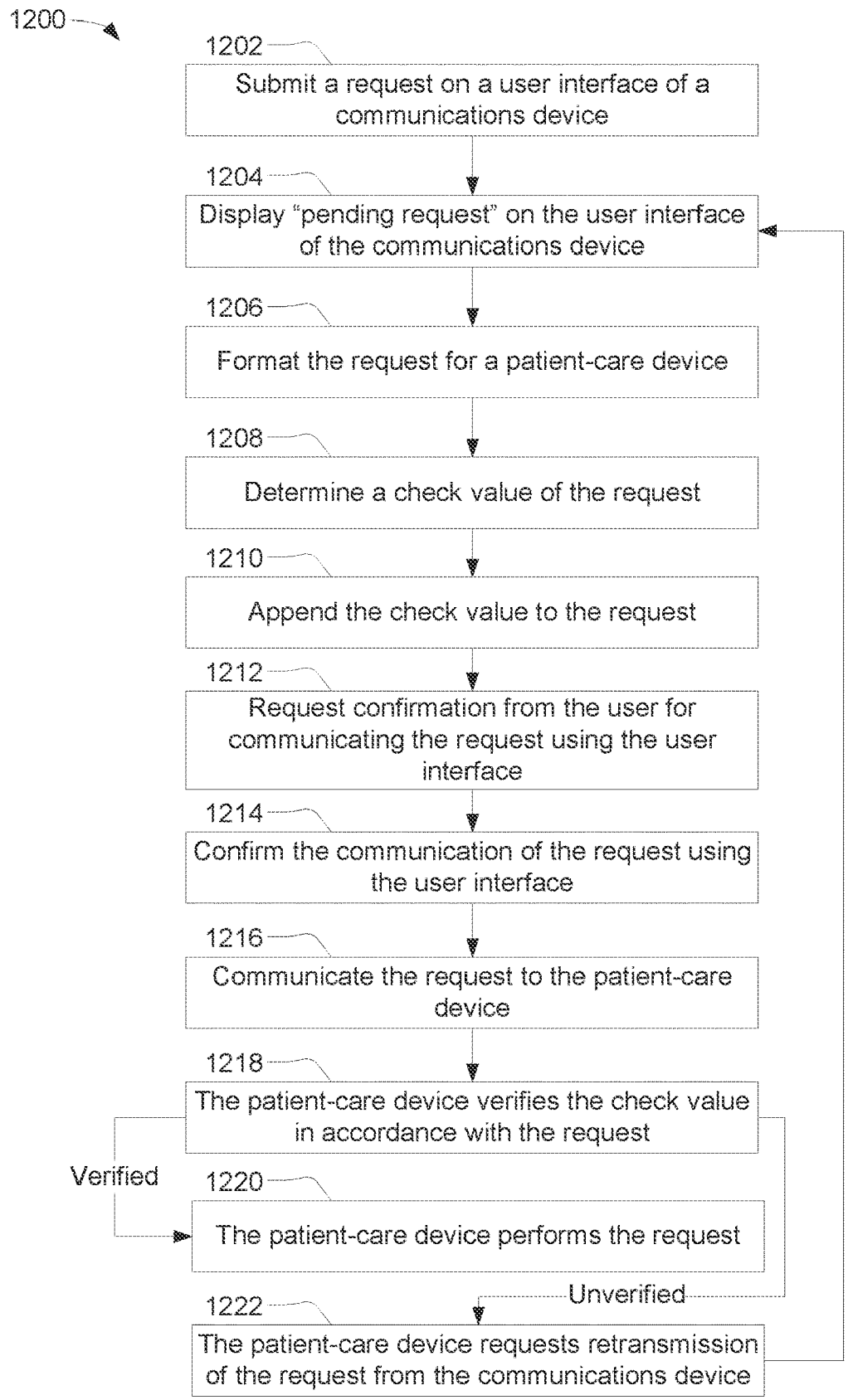
FIG. 17 is a flow chart diagram of a method of ensuring data integrity when communicating data for a patient-care device in accordance with an embodiment of the present disclosure.

FIG. 17 is a flow chart diagram of a method 1200 of ensuring data integrity when communicating data (e.g., requests) for a patient-care device in accordance with an embodiment of the present disclosure. Method 1200 includes acts 1202-1222. In some embodiments, each of the acts 1202-1222 is optional. The patient-care device of method 1200 may be any patient-care device disclosed herein, for example patient-care devices 7, 14, 15, 16, 17, 35, 126, 128, 130, 148, of FIG. 1, 3, 5, or 7, patient-care devices 14, 15, 16, 17, 830, 810, 812, 814 of FIG. 8, patient-care devices 14, 15, 16, 17 904, 906, 908 of FIG. 9, or other patient-care device disclosed herein.

The request may optionally originate from any authorized, authenticated, and/or identified monitoring client, such as, for example, a monitoring client 1 or 4 of FIG. 1, 3, 5, 7 or 8, a remote communicator 11 of FIG. 1, 3, 5, 7, 8 or 9, a cell phone, a handled computer, a tablet computer, a laptop computer, a personal computer, a personal digital assistant, and the like.

Act 1202 submits a request for a patient-care device using a user interface of a monitoring client. For example, using the touchscreen of the monitoring client 1 of FIG. 1, a user submits an infusion rate for the infusion pump 7. In some embodiments, the request may optionally be a parameter related to the patient-care device, e.g., a bolus amount, an infusion flow rate, a total fluid for delivery, a start time for drug delivery, a stop time for drug delivery, a flow-delivery-rate profile, a pill dispense command to dispense a pill, a pill-type, a pill dispensing schedule, and/or a max pill-dispensing criteria.

Act 1204 is optional, and act 1204 displays "pending request" on the user interface of the monitoring client. Act 1206 formats the request for a patient-care device. For example, act 1206 may prepare the request such that it conforms to the communications requirements of the patient-care device.

Act 1208 determines a check value of the request. For example, a cyclic-redundancy-check algorithm is used to determine a check value that corresponds to the request. The check value calculated by the cyclic-redundancy-check algorithm is dependent upon the request. A change in one bit of the request will also change the check value as calculated by the cyclic-redundancy-check algorithm. Likewise, changing several bits will also change the check value. Additionally or alternatively, in other embodiments, a parity bit (even or odd) or other data integrity checks may be used.

Act 1210 appends the check value to the request. Action 1212 is optional, and act 1212 requests confirmation from the user for communicating the request using the user interface. The request for confirmation may be a pop-up dialog box on a touchscreen that displays "confirm infusion rate of 90 milliliters/hour?" with a box for selecting "confirmed." The text and format shown in act 1212 may be of a different font, different font size, and/or different display position than other displayed information, e.g., as displayed during the entering of the request or otherwise, to provide an additional safeguard against bad display pixels, a corrupted font table, user misunderstanding, and the like. Act 1214 confirms the request for communication of the request using the user interface. The user can touch the "confirmed" box to confirm the request for communication of the request, according to some embodiments of the present disclosure.

Act 1216 communicates the request to the patient-care device. The communication may be made via wired, wireless, guided, or fiber optic communications, or the like. The patient-care device receives the request during act 1216. During transit of the request, it is possible that one or more bits in the request have been corrupted, e.g., a bit has changed its value, a bit has been lost, a bit has been added, and the like; this or other data corruption is undesirable.

Act 1218 of method 1200 facilitates the detection of corrupted data. During act 1218, the patient-care device verifies the check value in accordance with the request. In act 1218, the patient-care device may use the same cyclic-redundancy-check algorithm as in act 1208 on the request to calculate an additional check value. The check value in act 1216 as calculated by the patient-care device will be identical to the check value calculated in act 1208 only if the data in the request is identical. That is, the check value in act 1216 and the check value in act 1208 will be different only if the data of the request has become corrupted, has fewer or more bits, or otherwise is not identical to the digital data used to determine the check value of act 1208.

If the check value of the request was not verified, in act 1222 the patient-care device requests retransmission of the request from the monitoring client. Although FIG. 17 shows act 1222 as proceeding to act 1204 of method 1200, in other embodiments, method 1200 may proceed to any of acts 1202-2116. If retransmission of the request is not successful, method 1200 can communicate an error, an alarm, or an alert (not shown) to the monitoring client. Otherwise, if the check value is verified as indicating no data corruption, in act 1220 the patient-care device performs the request.

In alternative embodiments, the request in act 1218 is additionally sent back to the monitoring client after verification from the patient-care device and may include additional CRC checking during the transmission. The patient-care device during verification may perform, in this alternative embodiment, checks to determine if the request is within predetermined ranges (e.g., the infusion rate for the particular drug is safe, etc.). The monitoring client, in this alternative embodiment, can either compare the request as received from the patient-care device with the original request as stored in memory (the requests may be associated with each other), and/or the monitoring client can display the request to the user for confirmation. The request for confirmation may be a pop-up dialog box on a touchscreen that displays "confirm infusion rate of 90 milliliters/hour?" with a box for selecting "confirmed." The text and format shown in this alternative embodiment for the confirmation may be of a different font, different font size, and/or different display position than other displayed information, e.g., as displayed during the entering of the request or otherwise, to provide an additional safeguard against bad display pixels, a corrupted font table, user misunderstanding, and the like. In this alternative embodiment, the user can confirm the request for communication of the request using the user interface. The user can touch the "confirmed" box to confirm the request for communication of the request, according to some embodiments of the present disclosure.

Thereafter, in this alternative embodiment, the request is resent to the patient-care device for performing; additionally or alternatively, in this alternative embodiment, an action message is sent to the patient-care device, and the action message contains information linking it to the original request (e.g., "This is the "action" for the 90 milliliters/hour request that was just sent").

Figure 18:
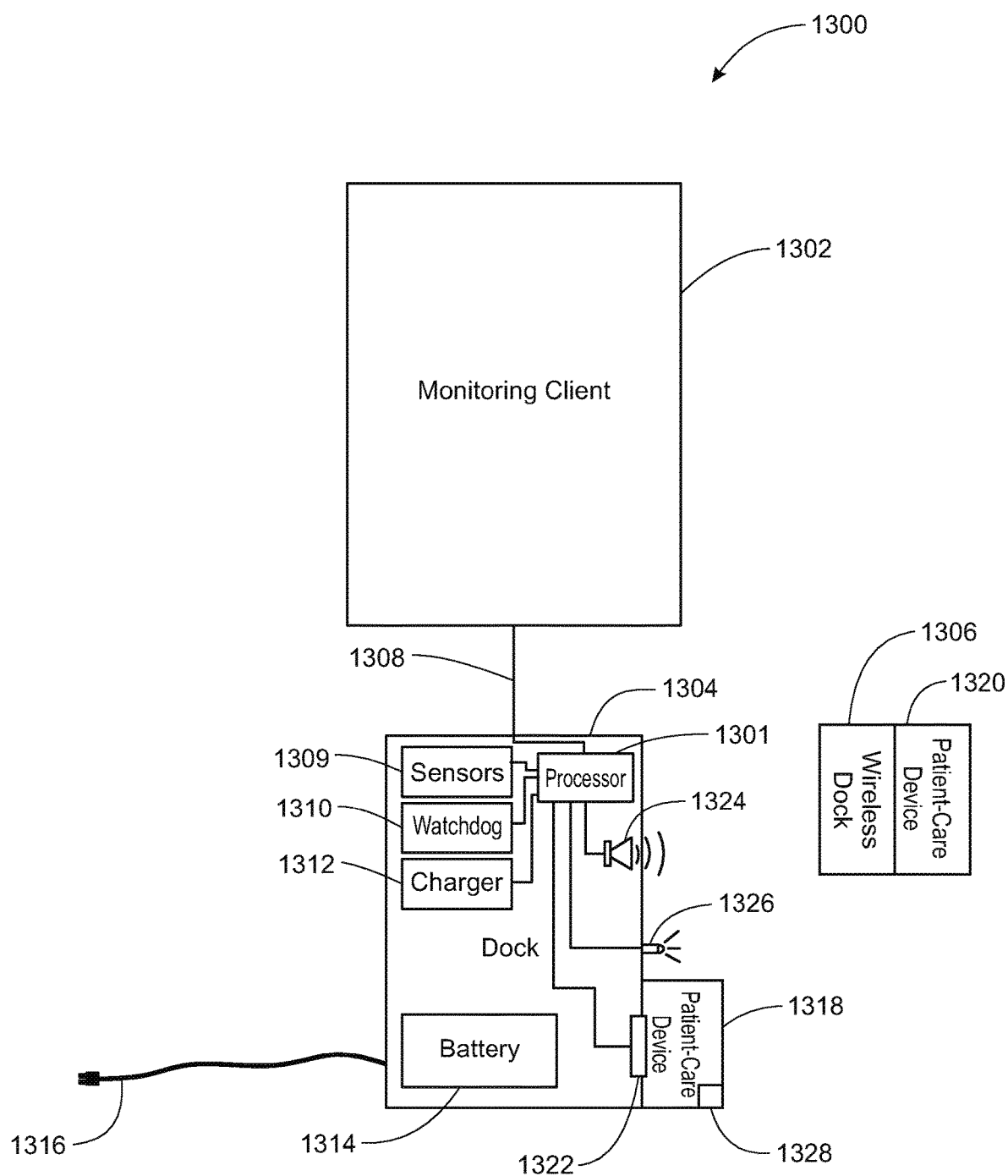
FIG. 18 is a block diagram of an electronic patient-care system in accordance with yet another embodiment of the present disclosure.

FIG. 18 is a block diagram of an electronic patient-care system 1300 in accordance with yet another embodiment of the present disclosure. System 1300 includes a monitoring client 1302, a dock 1304, and a wireless dock 1306. Optionally, in some embodiments, the dock 1304 may act as a hub as described herein.

The patient care device may be any patient-care device described herein, such as one of the patient-care devices 7, 14, 15, 16, 17, 35, 126, 128, 130, 148, of FIG. 1, 3, 5, or 7, the patient-care devices 14, 15, 16, 17, 830, 810, 812, 814 of FIG. 8, or the patient-care devices 14, 15, 16, 17 904, 906, 908 of FIG. 9. The monitoring client 1302 may be substituted for any monitoring client described herein, such as monitoring clients 1, 4, or 11 of FIGS. 1, 3, 5, 7, 8, monitoring clients 9, 4, or 11 of FIG. 9, a tablet, a smart phone, a PDA, or the like.

The dock 1304 may include a shaped receiving portion for receiving the monitoring client 1302 for connecting electrical contacts of the monitoring client 1302 to the docket 1304 through a cable 1308. The cable 1308 may be integrated together with the dock 1304 and/or the monitoring client 1302. The cable 1308 may provide, for instance, USB or other standard communications between the dock 1304 and the monitoring client 1302.

The dock 1304 optionally includes a processor 1301, sensors 1309, a watchdog 1310, a charger 1312, a battery 1314, and an alternating-current ("AC") power cord 1316. The processor 1301 controls the operation of the dock 1304. A patient-care device 1318 is dockable to the dock 1304. System 1300 also includes a wireless dock 1306 having a patient-care device 1320 docked thereto. The wireless dock 1306 may be identical or similar to the dock 1304, however, the wireless dock 1306 wirelessly communicates with the monitoring client 1302, in some embodiments.

The battery 1314 can power the dock 1304 and the patient-care device 1318 when the AC power cord 1316 is unplugged from an AC outlet (not shown). In some embodiments, the dock 1304 may be the sole source of power for the monitoring client 1302 or the patient-care device 1318. Additionally or alternatively, the monitoring client 1302 and/or the patient-care device 1318 may include an on-board battery or a separate AC power cord (not shown).

In some example embodiments, the dock 1304 may provide IEC-60601 compliant power to the patient-care device 1318. Additionally or alternatively, the dock 1304 can provide a variable DC voltage as requested by the patient-care device 1318. For example, the dock 1304 may include a programmable buck-boost power supply (not shown) that can provide a DC voltage from 1 Volt to 24 Volts as requested by the patient-care device 1318 for a specific connector pin of a connector 1322.

The battery 1314 may be charged by the charger 1312 when the power cord 1316 is plugged into an AC outlet (not shown). The battery 1314 provides uninterrupted power to the patient-care device 1318 when the AC power cord 1316 is unplugged from an AC outlet (not shown). For example, the patient-care device 1318 may be an infusion pump which continues to operate after the AC power cord 1316 is unplugged because the battery 1314 automatically supplies replacement power to the patient-care device 1318 when the AC power cord 1316 is unplugged.

The sensors 1308 may optionally include one or more of an ambient temperature sensor, an ambient pressure sensor, an ambient humidity sensor, and the like. The sensors 1308 may optionally include redundant sensors, such as two temperature sensors, and the dock 1304 may use the redundant sensors to determine if one or both has malfunctioned, e.g., by comparing the readings of the two sensors to each other. The dock 1304 may communicate with the sensors 1308 and/or other peripherals to ensure their proper operation, to perform data integrity checks, to provide the patient-care device 1318 with their measurements, e.g., the ambient temperature.

The watchdog 1310 can optionally ensures that the patient-care device 1318 is properly operating by performing interrogations mentioned above, monitoring the outputs of the patient-care device 1318 to determine if they are within predetermined ranges (e.g., physically possible or likely ranges), have feedback that is in accordance with applied input, and is otherwise operating properly. Additionally or alternatively, the system monitor 13010 may optionally monitor the operation of the monitoring client 1302 through the cable 1308. Although one watchdog 1310 is described herein, one or more watchdogs 1310 may be used, e.g., a plurality of watchdogs 1310. In some example embodiments, the patient-care device 1318 communicates with the watchdog 1310 at fixed intervals. The fixed intervals are optionally configurable using a user interface of the monitoring client 1302 or using a computer attached to the cable 1308. If the patient-care device 1318 fails to communicate with the watchdog 1310 during the fixed interval, the watchdog 1310 determines that an error has occurred within the patient-care device 1318 and issues an alert or alarm, e.g., an audible sound using a speaker 1324 or flashes an LED 1326 red. The action for response to not receiving a communication within the interval may be configurable and/or program, e.g., using a user interface of the monitoring client 1302 or using a computer attached to the cable 1308; for example, for non-critical patient-care devices, a failure to respond to the watchdog 1310 may cause the LED 1326 is flash RED, and an action to a critical patient-care device may additionally cause the dock 1304 and/or monitoring client 1302 to audibly and visually alarm and sent a notification to a nursing station and/or a remote communicator, e.g., remote communicator 11 of FIG. 1, 3, 5, 7, 8, or 9, a smartphone, a laptop computer, another patient-care device, and the like. Additionally or alternatively, the LED 1326 may optionally flash green if the patient-care device 1326 is operating properly or is presently treating a patient. Additionally or alternatively, a speaker within the monitoring client 1302 may issue an audible alert or alarm. If appropriate, the patient-care device can be disabled or swapped out until the error condition is resolved.

Additionally or alternatively, the watchdog 1310 may ensures that the monitoring client 1302 is properly operating by requiring it to communicate with the watchdog 1310 at a fixed, predetermined, or preprogrammed interval. If the monitoring client 1302 fails to communicate with the watchdog 1310 during the fixed interval, the watchdog 1310 may determine that an error has occurred within the monitoring client 1302 and issues an alert or alarm similar to the one described above with regards to the patient-care device 1318, e.g., an audible sound using a speaker 1324 or flashes an LED 1326 red. In some embodiments, a speaker within the monitoring client 1302 may issue an audible alert. In some embodiments, a speaker within the monitoring client 1302 may serve as a backup speaker to the dock 1304, and the speaker 1324 of the dock 1304 may serve as a backup speaker to the monitoring client 1302.

The charger 1312 can charge the battery 1314 using AC power supplied through the AC power cord 1316. Additionally or alternatively, the charger 1312 can charge a battery 1328 within the patient-care device 1318.

In some embodiments, the wireless dock 1306 may include the same hardware as the dock 1304 and may or may not include the AC power cord 1316. For example, the wireless dock 1306 may include a plurality of contacts for positioning the wireless dock in a recharging cradle that includes a plurality of contacts that engage the contacts of the wireless dock 1306 for charging a battery therein.

Figure 19:
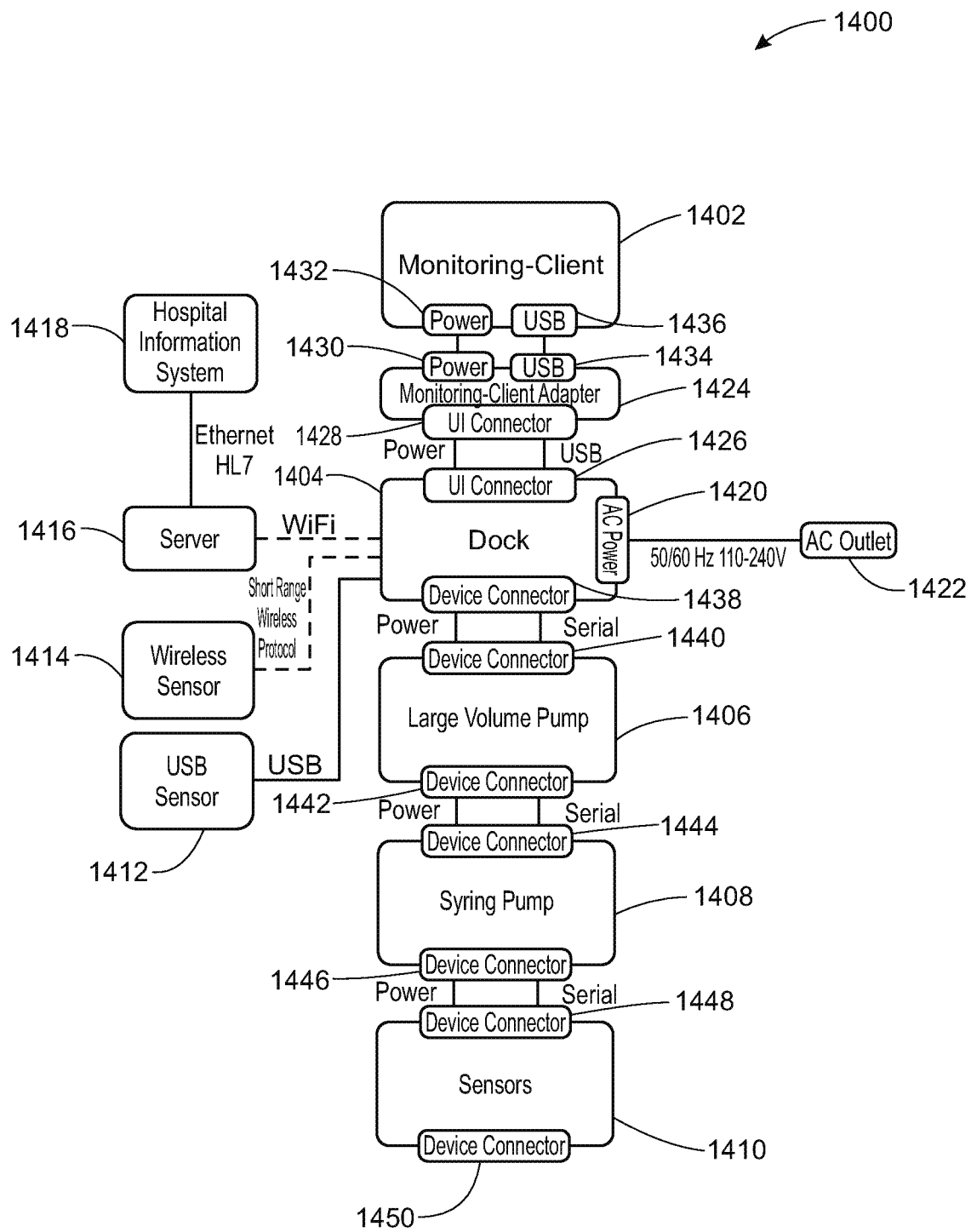
FIG. 19 is a block diagram of an electronic patient-care system in accordance with another embodiment of the present disclosure.

FIG. 19 is a block diagram of an electronic patient-care system 1400 in accordance with another embodiment of the present disclosure. System 1400 includes a monitoring client 1402, a dock 1404, a large volume pump 1406, a syringe pump 1408, and sensors 1410. System 1400 also include a USB sensor 1412 coupled to the dock 1404 through a USB cable, a wireless sensor 1414 in wireless communication with the dock 1404, a server 1416, and a hospital information server 1418. The monitoring client 1402 may be any monitoring client, such as one of the monitoring clients 1, 4, or 11 of FIGS. 1, 3, 5, 7, 8, the monitoring clients 9, 4, or 11 of FIG. 9, a tablet, a smartphone, a PDA, a laptop, and the like. The dock 1404 can communicate via the electrical conductor shown in FIG. 19 and/or via wireless to one or more of the large volume pump 1406, 1408, and/or the sensors 1410 to receive parameters and/or to control the devices.

The dock 1404 receives AC power 1420 from an AC outlet 1422. The dock 1404 is in operative communication with the monitoring client 1402 using a monitoring-client adapter 1424. The monitoring-client adapter 1424 is coupled to the dock 1404 through UI connectors 1426, 1428. The UI connectors 1426, 1428 provide power to the monitoring-client adapter 1424 and data through a USB link. The monitoring-client adapter 1424 is coupled to the monitoring client 1402 through several connectors 1430, 1432, 1434, 1436. Two of the connectors 1430, 1434 provide power from the monitoring-client adapter 1424 to the monitoring client 1402, while two other connectors 1434, 1436 provide a USB connection therebetween to facilitate digital communications between the dock 1404 and the monitoring client 1402. Note that other embodiments may employ connections other than the USB-type.

Connectors 1438-1450 allow the dock 1404 to operatively provide power to the large volume pump 1406, the syringe pump 1408, and sensors 1410. Additionally or alternatively, connectors 1438 and 1440 provide serial communications between the dock 1404 and the large volume pump 1406; connectors 1442 and 1444 provide serial communications between the large volume pump 1406 and the syringe pump 1408; and, connectors 1446 and 1448 provide serial communications between the syringe pump 1408 and the sensors 1410. Connector 1450 provides optional expansion for additional devices (not shown).

System 1400 shows a daisy-chained system for coupling together several devices together. Each device either digitally routes data destined for another device to a subsequent device, or each device includes electrical conductors such that both of its connectors include electrical connections to respective pins.

The dock 1404 can communicate with the wireless sensor 1414 using, for example, Bluetooth, Bluetooth low energy, Zigbee, Xbee, ANT, ANT Plus, and the like. The sensors 1412, 1414, and/or 1410 may be a patient-monitoring device, or one or more environment sensors, such as a temperature sensor, humidity sensor, a camera, a microphone, an ambient light sensor, a vibration sensor, and the like.

The server 1416 can communicate with the hospital information system 1418. The server 1416 provides a WiFi router such that the dock 1404 is in operative communication with the hospital information system 1418. Information may be transferred to and from the hospital information system 1418 through the server 1416, which can translate protocols of the dock 1404 to and from the hospital information system 1418 or Health Level 7 ("HL7"). The server 1416 (and/or the hospital information system 1418) may include a drug error reduction system ("DERS") system that checks to determine that any treatments being applied to a patient using the system 1400 is safe for the patient. The server 1416 may be the monitoring server 3, and the hospital information system 1418 may be the facility services 8 of FIGS. 1, 3, 5, 7, 8, and/or 9.

Figure 20:
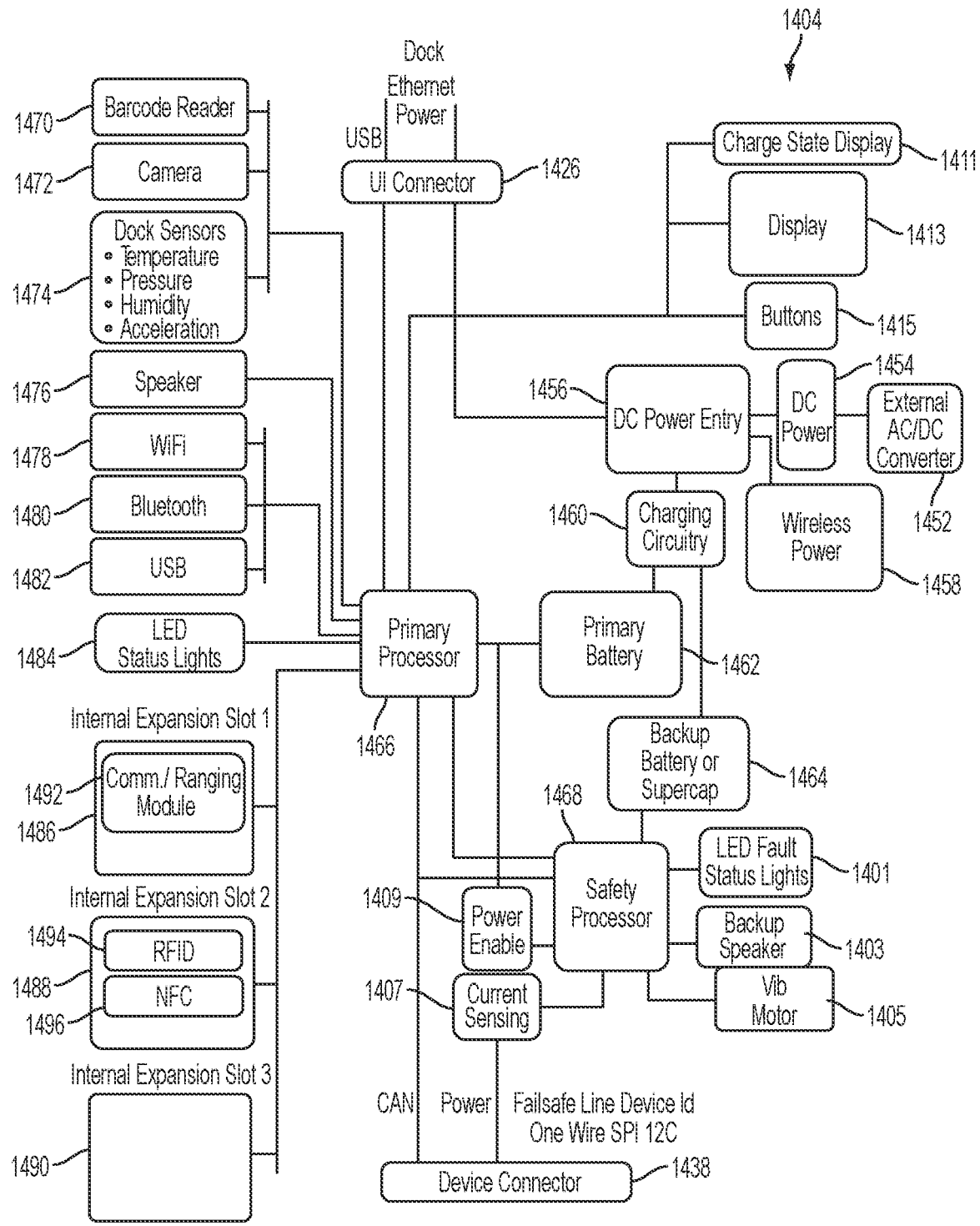
FIG. 20 is a block diagram of a dock of the electronic patient-care system of FIG. 19 in accordance with an embodiment of the present disclosure.

FIG. 20 is a block diagram of the dock 1404 of the electronic patient-care 1400 system of FIG. 19 in accordance with an embodiment of the present disclosure. In some embodiments, each of the components shown in FIG. 20 is optional.

Dock 1404 includes an AC/DC converter 1452 for receiving the AC power 1420 (see FIG. 19). The AC/DC converter 1452 may include rectifier circuitry, smoothing circuitry, a switched-mode power supply, a linear regulator, and the like to convert the AC power to DC power 1454. In some embodiments of the present disclosure, the AC/DC converter 1452 may be external to the dock. In other embodiments, the AC/DC converter 1452 is located within the dock 1404.

The DC power 1454 is received at the DC power entry 1456, which may be a connector to connect the positive and negative leads of the DC power 1454 to power and ground planes of a PCB board, respectively. The DC power entry 1454 provides power to the circuitry of the dock 1404. The DC power entry 1456 may also receive wireless power 1458.

The power received via the DC power entry 1456 is sent to charging circuitry 1460. The charging circuitry 1460 charges a primary battery 1462 and a backup battery or super-capacitor 1464. The charging circuitry 1460 may employ various charging techniques, for example, a constant-current/constant-voltage charging algorithm.

The dock 1404 includes a primary processor 1466 and a safety processor 1468. The primary processor 1466 is powered by the primary battery 1462. The safety processor 1468 is also powered by the primary battery 1462, but also can receive power from the backup battery or super-capacitor 1464.

In this example embodiment, the primary processor 1466 interfaces with a barcode reader 1470, a camera 1472, dock sensors 1474, a speaker 1476, a WiFi transceiver 1478, a Bluetooth transceiver 1480, a USB controller 1482, LED status lights 1484, and three internal expansion slots 1486, 1488, and 1490 (each of which is optional).

The internal expansion slots 1486, 1488, and 1490 can receive additional circuitry. For example, as shown in FIG. 20, the internal expansion slot 1486 has a communications/ranging module 1492, and the internal expansion slot 1488 has a RFID reader 1494 and a near-field communicator 1488 inserted therein (each of which is optional).

The safety processor 1468 provides a watchdog function to the primary processor 1466. For example, the safety processor 1468 can communicate with the primary processor at predetermined intervals, or expects a communication from the primary processor 1466 at predetermined intervals. If the safety processor 1468 does not receive the expected response or communication, it may determine that an error has occurred. The safety processor 1468 in response to the error may indicated a fault using LED Fault status lights 1401, generating an audible sound using a backup speaker 1403, or vibrate the dock 1404 using a vibration motor 1405. As will be appreciated in light of this disclosure, numerous fault notifications (e.g., telephone call, email, text message, etc) can be issued to numerous personnel (e.g., nurses and/or physicians, facility maintenance, etc).

The safety processor 1468 can monitor the power supplied through the device connector using current sensing circuitry 1407. If the safety processor 1468 determines that the current supplied to the device connector 1438 exceeds a predetermined threshold or is otherwise out of specification, the safety processor 1468 signals power enable circuitry 1409 to disengage the power supplied from the primary battery 1462 to the device connector 1438. The power enable circuitry 1409 may include relays, switches, solid-state switches, contactors, and the like to connect and disconnect the primary battery 1462 from the device connector 1438.

The primary processor 1466 is also electrically coupled to a optional charge-state display 1411 and a optional display 1413. The charge-state display 1411 can display the charge state of the primary battery 1462. The display 1413 may be a touchscreen and/or may display the operational status of the dock 1404. The dock 1404 receives user input via optional buttons 1415.

The communications/ranging module 1492 can communicate with other communications/ranging modules 1492, e.g., on a patient-care device, other dock, or monitoring client, to determine the distance therebetween. For example, two communications/ranging module (e.g., communications/ranging module 1492 and another communications/ranging module), may wirelessly communicate, for example, via ultrasound, RF, UHF, electromagnetic energy, optically, and the like, to determine the distance between them. In accordance with one embodiment, one or more of a patient-care device, a monitoring client, a patient's watchdog, a remote communicator, etc. may not operate unless each of them having a communications/ranging modules 1492 determines they are within a predetermined distance relative to each other.

Figure 21:
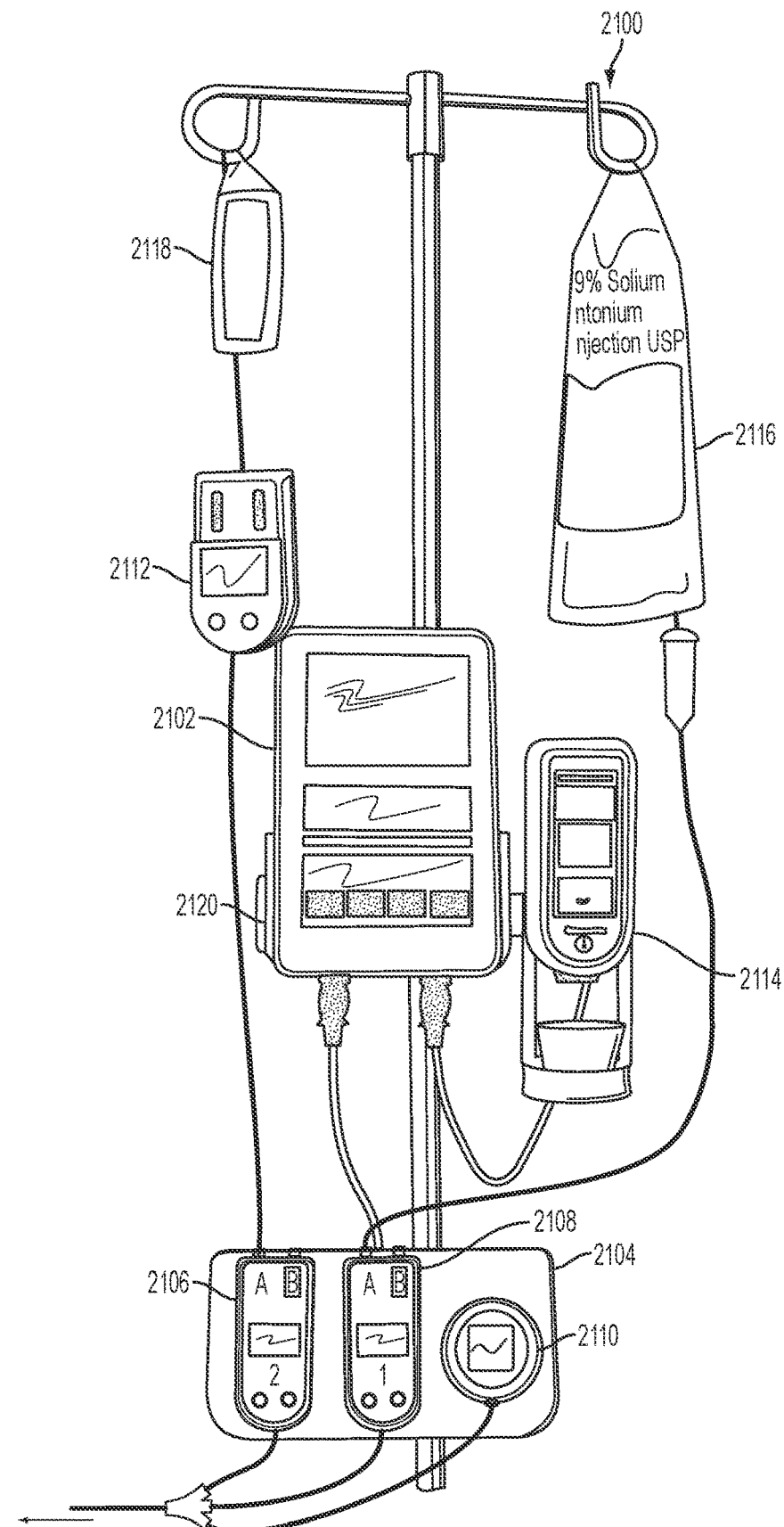
FIG. 21 shows an electronic patient-care system having a tablet docked into a dock having a cable electrically coupled to patient-care devices in accordance with an embodiment of the present disclosure.

FIG. 21 shows an exemplary arrangement of a system 2100 in which a monitoring client 2102 is linked to a number of patient-care devices via a dock 2120, including an infusion pump 2106 connected to and delivering from a smaller bag of fluid 2118, an infusion pump 2108 connected to and delivering from a larger bag of fluid 2116, a drip detection device 2112 connected to tubing from the smaller bag 2118, a pill dispenser 2114, and a microinfusion pump 2110. The monitoring client 2102 may communicate with these patient-care devices in a wired fashion, as shown for the infusion pumps 2106, 2108, the microinfusion pump 2110 (via docks 2120, 2104), and the pill dispenser 2114. Alternatively, the monitoring client may communicate wirelessly with patient-care devices, as suggested by the absence of a wired connection between the drip detection device 2112 and the monitoring client 2102. In an embodiment, a wired connection between the monitoring client 2102 and a patient-care device also affords an opportunity for electrical power to be supplied to the patient-care device from the monitoring client 2102. In this case, the monitoring client 2102 may include the electronic circuitry necessary to convert the voltage to power the patient-care device from either a battery attached to the monitoring client 2102 or from line voltage fed into the monitoring client 2102 from a power outlet (not shown) in a patient's room. Additionally or alternatively, the dock 2104 supplies power to the infusion pumps 2106, 2108 and the microinfusion pump 2110.

In an embodiment, the monitoring client 2102 is capable of receiving information about each patient-care device with which it is linked either directly from the device itself, or via a docking station, such as, for example, the dock 2104 onto which the patient-care device may be mounted. The dock 2104 may be configured to receive one or more patient-care devices via a standardized connection mount, or in some cases via a connection mount individualized for the particular device. For example, in FIG. 21, infusion pumps 2106 and 2108 may be mounted to the dock 2104 via a similar connection mount, whereas the microinfusion pump 2110, for example, may be mounted to the dock 2104 via a connection mount configured for the particular dimensions of the microinfusion pump's 2110 housing.

The dock 2104 may be configured to electronically identify the particular patient-care device being mounted on the docking station, and to transmit this identifying information to monitoring client 2102, either wirelessly or via a wired connection. Additionally, the particular patient-care device may be preprogrammed with treatment information (e.g., patient-treatment parameters such as an infusion rate for a predetermined infusion fluid) that is transmitted to the monitoring client 2102. In some embodiments of the present disclosure, the monitoring client 2102 communicates with EMR records to verify that the preprogrammed treatment information is safe for an identified patient and/or the preprogrammed treatment information matches the prescribed treatment stored in the EMR records.

In some embodiments, the drip detection device 2112 may communicate with the monitoring client 2102 either wirelessly or in a wired connection. If an aberrant fluid flow condition is detected (e.g., because the tubing to the patient has become occluded), a signal may be transmitted to monitoring client 2102, which (1) may display the flow rate of fluid from fluid container 2118 in a user interface either locally on monitoring client 2102, or more remotely to a user interface at a nurse's station or a handheld communications device, (2) may trigger an auditory or visual alarm, (3) may alter the rate of infusion of a pump 2108 connected to bag 2118, by either terminating the infusion or otherwise changing the pumping rate, or (4) may cause an audible alarm (and/or vibration alarm) on the infusion pump 2106. The alarms may occur simultaneously on several devices or may follow a predetermined schedule. For example, when an occlusion occurs in a line connected to the infusion pump 2106, (1) the drip detection device 2112 alarms using its internal speaker and an internal vibration motor, (2) thereafter, the infusion pump 2106 alarms using its internal speaker and an internal vibration motor, (3) next, the monitoring client 2102 alarms using its internal speaker and an internal vibration motor, and (4) finally, a remote communicator 11 (e.g., see FIGS. 1, 3, 5, 7, 8, 9) alarms using its internal speaker and an internal vibration motor.

In some embodiments, an individual pump may be programmable to allow for continued operation at a predetermined pumping rate should communications fail between the monitoring client 2102 and the pump, either because of a malfunction in the monitoring client 2102, in the communications channel between the monitoring client 2102 and the pump, or in the pump itself. In some embodiments, this independent function option is enabled when the medication being infused is pre-designated for not being suspended or held in the event of a malfunction in other parts of the system. In some embodiments, a pump programmed to operate independently in a fail safe mode may also be configured to receive information from a drip detection device 2112 directly, rather than through a monitoring client 2102. With this option, the pump may be programmed, in some embodiments, to stop an infusion if the drip detection device 2112 detects an aberrant flow condition (such as, e.g., a free-flow condition or an air bubble present in the infusion line). In some embodiments, one or more of the pumps 2106, 2108, and 2110 may have internal fluid flow meters and can operate independently as a stand-alone device.

Figure 22:
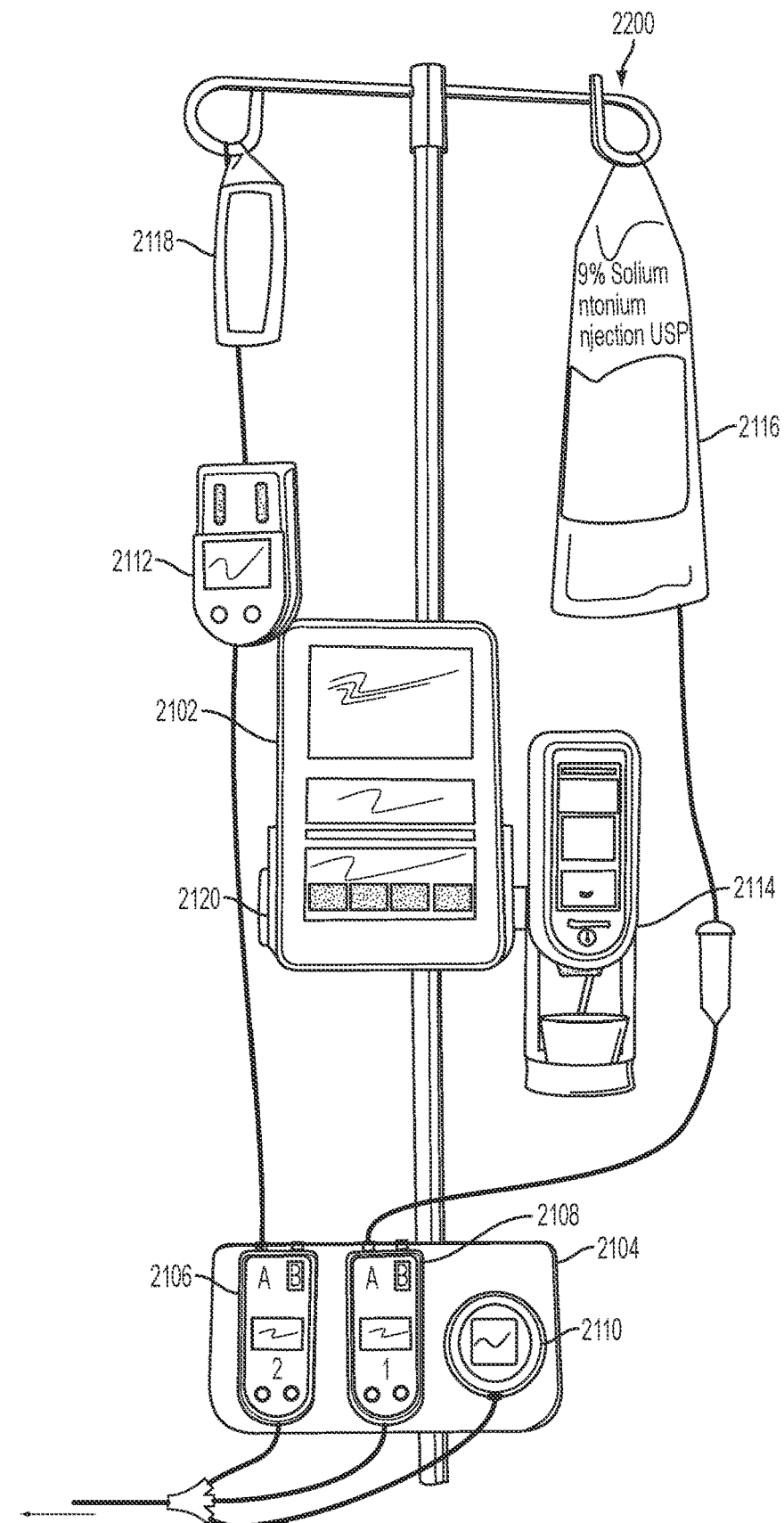
FIG. 22 shows an electronic patient-care system having a tablet docked into a dock for wirelessly communicating with patient-care devices in accordance with an embodiment of the present disclosure.

FIG. 22 shows an electronic patient-care system 2200 having a tablet 2102 docked into a dock for wirelessly communicating with patient-care devices 2106, 2108, 2110, 2112, 2114 in accordance with an embodiment of the present disclosure. The monitoring client 2102 may communicate with the patient-care devices 2106, 2608, 2110, 2112 wirelessly or through a wireless transceiver on the dock 2120. For example, the monitoring client 2102 may communicate to a transceiver within the dock 2104. Additionally or alternatively, the dock 2120 include a transceiver for use by the monitoring client 2102 for communicating with the dock 2104 and/or directly via a wireless connection to the patient-care devices 2106, 2108, 2110, 2112, 2114.

Figure 23:
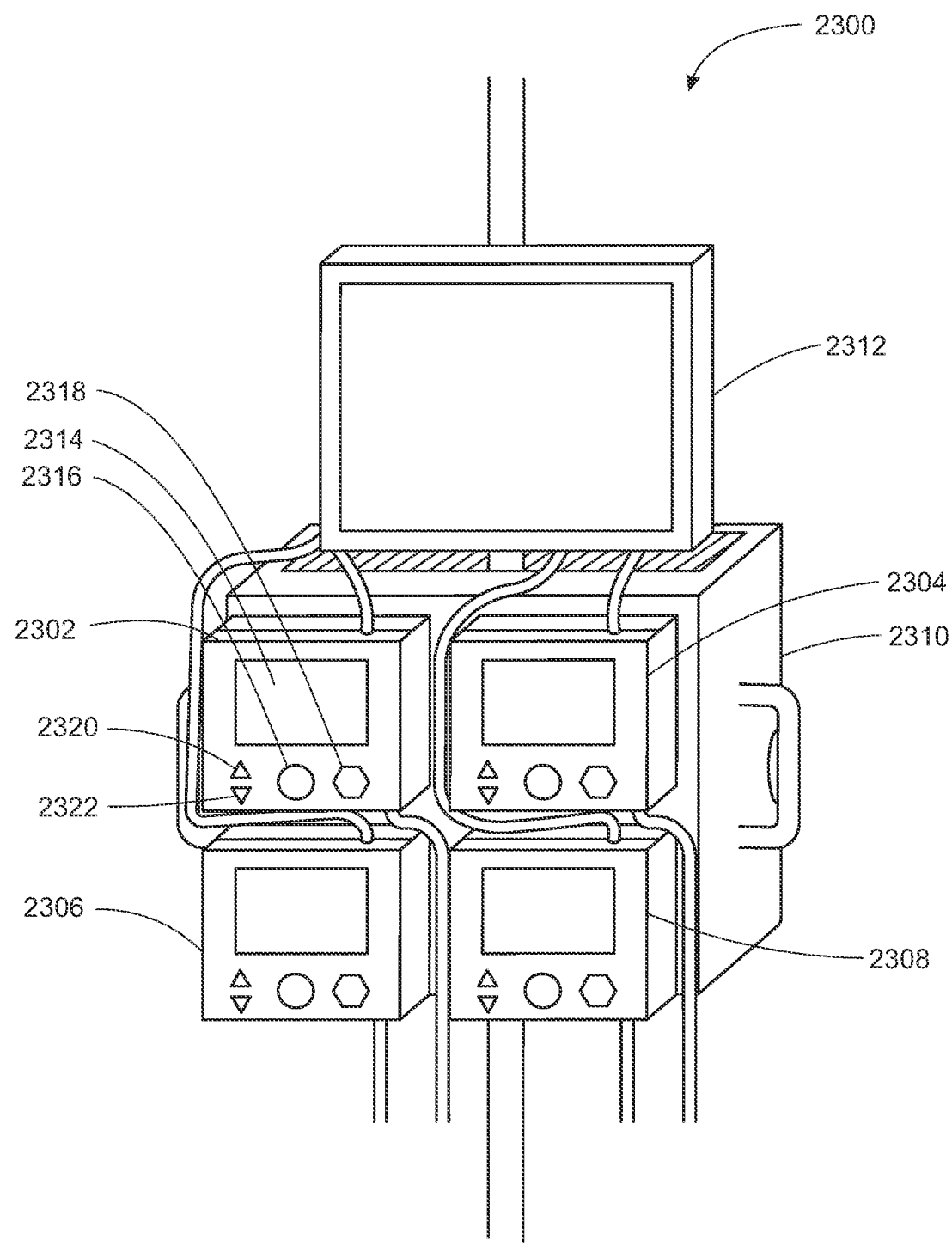
FIG. 23 shows an electronic patient-care system having modular infusion pumps that dock into a dock having a monitoring client with a retractable user interface in accordance with an embodiment of the present disclosure.
Figure 24:
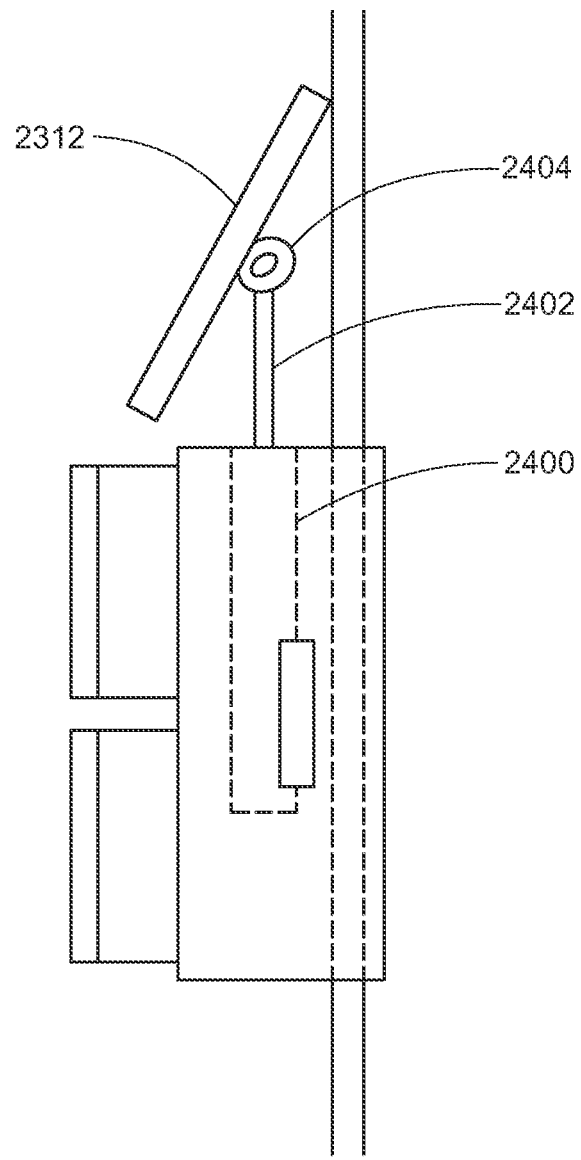
FIG. 24 shows a side-view of the electronic patient-care system of FIG. 23 in accordance with an embodiment of the present disclosure.

FIG. 23 shows an electronic patient-care system 2300 having modular infusion pumps 2302, 2304, 2306, 2308 that dock into a dock 2310 having a monitoring client 2312 with a retractable user interface in accordance with an embodiment of the present disclosure. The modular infusion pumps 2302, 2304, 2306, 2308 have standardized connectors so that they may be snapped into the dock 2310. Each of the modular infusion pumps 2302, 2304, 2306, 2308 includes a user interface. For example, the modular infusion pump 2302 includes a touchscreen 2314, a start button 2316, a stop button 2316, an increase-infusion-rate button 2320, and a decrease-infusion-rate button 2322. FIG. 24 is a side-view of the electronic patient care system 2300 of FIG. 23 and shows an outline of a cavity 2400 in which the monitoring client 2312 can retract into because the mounting pole 2402 is movable such that the monitoring client 2312 can be rotated along pivot 2404 and pushed down into the cavity 2400.

Figure 25:
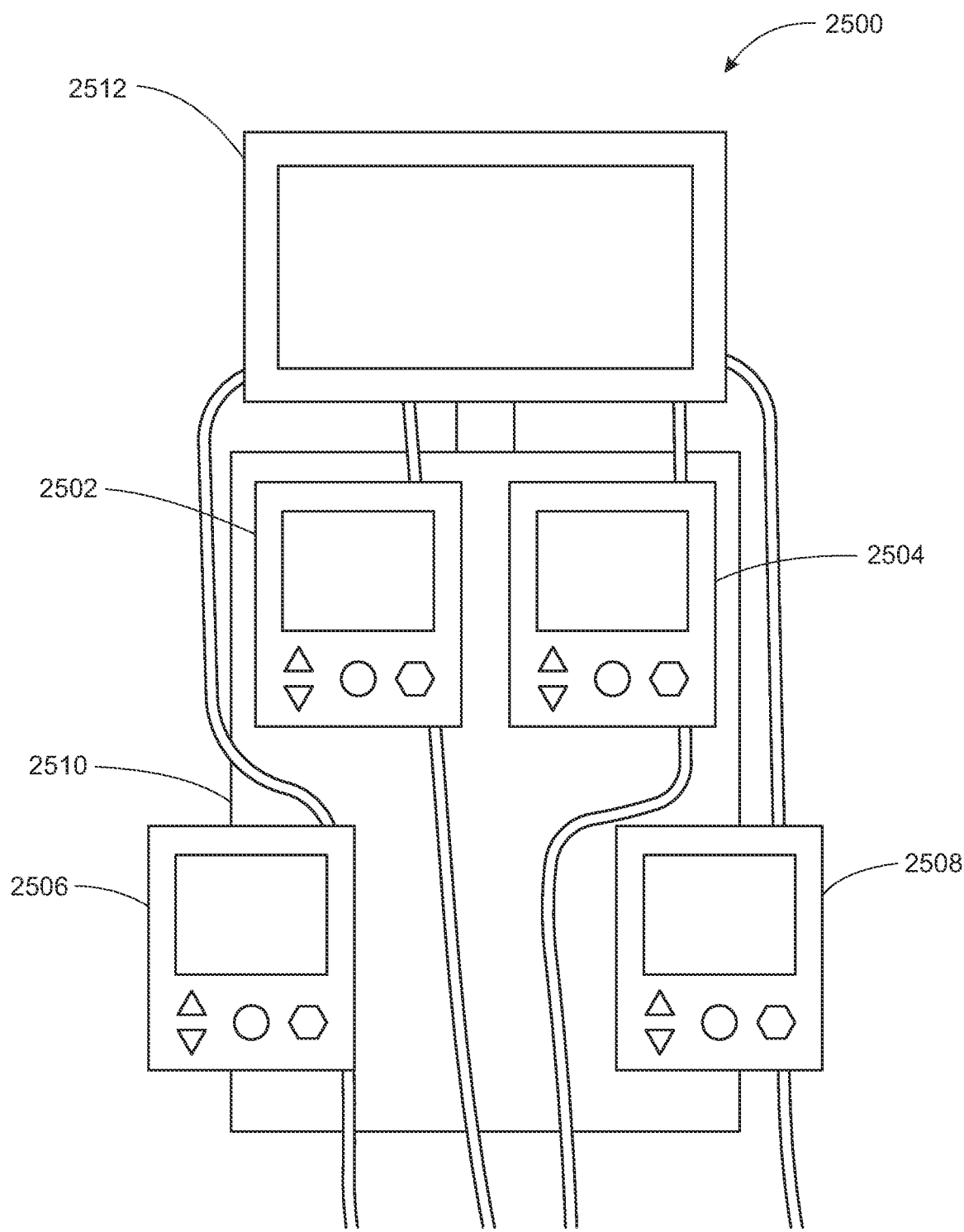
FIG. 25 shows an electronic patient-care system having modular infusion pumps that dock into a dock having a monitoring client with a retractable user interface, the infusion pumps are arranged in a staggered fashion in accordance with another embodiment of the present disclosure.

FIG. 25 shows an electronic patient-care system 2500 having modular infusion pumps 2502, 2504, 2506, 2508 that dock into a dock 2510 having a monitoring client 2512 with a retractable user interface, the infusion pumps 2502, 2504, 2506, 2508 are arranged in a staggered fashion in accordance with another embodiment of the present disclosure. System 2500 of FIG. 25 may be similar to the system 2300 of FIG. 23, except that system 2500 of FIG. 25 has the module infusion pumps 2502, 2504, 2506, 2508 arranged in a staggered fashion. The staggering of the modular infusion pumps 2502, 2504, 2506, 2508 may provide more room for tube routing.

Figure 26:
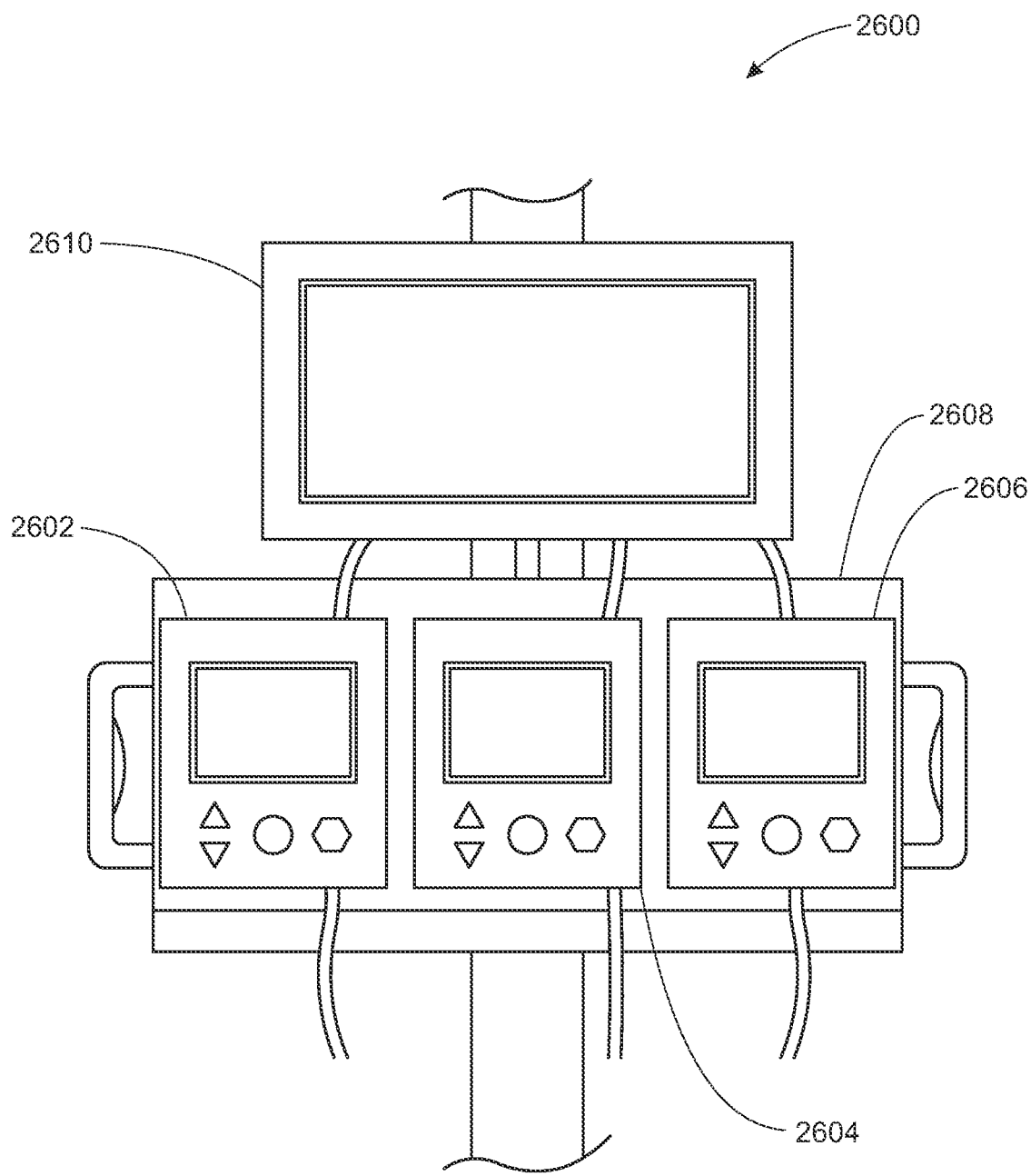
FIG. 26 shows an electronic patient-care system having modular infusion pumps that dock into a dock along a common horizontal plane and the dock includes a monitoring client with a retractable user interface in accordance with yet another embodiment of the present disclosure.
Figure 27:
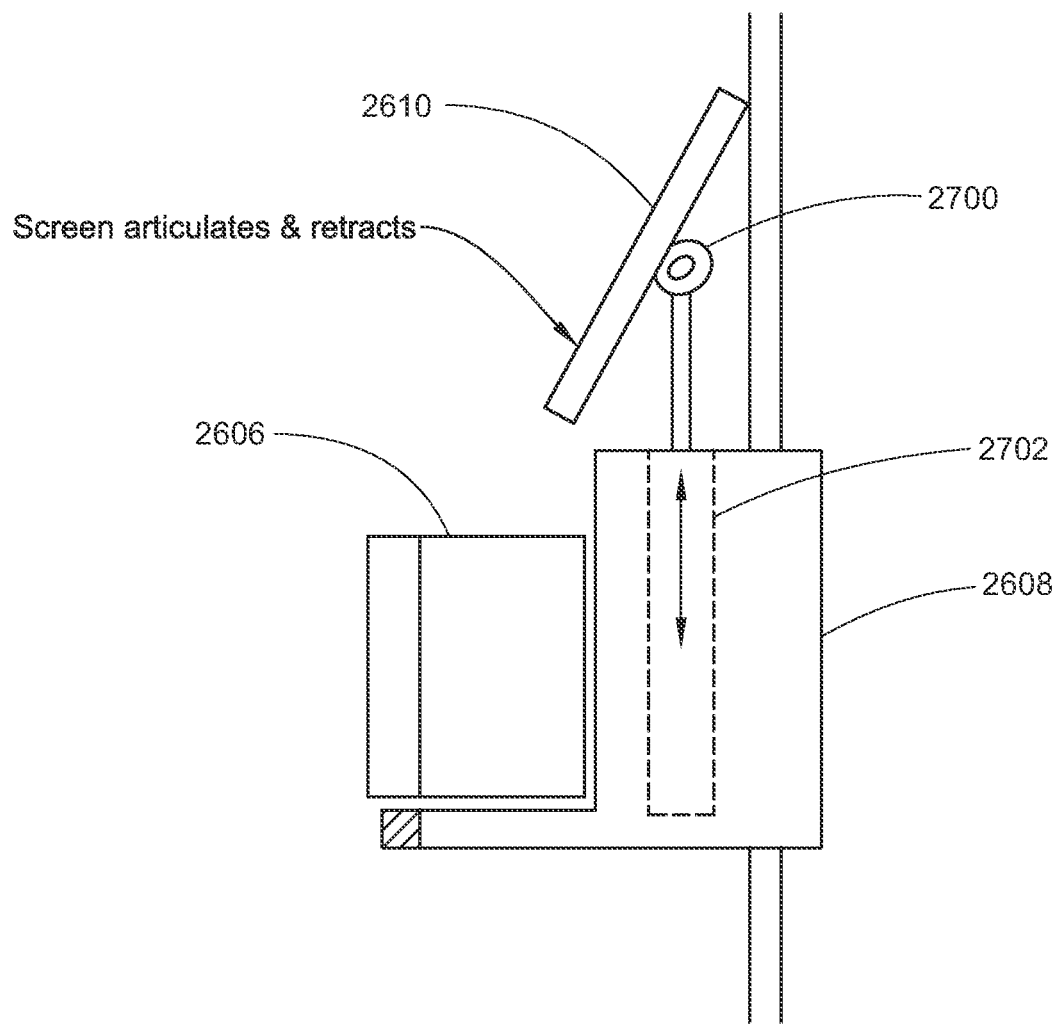
FIG. 27 shows a side-view of the electronic patient-care system of FIG. 26 in accordance with another embodiment of the present disclosure.

FIG. 26 shows an electronic patient-care system 2600 having modular infusion pumps 2602, 2604, 2606 that dock into a dock 2608 along a common horizontal plane. The dock 2608 includes a monitoring client 2610 that is retractable into the dock 2608. The monitoring client 2610 may be wholly retractable into the dock 2608 and/or some of the monitoring client 2610's circuitry may be housed in the dock 2608. As is easily seen from FIG. 27 which shows a side-view of the electronic patient-care system 2600 of FIG. 26, the monitoring client 2610 pivots along a pivot 2700 for retracting the monitoring client 2610 into a cavity 2702 inside of the dock 2608.

Figure 28:
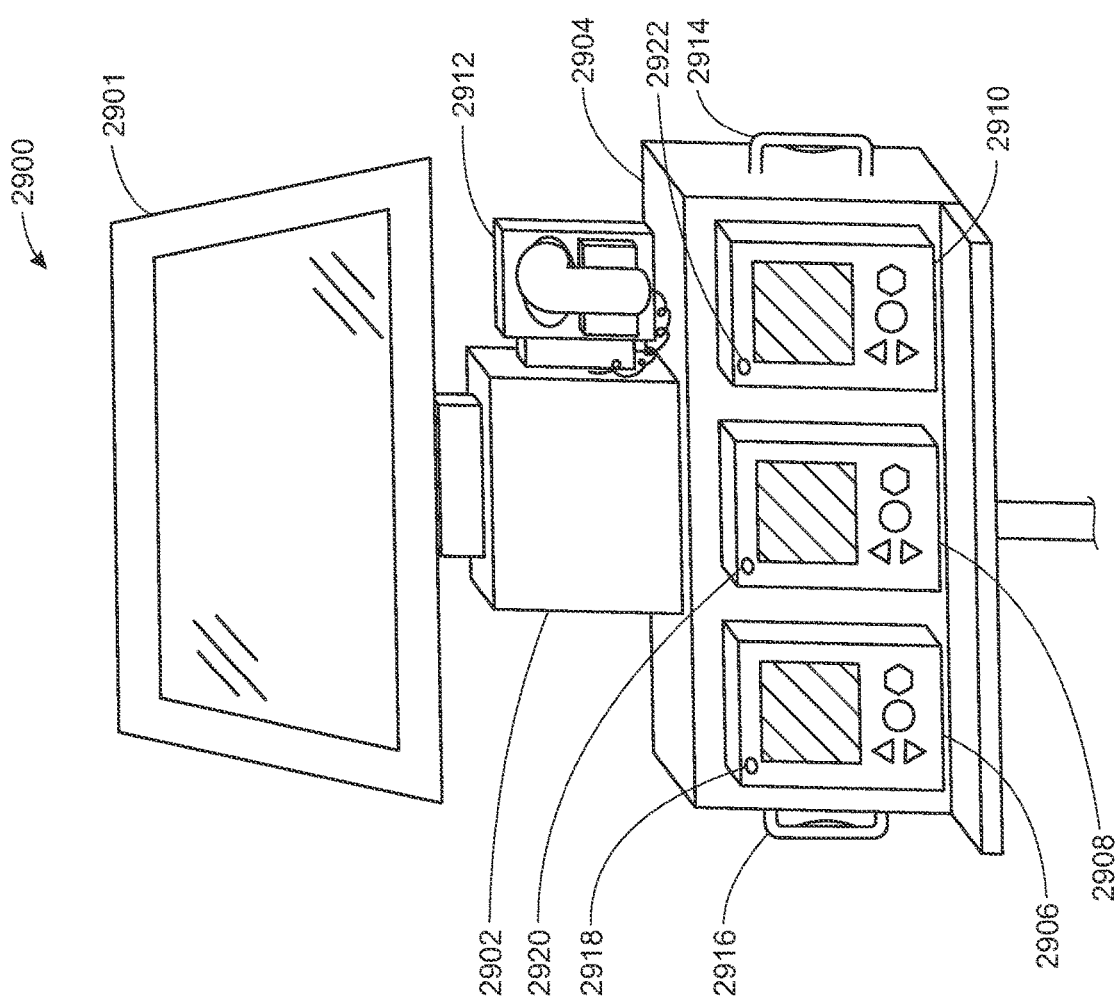
FIG. 28 shows an electronic patient-care system having a hub coupled to a scanner and a dock, the electronic patient-care system also includes modular infusion pumps that dock into the dock along a common horizontal plane, and the dock includes a monitoring client with a retractable user interface in accordance with yet another embodiment of the present disclosure.
Figure 29:
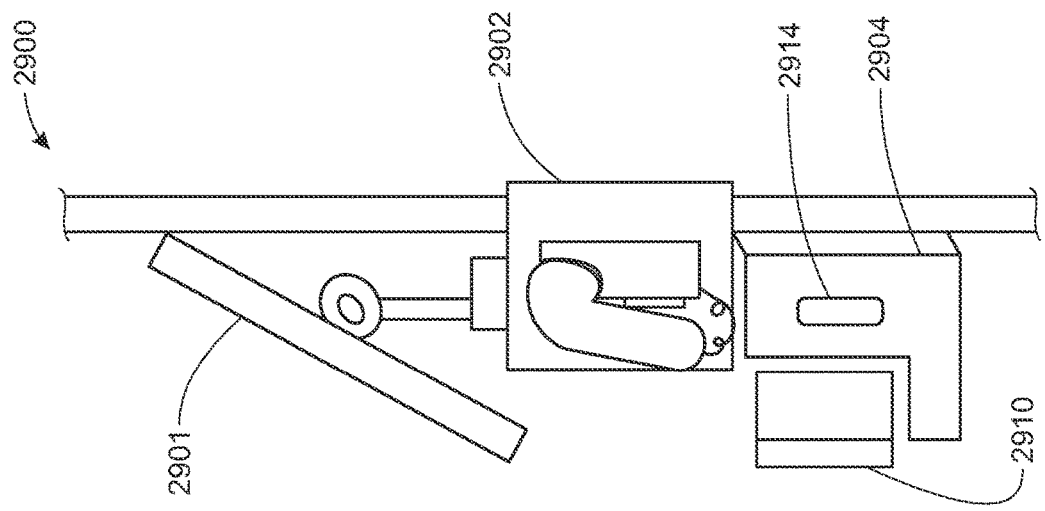
FIG. 29 shows a side-view of the electronic patient-care system of FIG. 28 in accordance with another embodiment of the present disclosure.

FIG. 28 shows another embodiment of an electronic patient-care system 2900 including a hub 2902 coupled to a device dock 2904. FIG. 29 shows a side-view of the electronic patient-care system 2900 of FIG. 28. The monitoring client 2901 is integrated with the hub 2902. In alternative embodiments, the hub 2902 is a cradle for the monitoring client 2901 and only provides electrical connections to the dock 2904 and the scanner 2912. Modular infusion pumps 2906, 2908, 2910 are shown as docked into the device dock 2904. The system 2900 also includes a scanner 2912 coupled to the hub 2902. The dock 2904 includes quick release handles 2914 and 2916 on the left and right side of the dock 2904, respectively. Also shown in the upper left corner of each of the modular infusion pumps 2906, 2908, and 2910 pumps is a respective button 2918, 2920, and 2922 that lights up when that patient-care device is the focus of interaction on the monitoring client 2901 (shown as a tablet, a type of monitoring client) or is selected for control by a user. Either the tablet can select the specific modular infusion pumps or the user can push the respective button of the buttons 2918, 2920, and 2922 of the modular infusion pumps 2906, 2908, and 2910 to select it for manipulation on the monitoring client 2901.

Figure 30:
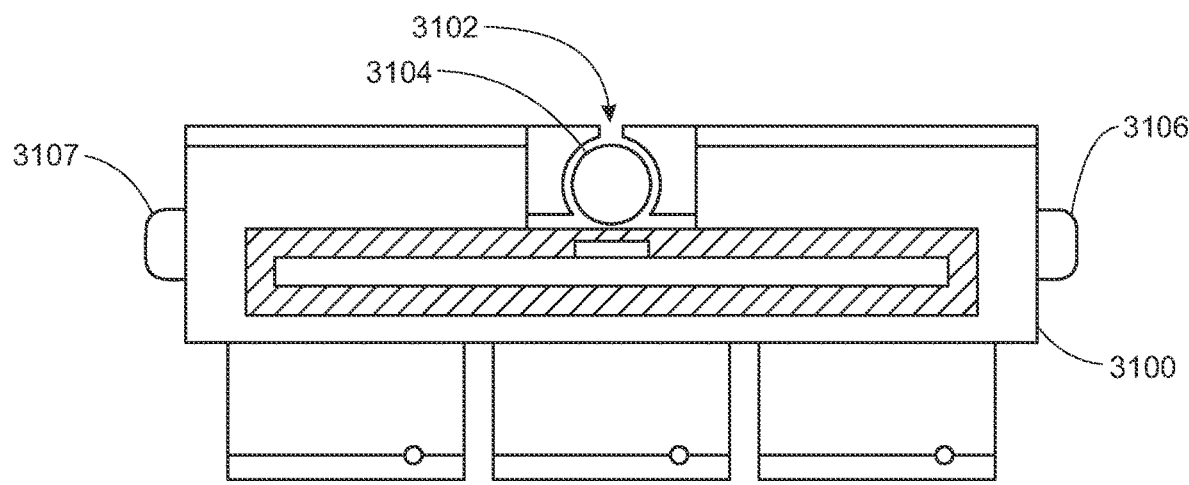
FIGS. 30-32 show several views illustrating a clutch system for mounting an electronic patient-care system on a pole in accordance with an embodiment of the present disclosure.
Figure 31:
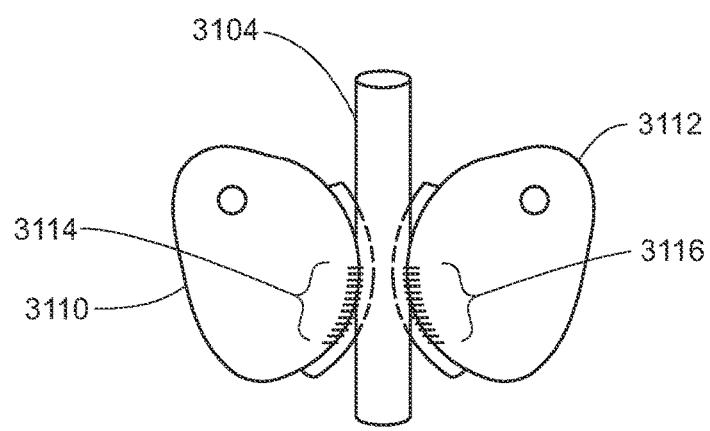
Figure 32:
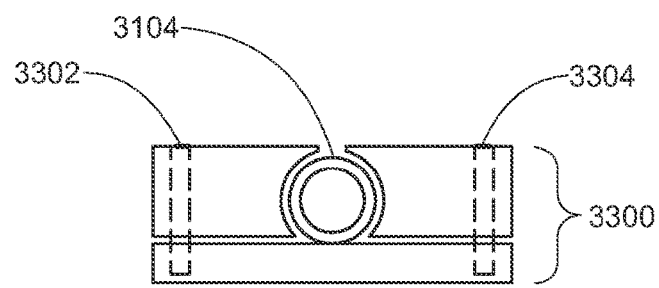

FIGS. 30-32 show several views illustrating a clutch system for mounting an electronic patient-care system on a pole in accordance with an embodiment of the present disclosure. FIG. 30 shows a top view of a dock 3100 having a hole 3102 for receiving a pole 3104. The clutches 3110 and 3112 are shown in FIG. 31. In some embodiments, the clutches 3110, 3112 include cleats 3114, 3116. The handles 3106 and 3107 may be used, individually or together, to release the clutches 3110 and 3112 from the pole 3104 (e.g., by pulling on the handles). Additionally or alternatively, the handles 3106 and 3107 may be used for locking the clutches 3110 and 3112 to the pole 3104 (e.g., by pushing on the handles 3106, 3107). As is easily seen from FIG. 31, a downward force, e.g., from gravity, further compress the clutches 3110, 3112 against the pole 3104. Although two clutches 3110, 3112 are shown in FIG. 31, one clutch may be used to press the pole 3104 against a friction surface. FIG. 32 shows an alternative pole mounting structure 3300 in which two fasteners 3302 and 3304 are used to clamp down on the pole 3104.

Figure 33:
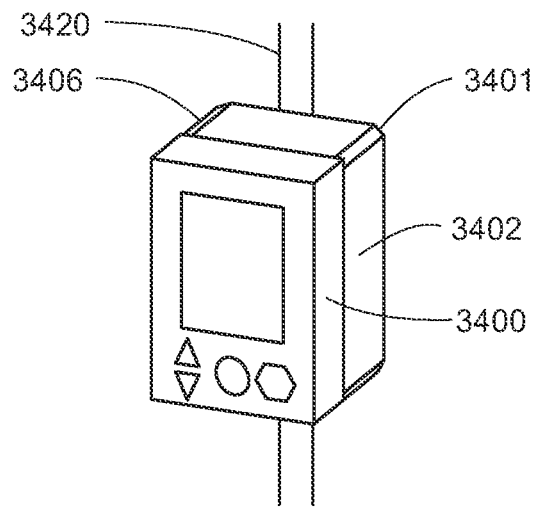
FIG. 33 shows an infusion pump and a dock coupled to a pole in accordance with an embodiment of the present disclosure.
Figure 34:
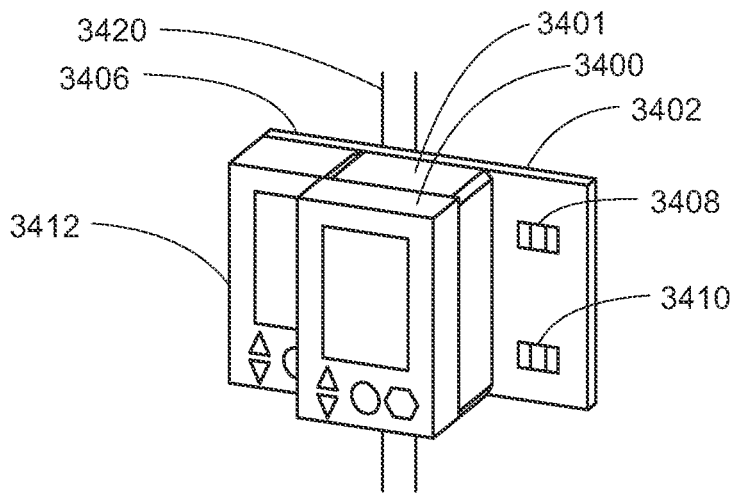
FIG. 34 shows the infusion pump with another infusion pump coupled to an open connector and an open connector in accordance with an embodiment of the present disclosure.
Figure 35:
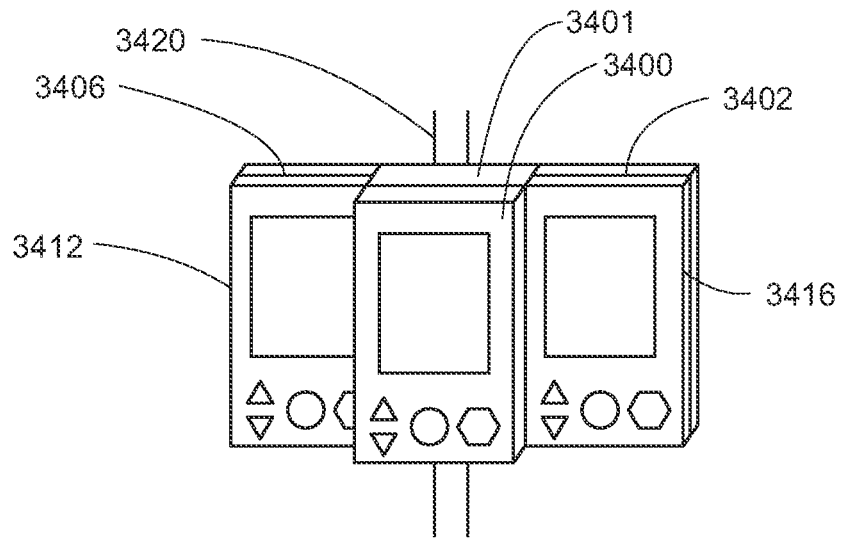
FIG. 35 shows the infusion pump of FIG. 33 with two additional infusion pumps each coupled to a respective open connector in accordance with an embodiment of the present disclosure.

FIG. 33 shows an infusion pump 3400 and retractable connectors 3402, 3406 in accordance with an embodiment of the present disclosure. In FIGS. 33-35, a hub 3401 is shown as having the retractable connectors 3402 and 3406. The hub 3401 has docking connectors making it also a dock. The retractable connectors 3402 and 3406 are shown as closed in FIG. 33. However, in alternative embodiments, the retractable connectors 3402 and 3406 may be connected directly to the infusion pump 3400, the infusion pump 3412, and/or additional infusion pumps. The hub 3401 may have a pole mounting mechanism that is enveloped by the hub 3401 (see FIG. 36). The hub 3401, in some embodiments, may be a dock or a cradle, and may optionally include a handle coupled to the top thereof; the handle may be integrated into the pole attachment mechanism such that picking up the handle also releases the hub 3401 from the pole. Alternatively, in some embodiments, the hub 3401 could support a cradle to attach it to a monitoring client, e.g., a tablet, or the monitoring client could be attached to the pole separately. The retractable connectors 3402 and 3406, in some embodiments, could have a support mechanism (e.g., a lip) on the bottom of the retractable connectors 3402 and 3406 to support an infusion pump when attached. In this example embodiment, the lip may also be the mechanism for electrical connection.

Figure 36:
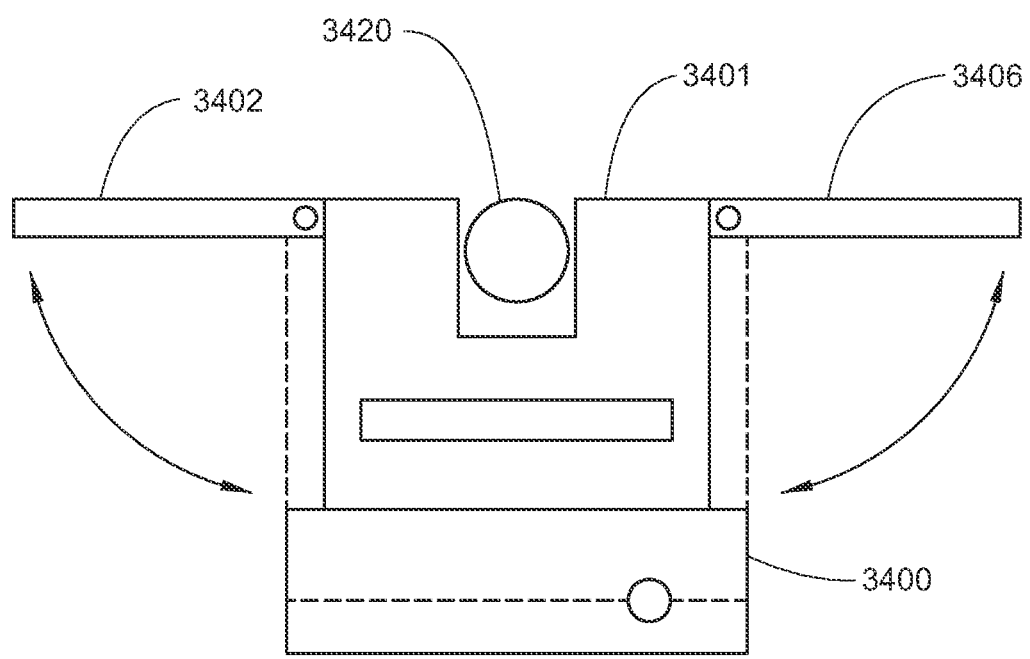
FIG. 36 shows a top view of one of the infusion pumps of FIGS. 33-35 and a hub in accordance with an embodiment of the present disclosure.

In FIG. 34, the retractable connector 3402 is shown as open, and connectors 3408 and 3410 are shown. Although the connectors 3408 and 3410 are shown on the retractable connector 3402, in other embodiments, the connectors 3408 and 3410 are on the hub 3401 or infusion pump 3400 and 3402 is a cover to cover the connectors 3408 and 3410. The retractable connector 3406 has an infusion pump 3412 docked thereto. FIG. 35 shows an infusion pump 3416 docked to the retractable connector 3402, and the infusion pump 3412 is docked to the retractable connector 3606. The infusion pumps 3400, 3412, and 3416 are electrically connected together in FIG. 35 via the hub 3401. FIG. 36 shows a top view of the infusion pump 3400 and the hub 3401 as attached to the pole 3420 of FIGS. 33-35. The retractable connectors 3402 and 3406 are shown in the open configuration.

Figure 37:
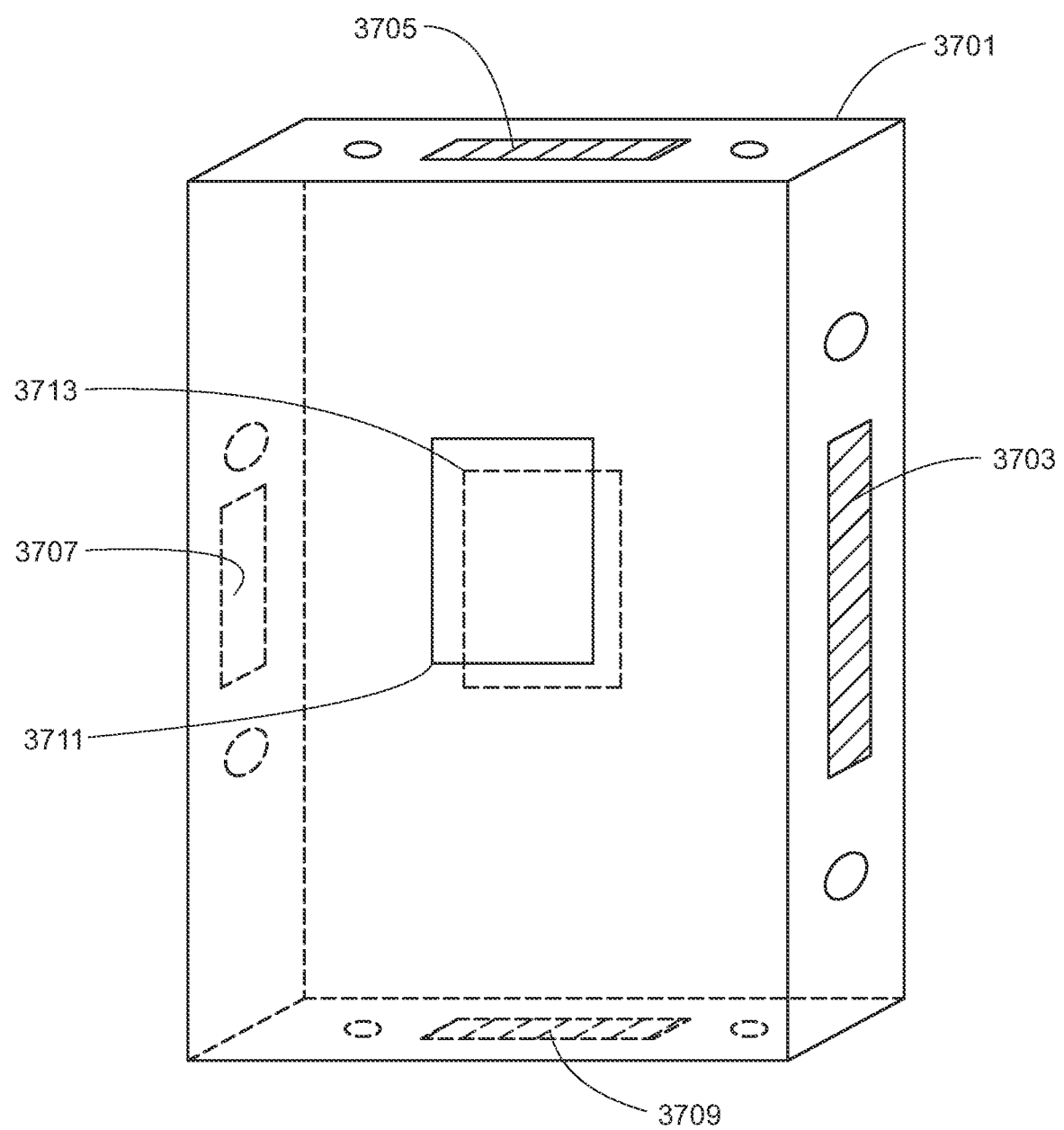
FIG. 37 shows a square-shaped hub having several connectors in accordance with an embodiment of the present disclosure.

FIG. 37 shows a square-shaped hub 3701 having several connectors 3703, 3705, 3707, 3709 in accordance with an embodiment of the present disclosure. Each of the connectors 3703, 3705, 3707, and 3709 may be used to connect additional batteries, communication modules, scanners, a monitoring client, a monitoring client's UI, patient-care devices, and the like. Each of the connectors 3703, 3705, 3707, and 3709 may use a standard pin-out in which the modules attached thereto use a subset. In some embodiments, each of the connectors 3703, 3705, 3707, and 3709 may use a subset of the available pins that are unique to the device that is connected based upon the type of device, e.g., as determined from a signal. A pole mounting mechanism could be located on the back of the square-shaped hub 3701. The square-shaped hub 3701 may also include front 3711 and back 3713 connectors. The mechanical attachments associated with each of the connectors 3703, 3705, 3707, 3709, 3711, 3712 may be permanent attachments (e.g. screws) or quick-release mounting points (e.g. latches).

Figure 38:
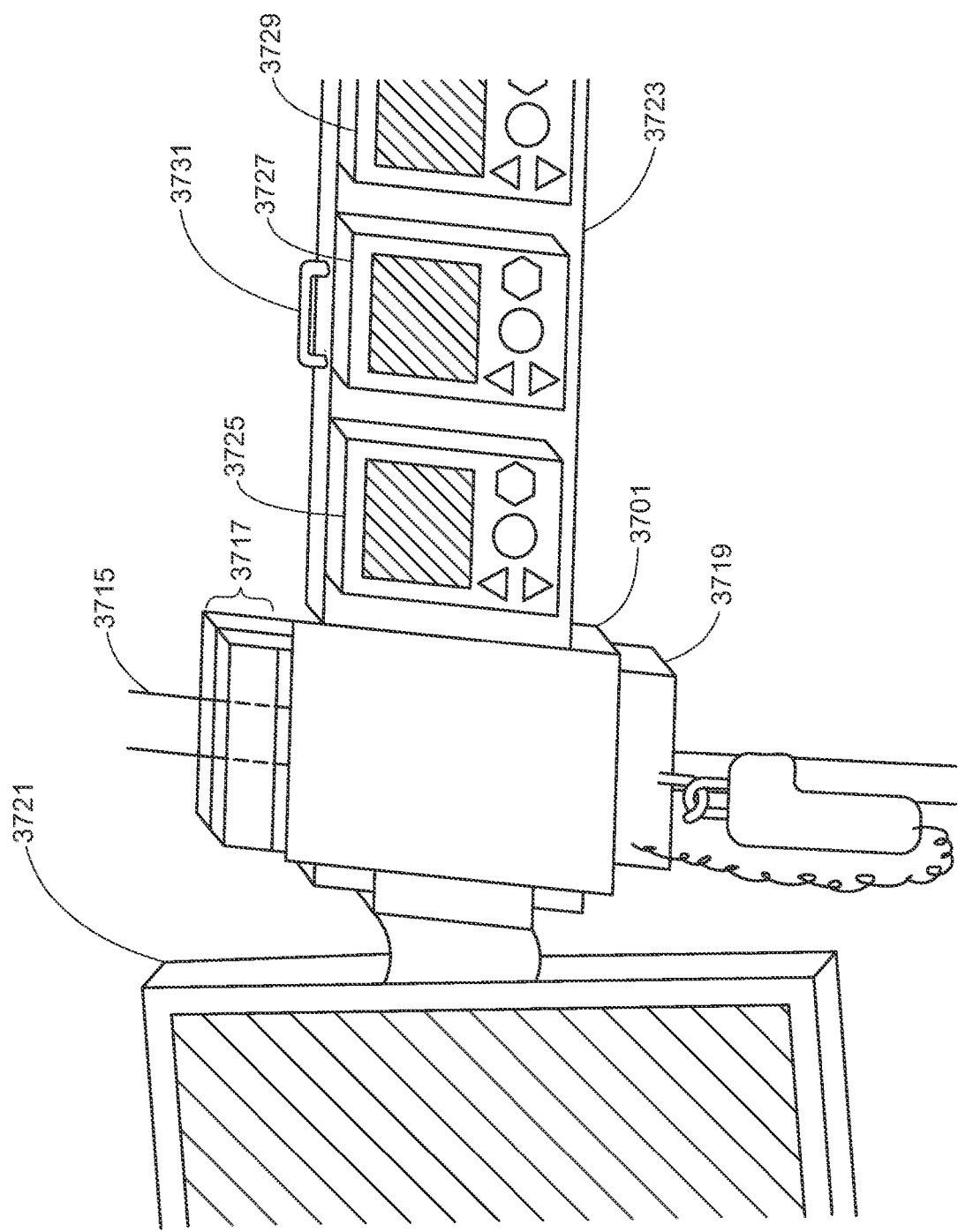
FIG. 38 shows an electronic patient-care system having a hub coupled to a pole in accordance with another embodiment of the present disclosure.

FIG. 38 shows an electronic patient-care system having a hub 3701 coupled to a pole 3715 in accordance with another embodiment of the present disclosure. FIG. 38 shows an articulating monitoring client 3712 on the left, an extended battery/communication module 3717 on top, a barcode scanner module 3719 on the bottom, and a pump dock 3723 on the right of the hub 3701. The pump dock 3723 is removable for transportation with all the infusion pumps 3725, 3727, 3729 attached such that they all may be transported as one unit. A quick-release handle 3731 may be located on top of the pump dock 3727 to allow easy detachment from the hub 3701. Alternatively, in other embodiments, the infusion pumps 3725, 3727, 3729 may be daisy chained together. The articulating monitoring client 3721 (e.g., a tablet) may be attached permanently to the hub 3701, which could make up a "Zero-Channel Pump" when the dock 3723 is removed. For example, the monitoring client 3721 may continue to operate and monitor various patient-care devices when no pump is attached to and/or is in operative communication with the monitoring client 3721.

Figure 39:
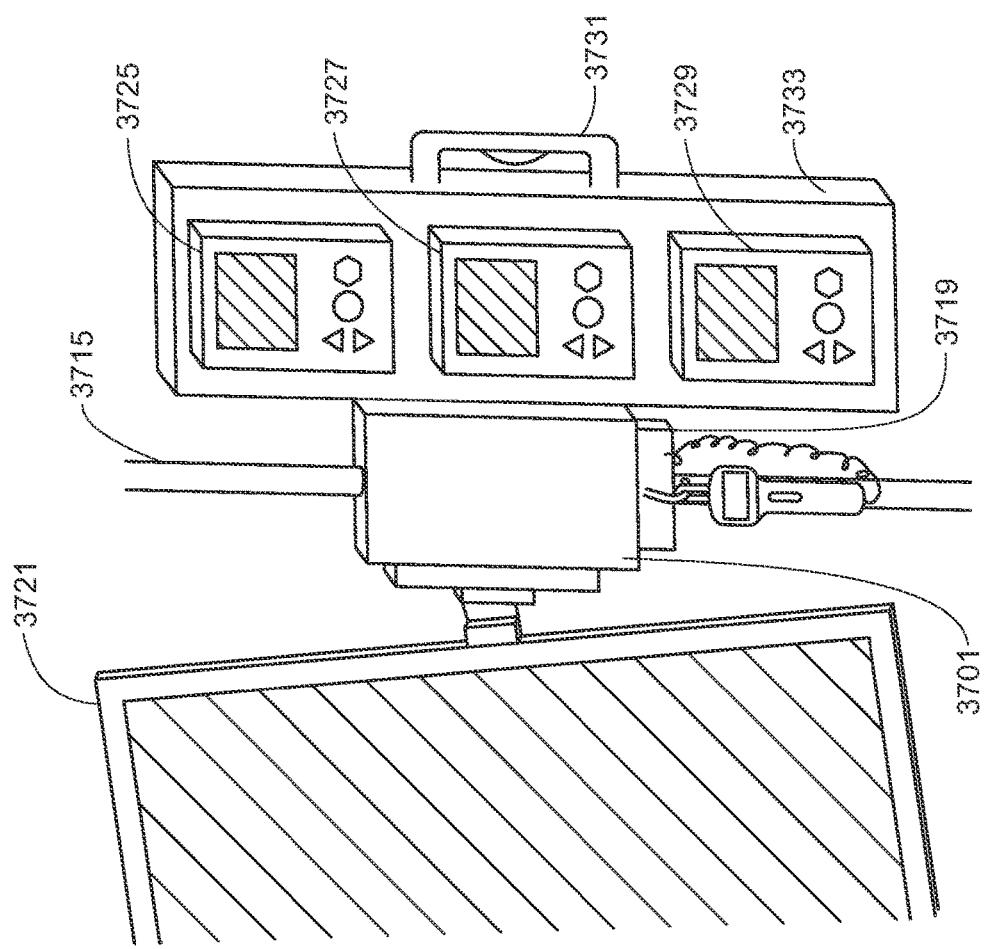
FIG. 39 shows an electronic patient-care system having a hub coupled to a pole and a portable dock that include a quick-release handle to detach the portable dock from the hub in accordance with another embodiment of the present disclosure.

FIG. 39 shows an electronic patient-care system having a hub 3701 coupled to a pole 3715, and a portable dock 3733 that includes a quick-release handle 3731 to detach the portable dock 3733 from the hub 3701 in accordance with another embodiment of the present disclosure. The hub 3701 allows for devices to be connected thereto using an adaptor plate 3735 as shown in FIG. 40.

Figure 40:
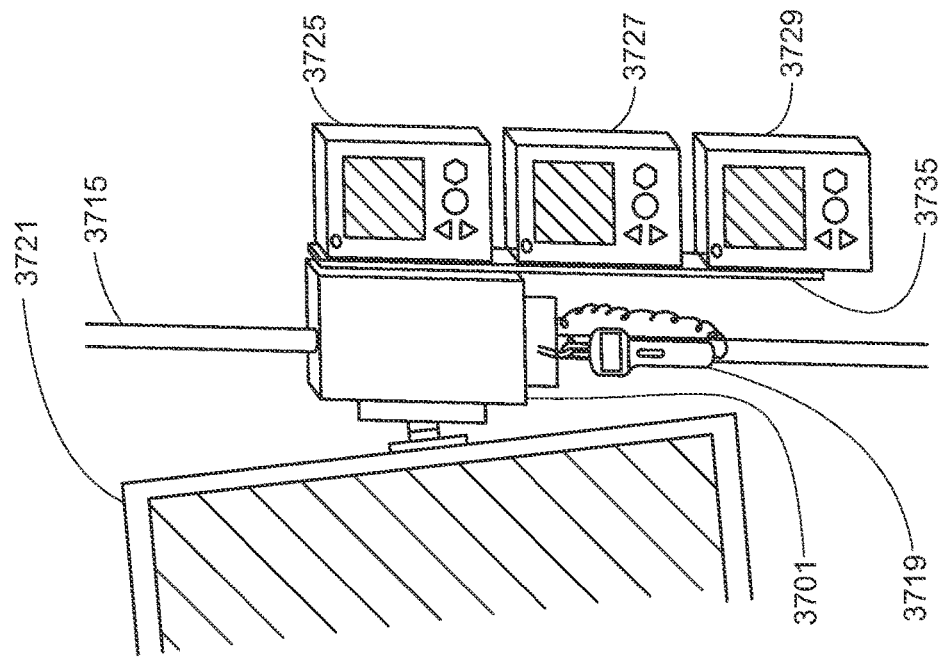
FIG. 40 shows an electronic patient-care system having a hub coupled to a pole and a dock coupled to the hub in accordance with another embodiment of the present disclosure.

FIG. 40 shows an electronic patient-care system having a hub 3701 coupled to a pole 3715 and a dock 3735 coupled to the hub 3701 in accordance with another embodiment of the present disclosure. The dock 3735 of FIG. 40 is shown as a connector plate. That is, the dock 3735 is shown as an adaptor or connector plate adapted to facilitate the connection of the infusion pumps 3725, 3727, 3729 to the hub 3701 using the generic connector provided by the hub 3701. The dock 3701 provides sufficient signals and sufficient mechanical alignment and orientation for connecting to the dock 3735 and/or vice versa.

Figure 41:
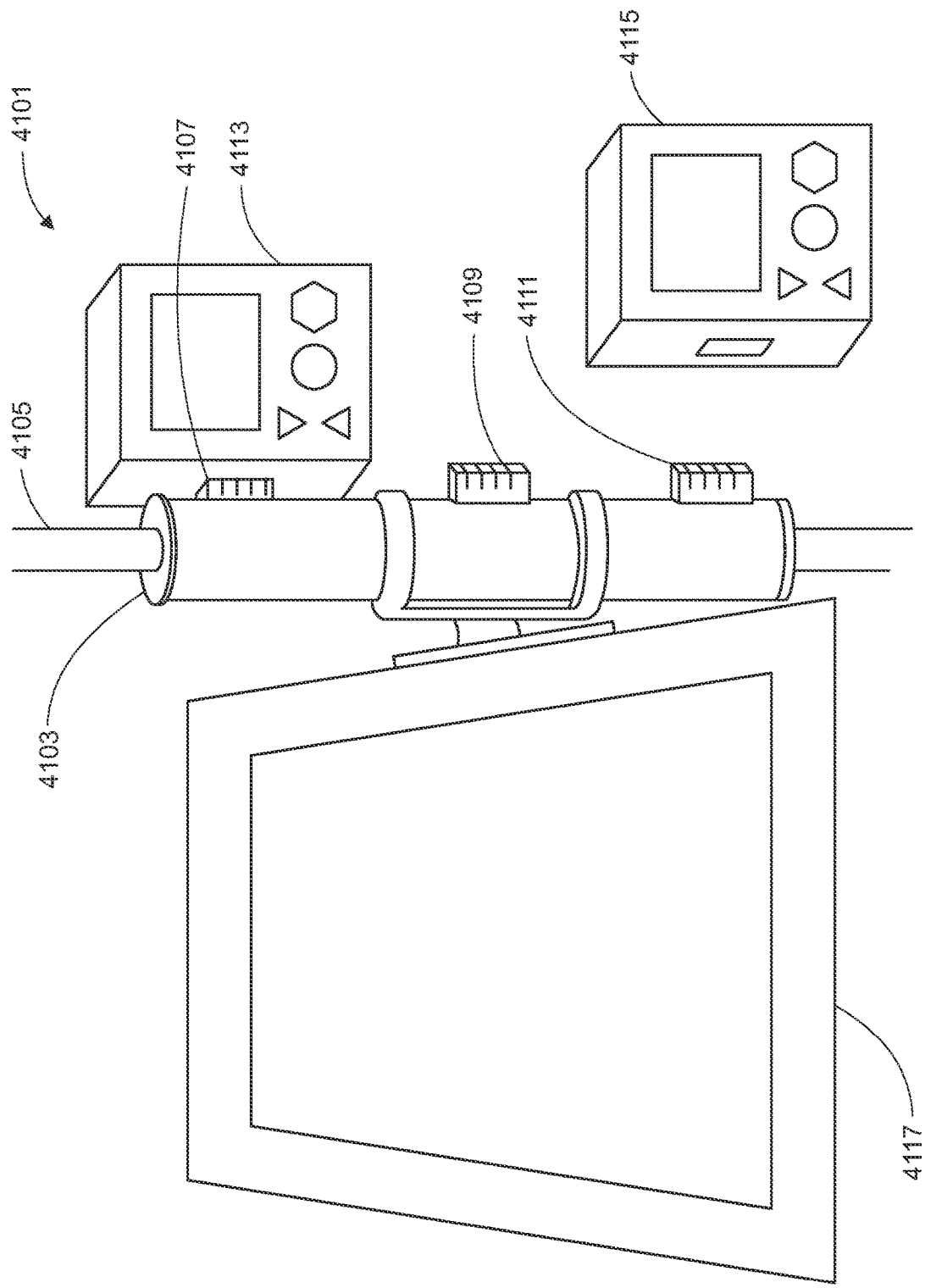
FIG. 41 shows an electronic patient-care system having a hub coupled to a pole in accordance with another embodiment of the present disclosure.

FIG. 41 shows an electronic patient-care system 4101 having a hub 4103 coupled to a pole 4105 in accordance with another embodiment of the present disclosure. The hub 4103 includes connectors 4107, 4109, and 4111 for receiving three respective infusion pumps, e.g., infusion pumps 4113 and/or 4115. The patient-care system 4101 includes a monitoring client 4117, e.g., a tablet, on one side of the pole 4105 and the infusion pumps attachable to the other side of the pole 4105 via the connectors 4107, 4109, and 4111. Although three connectors 4107, 4109, 4111 are shown, any arbitrary number of connectors may be used. Electronic patient-care system 4101 facilitates viewing of the monitoring client 4117 and the infusion pumps, e.g., infusion pumps 4113 and 4115, attached to the connectors 4107 4109, 4111. Additionally, electronic patient-care system 4104 facilitates routing of the tubes. The tubes may be inserted from top to bottom of the infusion pumps or may be routed from the monitoring client 4117's side (e.g., using a tube organizer on the pole 4105) on a side of the pole 4105. The monitoring client 4117 may be articulated. The pole mount of the hub 4103 may clamp to the pole 4105 or slip over the step in the pole 4105 that is available in some adjustable poles. The pole mount of the hub 4103, show here as being tubular shaped, may, in other embodiments, be a rectangular shape and/or may include the power supply, handle, and/or hub hardware. In some embodiments, the hub 4103 may be a cradle to route electrical connections.

Figure 42:
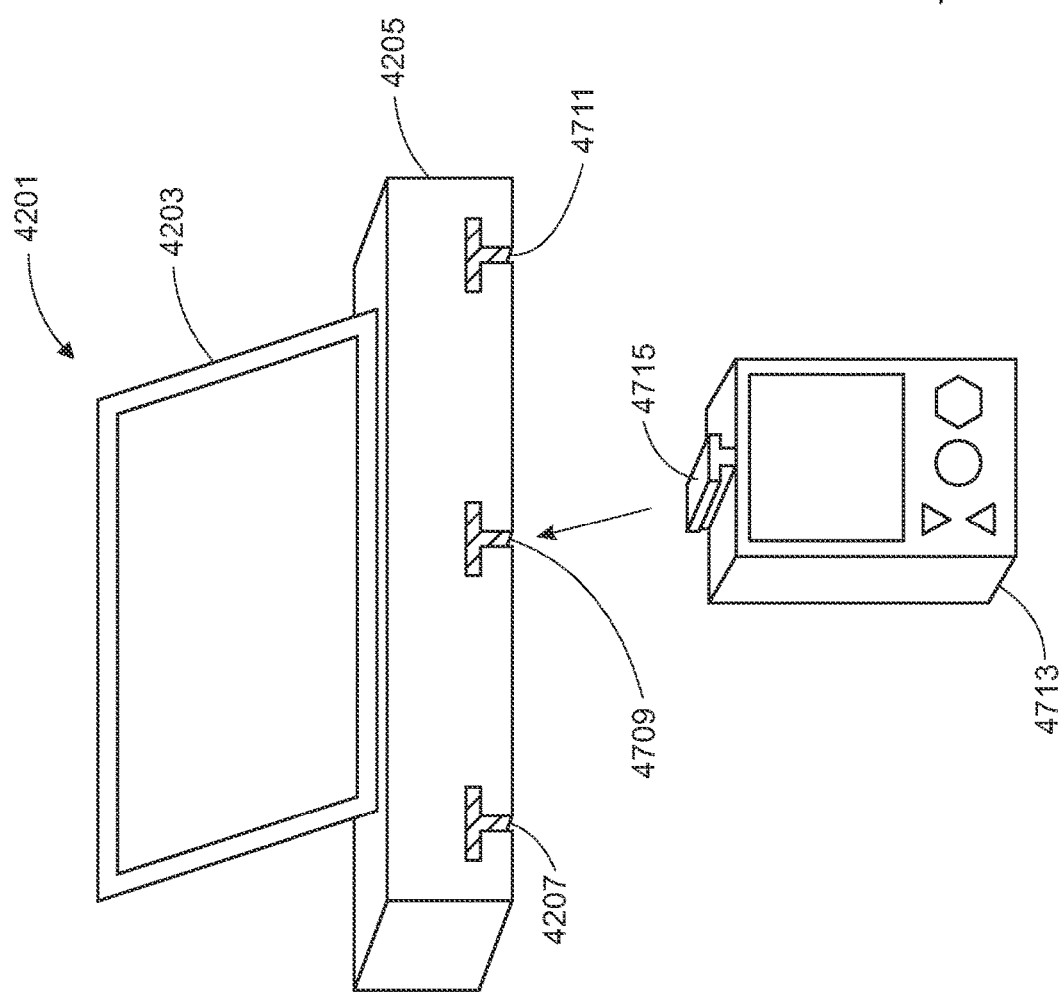
FIG. 42 shows an electronic patient-care system having a monitoring client coupled to a hub having notches for receiving patient-care devices in accordance with another embodiment of the present disclosure.
Figure 43:
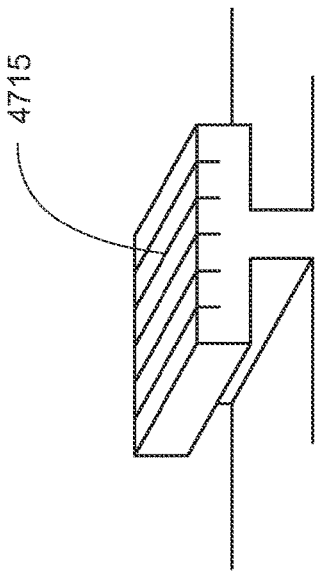
FIG. 43 shows a close-up view of a T-shaped connector for connecting with the notches of the hub as shown in FIG. 42 in accordance with another embodiment of the present disclosure.

FIG. 42 shows an electronic patient-care system 4201 having a monitoring client 4203 coupled to a hub 4205 having notches 4207, 4709, 4711 for receiving patient-care devices, e.g., an infusion pump 4713, in accordance with another embodiment of the present disclosure. This infusion pump 4713 includes a sliding connector 4715 that slides into one of the notches 4207, 4709, 4711. The connector 4715 may be structurally sufficient and/or additional structural support may be added. The monitoring client 4203 may fold down, e.g., flat with the dock 4205. The dock 4205 may include reliefs for routing tubes, e.g., from left to right or up to down. In alternative embodiments, the infusion pump 4713 may attach to the dock 4205 such that it is raised in front of the dock's 4205 front plane facilitating vertical routing of the tubes. FIG. 43 shows a close-up view of a T-shaped connector, e.g., connector 4715 of FIG. 42, for connecting with the notches 4207, 4709, 4711 of the hub 4205 as shown in FIGURE.

Figure 44:
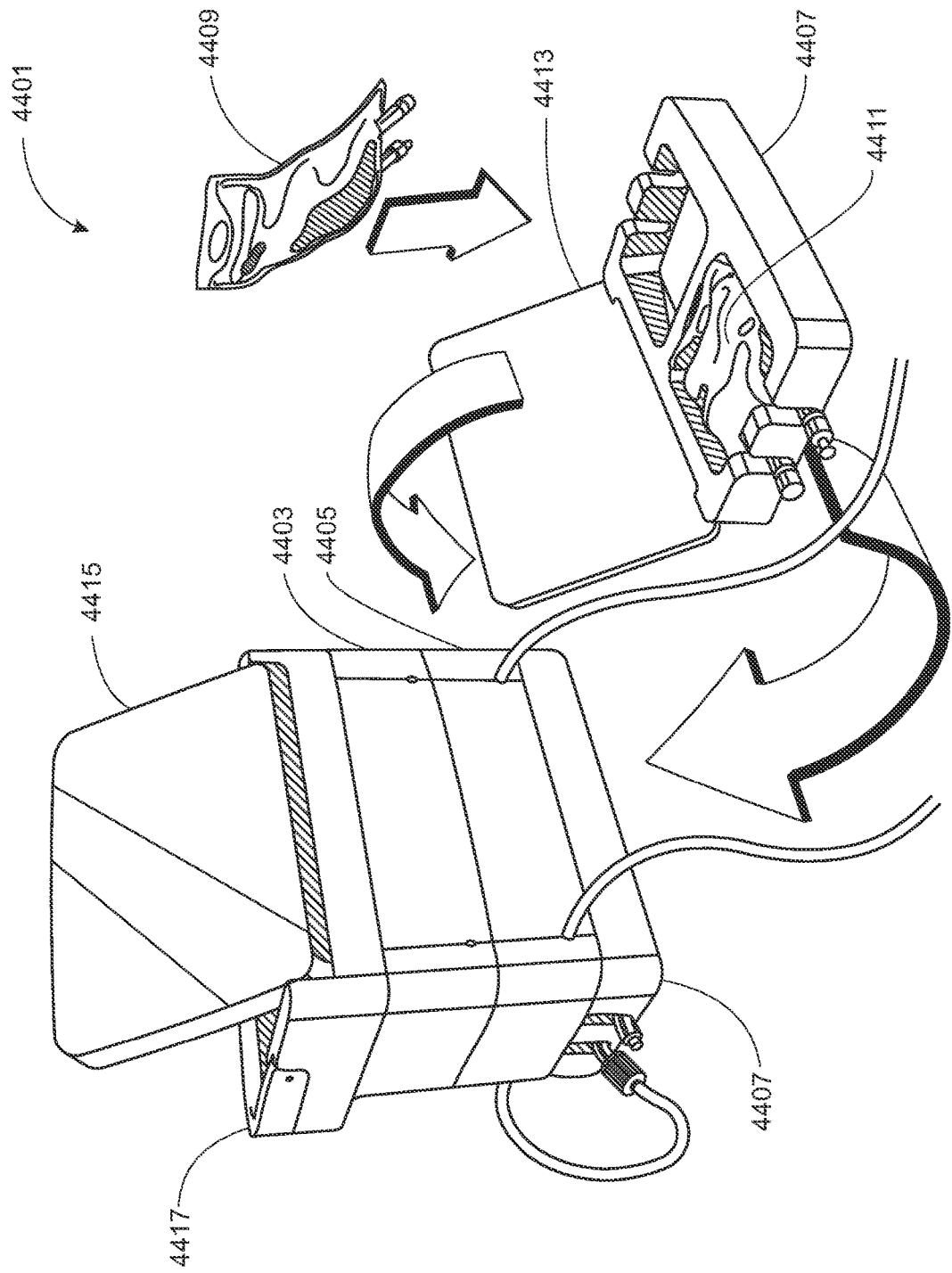
FIG. 44 shows an electronic patient-care system having stackable patient-care devices and a stackable container for housing an infusion bag in accordance with another embodiment of the present disclosure.

FIG. 44 shows an electronic patient-care system 4401 having stackable patient-care devices 4403, 4405 and a stackable container 4407 for housing an infusion bag, e.g., infusion bags 4411 and 4408, in accordance with another embodiment of the present disclosure. The stackable container 4407 includes a lid 4413 for securing the bags 4411, 4409 therein. The electronic patient-care system 4401 includes a monitoring client 4415 with a screen that may be folded down and a handle 4417 that may be pulled up for portability.

The infusion bags 4411 and 4407 may be microbags and may include an integrated flow rate monitor and/or an RFID tag embedded therein having a serial number or data (e.g., patient data) associated with the contents of the bags 4411 and/or 4407. In this specific embodiment, the microbags 4411 and 4407 may include an integrated flow rate meter, a drip counter, an integrated drip chamber, a communication link to communicate via the IV tube, and may include a power supply with or without a battery or AC/DC converter to power the electronics thereon. The IV communications may occur via an electrical conductor embedded into or attached to the intravenous tube, via electrical communication using the fluid within the intravenous tube as a conductive medium, using sounds waves traveling through the intravenous tube, or optically by using the fluid within the tube as an optical waveguide. The IV communications may be encrypted, e.g., using symmetric or asymmetric key encryption. The microbags 4411 and/or 4407 may include an optical communicator that communicates data (via an infusion tube) to an infusion pump describing a flow rate and/or the contents of the liquid contained therein. The microbags 4411 and/or 4407 may include an RFID and/or NFC tag at a pigtail that can interface with a drip counter which a reader may use to determine the contents and/or volume of the liquid inside of the microbags 4411 and/or 4407 (e.g., the information is encoded therein). The microbag 4411 and/or 4407 may include a bubble sensor (capacitive or ultrasonic) which communicates the estimation of bubble sizes to a monitoring client and/or hub. The microbags 4411 and/or 4407 may need to be within a predetermined distance from the patient as determined by NFC, and/or a ranging module before it will operate (e.g., open a valve and/or active an integrated flow rate meter, drip counter or drop chamber, a communication link, power supply etc.)

Figure 45:
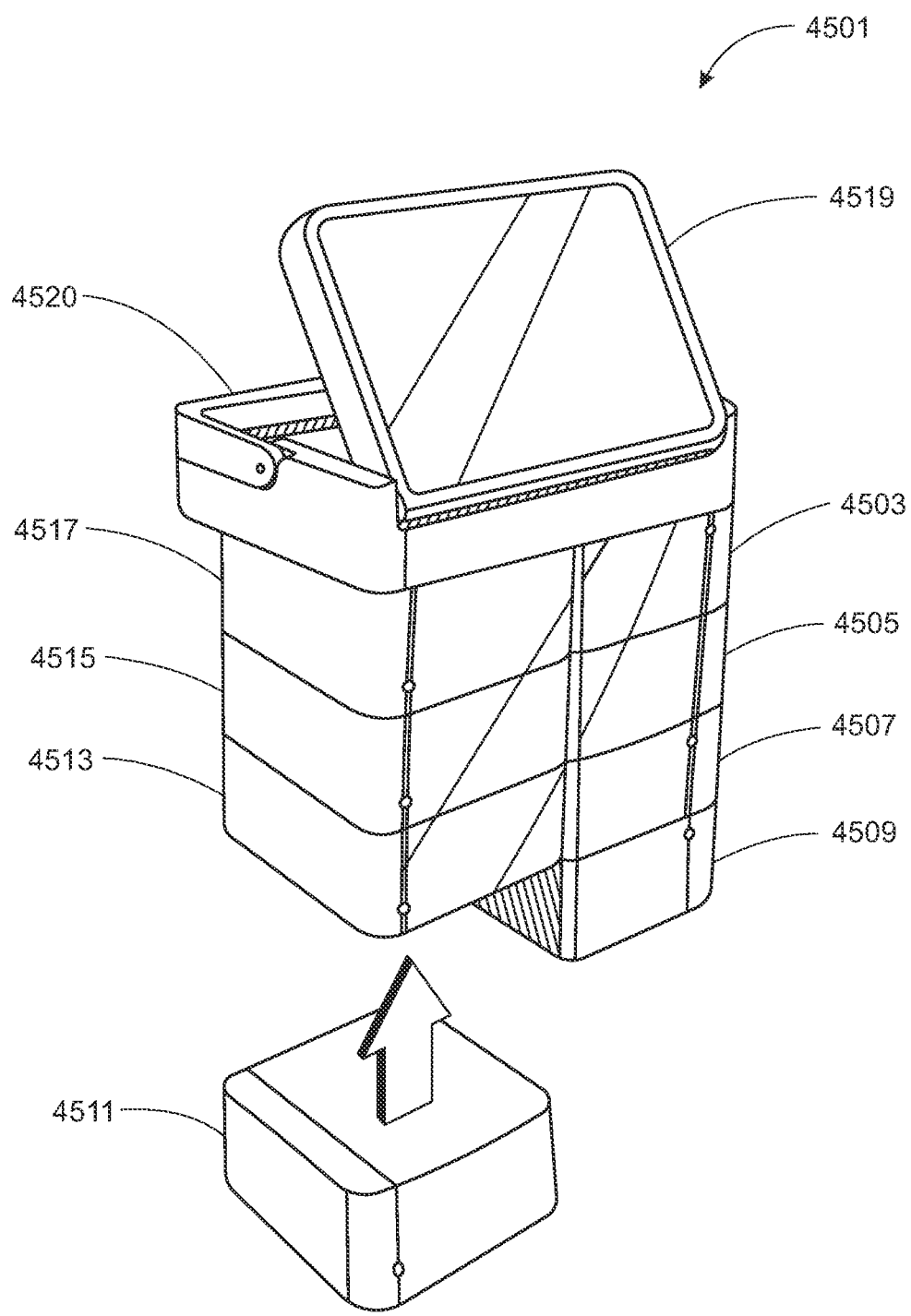
FIG. 45 shows an electronic patient-care system having stackable patient-care devices that are stackable next to another stack of patient care devices in accordance with yet another embodiment of the present disclosure.

FIG. 45 shows an electronic patient-care system 4501 having stackable patient-care devices 4503, 4505, 4507, 4509, 4511, 4513, 4515, 4517 that are stackable next to another one of the patient care devices in accordance with yet another embodiment of the present disclosure. The electronic patient-care system 4501 includes a monitoring client 4519 that includes a screen that may be folded down and a handle 4520 that may be pulled up for portability.

Figure 46:
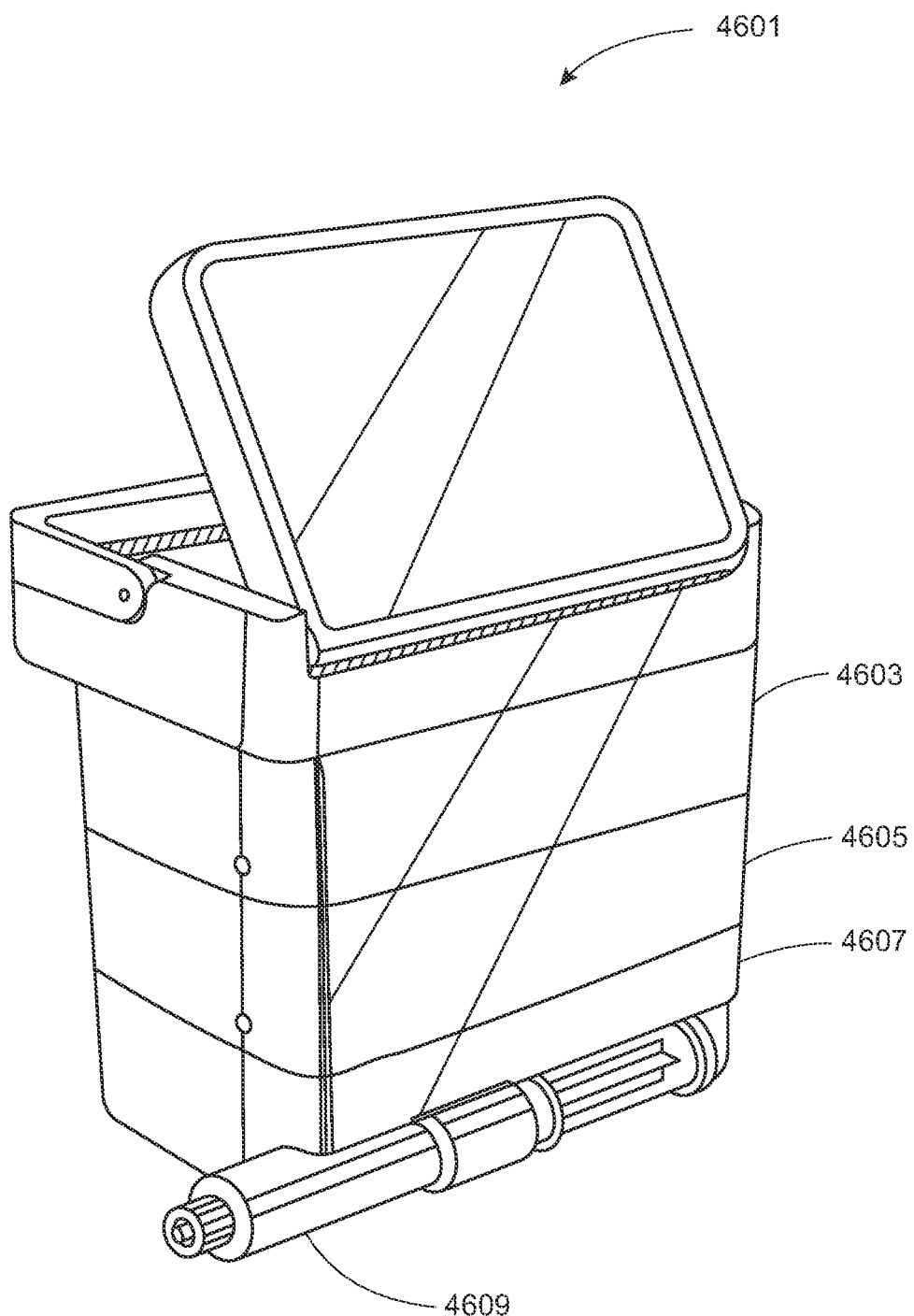
FIG. 46 shows an electronic patient-care system having stackable patient care devices with a syringe pump patient-care device having a single syringe in accordance with another embodiment of the present disclosure.

FIG. 46 shows an electronic patient-care system 4601 having stackable patient care devices 4603, 4605, 4607 with a syringe pump patient-care device 4607 having a single syringe 4609 in accordance with another embodiment of the present disclosure.

Figure 47:
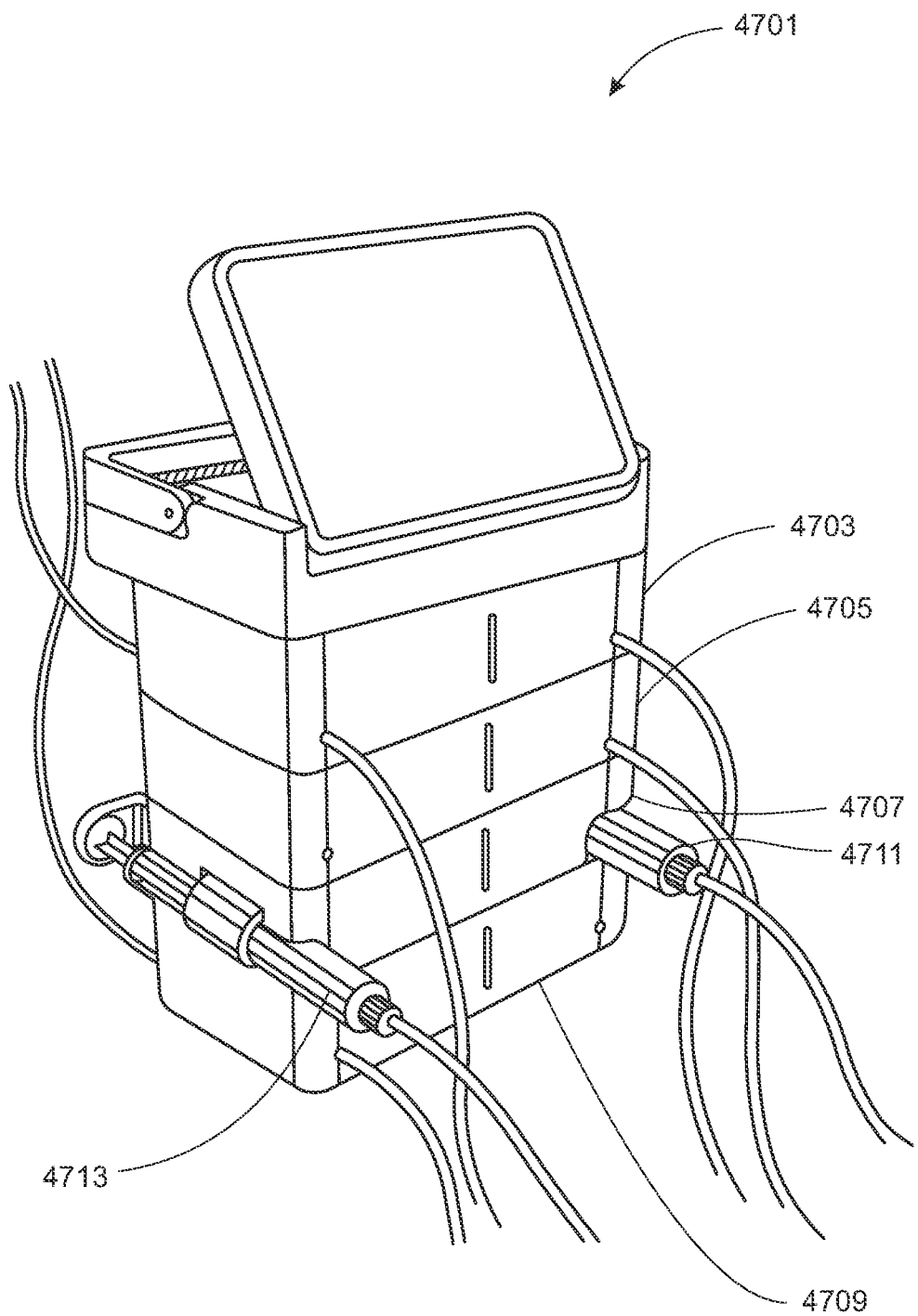
FIG. 47 shows an electronic patient-care system having stackable patient care devices with a syringe pump patient-care device having two syringes in accordance with another embodiment of the present disclosure.

FIG. 47 shows an electronic patient-care system 4701 having stackable patient-care devices 4703, 4705, 4707, 4709 with a syringe pump patient-care device 4707 having two syringes 4711, 4713 in accordance with another embodiment of the present disclosure.

Figure 49:
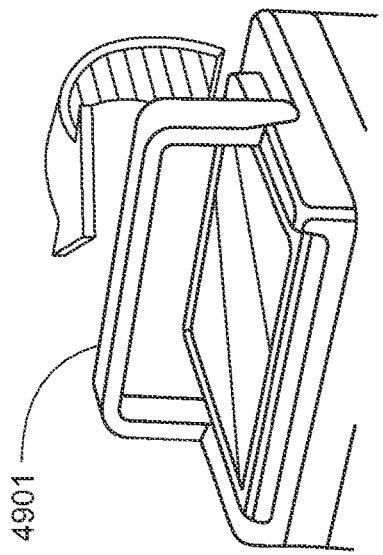
FIG. 49 is a close-up view of the handle of the electronic patient-care device of FIG. 48 in accordance with another embodiment of the present disclosure.
Figure 50:
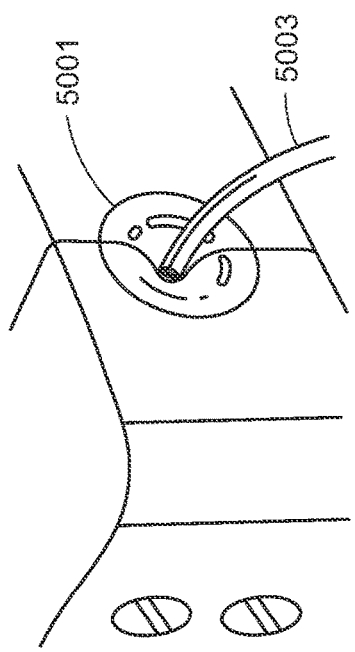
FIG. 50 is a close-up view of an infusion line port showing an infusion line positioned therethrough of the electronic patient-care system of FIG. 48 in accordance with another embodiment of the present disclosure.
Figure 48:
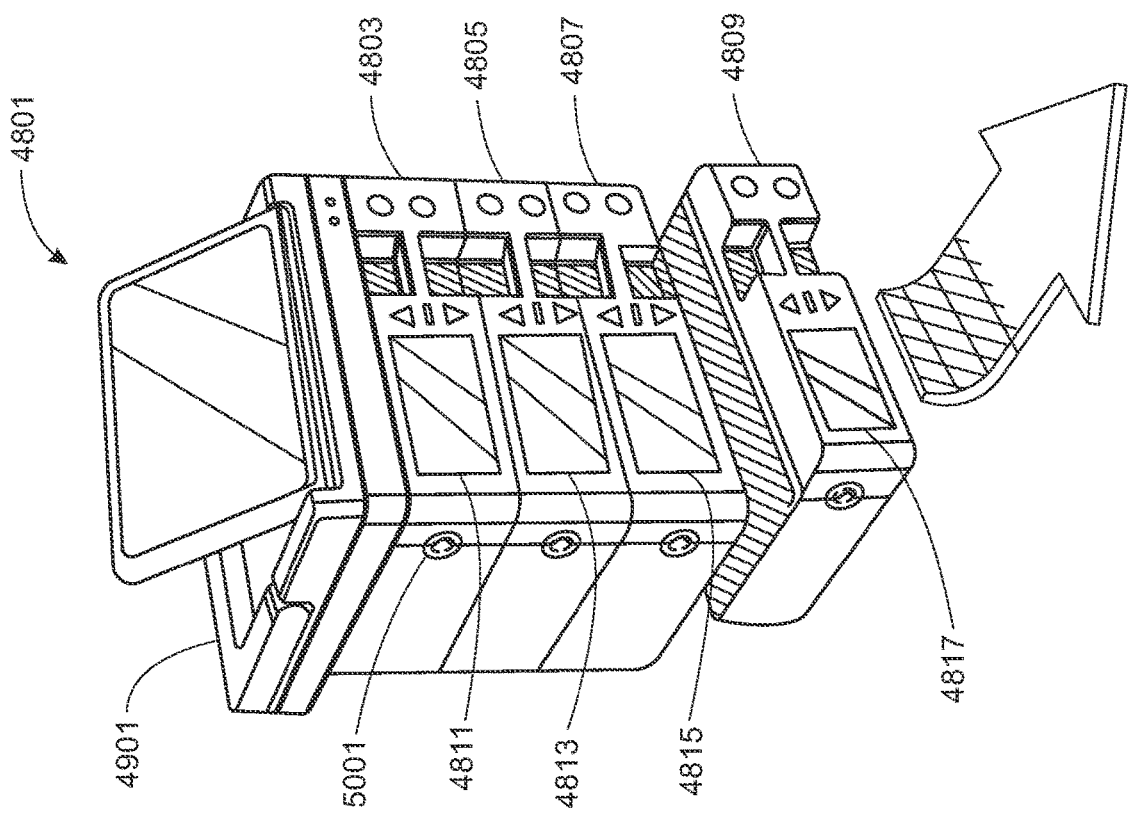
FIG. 48 shows an electronic patient-care system having stackable patient-care devices each having a display in accordance with another embodiment of the present disclosure.

FIG. 48 shows an electronic patient-care system 4801 having stackable patient-care devices 4803, 4805, 4807, 4809 each having a respective display (i.e., displays 4811, 4813, 4815, 4817) in accordance with another embodiment of the present disclosure. FIG. 49 is a close-up view of the handle 4901 of the electronic patient-care device of FIG. 48. FIG. 50 is a close-up view of an infusion line port 5001 showing an infusion line 5003 positioned therethrough of the electronic patient-care system 4801 of FIG. 48.

Figure 52:
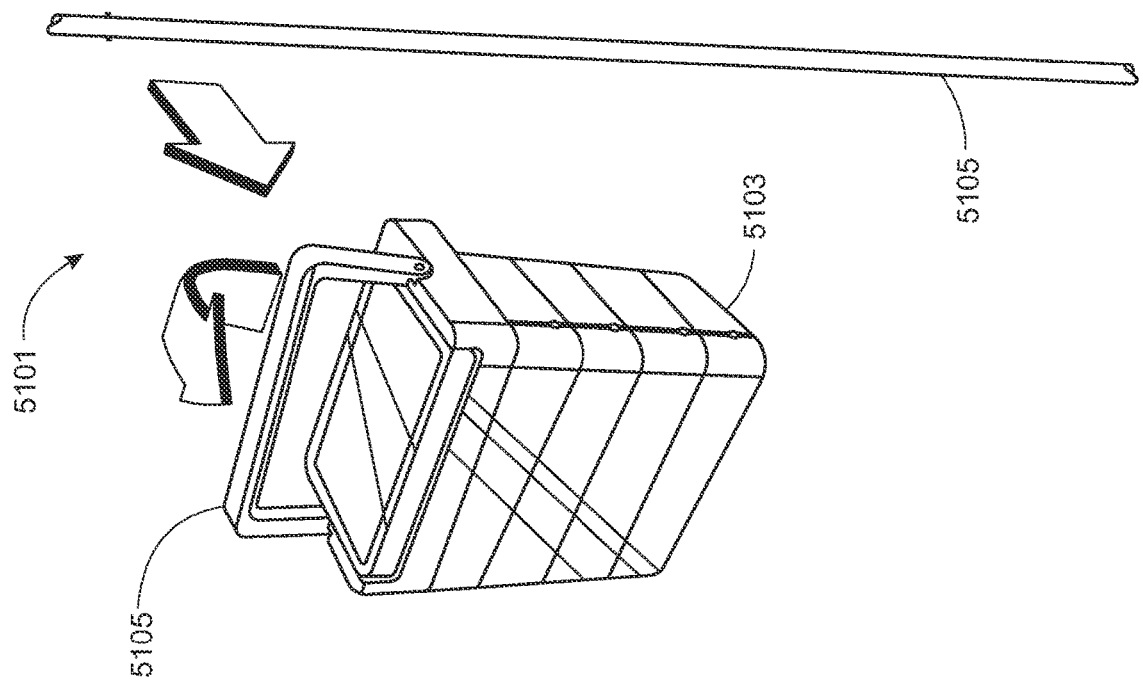
FIG. 52 shows an electronic-patient care system prepared for transport in accordance with another embodiment of the present disclosure.
Figure 51:
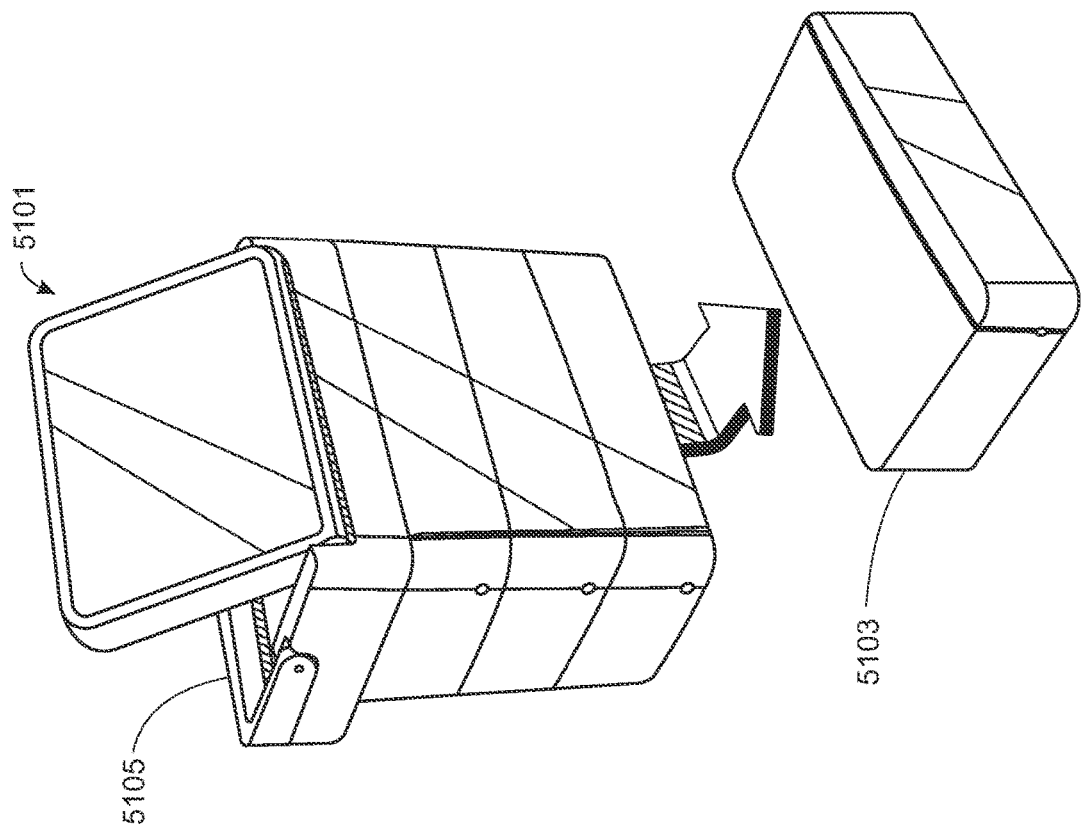
FIG. 51 shows another embodiment of an electronic patient-care system illustrating the removal of a stackable patient-care device in accordance with another embodiment of the present disclosure.

FIGS. 51-52 show another embodiment of an electronic patient-care system 5101 showing a removable stackable patient-care device 5102 in accordance with another embodiment of the present disclosure. FIG. 52 shows the handle 5103 being moved in a transport configuration to transport the electronic patient-care system 5101 with a pole 5105.

Figure 53:
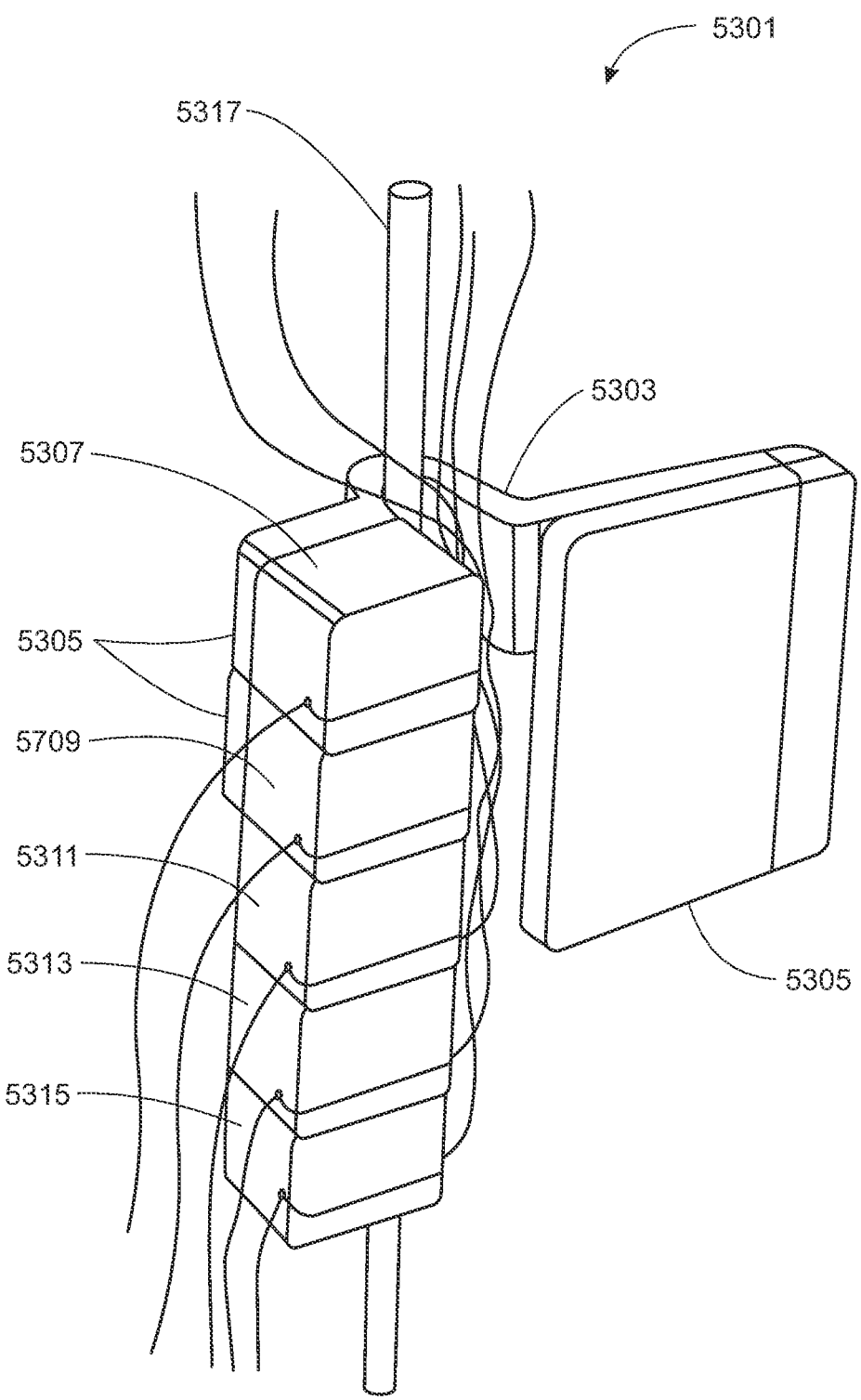
FIG. 53 shows an electronic-patient care system having stackable patient-care devices in accordance with another embodiment of the present disclosure.

FIG. 53 shows an electronic-patient care system 5301 coupled to a pole 5317 and having stackable patient-care devices 5307, 5309, 5311, 5313, 5315 that are coupled to a hub 5303 via a dock connectors 5305 in accordance with another embodiment of the present disclosure. The hub 5303 is coupled to a monitoring client 5305. The dock connectors 5305 connect to patient-care devices 5307 and 5309, which are connected to patient-care devices 5311, 5313, and 5315 via daisy-chained connections.

Figure 55:
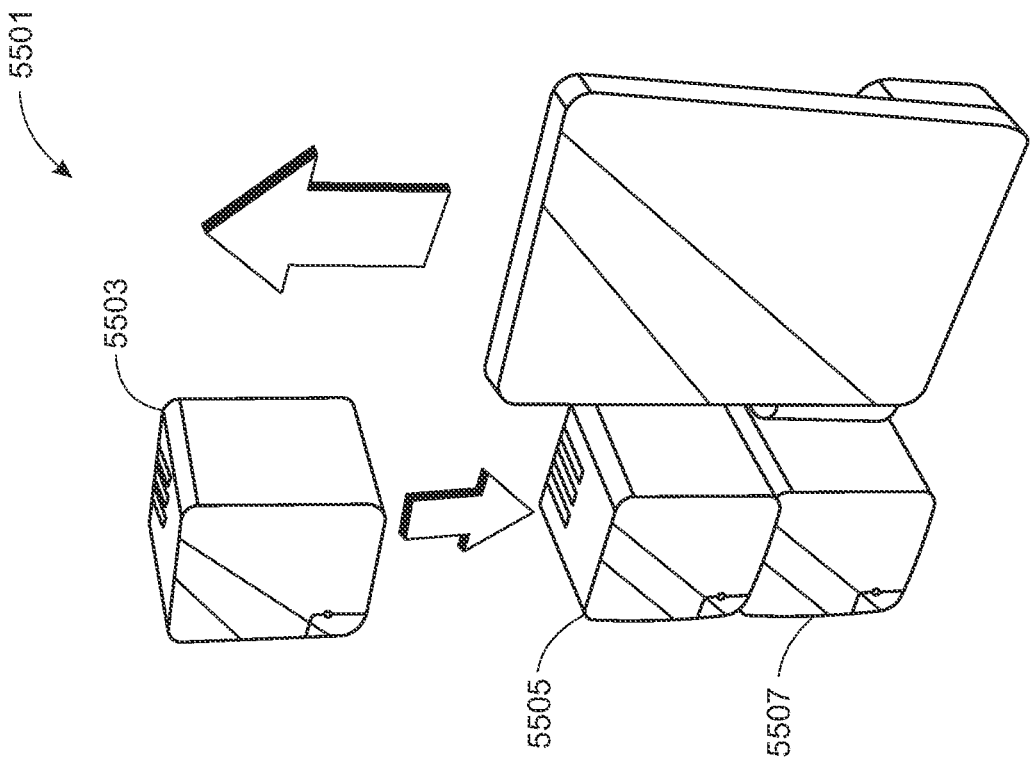
FIG. 55 shows an electronic-patient care system coupled to a pole and having stackable patient-care devices, stackable from the top down, in accordance with another embodiment of the present disclosure.
Figure 54:
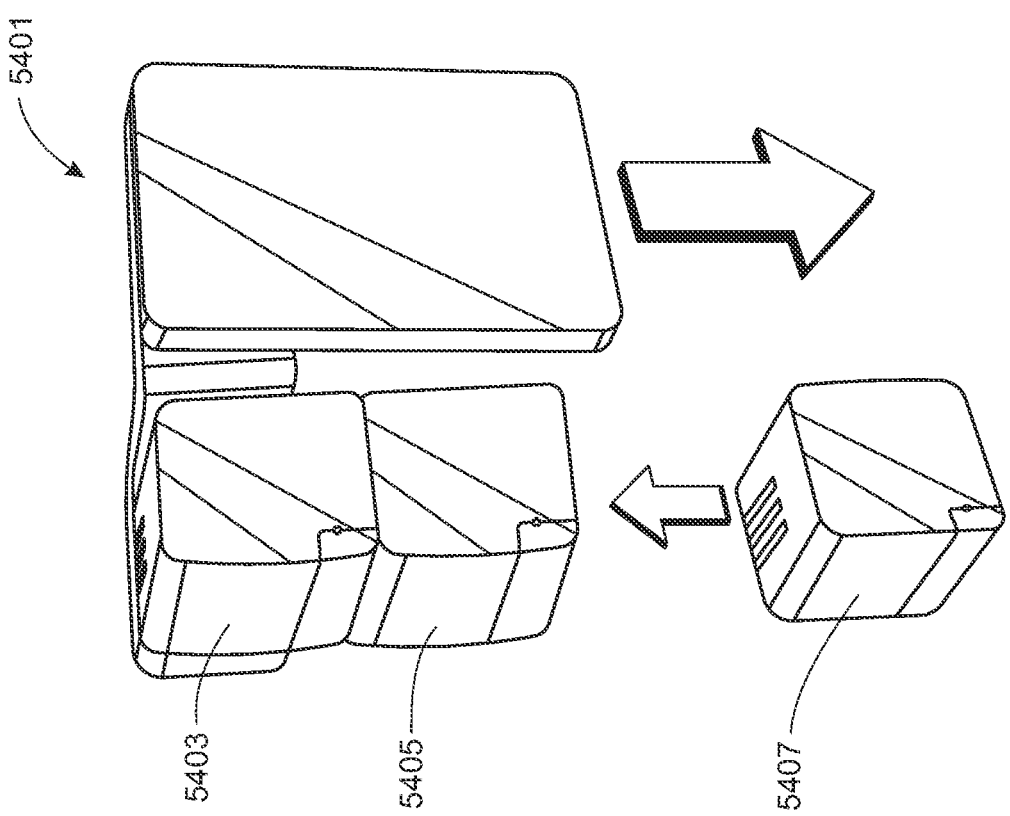
FIG. 54 shows an electronic-patient care system having stackable patient-care devices, stackable from the bottom up, in accordance with another embodiment of the present disclosure.

FIG. 54 shows an electronic-patient care system 5401 having stackable patient-care devices 5403, 5405, 5307, stackable from the bottom up, in accordance with another embodiment of the present disclosure. FIG. 55 shows an electronic-patient care system 5501 having stackable patient-care devices 5503, 5505, 5507 that are stackable from the top down, in accordance with another embodiment of the present disclosure.

FIG. 56 shows a perspective-view of a clutch system 5601 having a release handle 5603 for frictionally gripping to a pole 5605 in accordance with another embodiment of the present disclosure. FIG. 57 shows a back-view of the clutch system 5601 of FIG. 56 showing a transparent back for illustrating the use of the handle 5603 to engage clutches 5607 and 5609. FIG. 58 shows a top, cross-sectional view of the clutch system of FIG. 56.

Figure 59:
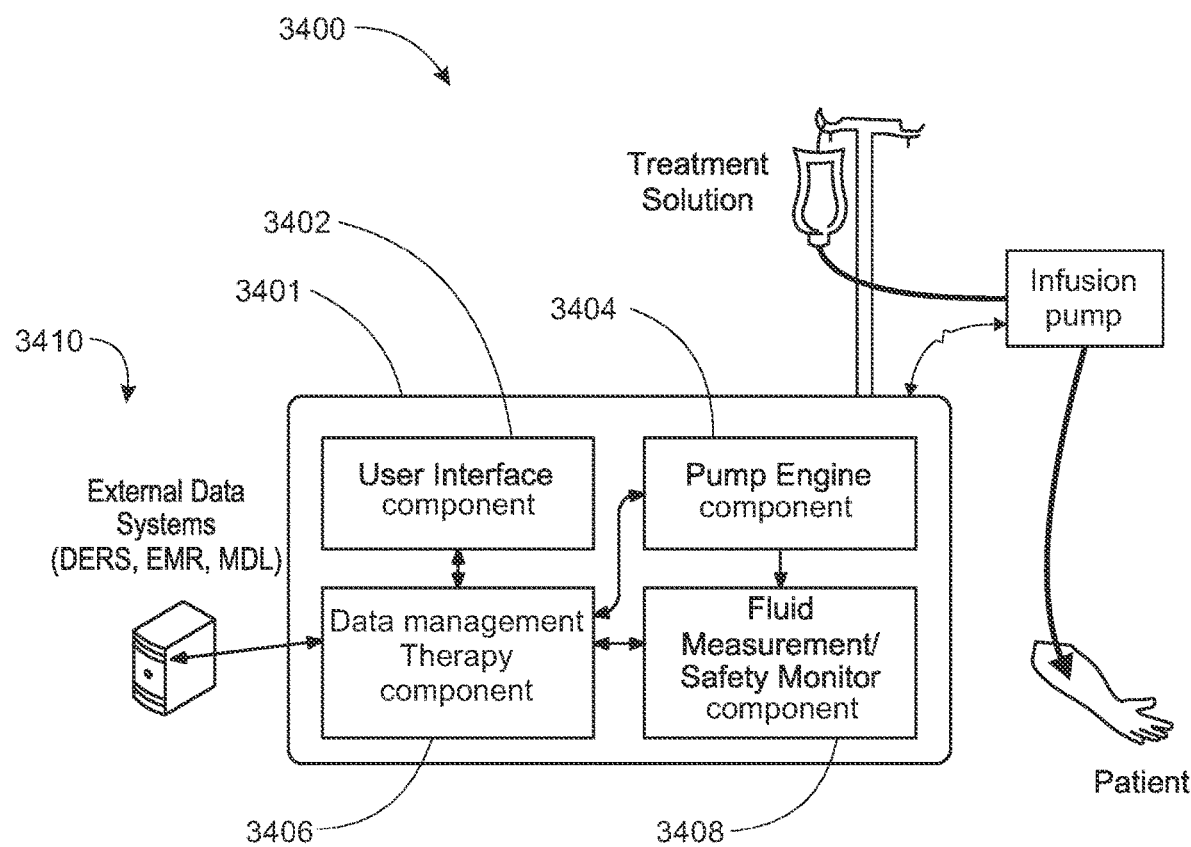
FIG. 59 is a block diagram of a system to control an infusion pump in accordance with an embodiment of the present disclosure.

FIG. 59 is a block diagram of a system 3400 to control an infusion pump in accordance with an embodiment of the present disclosure. System 3400 includes a user interface component 3402, a pump-engine component 3404, a data-management therapy layer component 3406, and a fluid measurement/safety monitor component 3408.

The components 3402, 3404, 3406, and 3408 may be implemented, for example, in hardware, software, software in execution, in digital logic, firmware, bytecode, in virtualization, using PLDs, FPGAs or PLAs, using one or more processors, or some combination thereof. For example, the components 3402, 3404, 3406, and 3408 may be an operative set of processor executable instruction configured for execution by one or more processors on a device 3401, e.g., the device 3401 may be a monitoring client disclosed herein. The components 3402, 3404, 3406, and 3408 may be stored on non-transitory, computer readable medium readable by one or more processor for execution by the one or more processors, e.g., the one or more processors may be in operative communication with the non-transitory, computer readable medium.

The user interface 3402 may be a touchscreen (or processor executable code to control a touchscreen) configured to receive user input, e.g., an infusion rate. The user interface 3402 may be used by an operator to set up treatment parameters and to see treatment status. The user interface 3402 can be used to adjust patient-treatment parameters during therapy, for guidance on the setup of the system 3400, and/or for post-treatment disassembly of the system 3400. The user interface 3402 may include a touchscreen and buttons. The user interface 3402 may be a resident software application on the device 3401 or may be executed by a remote or separate component, such as on a handheld device or a computer at a nurses' station. For example, the user interface 3402 may be implemented by the remote communicator 11 or the other monitoring clients 1, 4 of FIG. 1, 3, 5, 7, 8 or 9, a smartphone, a tablet, a pc, a tablet computer, or the like.

The data management therapy component 3406 can communicate with one or more external data systems 3410. For example, the data management therapy component 3406 may compare the a patient's 3412 ID with electronic medical records 3410 to determine if the therapy entered (e.g., an infusion rate) via the user interface component 3402 is: (1) safe for the patient; (2) conforms with the patient's 3412 ailment, condition, disease, and/or therapy plan; (3) is not contraindicated by another medication or treatment; (4) and does not require the presence of a specialists not-determined to be within the proximity to the patient 3412 (as determined by an RFID tag, voice authentication, facial-recognition, username/pas sword identification or verification, secure signatures, or the like).

The data management therapy component 3406 may include all treatment settings, may verify settings with the external data systems 3410, and can log treatment history such as flow rates, drug settings, vital signs, etc. to the electronic medical records of the external data systems 3410. The data management therapy component 3406 may also set parameters for any safety monitors. If the data management therapy component 3406 confirms the treatment, the setting is sent to the pump engine component 3404.

The pump engine component sends 3404 sends the patient-treatment parameters, e.g., an infusion rate, to the infusion pump 3414. The infusion pump 3414 may be any infusion pump disclosed herein. In some embodiments of the present disclosure, the pump engine component 3404 only sends an infusion rate to the pump 3414. The pump may have fluid measurement capability that is redundant to a flow meter or is the primary fluid measurement of the system 3406.

The fluid measurement/safety monitor component 3408 may serve as a watchdog for the other pump engine component 3404, can receive flow data from a flow meter (not shown), and may serve as a watchdog for the pump 3414. The fluid measurement/safety monitor component 3408 can determine if a fault or error condition exists, e.g., the infusion rate as measured is outside of a predetermined range or is beyond a threshold, and can communicate a stop command to the pump 3414 to stop the pump 3414. Additionally or alternatively, the fluid measurement/safety monitor component 3408 can communicate to a mechanical occlusion device (not shown) to stop the flow of the infusion fluid to the patient 3412.

Additionally or alternatively, the fluid measurement/safety monitor component 3408 may receive feedback on flow rate as well as patient-condition parameters, e.g., heart rate, temperature, vital signs, etc. If any of the parameters monitored by the fluid measurement/safety monitor component 3408 are outside of a predetermined range, an alert, such as a text message or email, is issued, e.g., to a monitoring device, a remote communicator, other monitoring clients, a smartphone, a tablet, a pc, a tablet computer, or the like. Additionally or alternatively, a mechanical fluid the fluid measurement/safety monitor component 3408 can communicate to a mechanical occlusion device (not shown) to stop the flow of the infusion fluid to the patient 3412.

Figure 60:
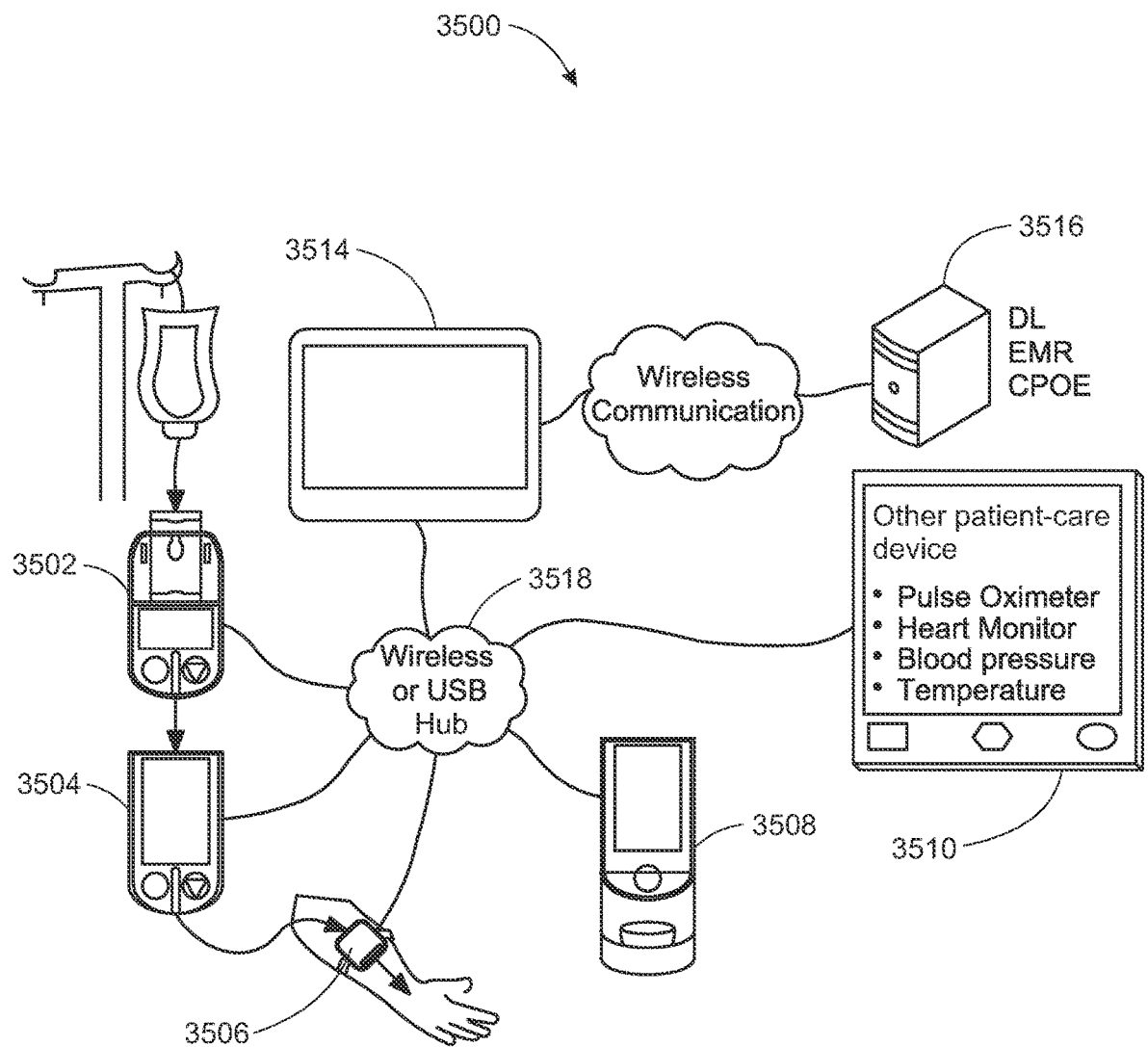
FIG. 60 is a block diagram of an electronic patient-care system having a hub for communicating with several electronic patient-care devices in accordance with an embodiment of the present disclosure.

FIG. 60 is a block diagram of system 3500 for communicating with several electronic patient-care devices 3502, 3504, 3506, 3508, 3510 in accordance with an embodiment of the present disclosure.

System 3500 includes a wireless or USB based dock or hub 3518. The dock 3518 is coupled to a drip counter 3502, an infusion pump 3504, a wearable system monitor 3506, a pill dispenser 3508, and other device 3510. The other device may be, for example, various patient-condition devices, such as a pulse oximeter device, a heart monitor device, a blood pressure device, and a temperature device. The devices 3502, 3504, 3506, 3508, 3510 communicate with the monitoring client, e.g., a tablet 3514, which in turn communicates with one or more servers 3516. The one or more servers 3516 may be, for example, a server of the facility services 8, the online drug databases 9 or drug adverse event network 9, the patient's personal HER 19', or a treatment outcomes database 10 of FIG. 1, 3, 5, 7, or 8.

The wireless communications between the wireless or USB dock 3518 and devices 3502, 3504, 3506, 3508, 3510 may be, for example, WiFi, Bluetooth, low energy Bluetooth, Zigbee, a communications link capable of ranging, near field communications, RFID communications, and the like.

The tablet 3514, in some embodiments of the present disclosure, may be the primary programming and monitoring interface. The tablet 3514 may be configured for a single patient or may be configured when docked into a dock 3518 or when the tablet 3514 identifies a patient (e.g., the tablet 3514 may download patient-treatment parameters after a patient's ID is entered into the tablet 3514 manually, through an RFID reader, a barcode reader, etc.).

The tablet 3514 may communicate patient-condition parameters or patient-treatment parameters to the one or more servers 3516. The one or more servers 3516 may store the patient-condition parameter or patient-treatment parameters. The tablet 3514 may communicate the patient-care parameters, e.g., the patient-condition parameters or the patient-treatment parameters, in real time (i.e., with at least one time constraint such as a deadline).

The tablet 3514 may connect to the dock 3518 wirelessly, through a USB cable, or may dock thereto. The tablet 3514, in some embodiments, receives power and data through one or more wired connections from the dock 3518.

The infusion pump 3504 may be a low rate infusion pump (e.g., can deliver 0.1-10 milliliters per hour), a medium flow rate infusion pump (e.g., can deliver 10-300 milliliters per hour), a high flow rate infusion pump (e.g., can deliver 300-1000 milliliters per hour), an infusion pump that switches between the various flow rate settings, or some combination thereof. The infusion pump 3504 may be inserted into the hub 3518 through a receiving portion; that is, the hub 3518 may also be a dock (not shown in FIG. 60). The infusion pump 3504, in some embodiments of the present disclosure, receives power and data through one or more wired connections from the hub 3518. The infusion pump 3504 may be configured to be undocked from the hub 3518 and can continue to operate while being carried by the patient. The infusion pump 3504 may be sent to a pharmacy for configuration and/or to be attached to an infusion bag (also referred to as an IV bag). In some embodiments, the infusion pump 3504 may be configured to operate only with a specific bag and/or a specific patient.

The wearable system monitor 3506 may be the wearable system monitor 131 of FIG. 1, 3, 5, 7, 8, or 9. In some embodiments, the wearable system monitor 3506 may read patient identification off of a smart arm-band, e.g., via RFID, can provide watchdog functionality for any of the other devices 3502, 3504, 3508, 3510, can track flow rate, detect air, monitor vitals, or include a call button integrated thereon. The wearable system monitor 3506 can occlude flow in response to an error condition. The wearable system monitor 3506 may communicate wirelessly with the hub 3518 or the infusion pump 3504.

Figure 61:
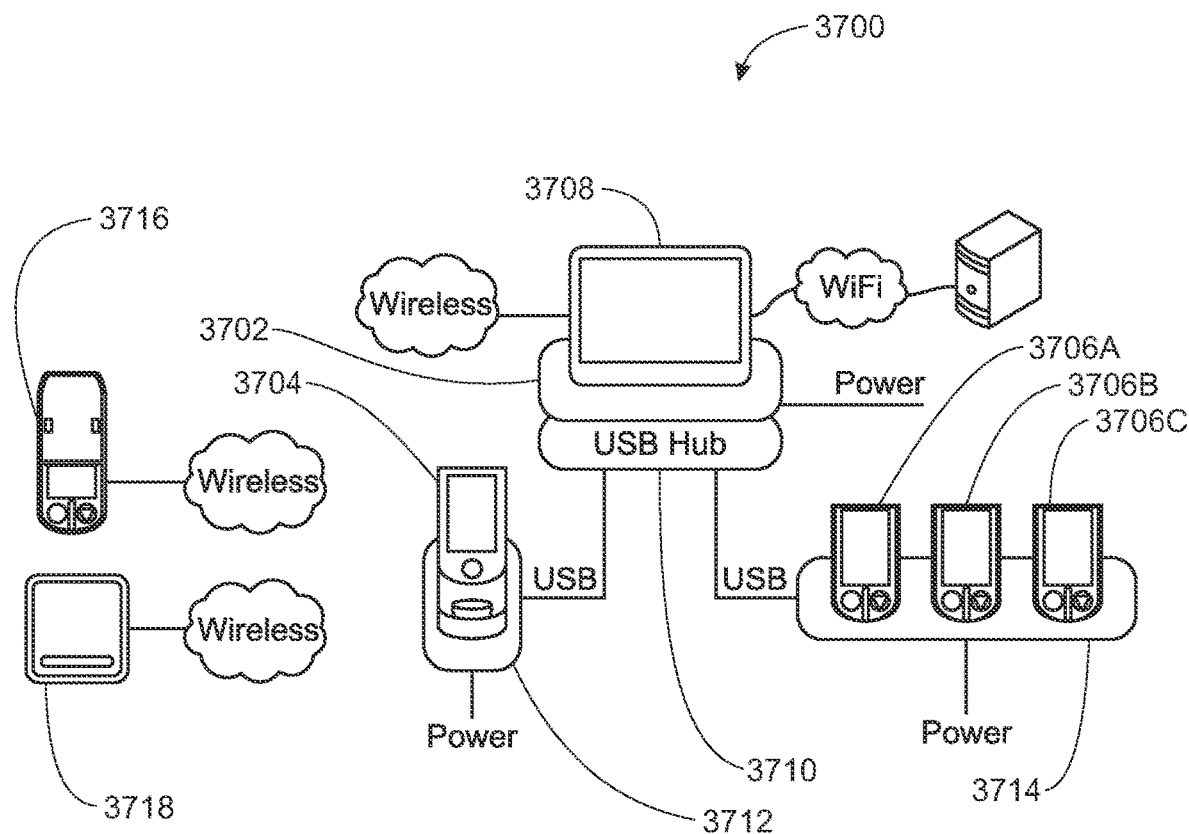
FIG. 61 is a block diagram of an electronic patient-care system having a dock connectable to patient-care devices through USB connections in accordance with an embodiment of the present disclosure.

FIG. 61 is a block diagram of an electronic patient-care system 3700 having a dock 3702 connectable to patient-care devices 3704, 3706A-3706C through USB connections in accordance with an embodiment of the present disclosure. System 3700 includes a dock 3702 which receives a tablet 3708. The dock 3702 is coupled to a hub 3710 which includes USB connections and can connect to docks 3712 and 3714 through USB connections. Dock 3712 receives the pill dispenser 3704. The dock 3714 receives infusion pumps 3706A-3706C. Docks 3712 and 3714 provide power to the devices 3704, 3706A-3706C docked thereto.

The dock 3702 supplies power to and charges the internal battery of the tablet 3708. The dock 3702 is also coupled to an USB hub 3710, which the tablet 3708 is a host. The flow meter 3716, e.g., a drip counter, and the wearable system monitor 3718 communicate wirelessly to the tablet 3708 via an antenna and transceiver on the tablet 3708 and/or via a transceiver and antenna on the dock 3702. As will be appreciated in light of this disclosure, flow meter 3716 and wearable system monitor 3718 may be operatively coupled with, or otherwise have integrated therein, transceivers and antennas such as communication modules 124 and antennas 122 of FIG. 1, so as to facilitate the wireless communication with the tablet 3708.

Figure 62:
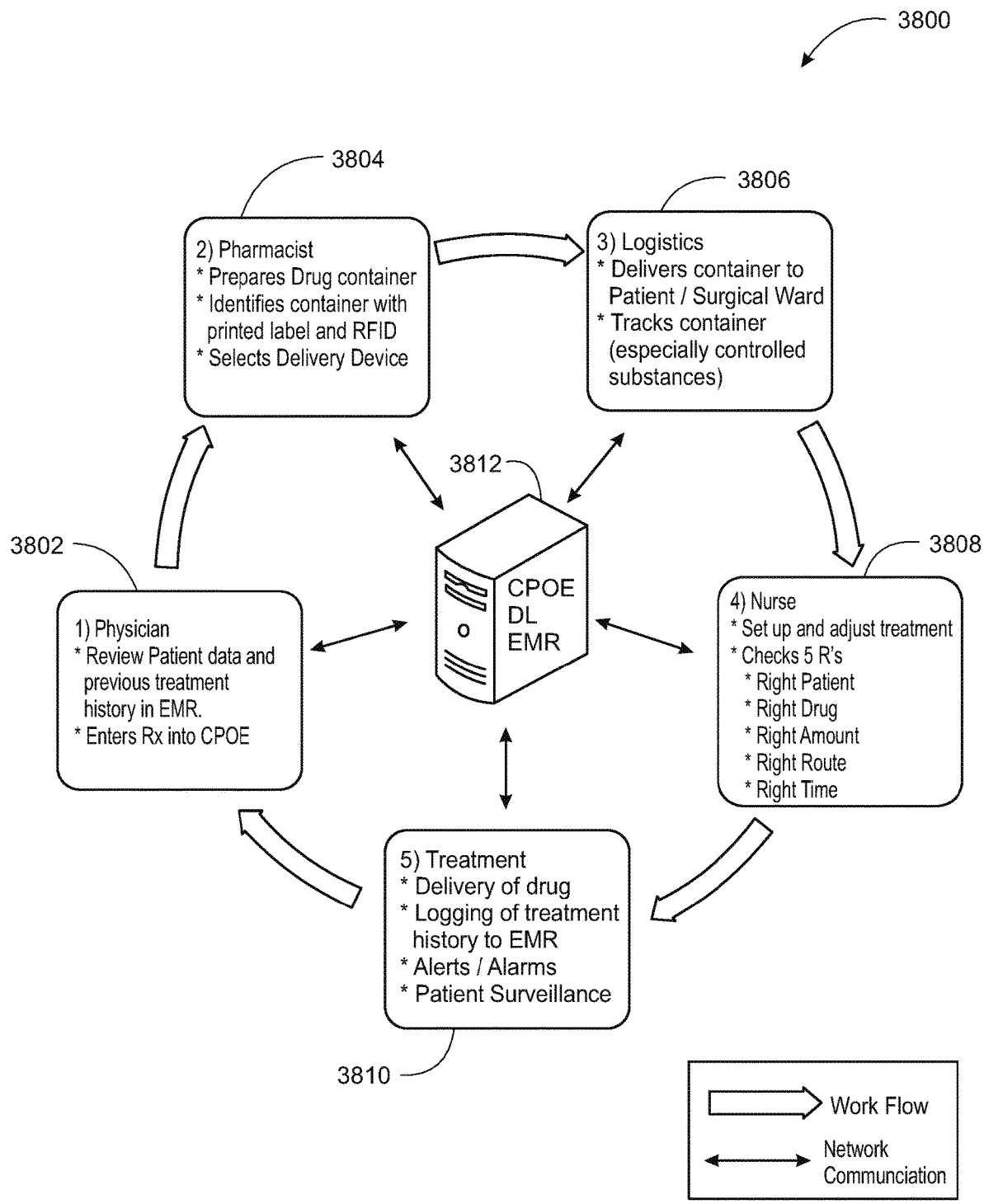
FIG. 62 is a process diagram showing several stages of electronic patient-care in accordance with an embodiment of the present disclosure.

FIG. 62 is a process diagram 3800 showing several stages of electronic patient-care in accordance with an embodiment of the present disclosure. The process diagram 3800 may be a method for electronic patient-care for use, for instance, with the example systems of FIGS. 1, 3, 5, 7, 8, and 9. Process diagram 3800 includes stages 3802-3810. Stage 3802 includes the steps of a physician reviewing patient data and previous treatment history in electronic medical records, and entering a prescription into a computerized physician order entry server 3812.

Stage 3804 includes the steps of a pharmacist preparing a drug container, identifying a container with a printed label and/or an RFID, and selecting a delivery device. Stage 3806 includes the steps of delivering a container to a patient or a surgical ward, and tracking the container, e.g., a controlled substance. Stage 3808 includes the steps of a nurse setting up and adjusting treatment, and checking the 5R's (right patient, right drug, etc). Stage 3810 includes the steps of delivering the drug, logging the treatment history into an electronic medical records, issues and alerts or alarms, and patient surveillance, e.g., monitoring the patient.

Figure 63:
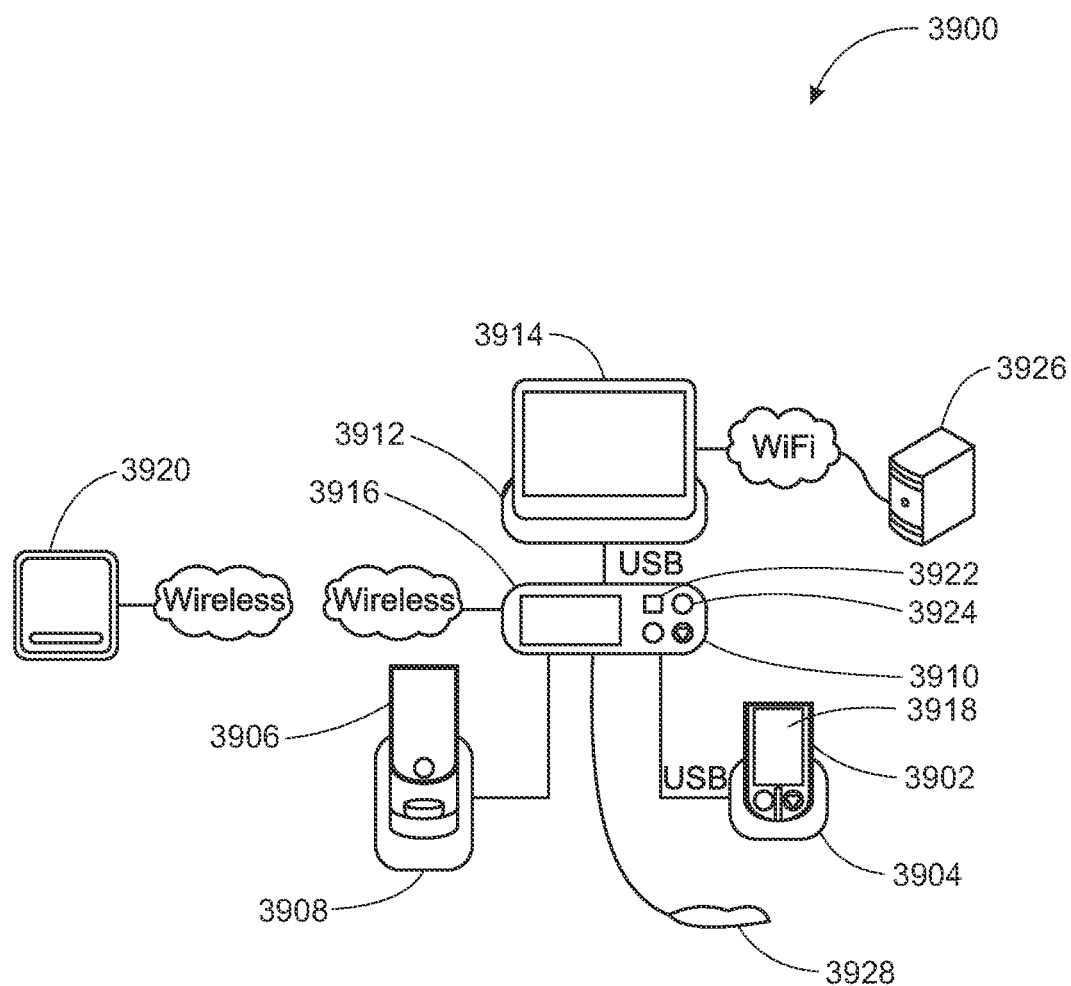
FIGS. 63-66 show several arrangements of an electronic patient-care system in accordance with an embodiment of the present disclosure.

FIG. 63 shows a system 3900 having an infusion pump 3902 docked to a dock 3904, a pill dispenser 3906 docked into a dock 3908, and a hub 3910 for interfacing with the docks 3904 and 3908 via USB cables. The hub 3910 also interfaces with a tablet dock 3912 that receives the tablet 3914. Additionally or alternatively, the tablet 3914 communicates with the hub 3910 wirelessly. The tablet 3914 may issue an alert and/or alarm when the mode or technology used for communicating changes, e.g., when changing from wired to wireless or from wireless to wired.

The hub 3910 includes a display 3916 and provides an interface between the tablet 3914 through the dock 3912. The hub 3910 can support a GUI displayed on the display 3916 (which may be a touchscreen) for programming, setup guidance, status, displaying alerts, displaying alarm, etc.

In some embodiments of the present disclosure, the hub 3910 includes all of the patient-safety circuitry enabling the system 3900 to be fully fault tolerant of any faults or errors that may occur within or regarding the tablet 3914, and the user interface necessary for patient safety is either on the hub 3910 or on a display of a patient-care devices 3906 and 3902 (e.g., the infusion pump 3902 include a display 3918, but not explicitly shown device 3906). For example, the hub 3910 may require user confirmation (e.g., via a touchscreen of the hub 3910) of an infusion rate and drug to be delivered prior to sending the request or command for the infusion rate to the infusion pump 3902. Additionally or alternatively, in some embodiments, the infusion pump 3902 requests user confirmation of the infusion rate and drug to be delivered prior to operation (e.g., via a touchscreen of the infusion pump 3902).

The hub 3910 may sound audible indicators for help guidance, alert prompts, alarm prompts, may include independent safety systems to monitor safety critical tasks, may be a fail-safe system for putting patient-care devices into a safety state when an alert or alarm condition occurs, may include independent sensors for critical sensors, may include an independent time base or real-time clock for time critical patient-care devices, e.g., real-time patient-care devices, may include a battery backup to power the patient-care devices through a USB cable, and may include a battery charging to circuit for charging the internal battery therein.

The hub 3910 may include a power entry module for AC or DC power supply and can receive power from a standard AC power outlet. The hub 3910 may satisfy the requirements for isolation and electromagnetic compatibility according to IEC-60601. The hub 3910 converts the AC power to a regulated DC power to be used to charge an internal backup battery, provide power to various circuitry therein, or to power the patient-care devices 3906, 3902 via their respective USB cables.

The hub 3910 may include IEC-60601 compliant power supply that is selectable or programmable to allow the attached patient-care device to request a power parameter, e.g., a voltage, duty cycle, DC or AC power etc., from the hub 3910. The hub 3910 may include one or more independent power supplies that are independent from the primary as defined by IEC-60601.

The hub 3910 includes a backup battery that may be used to supply power via the USB cables or other cables (not explicitly depicted). The hub 3910 may include its own battery charging circuit, e.g., a constant-voltage/constant-current charging circuit.

The display 3916 of the hub 3910 may display alarms or alerts based upon signals received from the patient-care devices 3902, 3906, 3920. For example, the hub 3910 may periodically query the patient-care devices 3902, 3906, 3920, and if the hub 3910 does not receive a response from one or more of the patient-care devices 3902, 3906, 3920 or the tablet 3914, or otherwise one or more of the patient-care devices 3902, 3906, 3920 or the tablet 3914 becomes unresponsive, the display 3914 displays an alert or alarm. The alarm may indicate to the user that the patient-care device is unresponsive. The patient-care device may be identified by the monitoring client via serial number, infusion pump channel, drug being delivered by the infusion pump, a letter or number being displayed on the patient-care device, via visual mapping of the patient-care devices on the monitoring device, and the like. For example, the monitoring client 3914 may display a layout diagram of the patient-care devices 3902, 3906, 3920 on its screen to provide visual mapping of the devices. Thereafter, the problem device, dock, or hub may thereafter be represented as a flashing red device indicating to the user the device that is the subject of the alert and/or alarm. The hub 3910 may also include status lights, LEDs, a speaker, a vibrator, or other visual/audio indicator.

The hub 3910 may include, for example, buttons or other input devices, such as switches, a stylus input, and the like. In some embodiments of the present disclosure, only the hub 3910 issues alerts and/or alarms for the patient-care devices; however, in other embodiments, the patient-care devices 3902, 3906, 3920, or the tablet 3914 issues alerts and/or alarms.

The hub 3910 may include two separate processors, each being a watchdog to each other. The hub 3910 may also include various sensors, such as an ambient temperature sensor, a pressure sensor, a humidity sensor, etc. The sensors of the hub 3910 may be redundant to the sensors on the patient-care devices 3902, 3906, 3920 or the tablet 3914, or the hub 3910 may give the patient-care devices 3902, 3906, 3920, or the tablet 3914 access to the measurement taken by the sensors of the hub 3910.

The hub 3910 may include, for example, WiFi capabilities, Zigbee, Bluetooth, Low Energy Bluetooth, Xbee, Near Field Communication, ranging devices, or the like. The hub 3910 may also include various wired interfaces, such as for example, RS-232, SPI, CAN, USB, Ethernet connectivity, etc.

The hub 3910 may also include a failsafe line that is coupled to one or more of the on the patient-care devices 3902, 3906, 3920 or the tablet dock 3912 which, when pulled low, can cause a safety circuit to cause all of the patient-care devices 3902, 3906, 3920 or the tablet dock 3912, or the particular device that cause the fault, to enter into a fail safe mode. For example, an electrical conductor (i.e., a wire or line) may exists between the hub 3910 and one or more of that is coupled to a voltage source via a resistor (i.e., the line is "high"), and another circuit can couple the conductor to a ground (the conductor may be so-called "pulled low."). In some embodiments, but not all embodiments, of the present disclosure, when a patient-care device disclosed herein, such one or more of the patient-care devices 3902, 3906, 3920, or a monitoring client, such as a tablet 3914, enters into a fail-safe mode, only critical (a predetermined set) of software routines are enabled and/or only critical circuitry (a predetermined set) is powered. In some embodiments, but not embodiments, for example, all circuitry except for the motor driver circuitry of an infusion pump may be disabled, such as radios, displays, display drivers, or other circuitry. Additionally or alternatively, in some embodiments, but not all embodiments, some software routines or functionality may be disabled that are not necessary when a specific fail safe mode is entered, such as in an infusion pump, the software that displays configuration information may be disabled.

The hub 3910 may also include a camera 3922 may be used to allow access to the system 3900, or identify a patient, nurse or drug using facial-recognition software, or by reading a barcode (2D or 3D). The camera 3922 of the hub 3910 may also read drug information and check it against the one or more servers 3926 for accuracy, and to ensure the drug is being delivered to the correct patient. Additionally or alternatively, the hub 3910 may also include a microphone 3924 to identify a patient, nurse, or caregiver using voice-recognition software.

The hub 3910 may also include a scanner 3928 that is a barcode reader, an RFID reader, or a magnetic strip reader. The scanner 3928 may be used to allow access to the system 3900, or identify a patient, nurse or drug. The scanner 3928 of the hub 3910 may also read drug information and check it against the one or more servers 3926 for accuracy, and to ensure the drug is being delivered to the correct patient.

The hub 3910 may also include one or more components for execution by one or more processors therein. The hub 3910 may include a watchdog component for verifying at given intervals that a patient-care device is responding to communication queries (for example, a call and response challenge to each patient-care device every 5 seconds or other suitable interval, and if the hub 3910 receives no response, the hub 3910 "pulls" the safety line, i.e., indicates that an error condition exists), a watchdog circuit to monitor health and check voltage levels of various power supply voltages, a data integrity check to verify that the data being transmitted through the hub 3910 is not corrupted and checks internal and routed packets to be sent to the tablet 3914 or a patient-care device disclosed herein, and a range checker to allow for checking of programmed thresholds. The hub 3910 may use data integrity checking.

The hub 3910 can monitor the tablet 3914 and can separately alarm when an error occurs on a patient-care device. In some embodiments of the present disclosure, the hub 3910 may include all of the safety-critical circuitry and software such that the system 3900 is wholly fault-tolerant of the tablet's 3914 failures and/or is wholly fault-tolerant of any failure modes of the tablet 3514.

The hub 3910 may include an application programming interface ("API") to display data on the display 3916 or the tablet 3914. The API may include a secure data class. A patient-care device can use the API to display on the display 3916 of the hub 3910. A patient-care device can send a message to the tablet 3914 instructing the tablet 3914 how to display an interface for the patient-care device. Additionally or alternatively, the hub 3910 sends a message to the tablet 3914 instructing the tablet 3914 to download an application from the one or more servers 3926 for displaying a user interface on the tablet 3914; the hub 3910 may send this message when a patient-care device is first connected to the hub 3910, either via a USB cable, or wirelessly (e.g., using pairing as described herein). Additionally or alternatively, the hub 3910 sends an instruction to the tablet 3914 for displaying a user interface for interfacing with the identified patient-care device.

Figure 64:
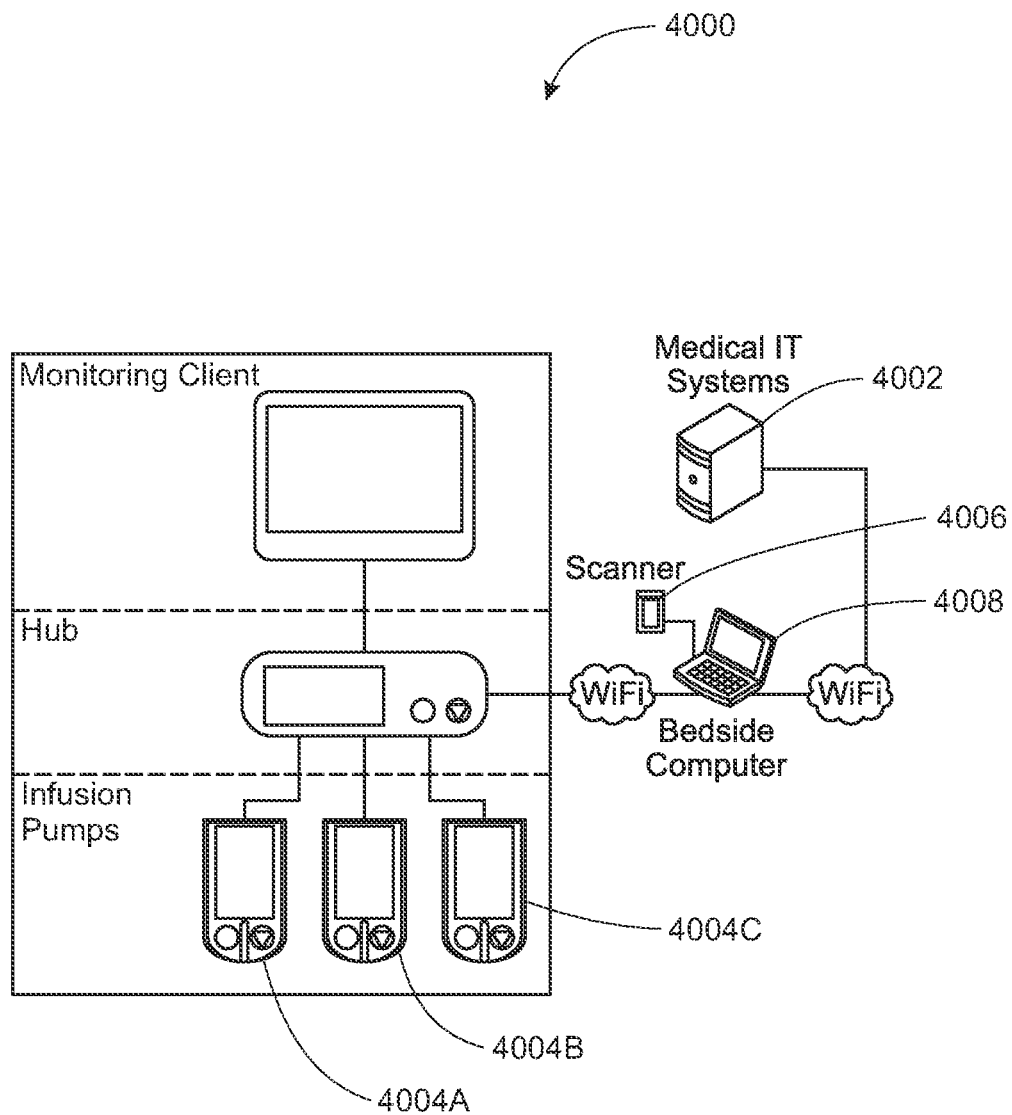
Figure 65:
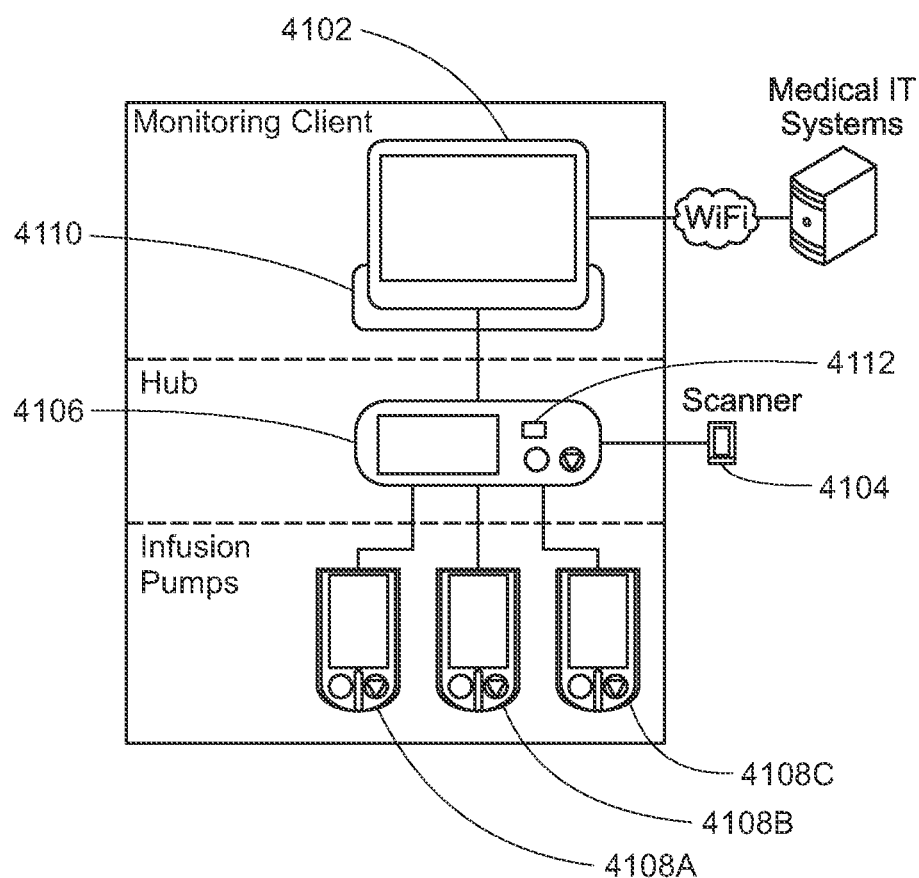

FIG. 64 shows a system 4000 for allowing an electronic medical records server of one or more servers 4002 to enter a prescription and send the prescription to an infusion pump of infusion pumps 4004A-4004C for confirmation using the scanner 4006 and/or using an interface of one or more of the infusion pumps 4004A-4004C. The prescription may be sent from EMR records on the server 4002 to the infusion pumps 4004A-4004C via an application. The application may on a bedside computer 4008 that can be used to determine clinician compliance with the prescription. In some embodiments, the application is on the monitoring client. The bedside computer 4008 may include an application for interfacing with an EMR server of the one or more servers 4002 through a standard API to download prescription and/or treatment regimes for use on the infusion pumps 4004A-4004C. The API may include a secure data class. In some additional embodiments, the hub communicates to the server 4001 through middleware as described above. Additionally or alternatively, referring to FIG. 65, the application for interfacing with the EMR server may be on the tablet 4102 as shown in FIG. 65. Although the scanner 4104 is shown as being coupled to the hub 4106, it may be attached to a patient-care device 4108A-4108C, or a tablet hub 4110. Rather than using the scanner 4104 to identify the medication, a camera 4112 may be used to identify the medication by reading a 2D or 3D barcode on the medication, e.g., on an infusion bag or pill container.

Figure 66:
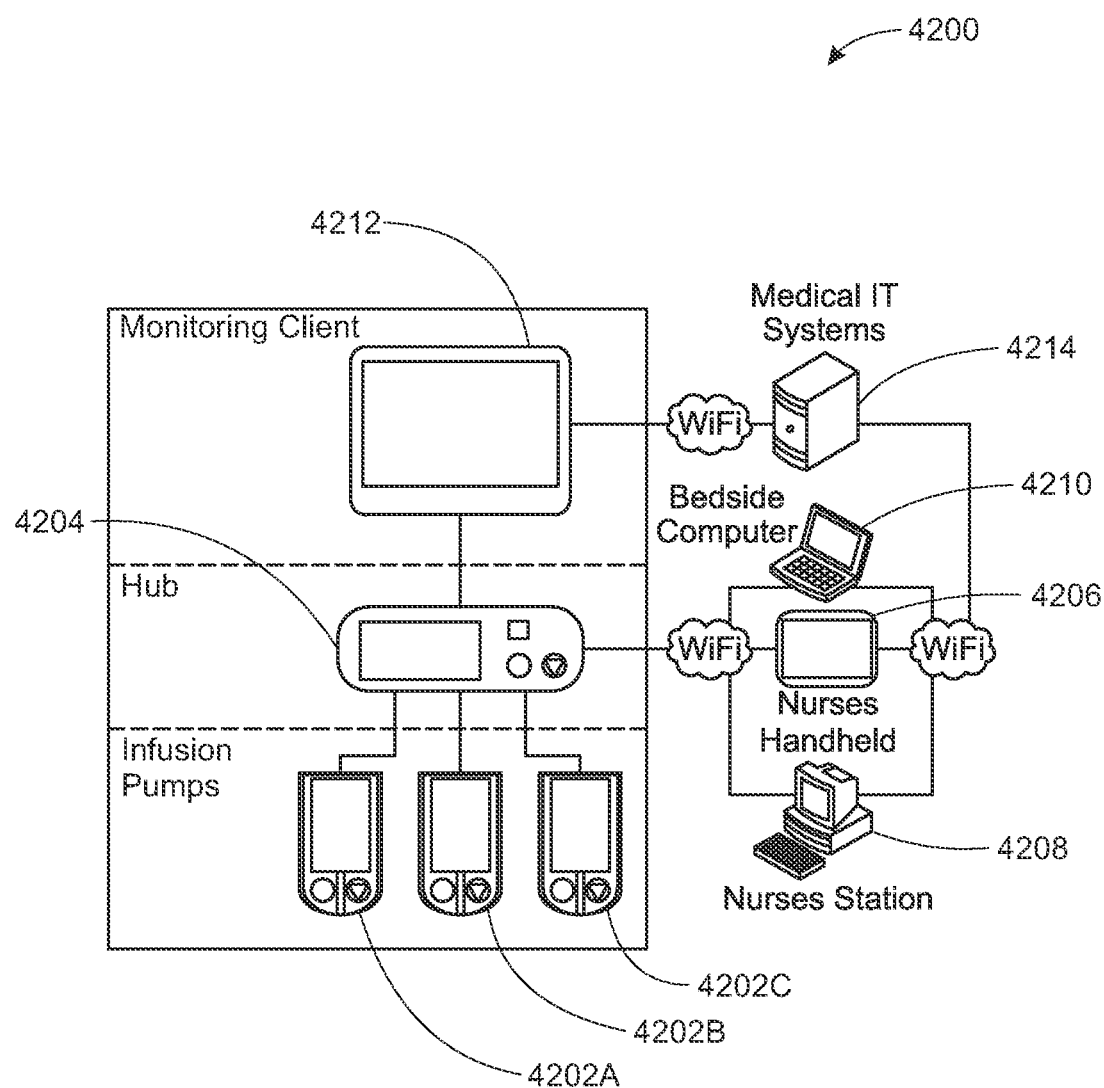

In FIG. 66, a system 4200 is shown. A patient-care device of the patient-care devices 4202A-4202C can broadcast patient-care parameters, e.g., a patient-treatment parameter such as an infusion rate to a subscribed device or a paired device (see FIG. 67). For example, the infusion pump 4202A, a hub 4204, a remote communicator 4206, a nurses' station 4208, or a bedside computer 4210 may receive the broadcasted signal, such as from a temperature probe (e.g., the infusion pump 4202A is subscribed to the temperature probe). The data may have different levels of encryption such that all data is not accessible to all clients (e.g., devices subscribing to another device may need to have a minimal level of security priority). The broadcasted signal may be the same signal received by the tablet 4212 or a subset thereof. The broadcasted messages may use a cross-platform protocol, e.g., http, https, etc.

Figure 67:
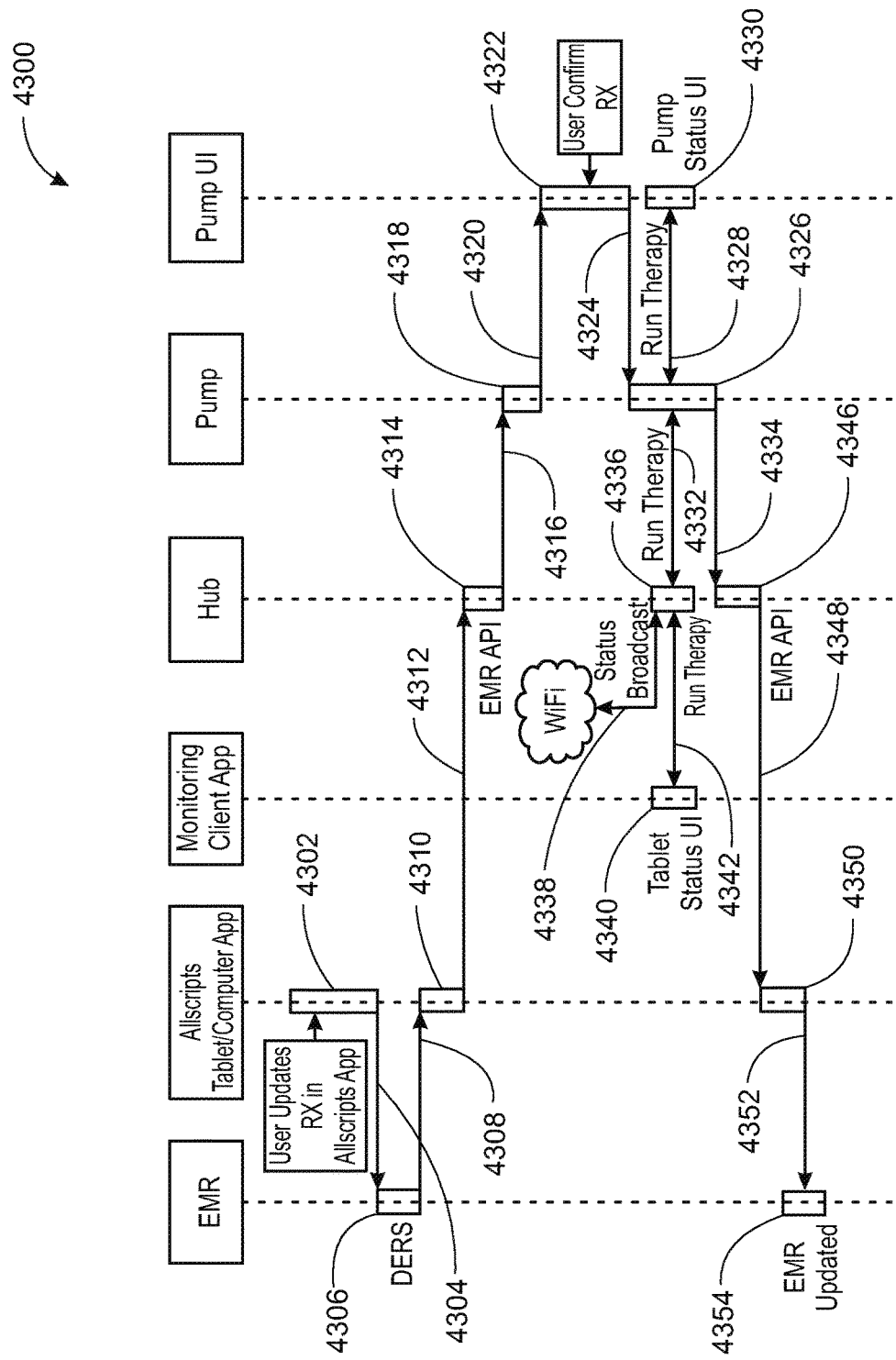
FIG. 67 shows a timing diagram of electronic patient-care treatment using an infusion pump in accordance with an embodiment of the present disclosure.

FIG. 67 shows a timing diagram 4300 of communications for the system 4200 of FIG. 66 in accordance with an embodiment of the present disclosure. The timing diagram 4300 illustrates the communications using an electronic medical records application programming interface executed on the tablet 4212. In some embodiments of the present disclosure, a drug error reduction system and/or Guardrails (or a cached version thereof) may be exists on the hub 4204 or an infusion pump of the infusion pumps 4202A-4202C to provide redundant patient safety when the system 4200 is not in operative communication with electronic medical records on the one or more servers 4214.

Timing diagram 4300 includes acts 4302 to 4354. During act 4302, a user updates a prescription in an application ("app") in a computer or a monitoring client, e.g., a tablet. Act 4304, the updated prescription is communicated to one or more servers in an EMR. Act 4306 checks the prescription in DERS to determine if it is safe for any patient or the particular patient, e.g., using predetermined criteria. Act 4308 communicates the safety information from the DERS system to the application on the monitoring client or computer application. Act 4310 receives the safety information. Act 4312 communicates the prescription from the tablet or computer application to an API of a hub, via an EMR application programming interface ("API") of the hub in act 4314. The API may include a secure data class. Act 4316 communicates the prescription to the pump in act 4318, which in turn, communicates the prescription to the pump in act 4320. Act 4322 requests user confirmation of the prescription on the pump user interface, e.g., via a touchscreen. After confirmation, the confirmation is communicated to the pump in act 4324, which is received in act 4326. During act 4326, therapy is started, and status information is communicated via act 4328 to the pump status UI, which is displayed to the user in act 4330.

Also, status information is communicated in acts 4332 and 4334. In act 4326, status information is received by the hub which broadcasts the status via WiFi in act 4338. The tablet application receives the status information during act 4340 from a communication of the status during act 4342. During act 4346, status information is interfaced via an EMR API, which is communicated to an tablet or computer app via act 4348, which is received in act 4350. The status information is communicated in act 4352 to the EMR database, which updates the EMR database in act 4354. In some embodiments communication between the EMR and the Allscripts Tablet/Computer App or the Hub is through middleware (e.g., middleware on the monitoring server 3 of FIG. 1).

Figure 68A:
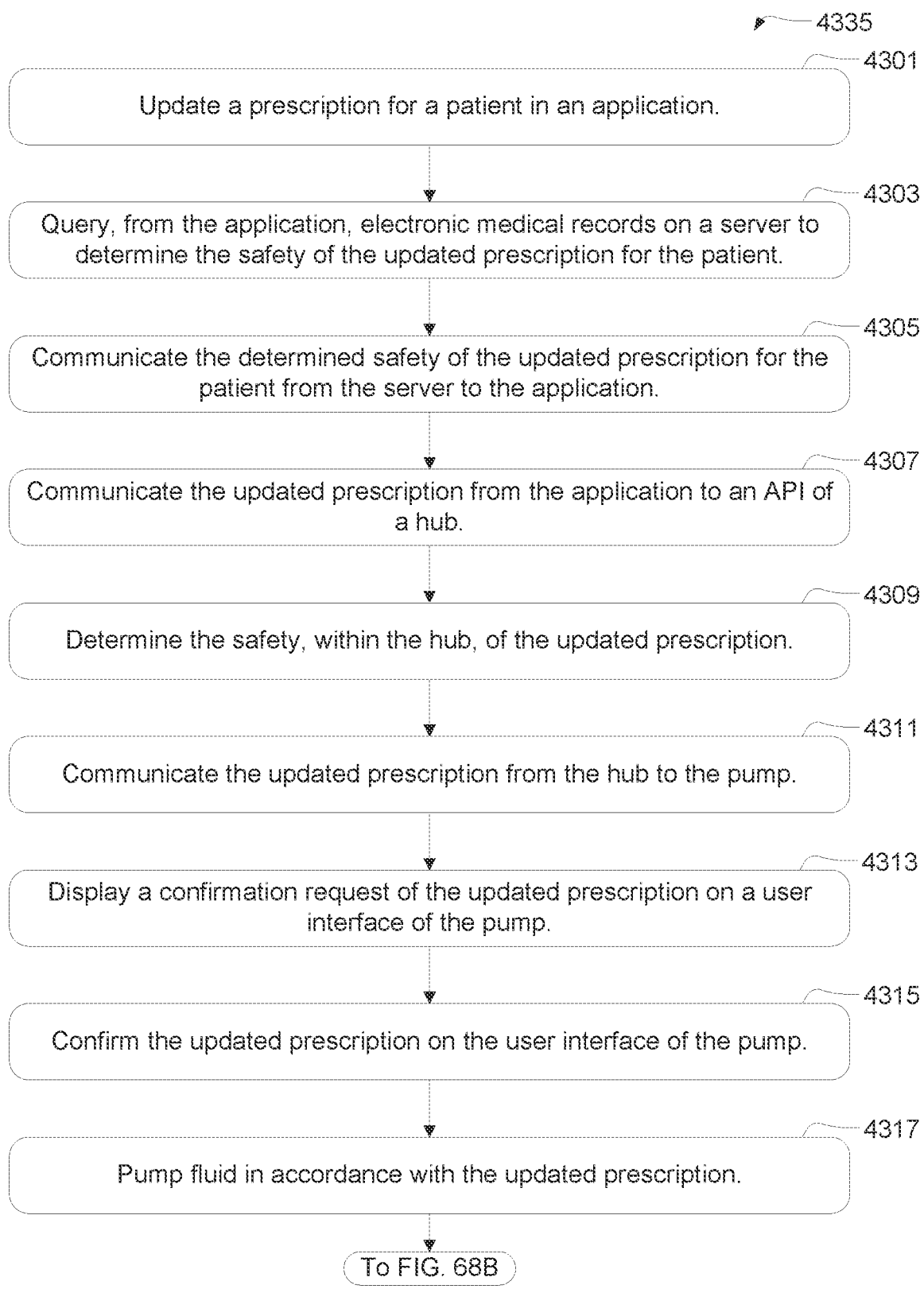
FIGS. 68A-68B show a flow chart diagram of a method illustrating the timing diagram of FIG. 67 in accordance with an embodiment of the present disclosure.
Figure 68B:
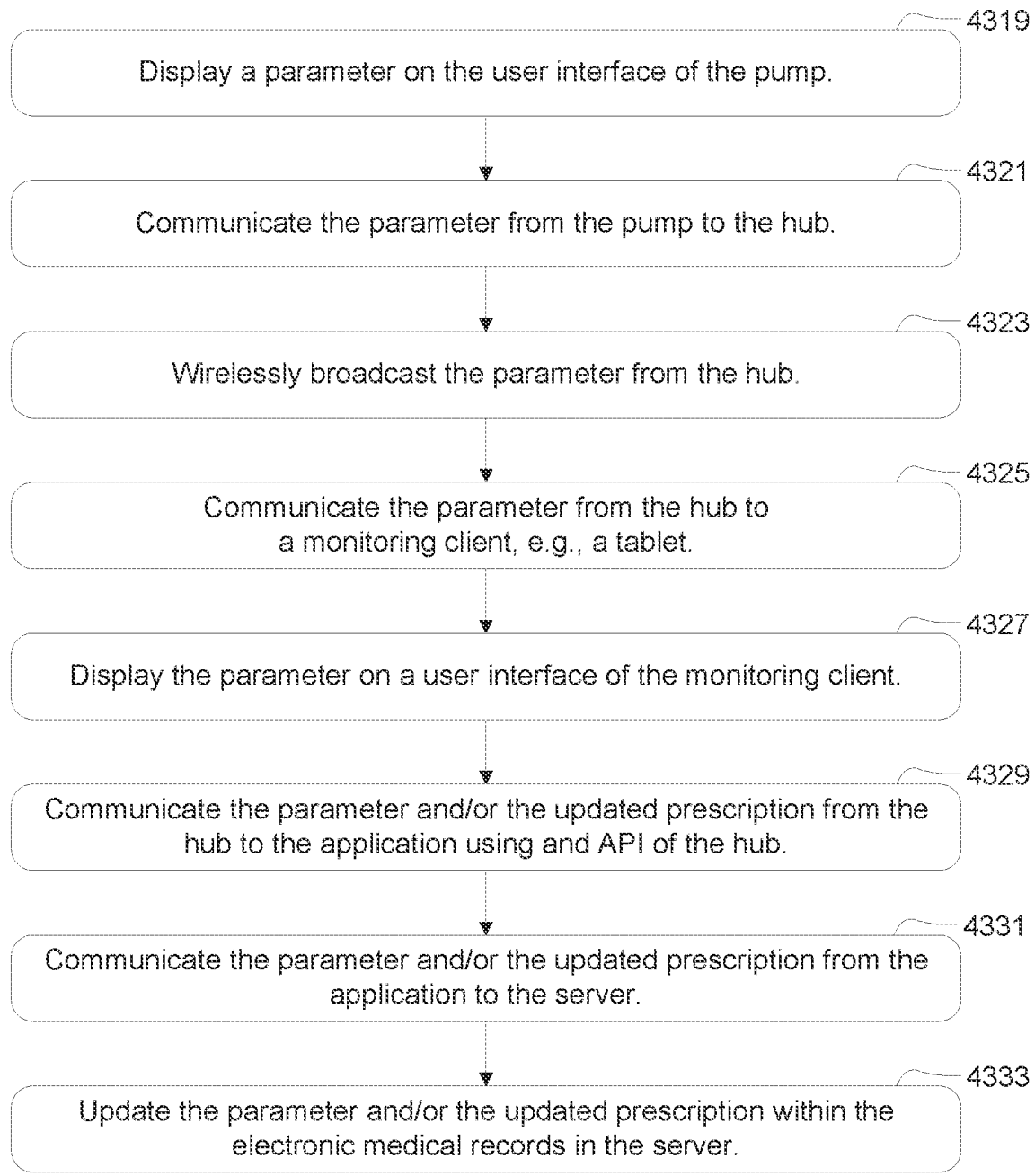

FIGS. 68A-68B show a flow chart diagram of a method 4335 illustrating the timing diagram of FIG. 67 in accordance with an embodiment of the present disclosure. Method 4335 includes acts 4301-4333.

Act 4301 updates a prescription for a patient in an application. Act 4303 queries, from the application, electronic medical records on a server to determine the safety of the updated prescription for the patient. Act 4305 communicates the determined safety of the updated prescription for the patient from the server to the application. Act 4307 communicates the updated prescription from the application to an API of a hub. The API may include a secure data class. In some embodiments, the communication of Act 4307 occurs through middleware (e.g., middleware on the monitoring server 3 of FIG. 1). Act 4309 determines the safety, within the hub, of the updated prescription (e.g., in some embodiments DERS checks and/or prescription checks). In some embodiments, Acts 4309 is optional. In some embodiments, Act 4311 communicates the updated prescription from the hub to the pump. Act 4311 is optional in some embodiments.

Act 4313 displays a confirmation request of the updated prescription on a user interface of the pump. Act 4315 confirms the updated prescription on the user interface of the pump. Act 4317 pumps fluid in accordance with the updated prescription. Act 4319 displays a parameter on the user interface of the pump. Act 4321 communicates the parameter from the pump to the hub. Act 4323 wirelessly broadcasts the parameter from the hub. Act 4325 communicates the parameter from the hub to a monitoring client, e.g., a tablet. Act 4327 displays the parameter on a user interface of the monitoring client. Act 4329 communicates the parameter and/or the updated prescription from the hub to the application using an API of the hub. Act 4331 communicates the parameter and/or the updated prescription from the application to the server. Act 4333 updates the parameter and/or the updated prescription within the electronic medical records in the server. In some embodiments, Act 4333 communicates through middleware (e.g., middleware on the monitoring server 3 of FIG. 1).

Figure 69:
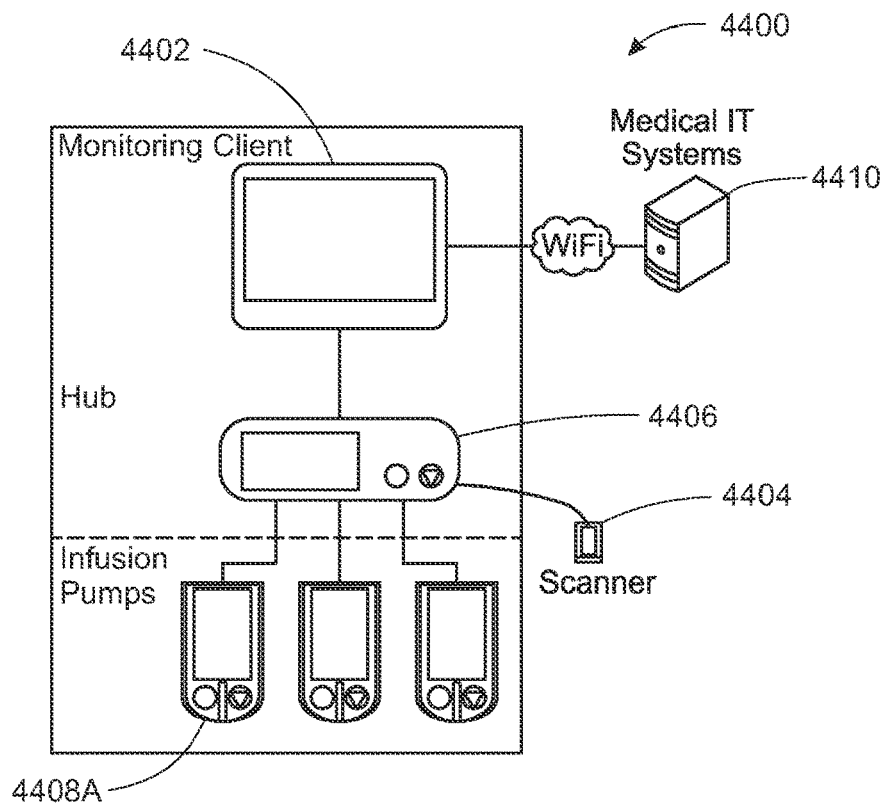
FIGS. 69-70 show additional arrangements of an electronic patient-care system in accordance with an embodiment of the present disclosure.
Figure 70:
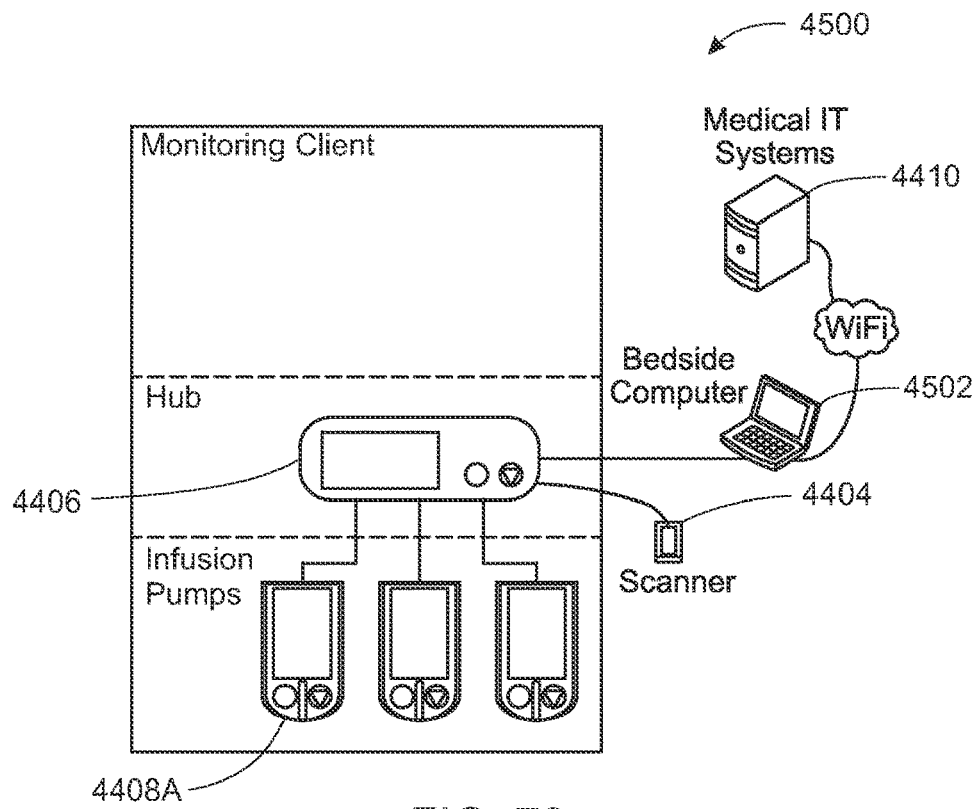

FIG. 69 shows an electronic patient-care system 4400 and FIG. 70 shows an electronic patient-care system 4500. In some embodiments, an electronic medical records application may reside on a tablet 4402 as shown in FIG. 69 and/or in a bedside computer 4502 of FIG. 70. Additionally or alternatively, in some embodiments, the electronic medical records application may reside in a hub, an infusion pump, a tablet, a patient-care device, some other device or apparatus, some combination thereof, or may not be utilized. The scanner 4404 may be used to determine if the medication, e.g., an infusion bag, matches the prescription prescribed for an identified patient, e.g., the patient may be identified using the scanner 4404.

Figure 71:
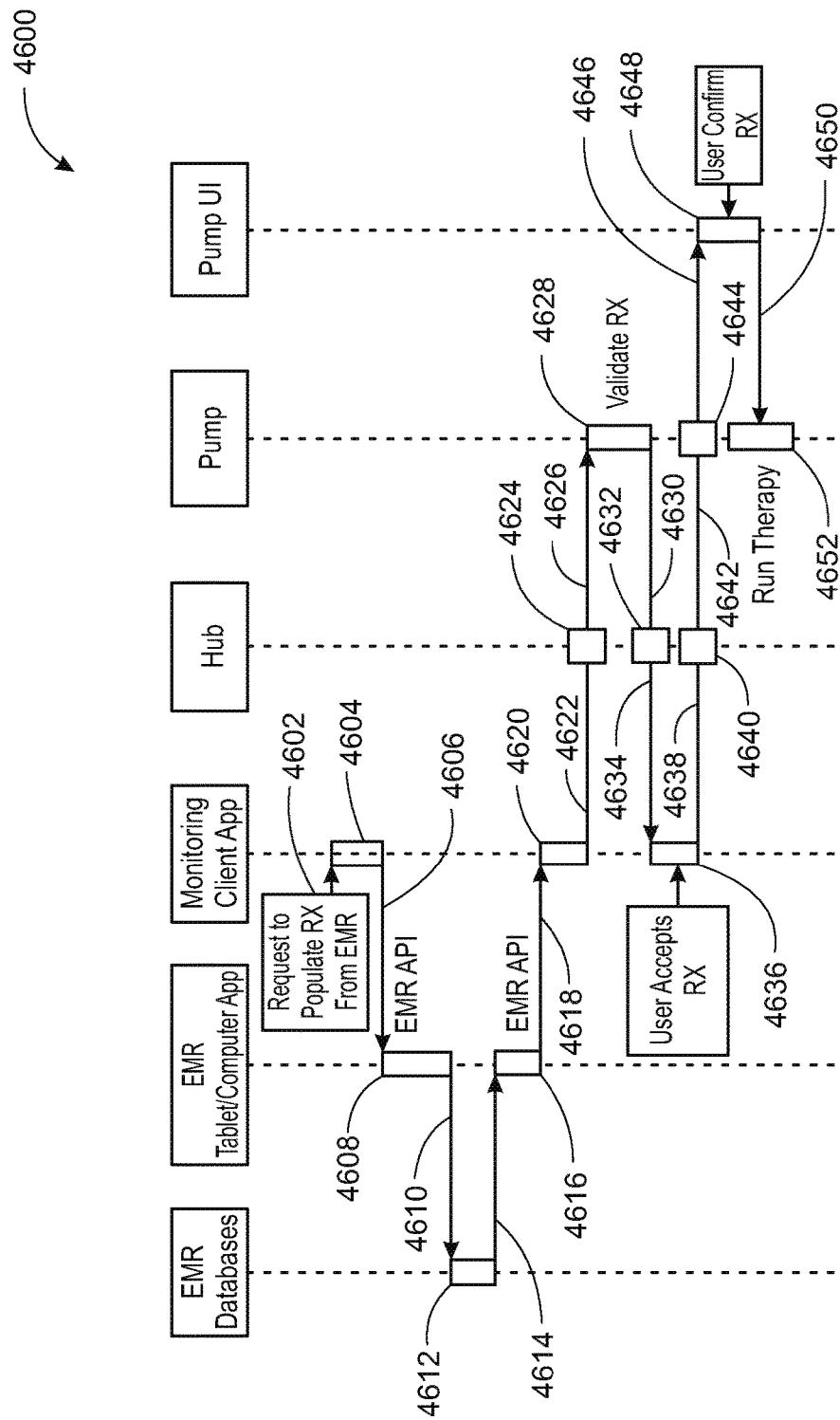
FIG. 71 shows a timing diagram of electronic patient-care treatment using an infusion pump in accordance with an embodiment of the present disclosure.

FIG. 71 shows a timing diagram 4600 illustrating, in accordance with some embodiments of the present disclosures, a method in which an infusion pump 4408A and/or a hub 4406 requests from the tablet 4402 which prescription was prescribed for a patient by querying an electronic medical records application executed on the tablet 4402. A user may enter the patient's identification or the patient's identification is scanned using the scanner 4404. The electronic medical records application executed on the tablet 4402 may request the prescribed medication from the one or more servers 4410. A tablet application may request the user to choose from a list of available prescriptions if there are multiple prescriptions, e.g., multiple infusion-pump-based prescriptions.

The timing diagram 4600 illustrates acts 4602-4652. Act 4602 requests, using a monitoring client during act 4604, a list of prescription for a patient after identifying the patient. Act 4602 "pulls" the prescription information from the monitoring client. The patient may be identified using a barcode scanner, an RFID interrogator, voice- or facial-recognition, or via manual entry. The tablet communicates the patient's ID during act 4606 using an EMR API to a tablet or computer application of 4608. The API may include a secure data class. The patient's identity is communicated in act 4610 to an EMR database, which in act 4612, communicates the list of prescription to an EMR API during act 4614, which is received by the EMR program running on the monitoring client or computer app in act 4616, which in turn communicates them in act 4618 to the monitoring client application. The communication between the EMR Tablet/Computer Application and the EMR database may be via middleware (e.g., middleware on the monitoring server 3 of FIG. 1).

The monitoring client, e.g., a tablet, in act 4620, can display the various prescriptions for the patient for user selection. The selected prescription is communicated in act 4622 to the hub, which can check the prescription in act 4624 and communicate the prescription to the pump in act 4626. The pump validates, either automatically by ensuring the prescription is within predetermined criteria, e.g., using DERS, in act 4628, or by requesting user validation. Additionally or alternatively, a user can validate the prescription using the pump UI.

The validated prescription of act 4628 is communicated in act 4630 to the hub, which in act 4632 communicates in act 4634 it to the monitoring client application. In act 4636, a user can accept the prescription, which is then communicated in act 4638 to the hub. The accepted prescription's communications occurs in act 4640 communicates it via act 4642 to the pump. In act 4644, the pump communicates the prescription to the pump UI in act 4646, in which the user can confirm the prescription in act 4642. The confirmation is sent to the pump in act 4650. Act 4652 runs the therapy.

Figure 72A:
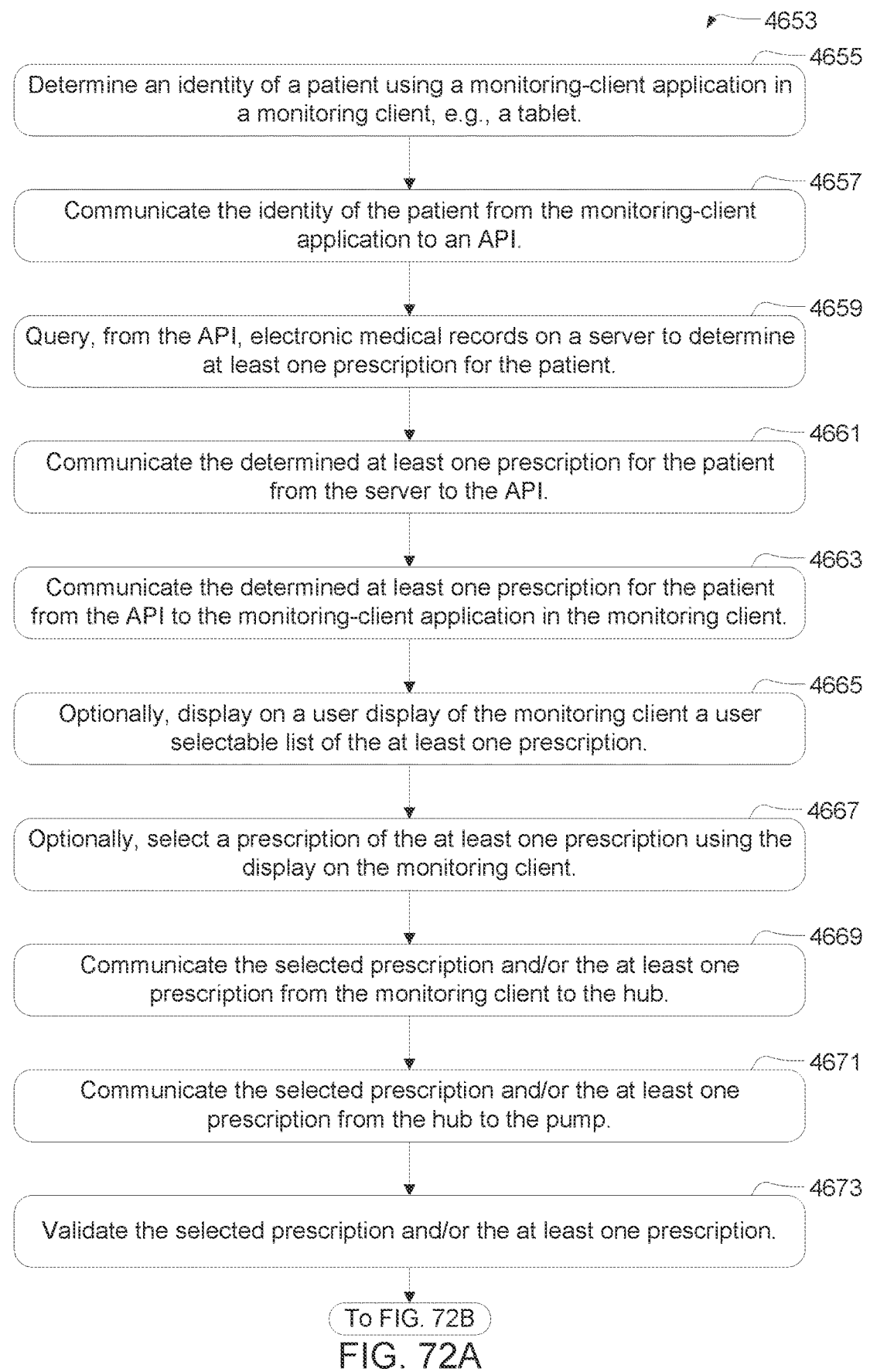
FIGS. 72A-72B show a flow chart diagram of a method illustrating the timing diagram of FIG. 71 in accordance with an embodiment of the present disclosure.
Figure 72B:
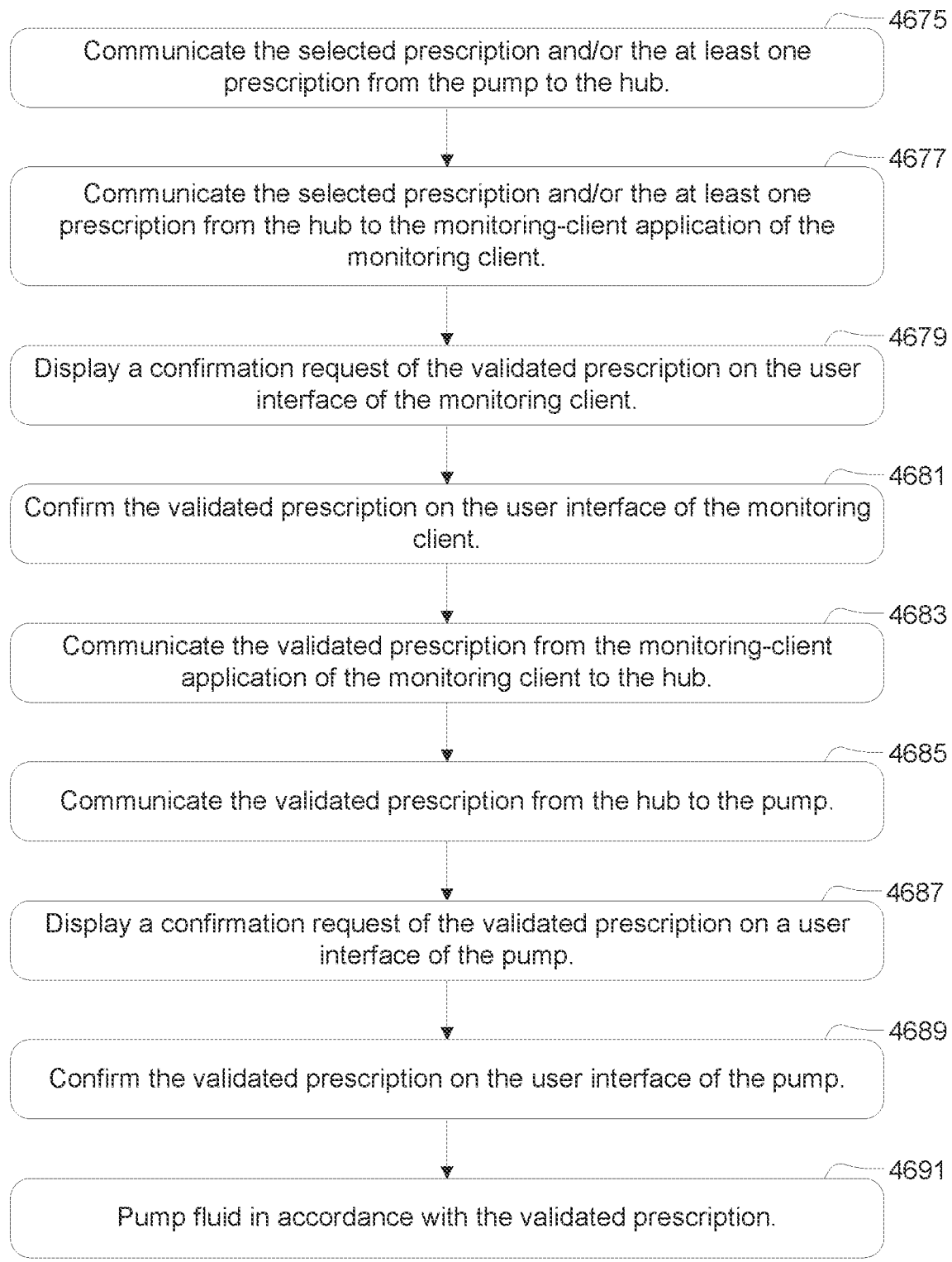

FIGS. 72A-72B show a flow chart diagram of a method 4653 illustrating the timing diagram of FIG. 71 in accordance with an embodiment of the present disclosure. Method 4653 includes acts 4655-4691.

Act 4655 determines an identity of a patient using a monitoring-client application in a monitoring client, e.g., a tablet. Act 4657 communicates the identity of the patient from the monitoring-client application to an API. Act 4659 queries, from the API, electronic medical records on a server to determine at least one prescription for the patient. In some embodiments, the Act 4659 queries through middleware (e.g., middleware on the monitoring server 3 of FIG. 1) to the electronic medical records. Act 4661 communicates the determined at least one prescription for the patient from the server to the API. Act 4663 communicates the determined at least one prescription for the patient from the API to the monitoring-client application in the monitoring client. Act 4665, optionally, displays on a user display of the monitoring client a user selectable list of the at least one prescription. Act 4667, optionally, selects a prescription of the at least one prescription using the display on the monitoring client. Act 4669 communicates the selected prescription and/or the at least one prescription from the monitoring client to the hub.

Act 4671 communicates the selected prescription and/or the at least one prescription from the hub to the pump. Act 4673 validates the selected prescription and/or the at least one prescription. Act 4675 communicates the selected prescription and/or the at least one prescription from the pump to the hub. Act 4677 communicates the selected prescription and/or the at least one prescription from the hub to the monitoring-client application of the monitoring client. Act 4679 displays a confirmation request of the validated prescription on the user interface of the monitoring client. Act 4681 confirms the validated prescription on the user interface of the monitoring client. Act 4683 communicates the validated prescription from the monitoring-client application of the monitoring client to the hub. Act 4685 communicates the validated prescription from the hub to the pump. Act 4687 displays a confirmation request of the validated prescription on a user interface of the pump. Act 4689 confirms the validated prescription on the user interface of the pump. Act 4691 pumps fluid in accordance with the validated prescription.

Figure 73:
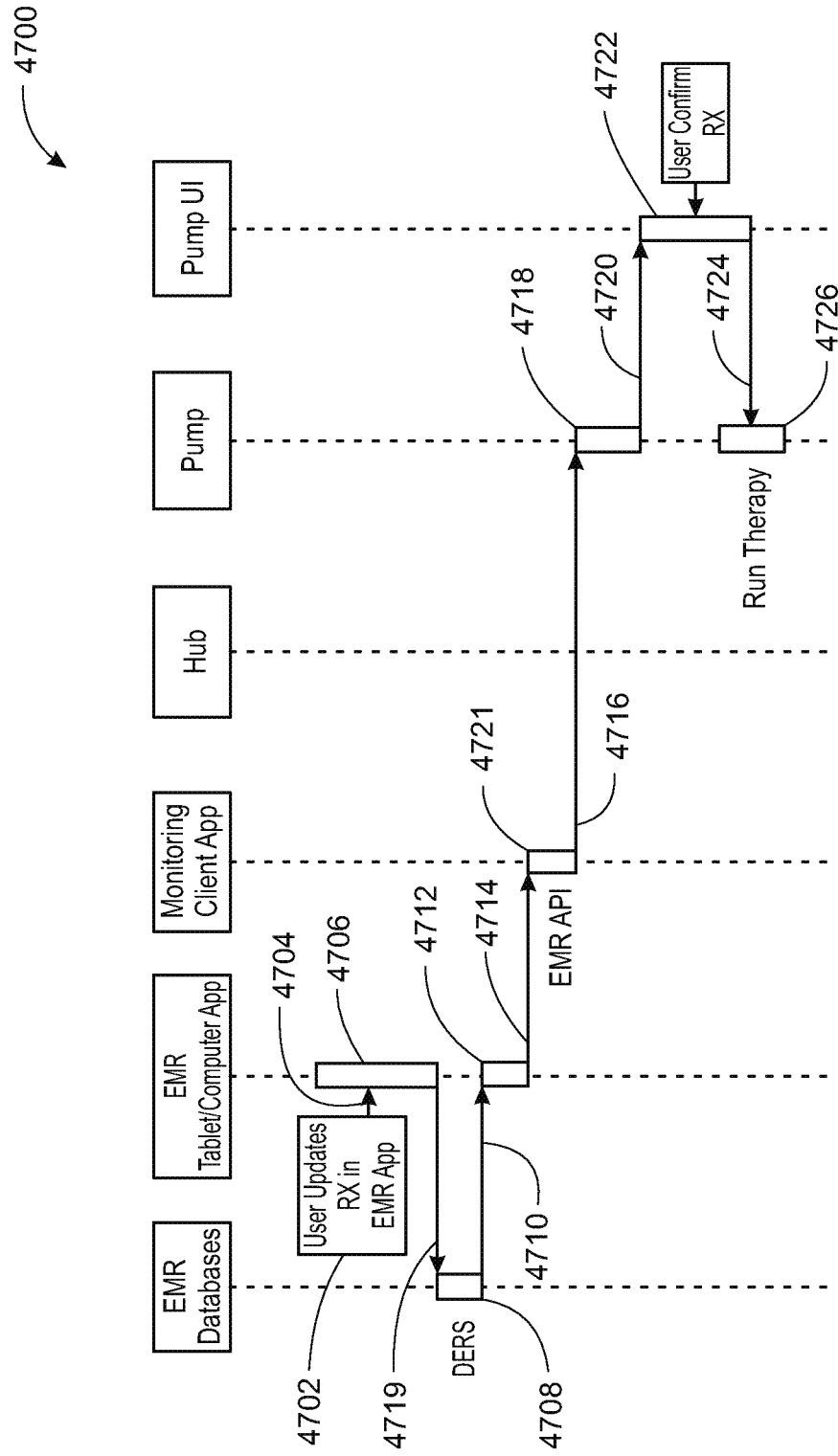
FIG. 73 shows another timing diagram of electronic patient-care treatment using an infusion pump in accordance with an embodiment of the present disclosure.

FIG. 73 shows a timing diagram 4700 in which a prescription is pushed to the infusion pump 4408A. Additionally or alternatively, the electronic medical records application also can be located on the device hub 4406 which maintain the electronic medical records application programming interface across multiple devices. Method 4700 includes acts 4702-4726. Middleware (e.g., middleware on the monitoring server 3 of FIG. 1) may be utilized, in some embodiments, between the EMR databases and the EMR tablet/computer application.

In act 4702, a user updates a prescription in an EMR application on a monitoring client, e.g., a tablet or a computer. The update may be a new prescription of a modified prescription. The updated prescription is communicated to the application in act 4704. The application processes the update in act 4706, and commutes it in act 4719 to the EMR database. In act 4708, DERS checks the updated prescription. The updated prescription is communicated, in act 4710, to the EMR monitoring client or computer application, which is processed in act 4712. After processing, in act 4714, the updated prescription is communicated via an EMR API to a monitoring client application, which is processed in act 4721. The monitoring client communicates it, in act 4716, to the pump. The pump processes the updated prescription in act 4718 and communicates it to the pump in act 4720. A user confirms the updated prescription in act 4722, which is communicated to the pump in act 4724. The therapy is applied in act 4726.

Figure 74:
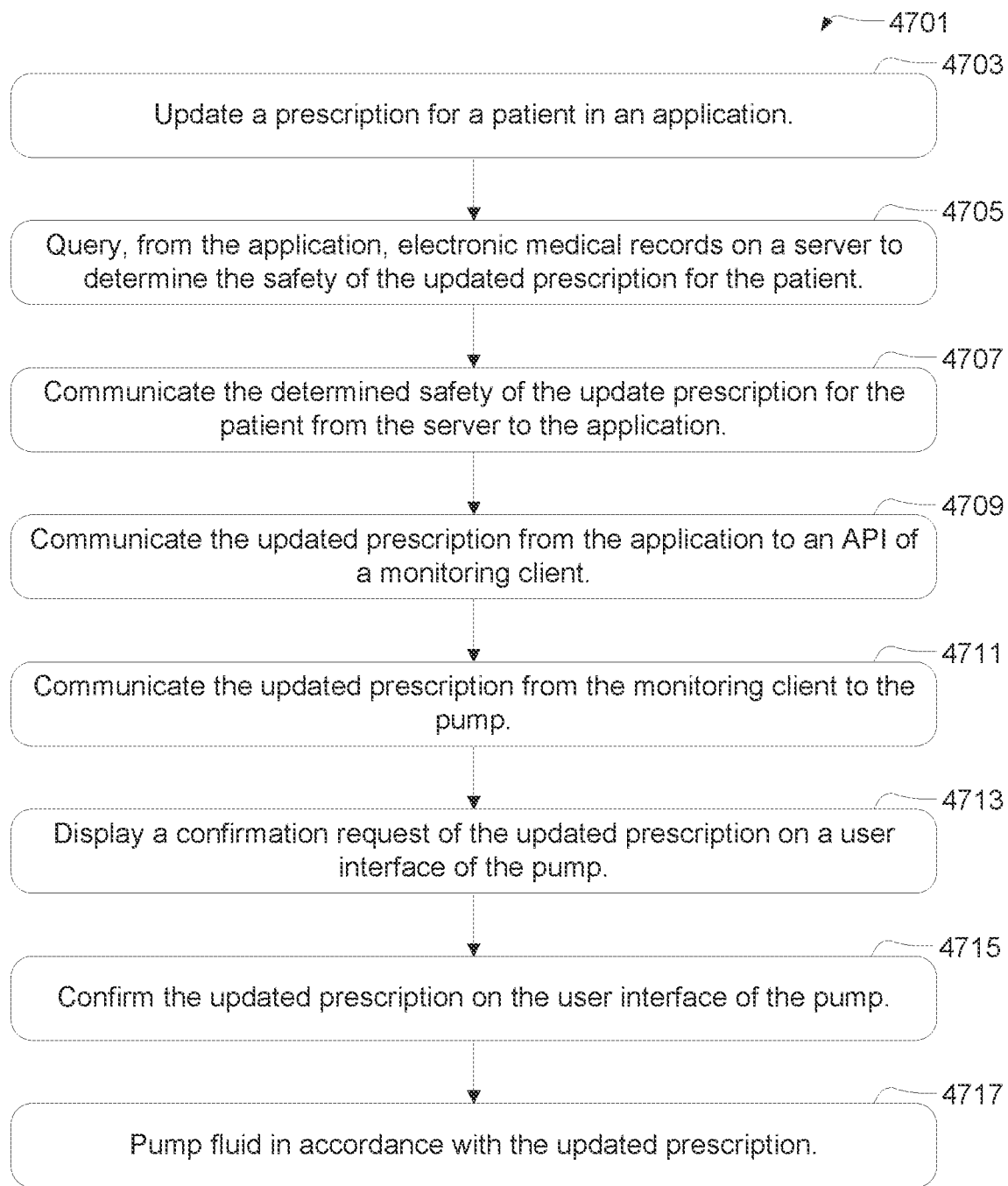
FIG. 74 shows a flow chart diagram of a method illustrating the timing diagram of FIG. 73 in accordance with an embodiment of the present disclosure.

FIG. 74 shows a flow chart diagram of a method 4701 illustrating the timing diagram of FIG. 73 in accordance with an embodiment of the present disclosure. Method 4701 includes acts 4703-4717.

Act 4703 updates a prescription for a patient in an application. Act 4705 queries, from the application, electronic medical records on a server to determine the safety of the updated prescription for the patient. Act 4707 communicates the determined safety of the updated prescription for the patient from the server to the application. Act 4709 communicates the updated prescription from the application to an API of a monitoring client. Act 4711 communicates the updated prescription from the monitoring client to the pump. Act 4713 displays a confirmation request of the updated prescription on a user interface of the pump. Act 4715 confirms the updated prescription on the user interface of the pump. Act 4717 pumps fluid in accordance with the updated prescription.

Figure 75:
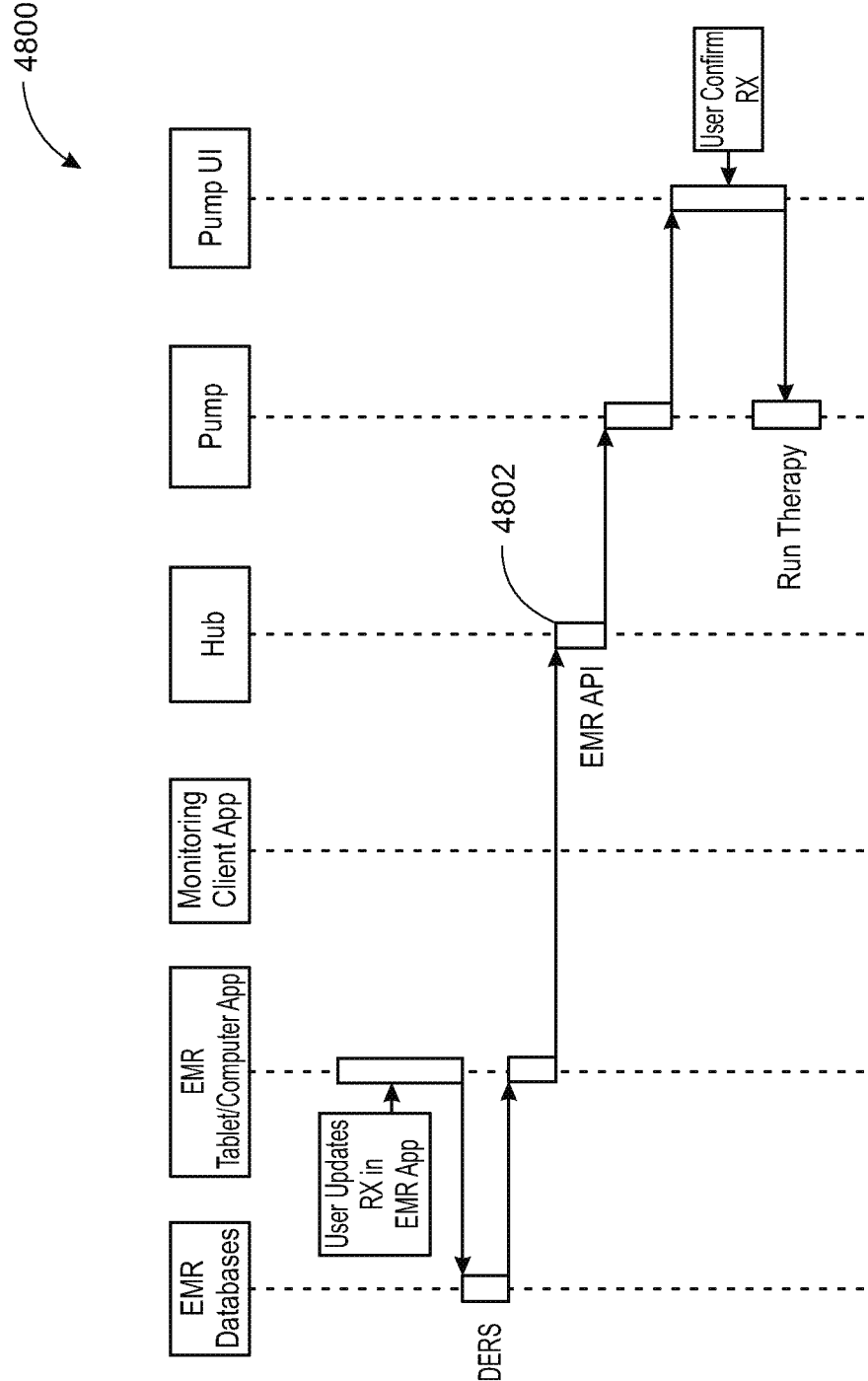
FIG. 75 shows yet another timing diagram of electronic patient-care treatment using an infusion pump in accordance with another embodiment of the present disclosure.

FIG. 75 shows a timing diagram 4800 in which the hub 4406 communicates to the infusion pump 4408A for user confirmation of the prescription. That is, the method 4800 of FIG. 75 is similar to method 4700 of FIG. 73; however, the hub includes the EMR API and processes it in act 4802.

Figure 76:
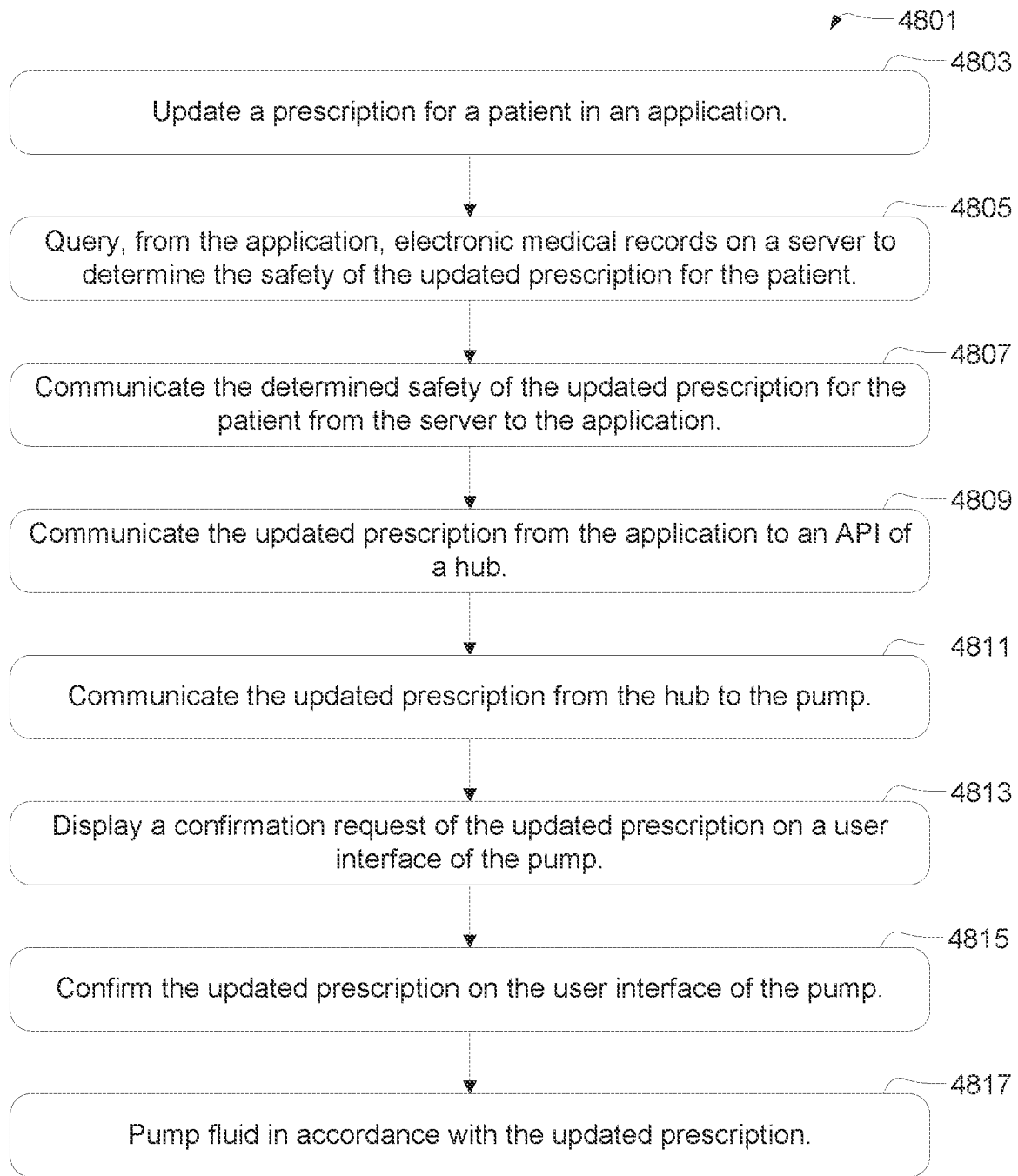
FIG. 76 shows a flow chart diagram of a method illustrating the timing diagram of FIG. 75 is accordance with an embodiment of the present disclosure.

FIG. 76 shows a flow chart diagram of a method 4801 illustrating the timing diagram of FIG. 75 is accordance with an embodiment of the present disclosure. Method 4801 includes acts 4803-4817.

Act 4803 updates a prescription for a patient in an application. Act 4805 queries, from the application, electronic medical records on a server to determine the safety of the updated prescription for the patient. Act 4807 communicates the determined safety of the updated prescription for the patient from the server to the application. Act 4809 communicates the updated prescription from the application to an API of a hub. Act 4811 communicates the updated prescription from the hub to the pump. Act 4813 displays a confirmation request of the updated prescription on a user interface of the pump. Act 4815 confirms the updated prescription on the user interface of the pump. Act 4817 pumps fluid in accordance with the updated prescription.

Figure 77:
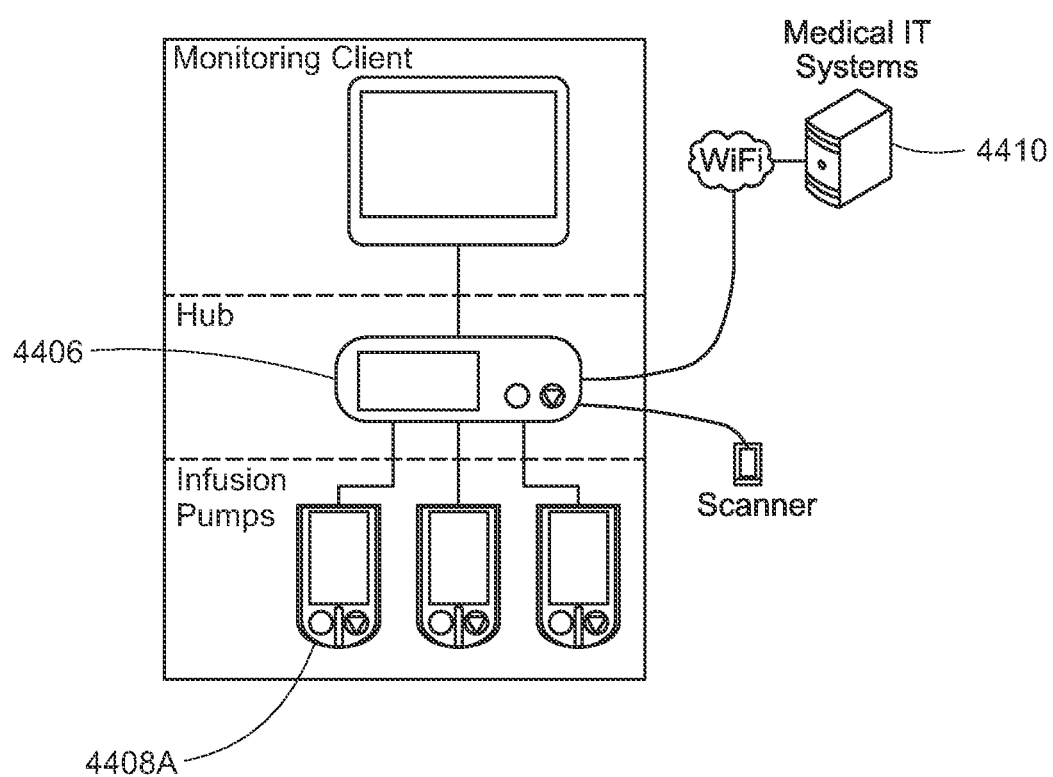
FIGS. 77-78 show several arrangements of an electronic patient-care system in accordance with an embodiment of the present disclosure.
Figure 78:
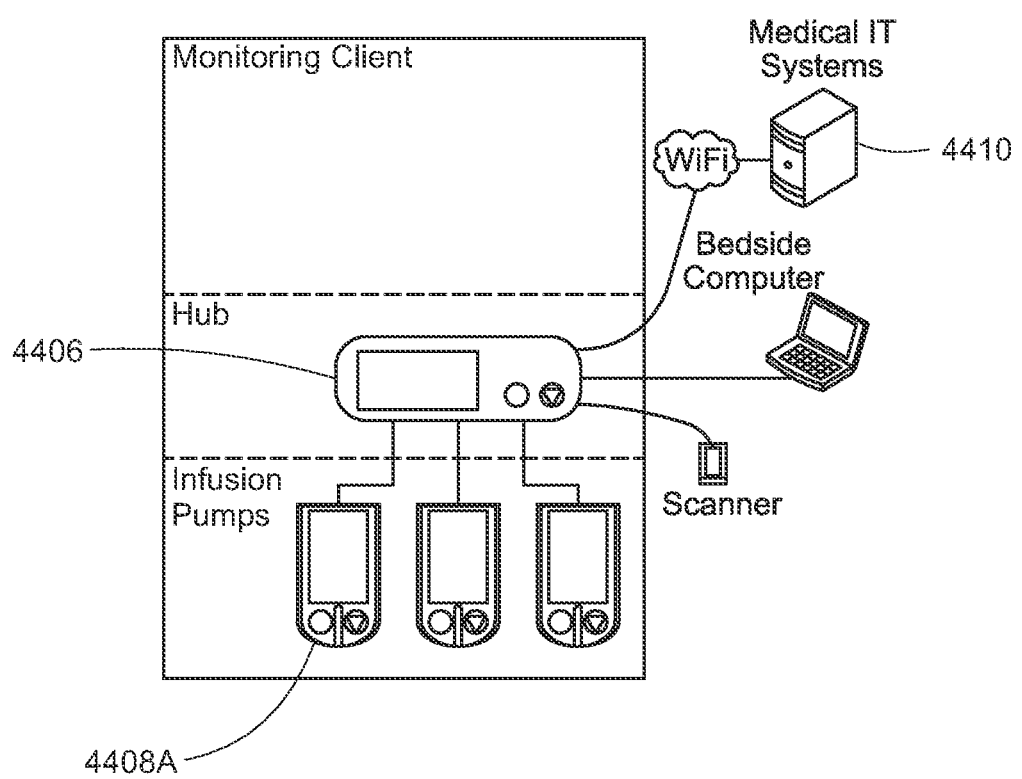

FIGS. 77 and 78 show embodiments in which the hub 4406 communicates with the one or more servers 4410, e.g., to determine if the prescription is safe for the patient, etc.

Figure 79:
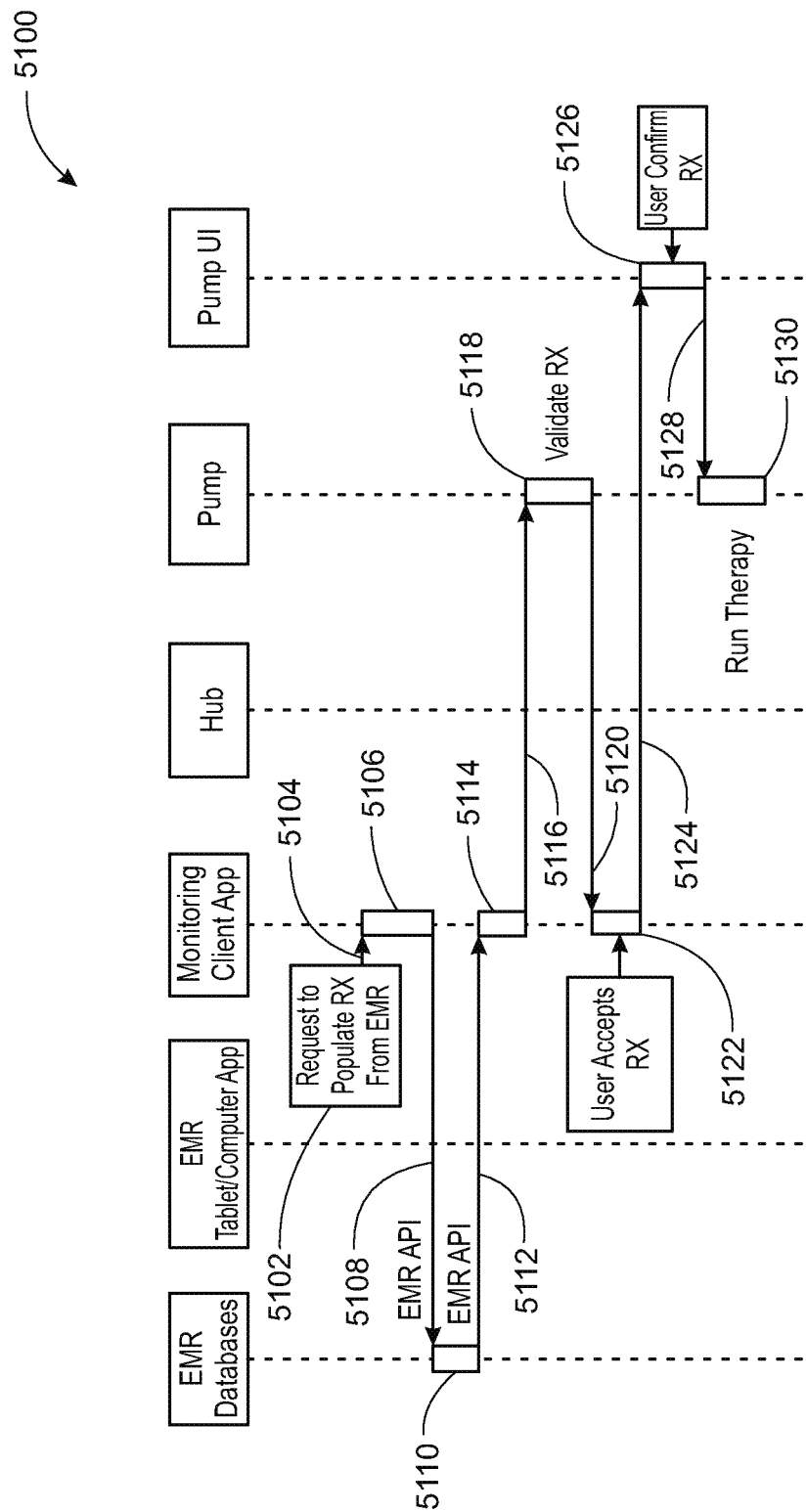
FIG. 79 shows another timing diagram of an electronic patient-care treatment using an infusion pump in accordance with another embodiment of the present disclosure.

FIG. 79 shows a timing diagram 5100 for user confirmation of the prescription on the pump's 4408A user interface. The timing diagram 5100 implements a method that includes acts 5102-5130. Act 5102 requests prescriptions from an EMR using a monitoring client's app, which is communicated in act 5104 and processed by act 5106. The request 5102 may be made via patient identification. The tablet communicates the request in act 5108 via an EMR API to the EMR database. Act 5110 processes the request and communicates back via the EMR API in act 5112. The monitoring client processes the prescriptions received from the EMR database in act 5114.

The monitoring client communicates the prescriptions in act 5116 to the pump, which validates the prescription in act 5118 and communicates it in act 5120 to the monitoring client's application. The user can accept the prescription in act 5122, which is communicated to the pump and the pump's UI in act 5124. In act 5126, a user can confirm the prescription on the pump. The confirmation is communicated to the pump in act 5128, which then is executed in acct 5130.

Figure 80A:
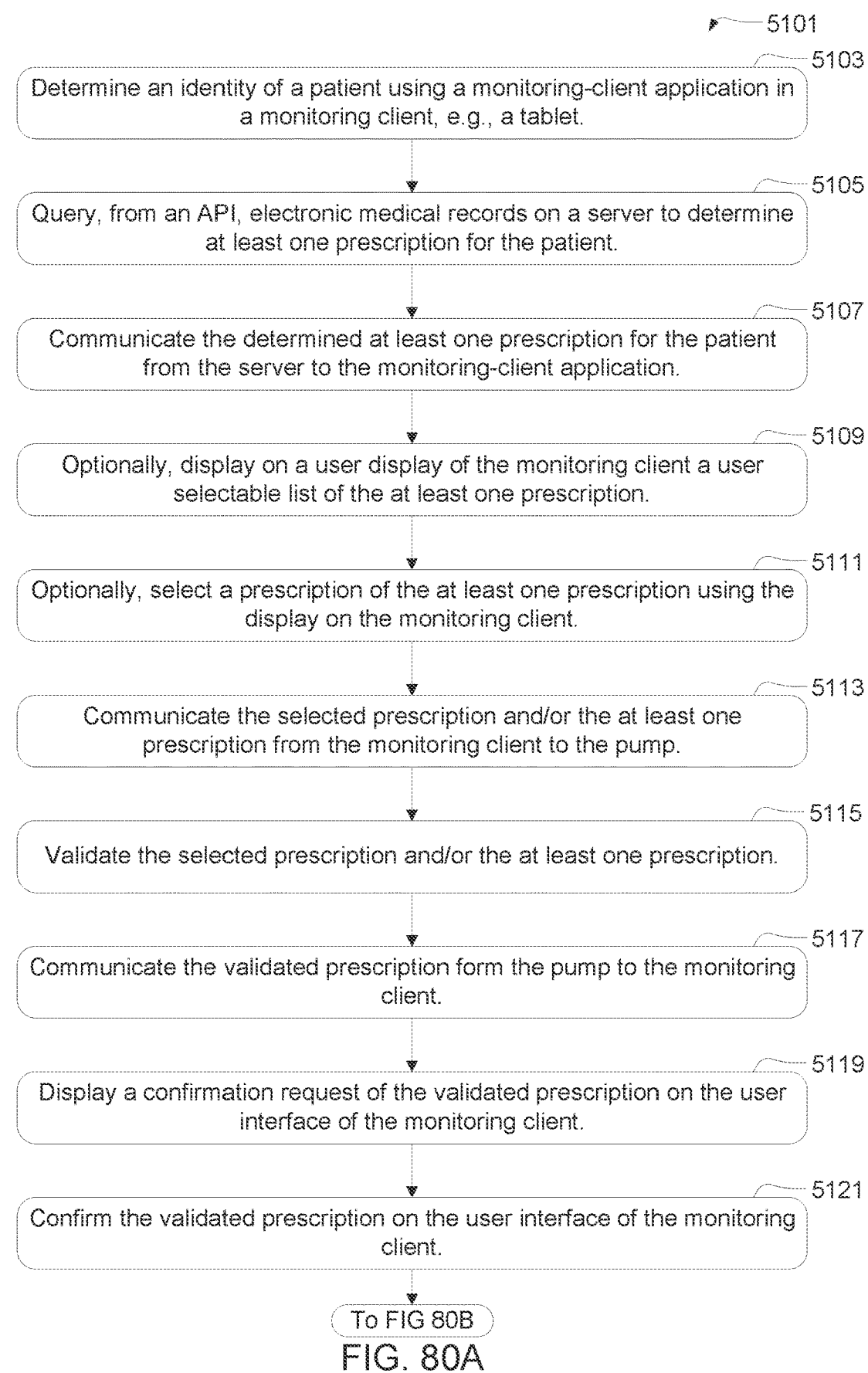
FIGS. 80A-80B show a flow chart diagram of a method illustrating the timing diagram of FIG. 79 in accordance with an embodiment of the present disclosure.
Figure 80B:
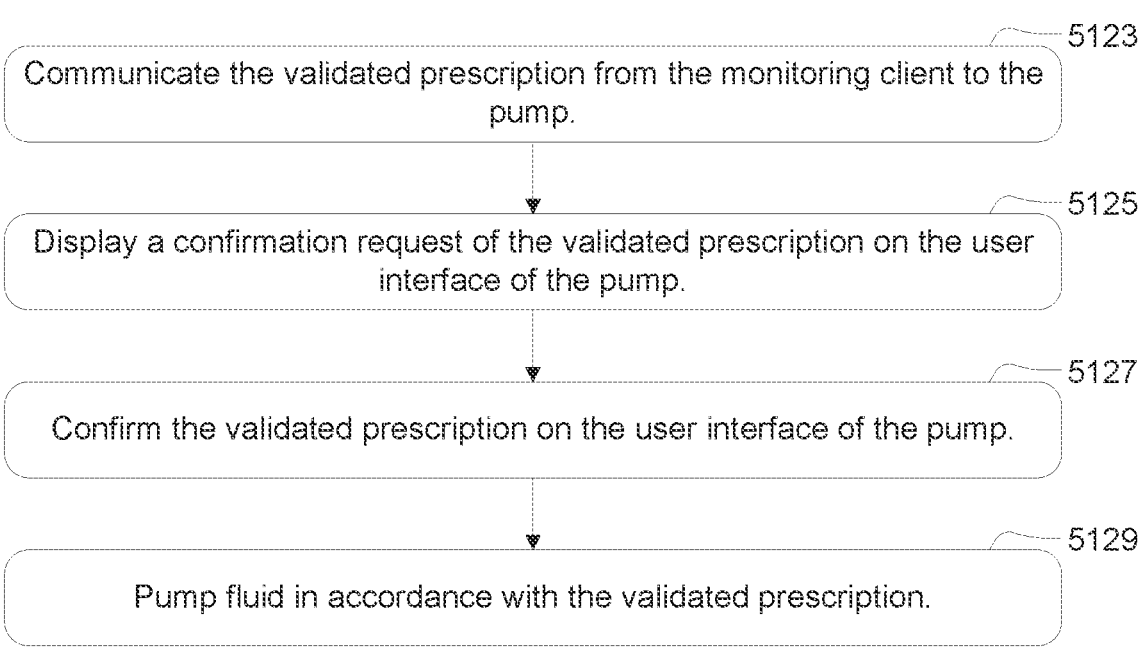

FIGS. 80A-80B show a flow chart diagram of a method 5101 illustrating the timing diagram of FIG. 79 in accordance with an embodiment of the present disclosure. Method 5105 includes acts 5103-515128.

Act 5103 determines an identity of a patient using a monitoring-client application in a monitoring client, e.g., a tablet. Act 5105 queries, from an API, electronic medical records on a server to determine at least one prescription for the patient. Act 5107 communicates the determined at least one prescription for the patient from the server to the monitoring-client application. Act 5109, optionally, displays on a user display of the monitoring client a user selectable list of the at least one prescription. Act 5111, optionally, selects a prescription of the at least one prescription using the display on the monitoring client. Act 5113 communicates the selected prescription and/or the at least one prescription from the monitoring client to the pump. Act 5115 validates the selected prescription and/or the at least one prescription. Act 5117 communicates the validated prescription from the pump to the monitoring client. Act 5119 displays a confirmation request of the validated prescription on the user interface of the monitoring client.

Act 5121 confirms the validated prescription on the user interface of the monitoring client. Act 5123 communicates the validated prescription from the monitoring client to the pump. Act 5125 displays a confirmation request of the validated prescription on the user interface of the pump. Act 5127 confirms the validated prescription on the user interface of the pump. Act 5129 pumps fluid in accordance with the validated prescription.

Figure 81:
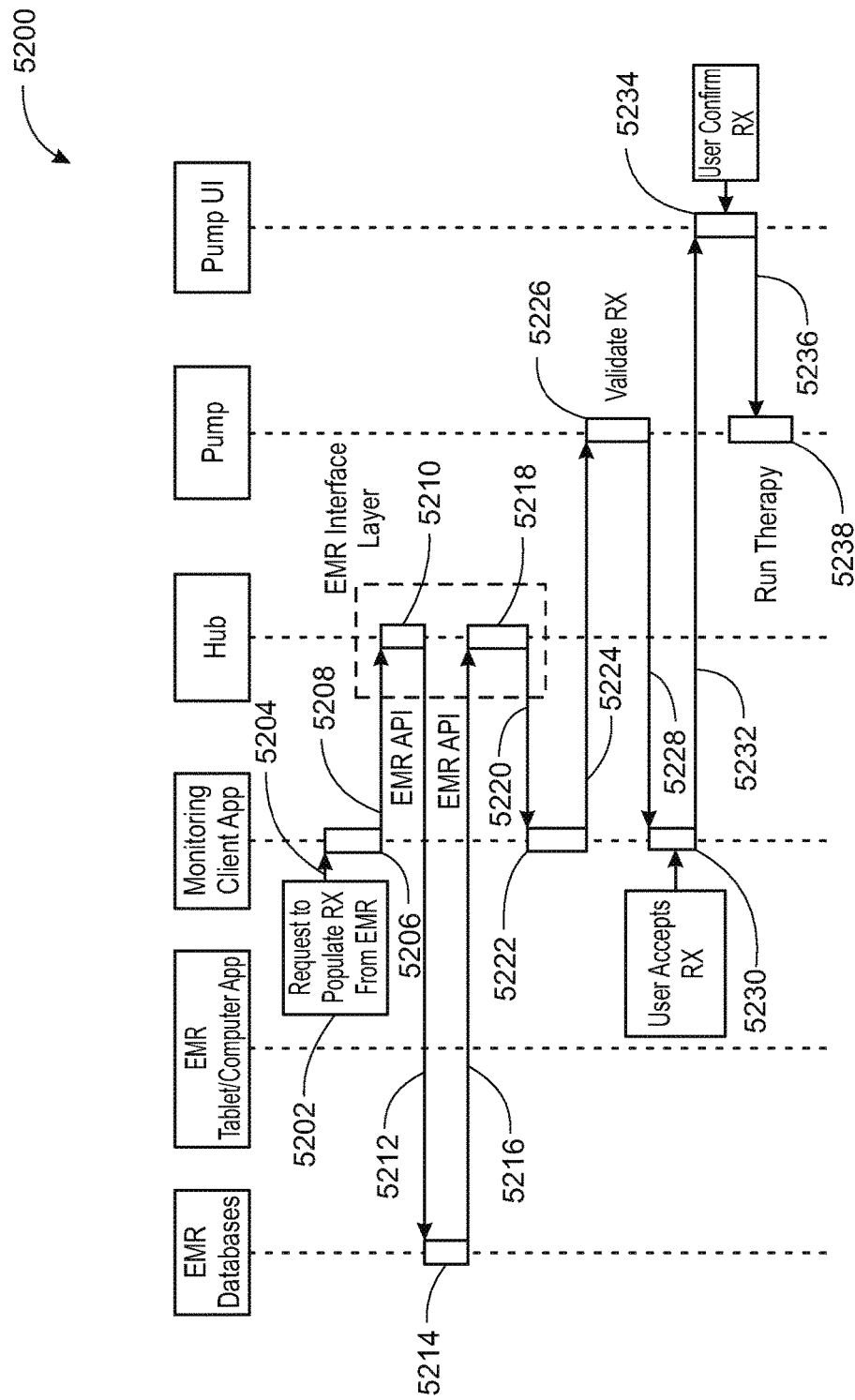
FIG. 81 shows another timing diagram of an electronic patient-care treatment using an infusion pump in accordance with another embodiment of the present disclosure.

FIG. 81 shows a timing diagram 5200 in which the hub 4406 communicates with the one or more servers 4410 to communicate with electronic medical records. The method implemented by the timing diagram 5200 includes acts 5202-5238. Middleware (e.g., middleware on the monitoring server 3 of FIG. 1) may be utilized, in some embodiments, between the EMR databases and the EMR tablet/computer application.

In act 5202, a user requests prescription from an EMR via a monitoring client application, which is communicated in act 5204 and processed by act 5206. The monitoring client application interfaces with the EMR API of the hub in act 5208, which is processed by act 5210. The EMR API requests in act 5212 the prescriptions, which is processed in act 5214.

The prescriptions are communicated in act 5216 to the hub, which processes them in act 5218 and communicates them in act 5220 to the monitoring client's application for processing in act 5222. The prescriptions are communicated in act 5224 to the pump for validation in act 5226. The validation is communicated in act 5228 for user acceptance in act 5230, which is communicated to the pump in act 5232. The user can confirm the prescription in act 5234, which is communicated in act 5236 for starting the therapy in the pump in act 5238.

Figure 82A:
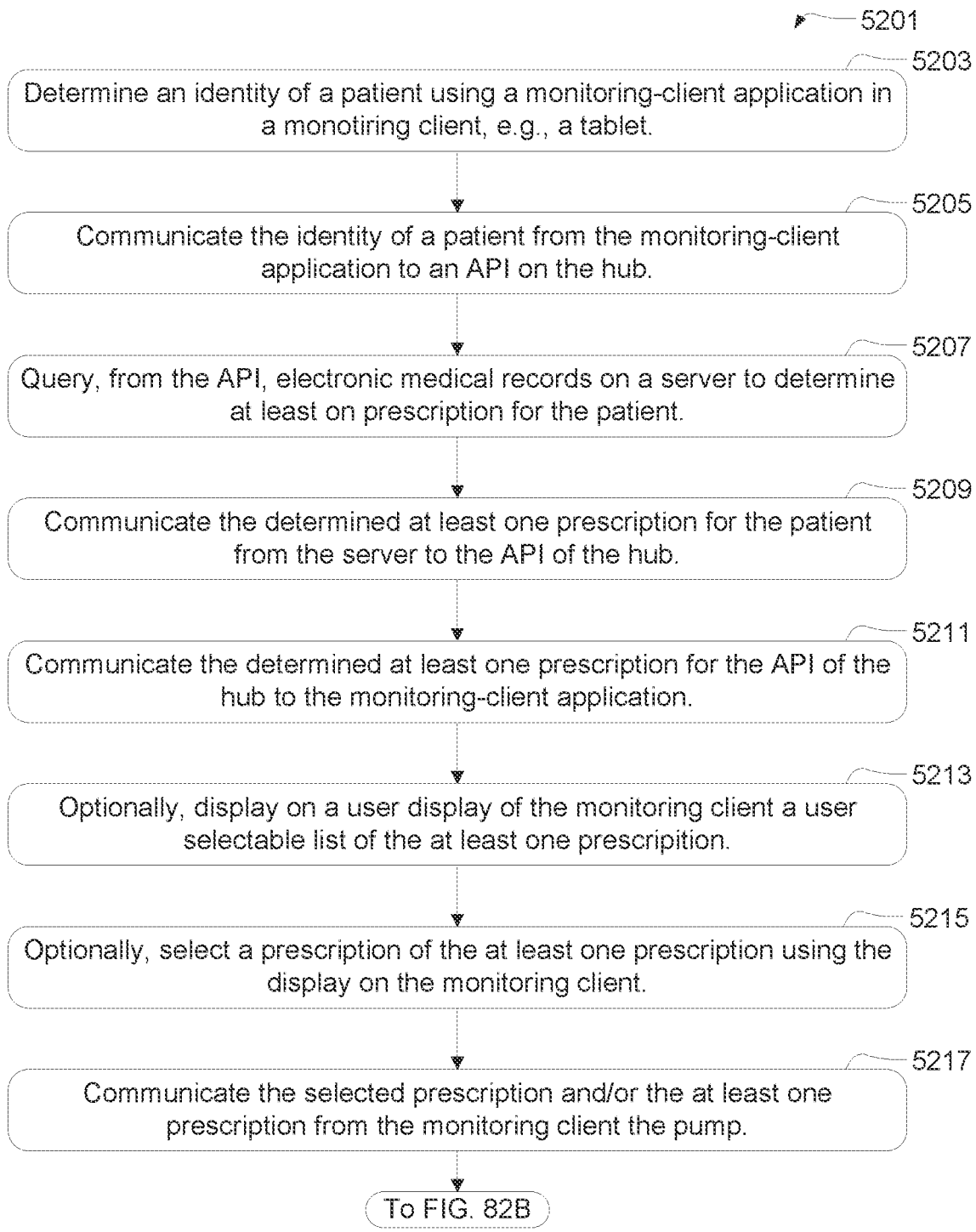
FIGS. 82A-82B show a flow chart diagram of a method illustrating the timing diagram of FIG. 81 in accordance with an embodiment of the present disclosure.
Figure 82B:
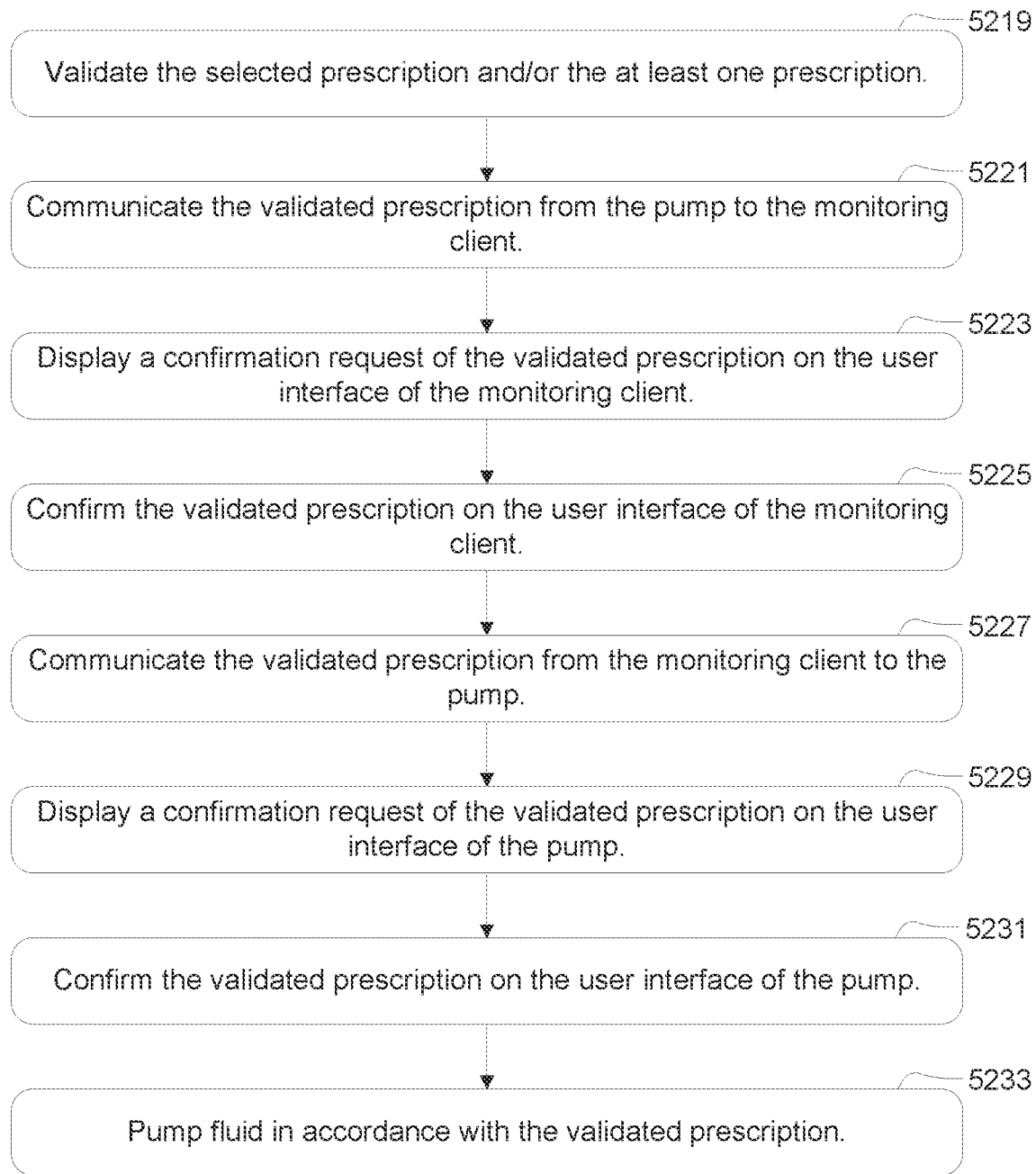

FIGS. 82A-82B show a flow chart diagram of a method 5201 illustrating the timing diagram of FIG. 81 in accordance with an embodiment of the present disclosure. Method 5201 includes acts 5203-5233.

Act 5203 determines an identity of a patient using a monitoring-client application in a monitoring client, e.g., a tablet. Act 5205 communicates the identity of a patient from the monitoring-client application to an API on the hub. Act 5207 queries, from the API, electronic medical records on a server to determine at least one prescription for the patient. Acts 5205 and/or 5207 may utilize middleware (e.g., middleware on the monitoring server 3 of FIG. 1). Act 5209 communicates the determined at least one prescription for the patient from the server to the API of the hub. Act 5211 communicates the determined at least one prescription from the API of the hub to the monitoring-client application. Act 5213, optionally, displays on a user display of the monitoring client a user selectable list of the at least one prescription. Act 5215, optionally, selects a prescription of the at least one prescription using the display on the monitoring client. Act 5217 communicates the selected prescription and/or the at least one prescription from the monitoring client to the pump. Act 5219 validates the selected prescription and/or the at least one prescription. Act 5221 communicates the validated prescription from the pump to the monitoring client. Act 5223 displays a confirmation request of the validated prescription on the user interface of the monitoring client.

Act 5225 confirms the validated prescription on the user interface of the monitoring client. Act 5227 communicates the validated prescription from the monitoring client to the pump. Act 5229 displays a confirmation request of the validated prescription on the user interface of the pump. Act 5231 confirms the validated prescription on the user interface of the pump. Act 5233 pump fluids in accordance with the validated prescription.

Figure 83:
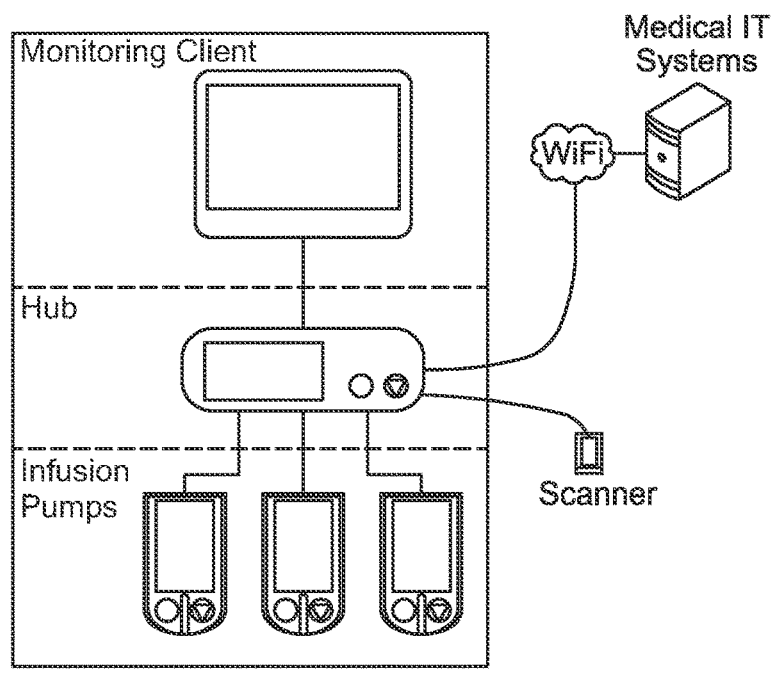
FIGS. 83-89 show several additional embodiments of an electronic patient-care system in accordance with several embodiments of the present disclosure.

FIG. 83-89 show several additional embodiments of an electronic patient-care system in accordance with several embodiments of the present disclosure. FIG. 83 shows a system 5300 where an electronic medical records application interfaces with electronic medical records on one or more servers 3516 to display some of the patient's electronic medical records on a user interface of a tablet 3514 and/or the hub 3804. A subset of the data from the electronic medical records received from the one or more servers 3516 may be displayed on a display on an infusion pump 3504 (e.g., the medication being delivered by the infusion pump 3504). Additionally or alternatively, in some embodiments, a subset of data from the electronic medical records may be cached on the hub. In some embodiments, the hub may communicate with the medical IT systems through middleware (e.g., middleware on the monitoring server 3 of FIG. 1).

Figure 84:
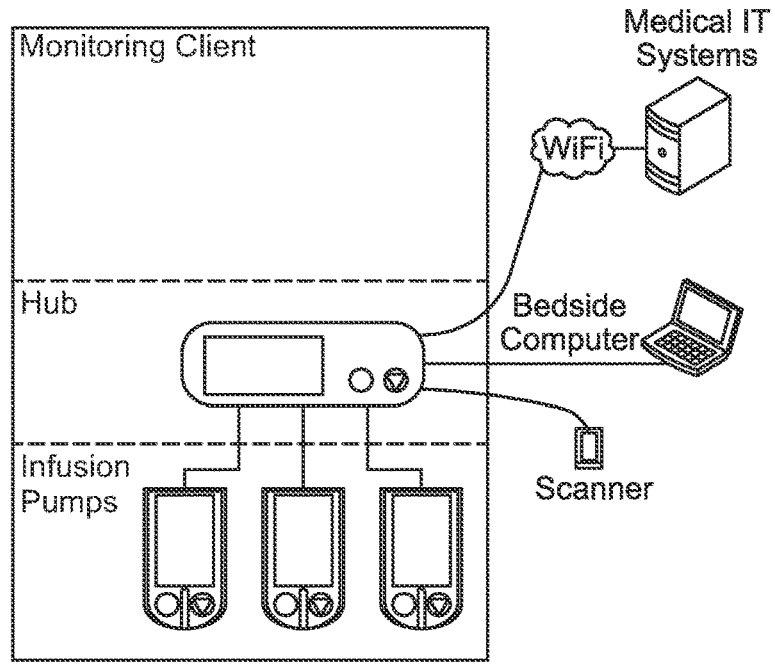

FIG. 84 shows a system 5400 where an electronic medical records application interfaces with electronic medical records on one or more servers 4410 to display some of the patient's electronic medical records on a user interface of a bedside computer 4204 and/or the hub 4406. A subset of the data from the electronic medical records received from the one or more servers 4410 may be displayed on a display on an infusion pump 4408A (e.g., the medication being delivered by the infusion pump 4408A). Additionally or alternatively, in some embodiments, a subset of data from the electronic medical records may be cached on the hub and/or the bedside computer. In some embodiments, the hub may communicate with the medical IT systems through middleware (e.g., middleware on the monitoring server 3 of FIG. 1).

Figure 85:
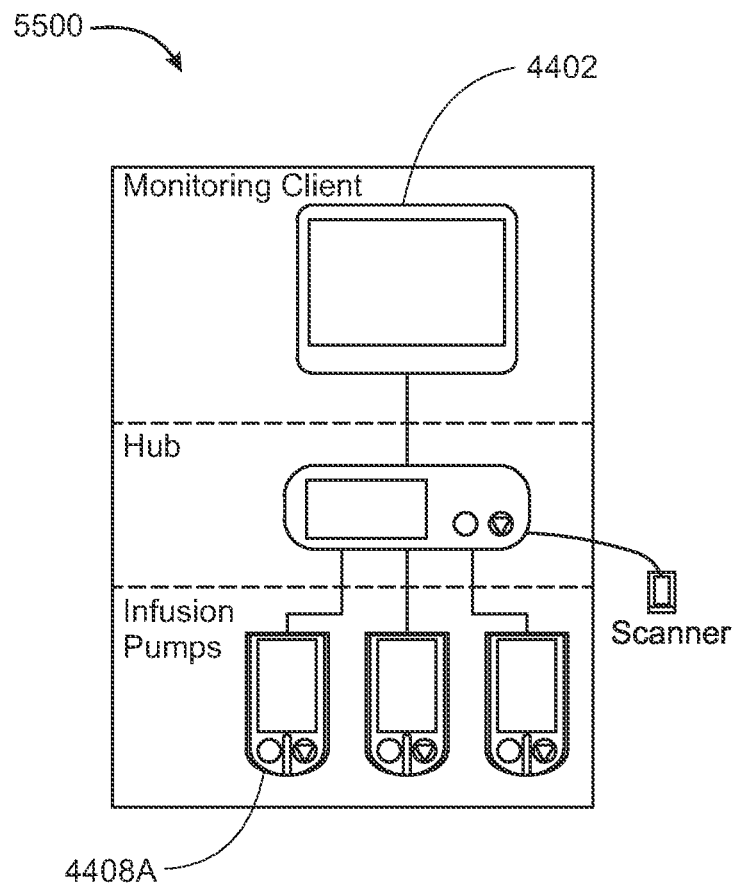
Figure 86:
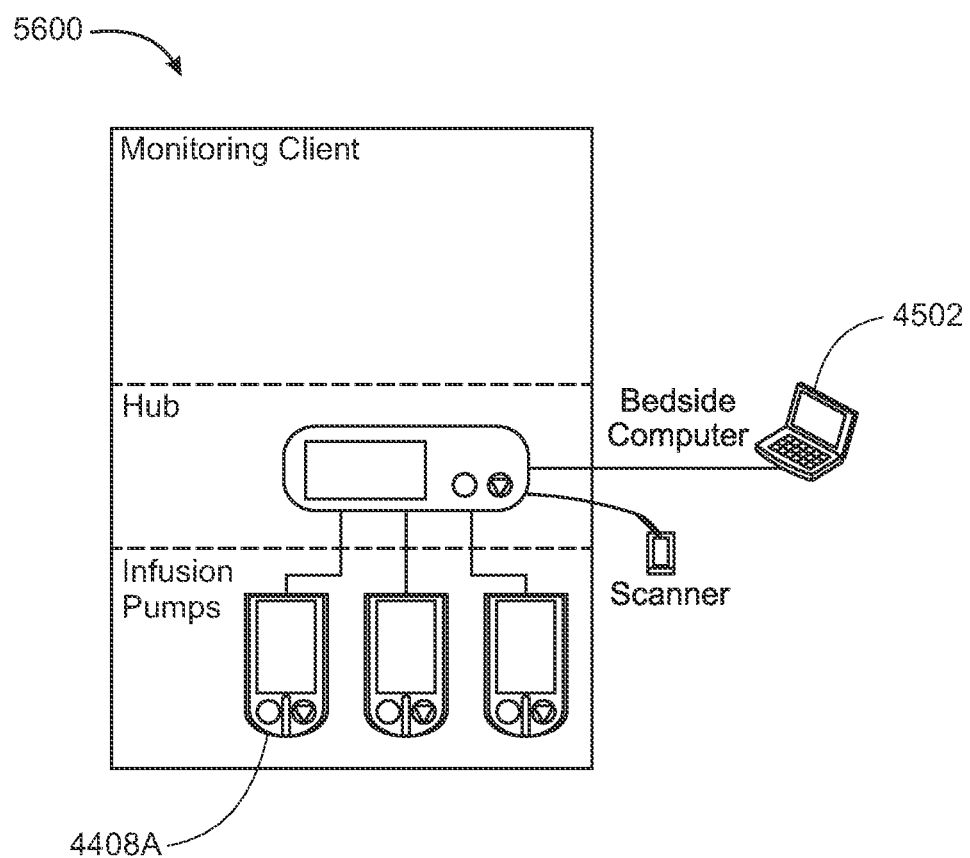

FIG. 85 shows a system 5500, which may be an independent system or is system 5400 of FIG. 84 when the communication with the one or more servers 4410 is interrupted. FIG. 86 shows a system 5600, which may be an independent system or is system 5400 of FIG. 84 when the communication with the one or more servers 4410 is interrupted. In FIGS. 85-86, the prescription may can to be programmed into the systems 5500, 5600 without access to an electronic medical records server of the one or more servers 4410. The prescription may be adjusted on the tablet 4402, the bedside computer 4502, or the infusion pump 4408A. The hub 5804 may communicate with the scanner, the bedside computer 4502, and/or the infusion pumps 4408A-4408C wirelessly and/or via a wired connection. In some specific embodiments, the monitoring client 4402, the hub, and/or the bedside computer can be programmed without EMR data, but may be compared to local version of Guardrails.

Figure 87:
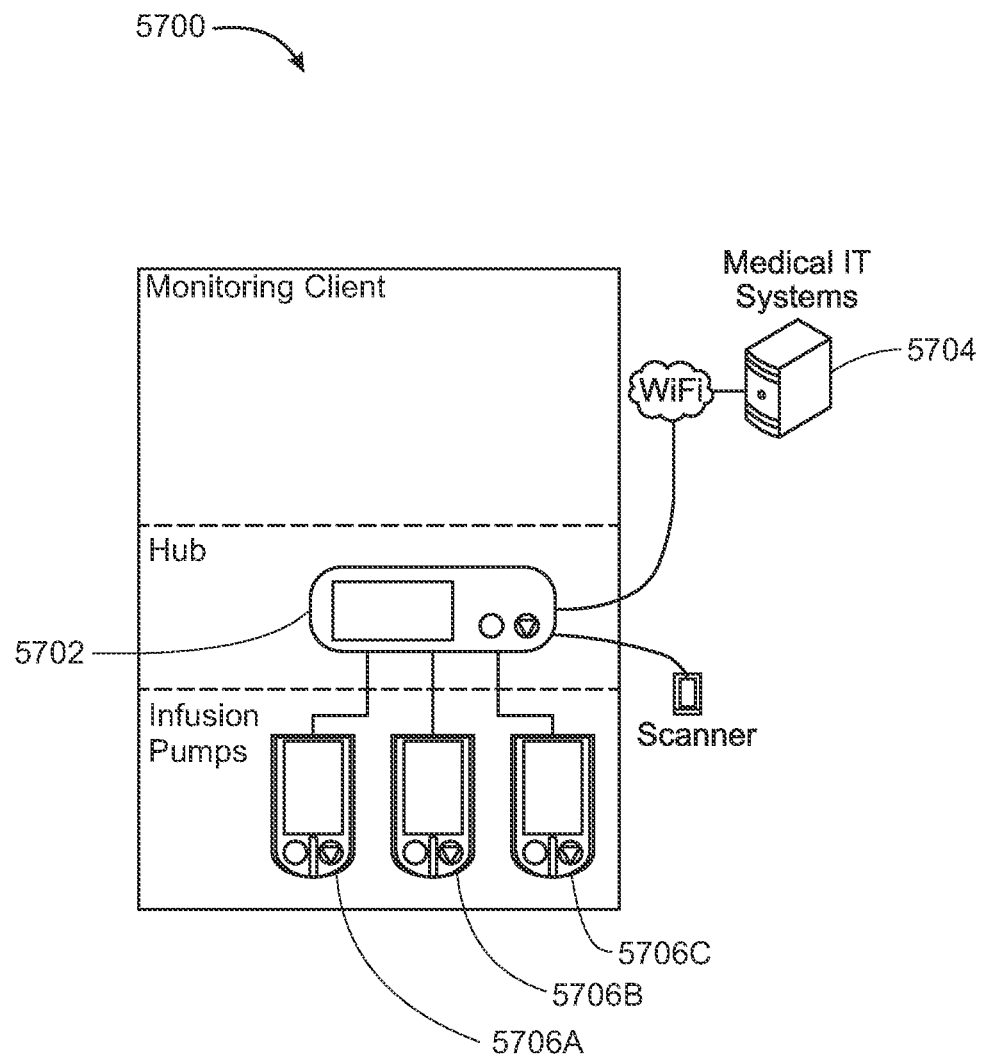

Referring to the drawings, FIG. 87 shows a system 5700 for electronically treating a patient. The hub 5702 communicates with the one or more servers 5704 using a networking API or a local API to a resident electronic medical records application that handles the communication to the one or more servers. The pumps 5706A-5706C are used to program and run the treatment. The hub 5702 may communicate with the scanner and/or the medical IT systems 5704 wirelessly and/or via a wired connection.

Figure 88:
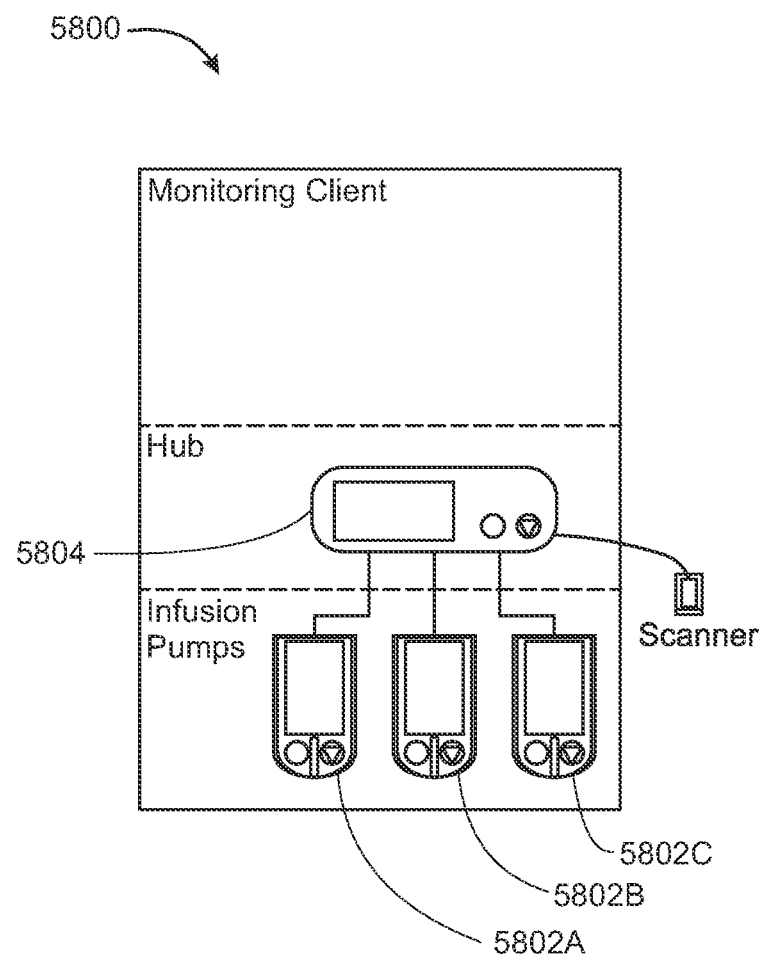

FIG. 88 shows a system 5800 not having a tablet, or a bedside computer. System 5800 may be system 5700 of FIG. 87 when communication to the one or more servers 5704 is unavailable 5704. The infusion pump 5802A is programmed using the user interface on the pump 5802A, and a cached set of predetermined safety criteria (e.g., Guardrails) exists in either the hub 5804 or in the pumps 5802A-5802C. The predetermined safety criteria may be based upon the drug delivered, the patient, allergies, or stored drug contraindications and may prevent unsafe treatment settings from being delivered to the patient. The hub 5804 may communicate with the scanner and/or the infusion pumps 5802A, 5802B, and/or 5802C wirelessly and/or via a wired connection.

Figure 89:
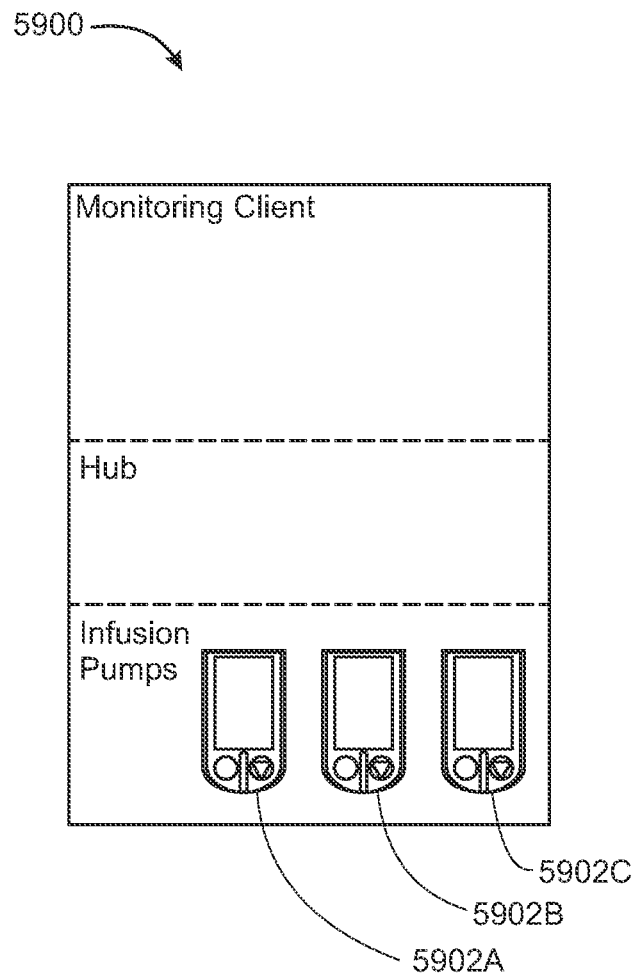

FIG. 89 shows a system 5900 with several infusion pumps. System 5900 may be system 5800 of FIG. 88 when communication with the hub is unavailable. The infusion pumps 5902A-5902C may be directly controlled using each respective user interface on the pump, and a set of predetermined criteria (e.g., DERS) may be cached therein to ensure the medication is not delivered outside predetermined criteria; in some embodiments, no DERS is cached within the infusion pumps 5902A-5902C, and/or permanent DERS data is stored internally within non-volatile memory.

Figure 90:
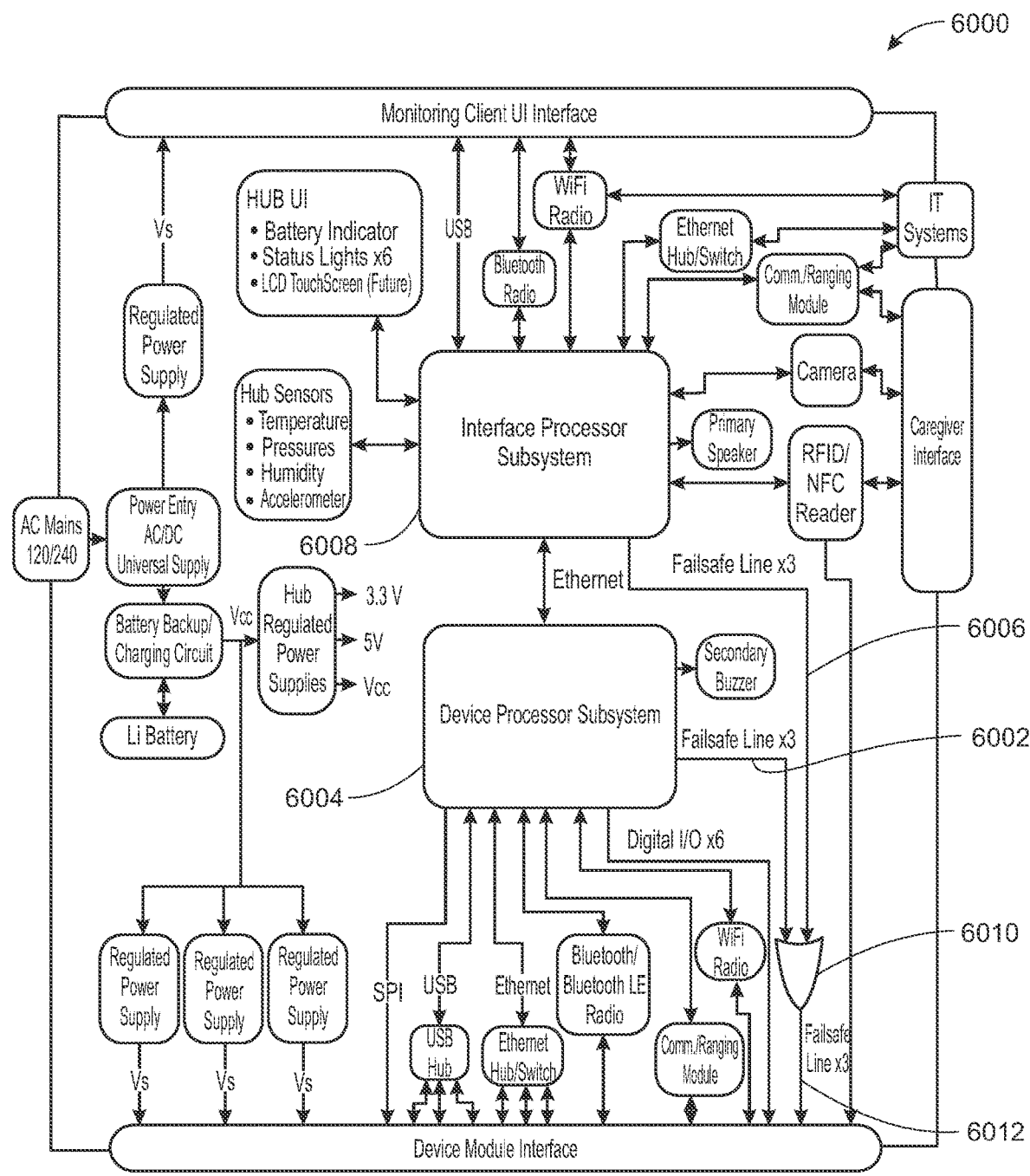
FIG. 90 shows a block diagram of electronic circuitry of embodiments of a hub in accordance with an embodiment of the present disclosure.

FIG. 90 shows a block diagram of circuitry 6000 of a hub disclosed herein. Additionally or alternatively, the circuitry 6000 may be used within a dock, a communication module, or a pump disclosed elsewhere herein. The circuitry 6000 may interface into a bus or hub to communicate with several devices via the device module interface and/or to provide power thereto. Circuitry 6000 includes a first failsafe line 6002 that may be activated by a device processor subsystem 6004, and a second failsafe line 6006 that may be activated by an interface processor subsystem 6008. The first and second failsafe lines 6002, 6006, are fed into an OR gate 6010, which has an output for an output failsafe line 6012. If ether the device process subsystem 6004 or the interface processor subsystem 6008 detects a fault or error, the first or second failsafe lines 6002, 6006 can activate the output failsafe line 6012. The failsafe line 6012 may be coupled to appropriate circuitry and/or devices in response to the output failsafe line 6012, e.g., an automatic occluding device that can automatically prevent fluid flow through an intravenous line when it receives a signal from the output failsafe line 6012. In some embodiments, a patient-care device coupled to the device module interface may request one or more voltages from the regulated power supplies, which each may be a buck, a boost, or a buck-boost power supply.

Figure 91:
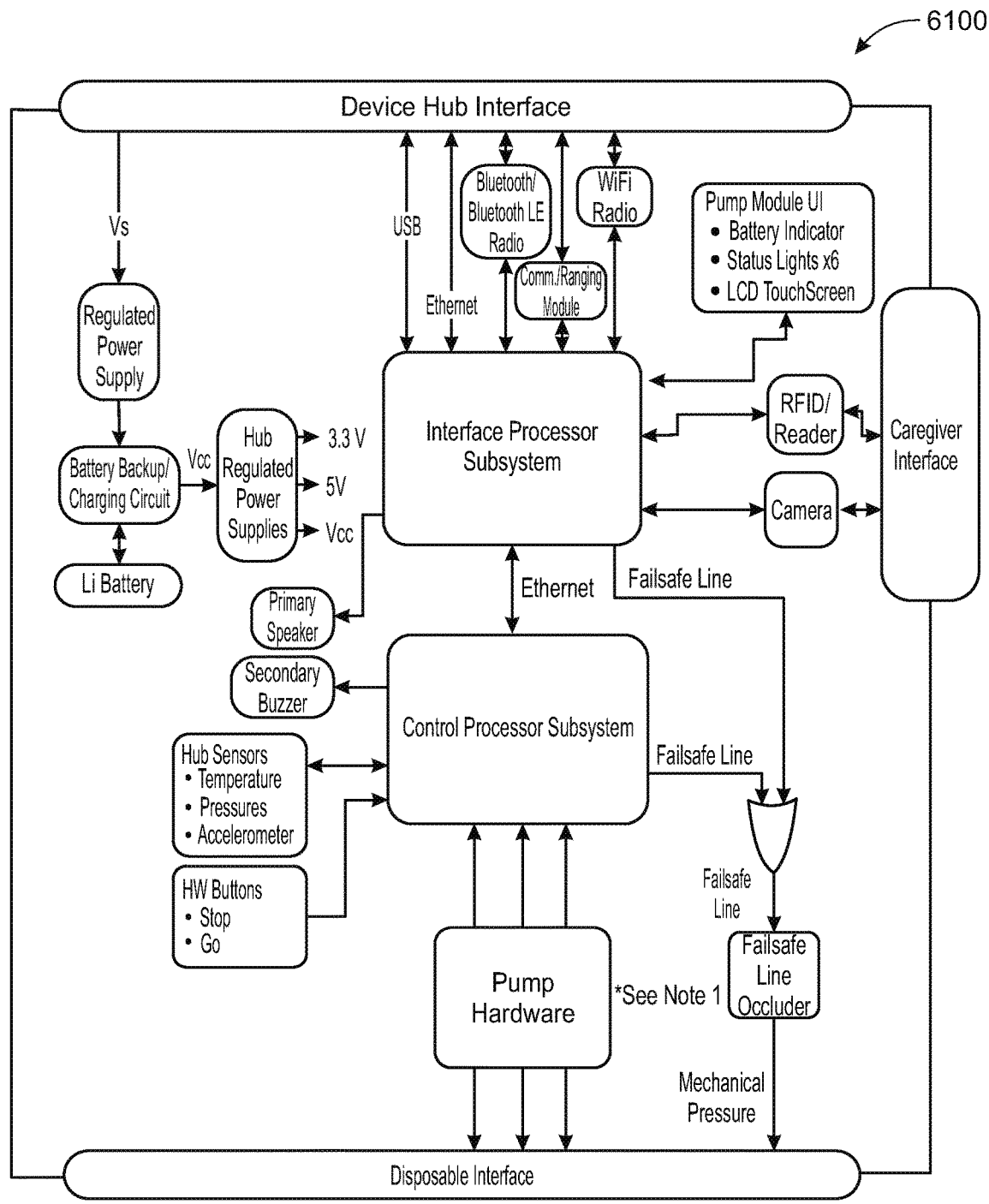
FIG. 91 shows a block diagram of electronic circuitry for interfacing with an infusion pump in accordance with an embodiment of the present disclosure.

FIG. 91 is a block diagram of circuitry 6100 for interfacing with an infusion pump. Additionally or alternatively, the circuitry 6100 may be in a dock or hub disclosed herein that connects to a pump and/or the circuitry 6100 may be an attachable module attachable to an infusion pump, e.g., a communications module. The circuitry 6100 may interface into a bus or hub to communicate with several devices via the device module interface and/or to provide power thereto. In some embodiments, the interface processor subsystem may communicate with device coupled to a device hub interface using a wireless link and/or near-field communications.

Figure 92:
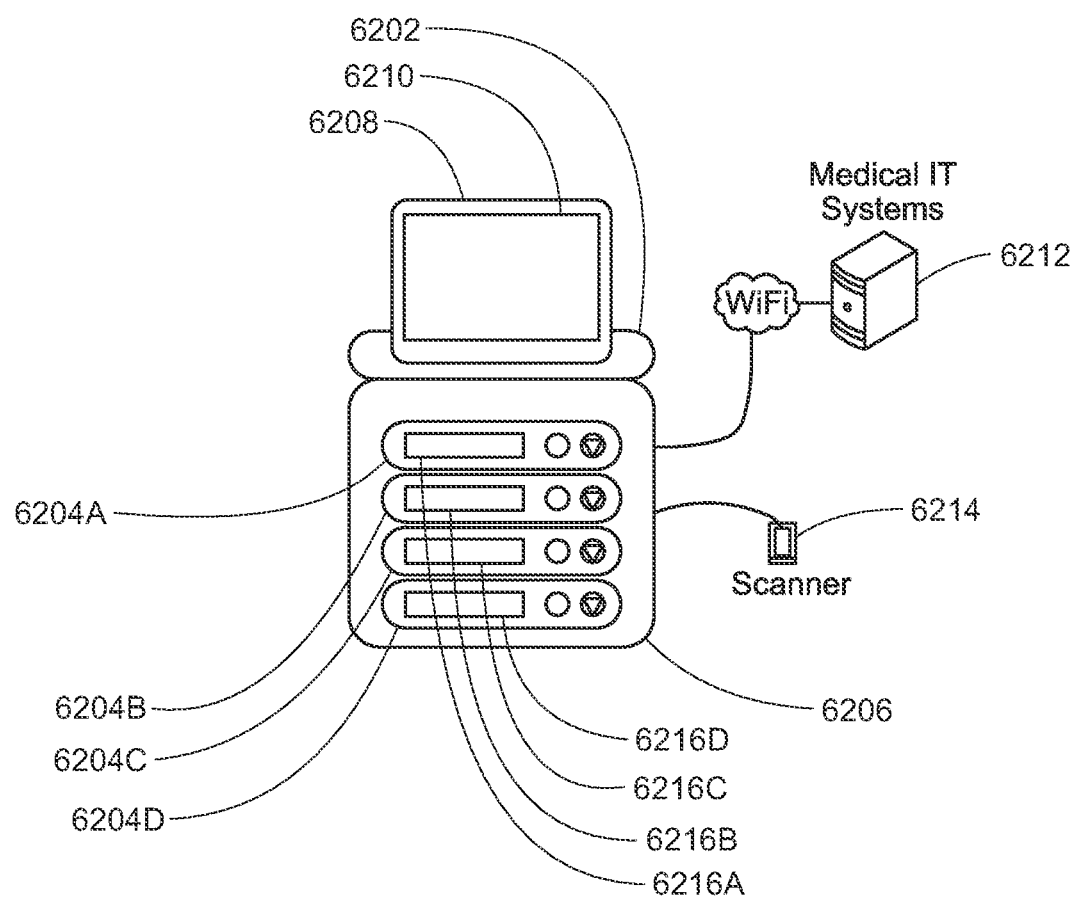
FIG. 92 shows another embodiment of an electronic patient-care system having vertically aligned patient-care devices docked in a dock in accordance with an embodiment of the present disclosure.

FIG. 92 shows a block diagram of an electronic patient-care system 6200 that includes a tablet dock 6202, infusion pumps 6204A-6204D, a dock 6206 for receiving the infusion pumps 6204A-6204D, and a tablet 6208. In alternative embodiments, the tablet 6208 is integrated into the tablet dock 6202. In additional embodiments, the docks 6202 and 6206 are integrated together. In yet additional alternative embodiments, the dock 6202, the dock 6206, and the tablet 6208 are integrated together. The tablet 6208 provides the primary user interface using a display 62010. The dock 6202 includes a memory for caching or storing a user interface template or a user interface program for displaying a user interface on the display 6210 for a patient-care device, e.g., infusion pumps 6204A-6204D. The tablet 6208 may be used to order a prescription or verify a prescription using one or more servers 6212 having a drug error reduction system, e.g., using the scanner 6214. In some embodiments, there may be middleware (e.g., middleware on the monitoring server 3 of FIG. 1) between the medical IT system 6212 and the dock 6206. The user interface template or a user interface program is configured to display on the display 6210 aggregate data from the infusion pumps 6204A-6204D, and acts as a backup alarm if one or more of the infusion pumps 6204A-6204D fails. Additionally or alternative, the dock 6206 alarms if one or more of the infusion pumps 6204A-6204D fails using an internal speaker and/or an internal vibration motor.

The dock 6206 may aggregate data from the infusion pumps 6204A-6204D and pass the aggregated data to the tablet 6208. Each of the infusion pumps 6204A-6204D includes a respective display 6216A-6216D. The displays 6216A-6216D can be used for adjusting flow rates during infusion (predetermined safety criteria may be loaded while programming a prescription through the tablet 6208). An infusion can be started without the drug error reduction system's predetermined safety criteria by adjusting the flow rate from zero on a user interface displayed on the displays 6216A-6216D. The displays 6216A-6216D may also displays alerts and alarms both visually and with auditory indication.

The dock 6206 includes a power entry module, medical grade power supplies, and a backup battery. The dock 6206 also contains all of the communications hardware to interface to the tablet 6208 and to the medical IT systems, i.e., the one or more servers 6212. The dock 6206 may include hardware for traveling, such as a pole, and pole mounting hardware.

During programming of a prescription, the personalized drug error reduction system setting, e.g., predetermined safety criteria, is received directly from the one or more servers 6212. The tablet 6208 may be used to facilitate entering in a patient's ID and medication. Communication between the tablet 6208 and the one or more server 6212 may occur through the dock 6206. The predetermined safety criteria from the general drug error reduction system is cached on the dock 6206 or in one or more of the infusion pumps 6204A-6204D. In case the drug error reduction system is unavailable from the one or more servers 6212, the locally cached predetermined safety criteria from the drug error reduction system is updated through the network (e.g., WiFi) when it is available again.

The dock 6206 has enough battery to support 8 hours of operation of the hub dock 6206 and of the infusion pumps 6114A-6114D. The tablet 6110 may or may not have its own battery. In some embodiments, the infusion pumps 6204A-6204D may have enough battery (or other backup power) to support saving data when being pulled out of the dock 6206 and for alarming. This alarming capability and separate battery may also be moved to the dock 6206.

The pump's UI display on a display of the displays 6216A-6216D may be small. For example, in some embodiments, the displays 6216A-6216D may be just large enough so that only flow rate may be adjusted. This will allow an infusion to be started without entering in any other information. Since the patient's ID and/or drug name may be entered before accessing the EMR, there is limited data from a drug error reduction system or guardrails from the one or more servers 6212 if infusion is started without the tablet 6208. If the infusion is programmed with the tablet and then later the tablet is removed from the system the pump can continue to implement the guardrails feature related to the current prescription.

Figure 93:
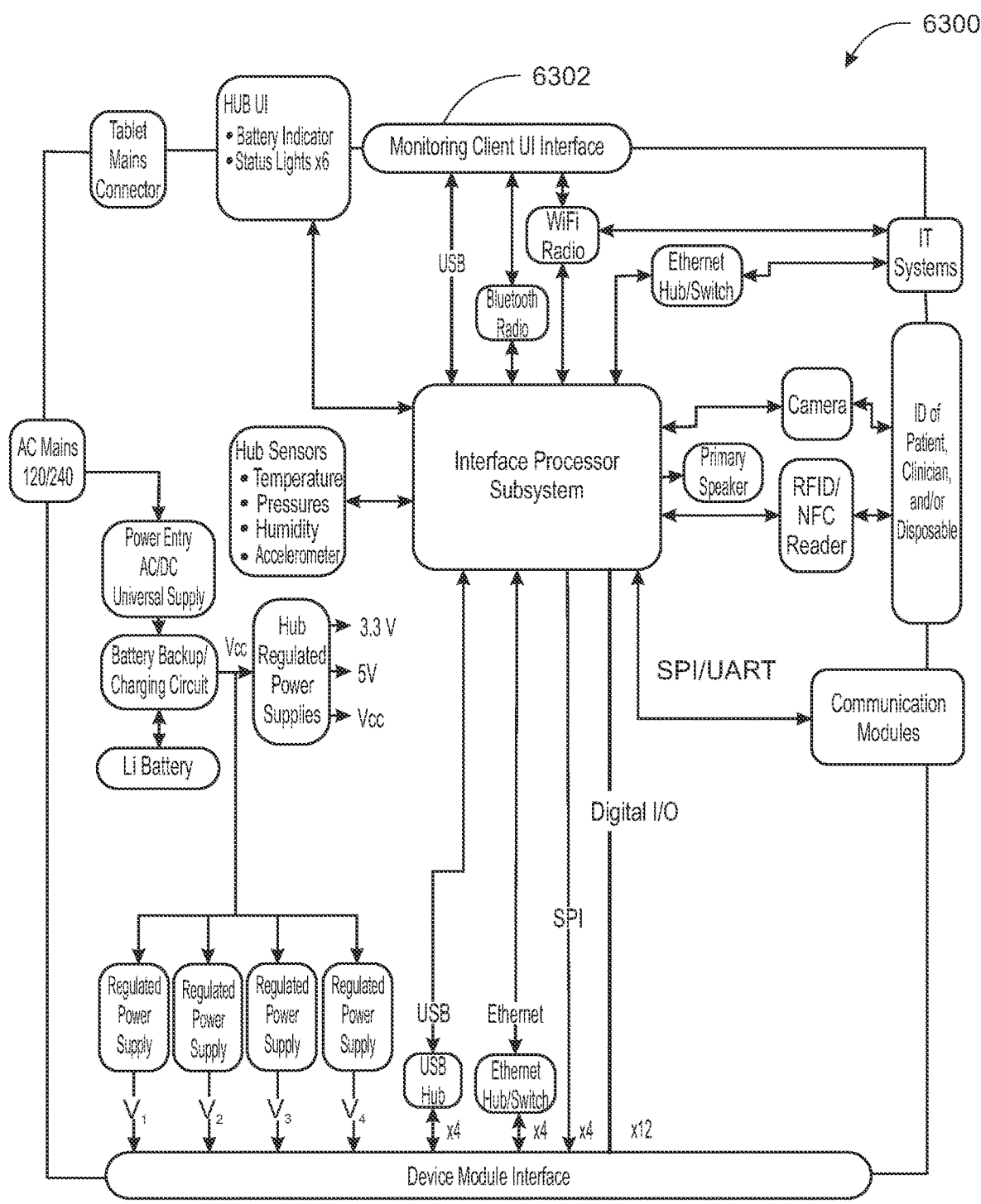
FIG. 93 shows a block diagram of electronic circuitry of an embodiment of a hub in accordance with an embodiment of the present disclosure.

FIG. 93 shows a block diagram of circuitry 6300 for the hub 6206 of FIG. 92, or for a communications module 124A-124K of FIG. 1, 3, 5, 7, 8, or 9. Additionally or alternatively, the circuitry 6300 may be used in a pump or a dock described herein. The circuitry 6300 may interface into a bus or hub to communicate with several devices via the device module interface and/or to provide power thereto. A tablet (not shown) coupled to a tablet UI interface 6302 may have its own power supply (not explicitly shown). In some embodiments of the present disclosure, the circuitry 6300 can supply power to a tablet.

Figure 94:
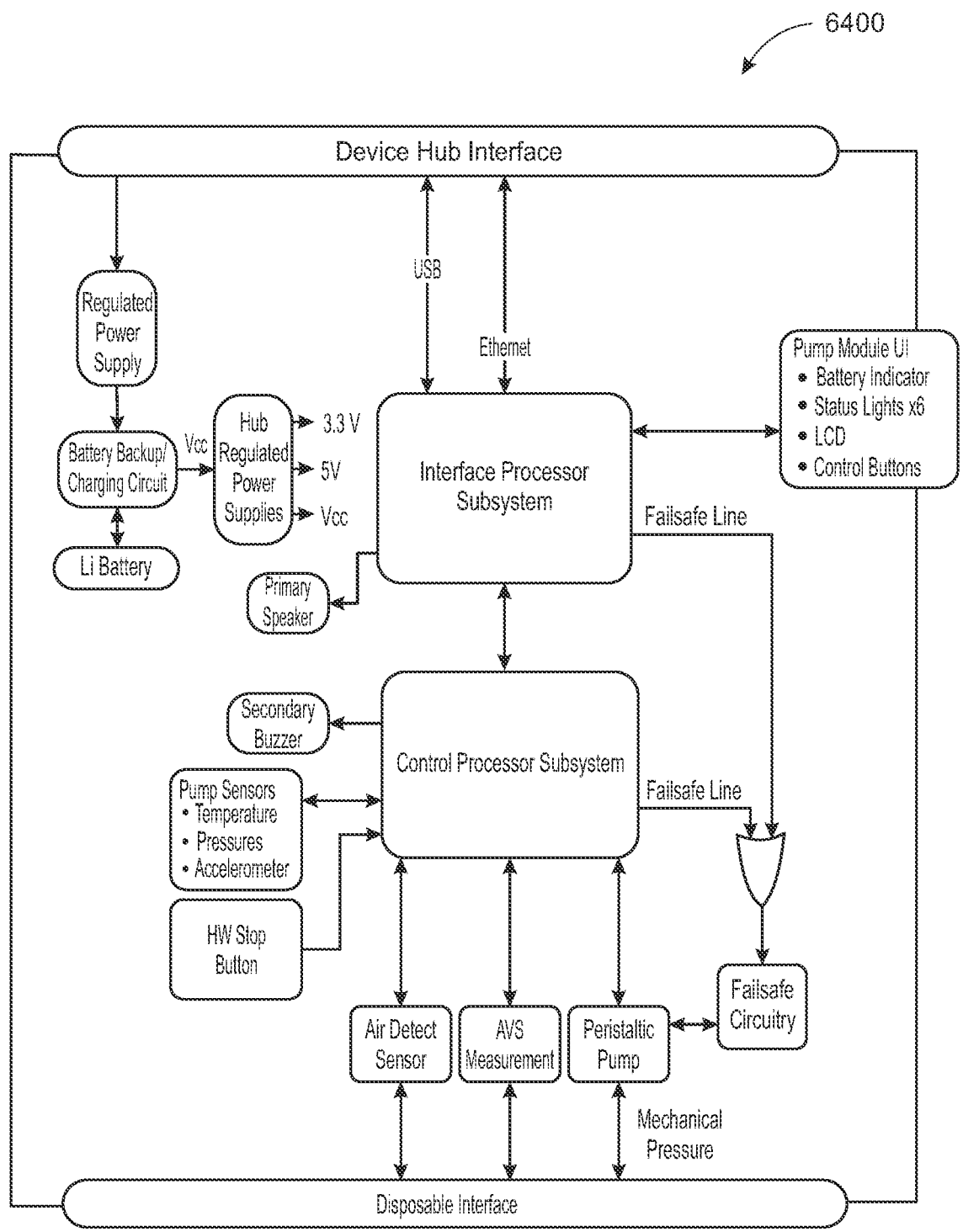
FIG. 94 shows a block diagram of electronic circuitry of a communication module in accordance with an embodiment of the present disclosure.

FIG. 94 shows a block diagram of circuitry 6400 for the hub 6206 of FIG. 92, or for a communications module 124A-124K of FIG. 1, 3, 5, 7, 8, or 9. Additionally or alternatively, the circuitry 6400 may be used in a dock or a pump described herein. The circuitry 6400 may interface into a bus or hub to communicate with several devices via the disposable interface and/or to provide power thereto. In some embodiments of the present disclosure, the circuitry 6300 can supply power to a tablet.

Figure 95:
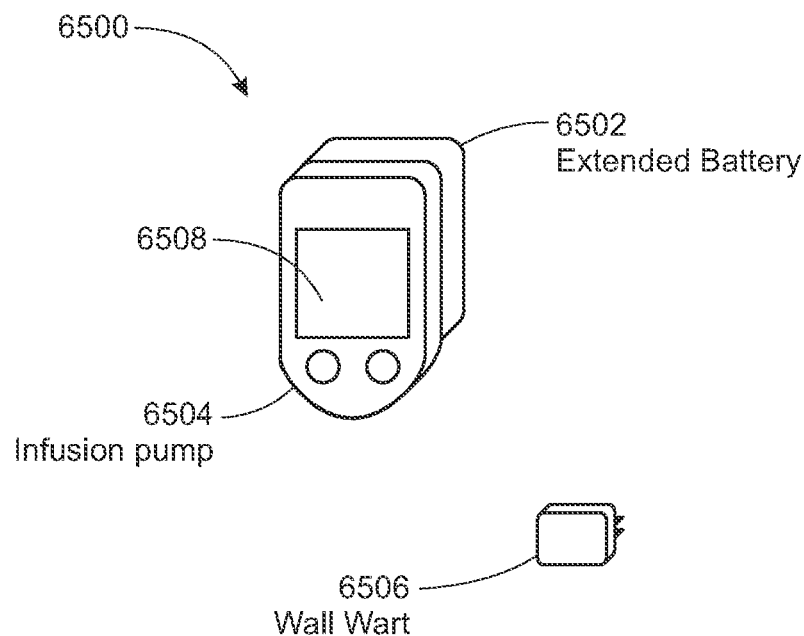
FIGS. 95-98 shows several embodiments of electronic patient-care systems having an infusion pump coupled with a communications module in accordance with several embodiment of the present disclosure.

FIG. 95 shows a system 6500 having an extended battery 6502, an infusion pump 6504, and a wall wart 6506. System 6500 may operate without a drug error reduction system from a server. A display 6508 on the infusion pump 6504 may be used to enter in drug information and control the infusion rate. In some embodiments, drug error reduction system data is cached in memory of the infusion pump 6504 and updated through docking.

Figure 96:
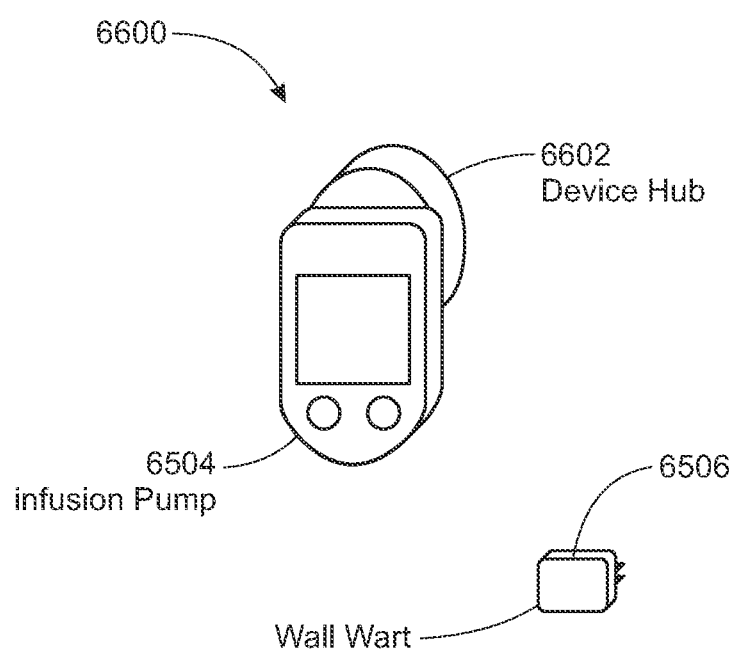

FIG. 96 shows a system 6600 having an infusion pump 6504 coupled to a device hub 6602. The infusion pump has 6504 has an ability to initiate delivery. Emergency modes with limited generic Drug Error Reduction System based on a subset of drugs easily picked from a list may be cached on the device hub 6602 and/or the infusion pump 6504. The infusion pump 6504 may be started without data from a drug error reduction system.

Figure 97:
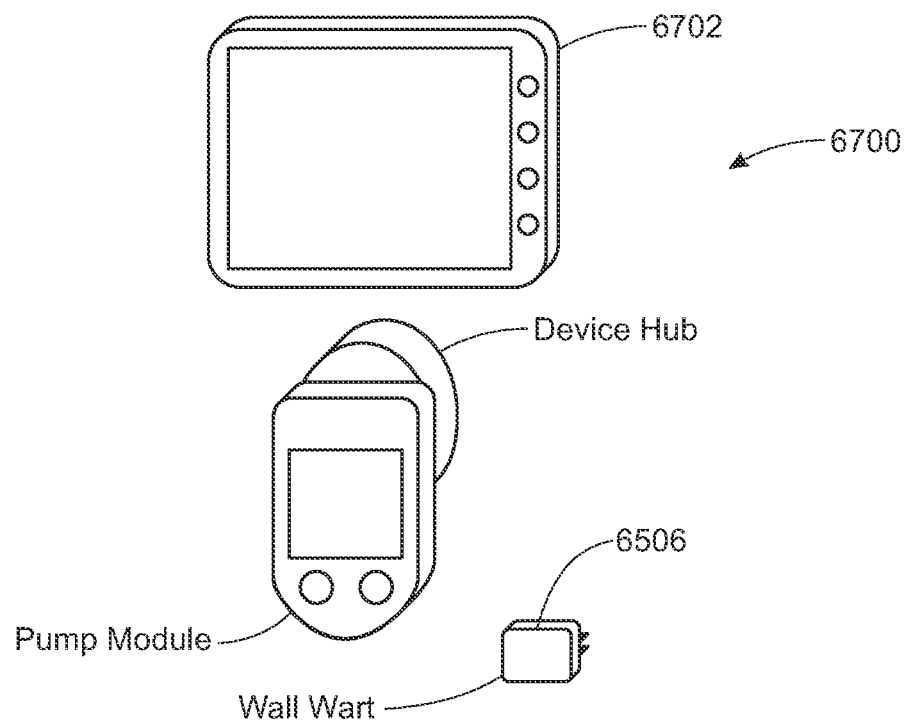

FIG. 97 shows a system 6700 having a tablet 6702 allowing access to the infusion pump 6504 through the tablet's 6702 interface. The tablet's 6702 user interface may reside in the device hub 6602. DERS may reside on the tablet 6702, on the device hub, and/or on the infusion pump 6504. A wall wart 6506 can supply power to the tablet 6702, the device hub 6602, and/or the infusion pump 6504.

The device hub 6602 may have a physical or wireless connection to the tablet 6702. The device hub 6602 may include a cradle (not shown) for the tablet 6702. The tablet 6702 could optionally be rigidly attached to the device hub 6602.

Figure 98:
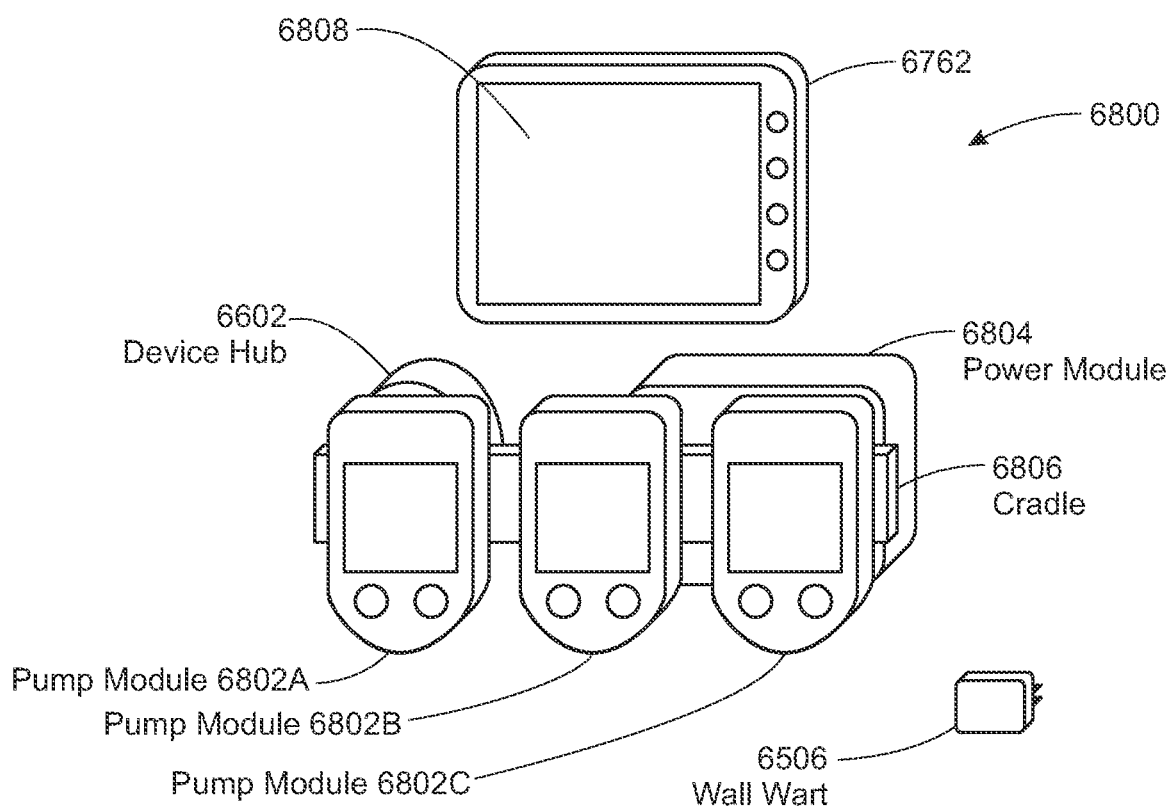

Referring to the drawings, FIG. 98 shows a system 6800 having a dock 6804 (which may be a cradle in some embodiments), pump modules 6802A-6802C, a device hub 6602, and tablet 6702 plug into a backplane of the dock 6804 (or in some embodiments, cradle). In addition, a power module 6804 includes power entry and extra battery that may be plugged into or is integrated into the dock 6806. The device hub 6602 is the master for communication between all other modules as well as IT systems via one or more servers (not shown). Although the infusion pumps 6802A-6802C are removable in the embodiment shown in FIG. 98, other components may be modular or integrated together in other embodiments.

The infusion pumps 3802A-3802C generally contain pumping mechanisms and electronics that can run a pumping mechanism. In one specific embodiment, the device hub 6602 includes backup power for one or more infusion pumps 3802A-3802C, a processor for aggregating data and hosting the tablet's 6702 UI model (e.g., a user-interface template) and modular communications hardware The tablet 6702 may include a touchscreen 6808. The wall wart 6506 provides AC-to-DC conversion, and is coupled to the power module 6804 which contains all the power entry module and an AC/DC power supply. The wall wart 6506 is optional and/or an AC-to-DC converted may be incorporated into the power module 6804. The power module 6804 may also include an extended battery to run multiple pump modules. The dock 6806 includes a back plane connecting together the various components.

Figure 99:
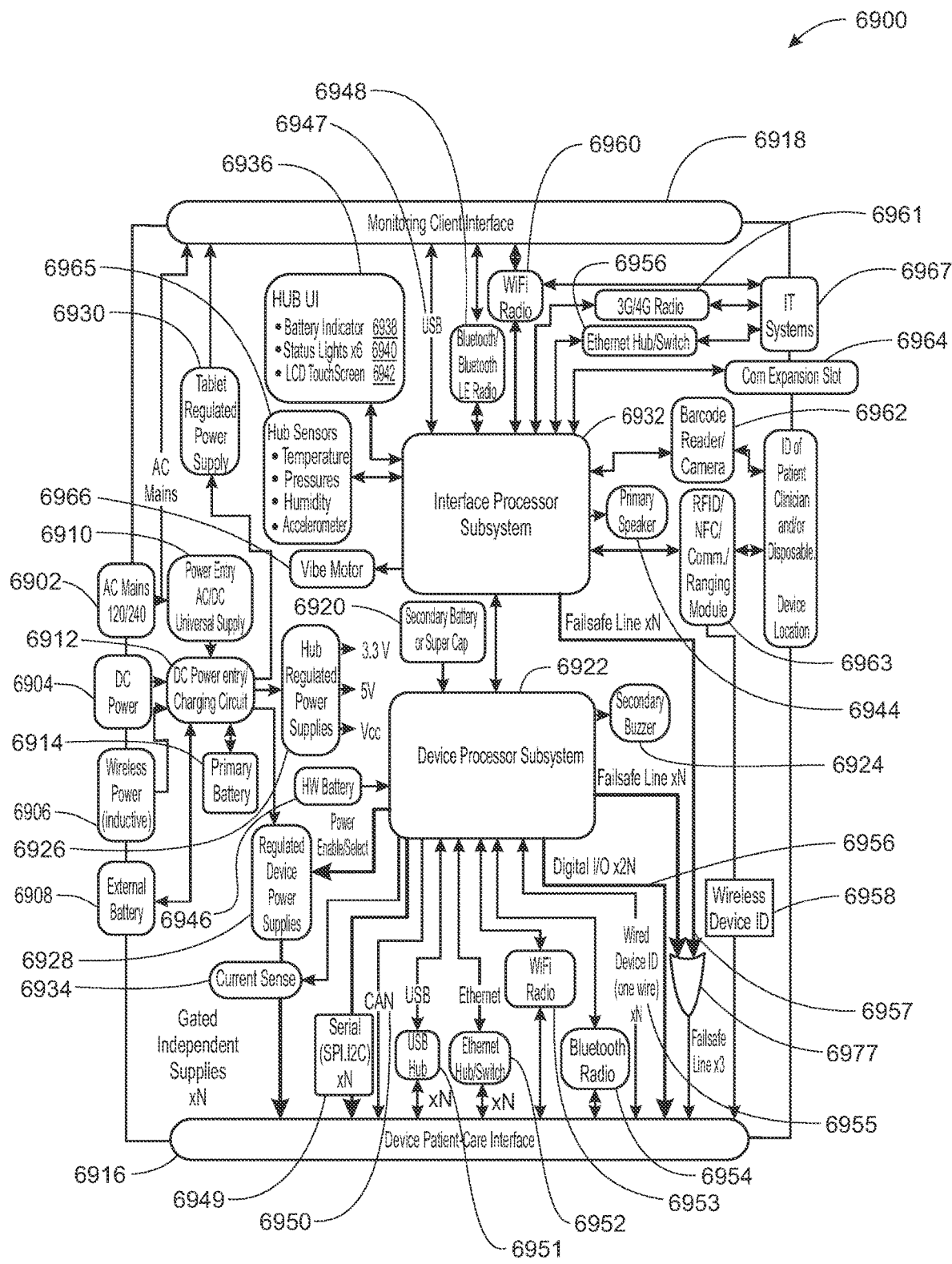
FIGS. 99-101 show several block diagrams of electronic circuitry of a dock in accordance with several embodiments of the present disclosure.

FIG. 99 shows electronic circuitry 6900 of a device hub, e.g., device hub 6602 of FIG. 96, in accordance with one embodiment of the present disclosure. Additionally or alternatively, the circuitry 6900 may be used in a pump, a dock or a communication module described herein. The circuitry 6900 may interface into a bus or hub to communicate with several devices via the device patient-care interface 6916 and/or to provide power thereto. Circuitry 6900 includes various power sources, a user interface, communications, sensors, and actuators. Circuit 6900 includes AC mains 6902, DC power 6904, wireless power 6906, e.g., inductive, and an external battery connection 6908.

The AC mains 6902 may be a direct connection to mains, such as through an AC outlet. The AC mains 6902 are coupled to a power entry and charging circuit 6910 which can rectify and convert the AC signal from the AC mains 6902 to a DC signal. The DC signal from the power entry AC/DC universal supply 6910 is fed into the DC power entry and charging circuit 6912.

The DC power 6904 receives DC power from a DC power source, such as the wall wart 6506 of FIG. 95 or from a backplane or another external battery (not explicitly shown).

The wireless power 6906 may receive energy wirelessly. For example, the wireless power 6906 may include a coil that receives a time-varying magnetic field such that a voltage across the coil is induced; the induced AC signal is rectified and smoothed via a smoothing circuit and coupled to the DC power entry/charging circuit 6910.

The circuitry 6900 also includes a primary battery 6914, an external battery 6908, and a secondary battery 6920. The primary battery 6914 is used to supply power to one or more patient-care devices coupled to the patient-care device interface 6916 and a tablet (not shown) coupled to a tablet interface 6918. The interface 6916 may connect to none, one, or a plurality of patient-care devices through one or more communications technologies. The tablet interface 6918 may couple directly to a tablet or is coupled to a user interface of a tablet. The external battery connection 6908 may be electrical connectors (not explicitly shown) that are adapted for electrical coupling with one or more battery cells located in a separate housing of the electronic circuitry 6900. The external battery 6908 may supplement the primary battery 6914 or replace the primary battery 6914 in the event the primary battery 6914 fails. The secondary battery 6920 may be a super-capacitor 6920. In some embodiments, the secondary battery 6920 may be used only in failure modes where power is otherwise unavailable, e.g., the AC mains 6902 fails and the external battery 6908 is removed or fails. The secondary battery 6920 supplies sufficient power for a device processor subsystem 6922 to alarm via a secondary buzzer 6824.

The circuitry includes various power supplies, such as hub regulated power supplies 6926, a gated independent supply from regulated device power supplies 6928, and a tablet regulated power supply 6930.

The hub regulated power supplies 6926 is used to for powering the electric and sensors of the circuitry 6900. For example, the hub regulated power supplies 6926 are used to provide a voltage for an interface processor subsystem 6932.

The regulated device power supplies 6928 may be gated and may provide one or more independent and regulated voltage supplies that are sent to one or more patient-care devices coupled to the patient-care device interface 6916. The one or more regulated device power supplies 6928 that are sent to one or more patient-care devices via the patient-care device interface 6916 are monitored by a current sense 6934 and are enabled by the device processor subsystem 6922. Additionally or alternatively, the regulated device power supplies 6928 may be programmable such that a patient-care device requests a voltage from device processor subsystem 6922, which is turn, programs the regulated device power supplies 6928 to supply the requested voltage to the patient-care device.

The tablet regulated power supply 6930 supplies DC power to a tablet coupled to the tablet interface 6918. Additionally or alternatively, the circuitry 6900 passes an AC signal from the through AC mains 6902 for use by an internal power supply of the tablet (not shown in FIG. 99).

The circuitry 6900 also includes a user interface 6936 including a battery indicator 6938, status indicators lights 6940, and a LCD touchscreen 6942. The battery indicator 6938 shows the charge state and battery state of the primary battery 6914. The status indicator lights 6940 show the status of the hub, tablet, and any patient-care devices coupled to the patient-care device interface 6916. The status indicator lights 6940 may include one or more lights, e.g., LEDs, for each patient-care device coupled to the patient-care device interface 6916. For example, the status indicator lights 6940 may include a LED to show an alarm state and another LED to show a run state.

In some embodiments of the present disclosure, the LCD touchscreen 6942 may be the main display and input method for patient-care devices coupled to the patient-care device interface 6916 which don't have displays. Additionally or alternatively, the LCD touchscreen 6942 displays verbose information about the hub, the hub's circuitry 6900, and/or patient-care devices coupled to the patient-care device interface 6916. In addition, the LCD touchscreen 6942 may be configured to passively output status information to a large display, such as an external TV screen.

The primary speaker 6944 may be used to provide voice guidance for patient-care devices coupled to the patient-care device interface 6916 that do not have displays or alarms when a tablet is not connected to the tablet interface 6918 and/or is otherwise not available. The secondary buzzer 6924 is a backup buzzer and provides safety in conditions in which the primary speaker 6944 is unavailable or broken and/or the interface processor subsystem 6932 is unavailable or broken.

In some embodiments of the present disclosures, hardware buttons 6946 may be used for additional safety input to stop or provide input into a patient-care device that does not have its own display and there is no tablet available.

The tablet interface 6918 is coupled to the interface 6932 such that the interface processor subsystem 6932 can communicate with a tablet coupled to the tablet interface 6918. The tablet interface 6918 is coupled to a USB interface 6947 and a Bluetooth interface 6948 (the Bluetooth interface 6948 may be a Bluetooth Low energy interface.

The patient-care device interface 6916 provides interfaces to a patient-care device including a serial interface 6949, which may be a SPI, I2C, RS232, RS485, or any other serial protocol. The patient-care device interface 6916 also provides a CAN interface 6950, a USB interface 6951, a Ethernet interface 6952, a WiFi Radio interface 6953, and a Bluetooth interface 6954.

The patient-care device interface 6916 may include a Wired Device ID 6955 that facilitates patient-care device discovery of type, serial number, class, or performance characteristics of the patient-care device and its location in a multichannel cradle, dock, and/or hub. The wired device ID 6955 may be used to determine an optimal or preferred communications protocol based upon predetermined criteria. Additionally or alternatively, a powering method may be chosen as a function of the wired device ID 6955 based upon predetermined criteria. The wire device ID 6955 may be determined by communicating with a patient-care device attached to the patient-care device interface 6916 using a "one wire" device. Additionally or alternatively, the patient-care device interface 6916 also includes a wireless device ID 6958 that facilitate patient-care device discovery which may utilize a RIFD interrogator, near field communications, or other wireless communications link to facilitate patient-care device discovery of the type, serial number, class, or performance characteristics of the patient-care device and its location in a multichannel cradle, dock, and/or hub.

The patient-care device interface 6916 also includes a digital I/O interface 6956. The digital I/O interface 6956 may include multiple lines per patient-care device coupled to the patient-care device interface 6916 that may be used for triggering actuators, enabling pins as part of a safety system, or for be used for status lights on a hub or cradle.

The patient-care device includes also includes failsafe lines 6957. Either of the interface processor subsystem 6932 or the device process subsystem 6922 can trigger one of the failsafe lines 6957 which are fed into a logical OR 6977. The output of the logical OR 6977 can be coupled to a electromechanical occluding device (not shown) coupled to the patient-care device interface 6916. In alternative embodiments, a logical AND is used in place of the logical OR 6977 such that both of the interface processor subsystem 6932 or the device process subsystem 6922 must agree, in this specific embodiment, (i.e., both provide a logical true) prior to a "true" signal being sent to the patient-care device interface 6916 as a failsafe line.

The circuitry 6900 includes several communications links to IT systems or one or servers 6967. The circuitry 6900 includes a WiFi interface 6960, a 3G/4G interface 6961, and an Ethernet hub or switch interface 6956. The 3G/4G interface 6961 facilitates operation of the hub having the circuit 6900 within a home environment. The 3G/4G interface 6961 may be any cellular technology or long-range communications transceiver, e.g., Code division multiple access ("CDMA"), Time-division multiplexing ("TDM"), WiMax, Evolution-Data Optimized ("EVDO"), Orthogonal frequency-division multiplexing ("OFDM"), Space-Division Multiple Access ("SDMA"), Time-Division Duplex ("TDD"), Time division multiple access ("TDMA"), Frequency-division duplexing ("FDD"), or the like.

The circuitry 6900 includes a barcode reader or camera 6962, which may be used for patient Identification, clinician identification, and/or solution/drug identification (e.g., by reading a 2-D barcode using the camera).

The circuit 6900 may also include a transceiver 6963 for RFID, NFC, or other communication protocol for patient identification, clinician identification, and/or solution/drug identification or to determine the location of a patient-care device.

The circuitry 6900 can also include a communications expansion slot 6964 so that future wired or wireless technologies may be modularily inserted into the slot 6964. The slot 6964 may include one or more expansion connectors and is internal to the case of the hub is externally connectable thereto. Additionally or alternatively, the expansion slot 6964 may be a connection for an additional modules having a plurality of functions, e.g., wireless communications functions, wired connections, and the like.

The circuitry 6900 may also include hub sensors 6965, such as a temperature sensor, a pressure sensor, a humidity sensor, and an accelerometer. The circuitry 6900 may also include a vibration motor 6966 for tactile feedback, e.g., when alarming or prompting a user for selection via a GUI on the tablet coupled to the tablet interface 6918.

Figure 100:
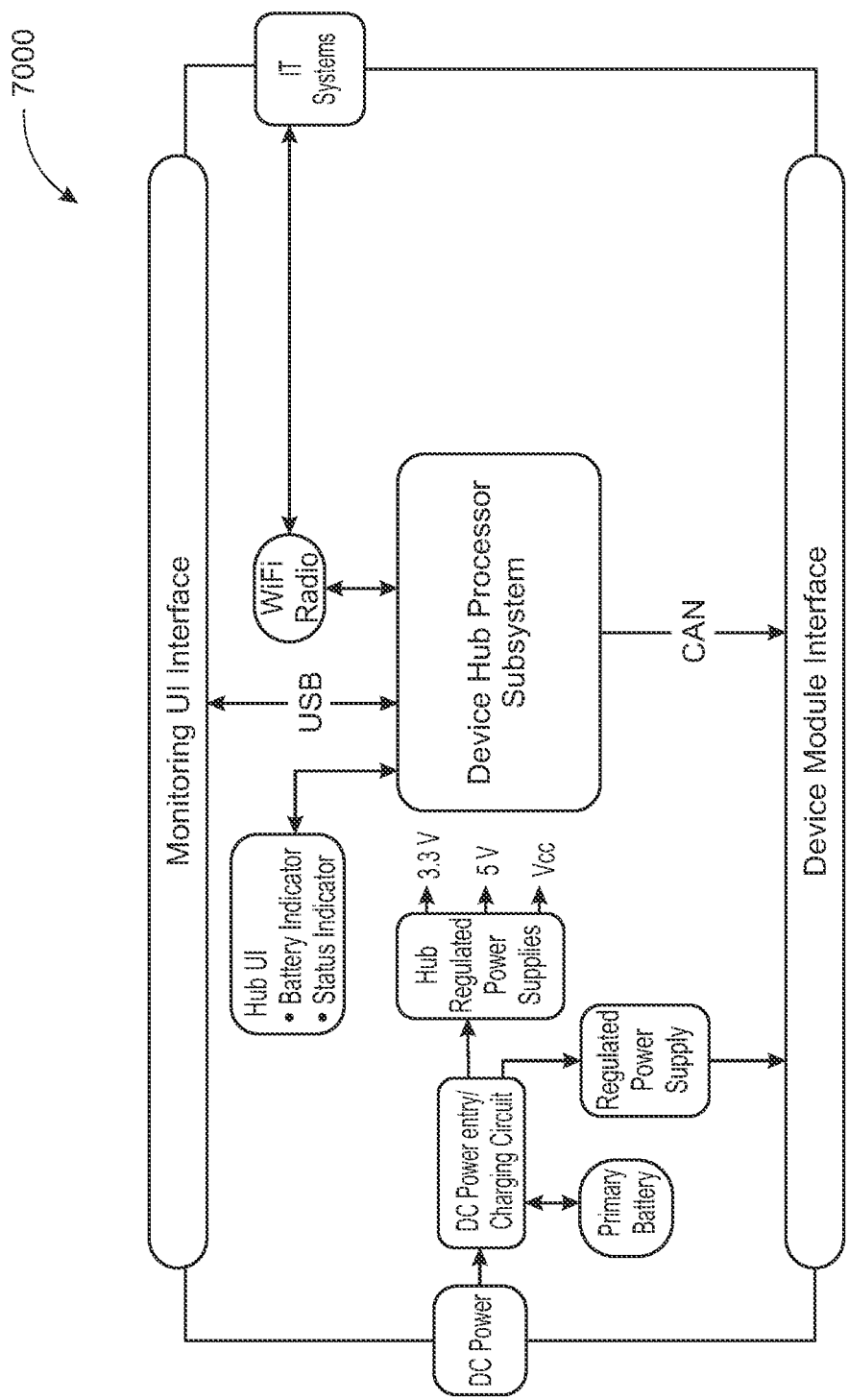

FIG. 100 shows a block diagram of circuitry 7000 which shows one embodiment of features that may be used for a patient-care device such as a pump. That is, the device module interface may interface with an infusion pump 7 of FIG. 1, for example. Additionally or alternatively, in some embodiments, the circuitry 7000 may be on a hub, a communication module, a dock, or an infusion pump described herein. The circuitry 7000 may interface into a bus or hub to communicate with several devices via the device module interface and/or to provide power thereto. Circuitry 7000 also includes various safety systems. This circuitry 7000 supplies a method of battery backed-up power and communications to the tablet and IT systems. The circuitry 7000 receives power from an external wall wart (not shown) power supply for the hub and for the tablet. In some embodiments, the device hub processor subsystem includes an Ethernet connection to the IT systems. In some embodiments, the device hub processor subsystem communicates with the monitoring client interface using Ethernet, WiFi, Bluetooth, Bluetooth Low Energy, near-field communications, etc.

Figure 101:
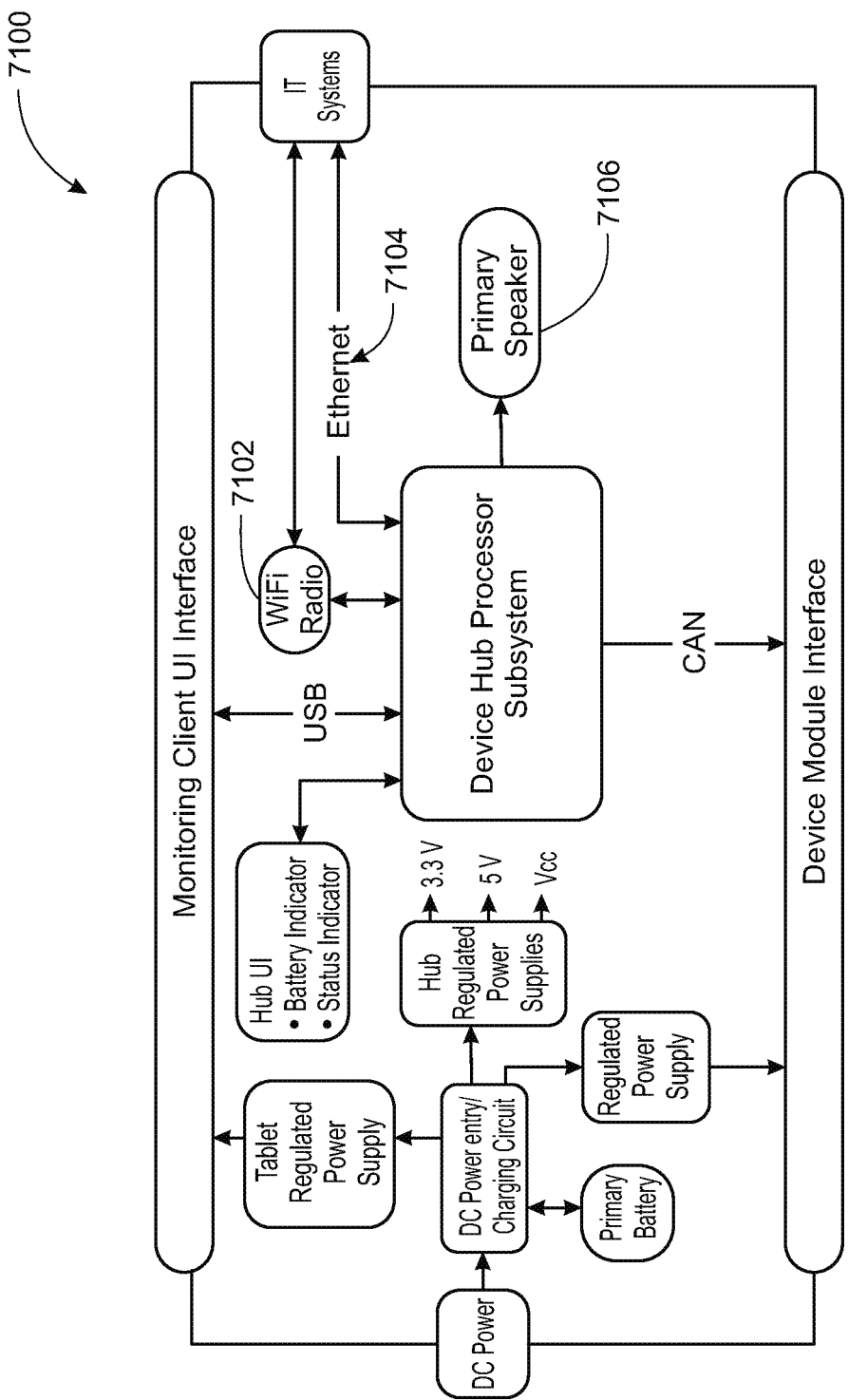
Figure 102:
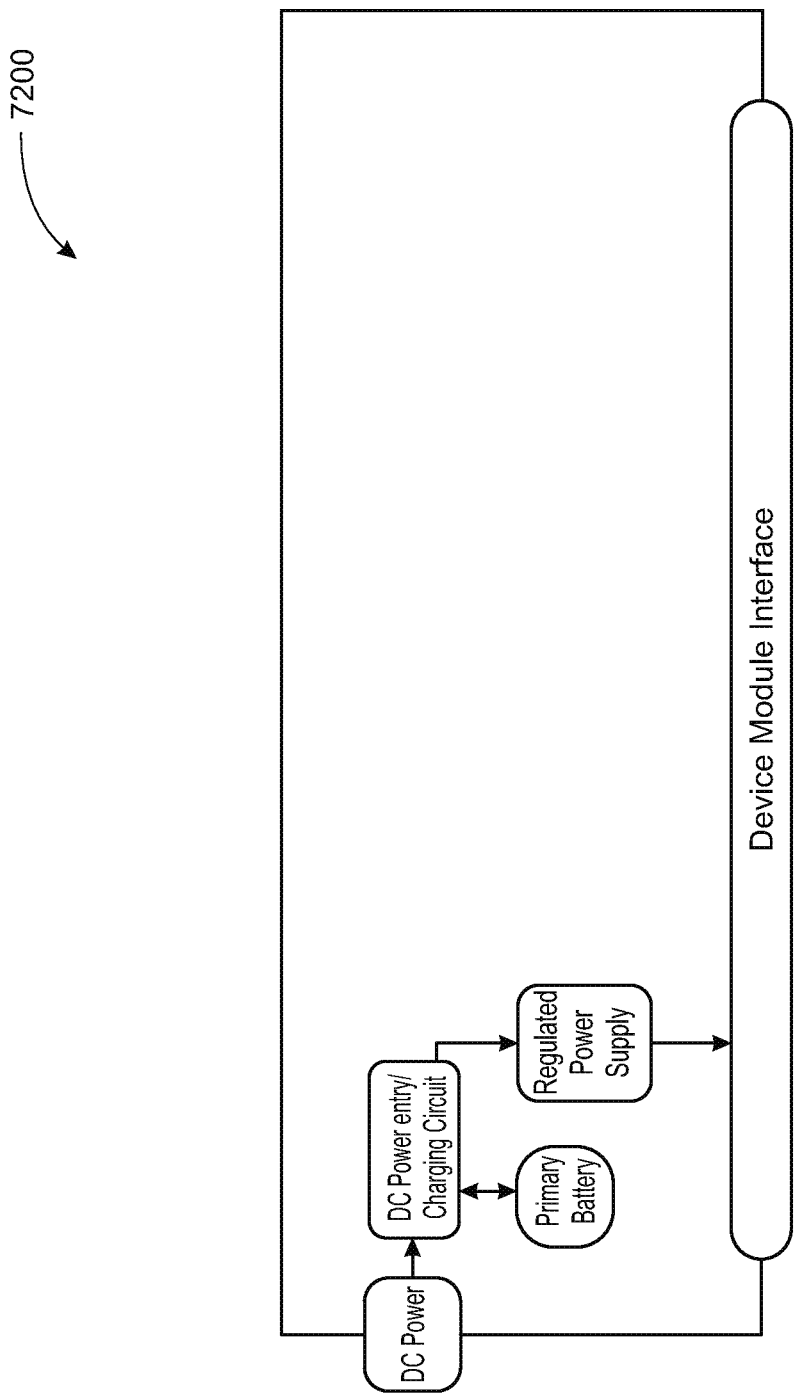
FIG. 102 shows a block diagram of a battery pack in accordance with an embodiment of the present disclosure.

FIG. 101 shows a block diagram of circuitry 7100. The circuitry 7100 may be on a hub. And, the device module interface may interface with an infusion pump 7 of FIG. 1, for example. Additionally or alternatively, in some embodiments, the circuitry 7100 may be on a hub, a communication module, a dock, or an infusion pump described herein. The circuitry 7100 may interface into a bus or hub to communicate with several devices via the device module interface and/or to provide power thereto. Circuitry 7100 includes a WiFi circuit 7102 and an Ethernet connection 7104 for communication with an IT system (e.g., as described herein) for flexibility in accordance with one embodiment of the present disclosure. The speaker 7106 may also be useful for enunciating problems with the hub or dropped connections to the IT system. The tablet regulated power supply is may facilitate the use of only one external power supply. In some embodiments, the device hub processor subsystem communicates via the monitoring client interface using Bluetooth, wifi, Bluetooth low energy, near-filed communications, etc. In some embodiments, the device hub processor subsystem communications with the patient-care device interface using Bluetooth, Bluetooth low energy, USB, near-field communications, etc. FIG. 102 shows a battery only version, i.e., an extended battery as previously described. That is, the circuitry 7200 of FIG. 102 may be the extended battery 6502 of FIG. 95 and may make the system 6500 wearable, for example. The extended batteries 6502 of FIG. 95 may be stackable together (e.g., the circuitry 7200 includes a transceiver, such as SPI or CAN) such that multiple extended batteries 6502 of FIG. 95 may be stacked together to power the infusion pump 6504. The circuitry 7200 may interface into a bus or hub to provide power to several devices (e.g., patient-care devices) via the device module interface.

Figure 103:
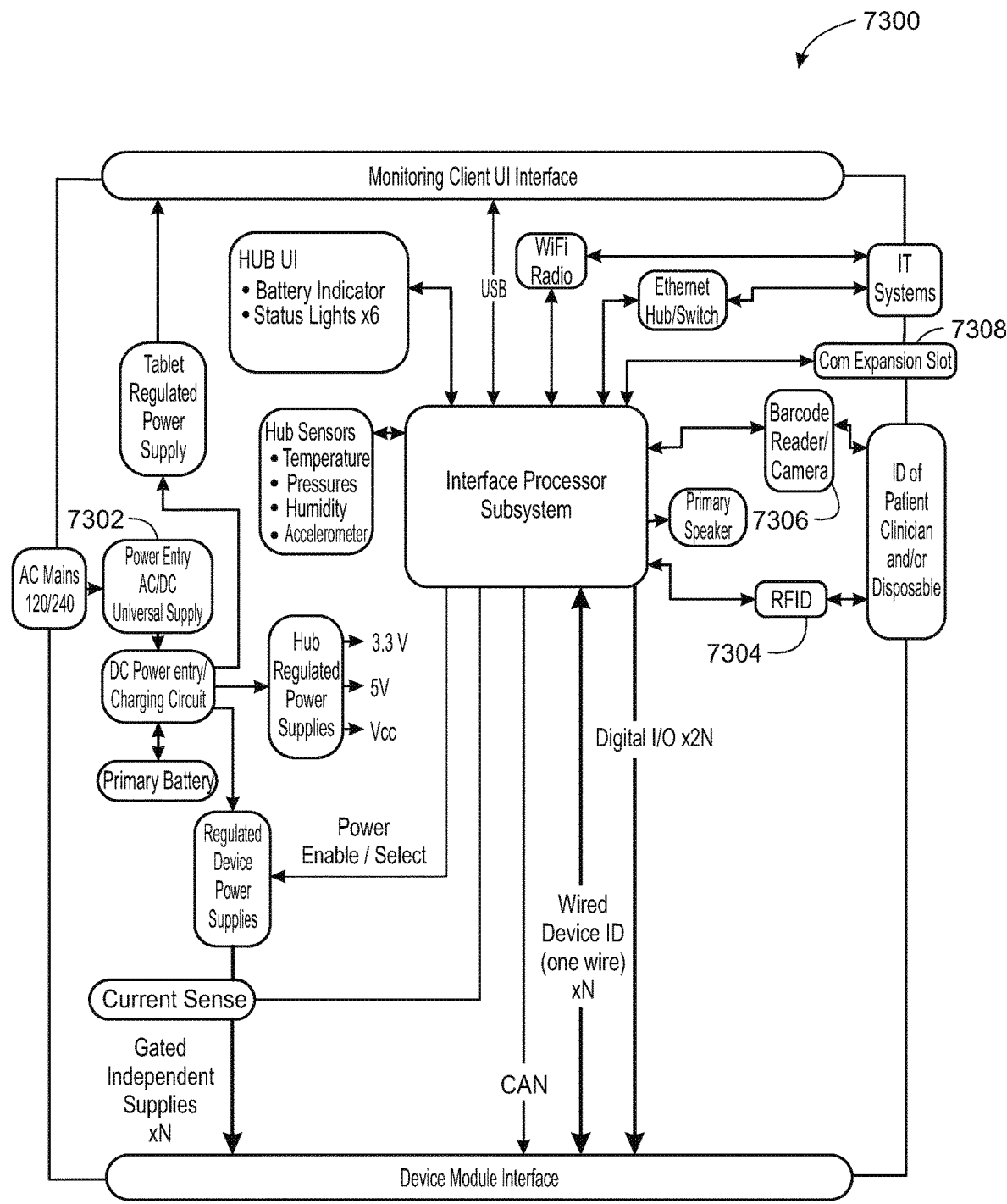
FIGS. 103-104 show additional embodiments of electronic circuitry of a dock in accordance with additional embodiments of the present disclosure.

FIG. 103 shows a block diagram of circuitry 7300 for controlling multiple infusion pumps with flexibility for expansion. For example, the device module interface may interface into multiple infusion pumps, one infusion pumps, or no infusion pumps. Additionally or alternatively, in some embodiments, the circuitry 7300 may be used in a dock, an infusion pump, a communication module, and/or a hub as described herein. The circuitry 7300 may interface into a bus or hub to communicate with several devices via the device module interface and/or to provide power thereto. In some embodiments, the monitoring-client interface may utilize Bluetooth, Bluetooth low energy, or other communication technology. In some embodiments, the device module interface (i.e., patient-care device interface) may be coupled to a patient-care device via Bluetooth, Bluetooth low energy, WiFi, and/or near-field communications. As can be seen with this example, CAN communication may be used as the wired protocol to communicate with the infusion pumps. Some digital are IOs utilized to add some functionality to the pump cradle, if necessary. The power entry and the AC/DC supply 7302 is inside the hub (i.e., inside of the circuitry 7300), and it supplies power to the tablet, hub, and one or more infusion pumps. The infusion pumps coupled to circuitry 7300 may be "stand-alone" safe. An RFID reader 7304 and the barcode reader/camera 7306 are included to authenticate a patient, or provider. The com expansion slot 7308 is included to expand the communication functionality when other methods are developed (e.g., peanut for authentication and location).

Figure 104:
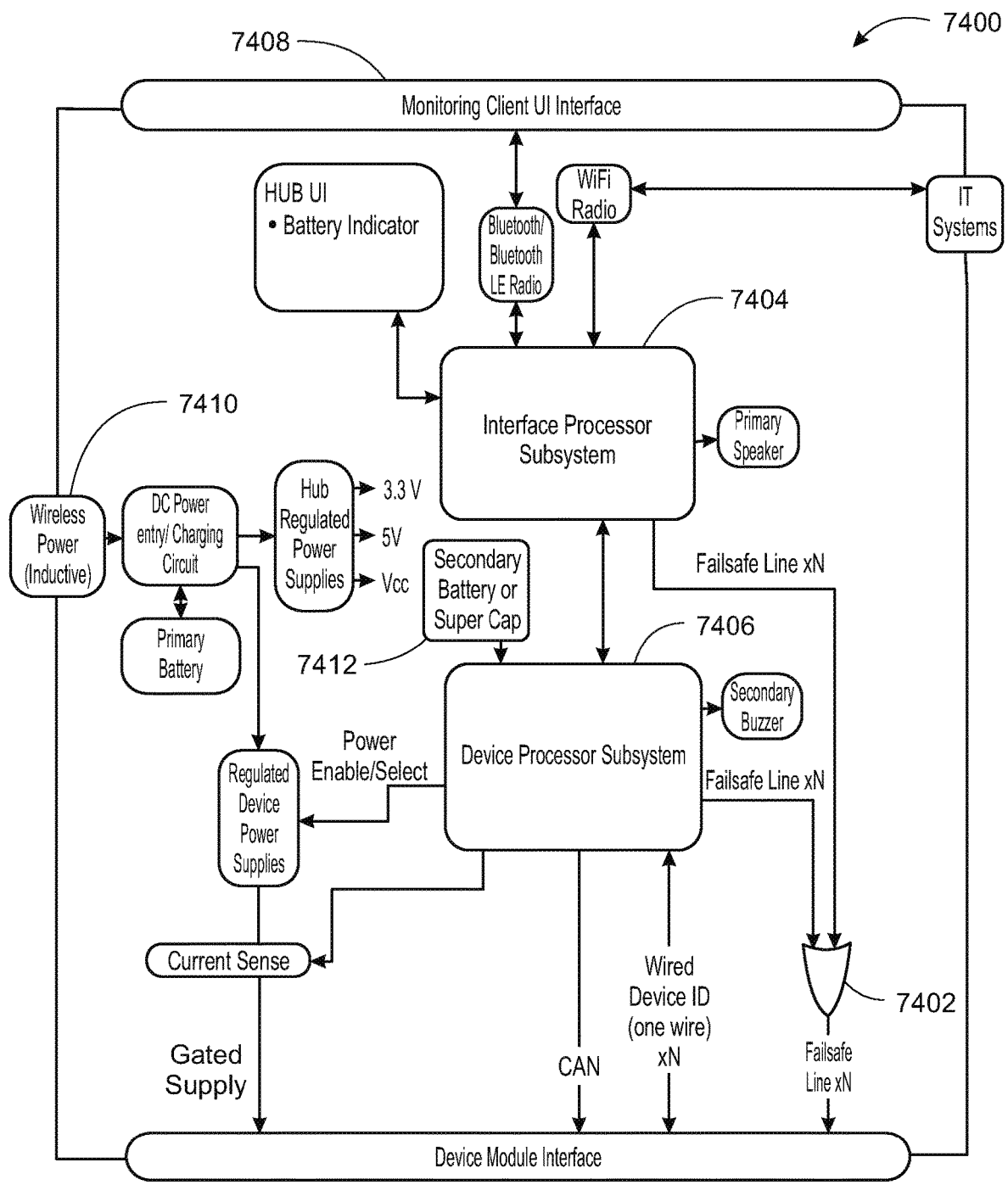

FIG. 104 shows circuitry 7400 for a hub described herein with a failsafe line 7402 and two processors 7404, 7406. Additionally or alternatively, in some embodiments, the circuitry 7400 may be used in a dock, an infusion pump, and/or a communication module as described herein. The circuitry 7400 may interface into a bus or hub to communicate with several devices (e.g., patient-care devices) via the device module interface and/or to provide power thereto. The processor 7406 may be a safety processor. The failsafe line 7402 may be activated by either of the two processors 7404, 7406. In some embodiments, the WiFi Radio may be an Ethernet interface. In some embodiments, the CAN interface may be a Bluetooth, Bluetooth low energy, WiFi, or other communications technology.

Additional safety is provided by the failsafe line 7402. For example, a pulse oximeter monitor can clamp a line if the pulse rate goes up or is too high. That is, the failsafe line output may be coupled to an electromechanical occluder. The hub circuitry 7400 could act as a watchdog and even monitor the output for range checking and send failsafe signals down to trigger the clamp if the process in the pulse oximeter is in error or is in a fault condition. The communication with a tablet may be wireless via the tablet UI interface 7408. The circuitry 7400 may be wirelessly charged via wireless power 7410. A vibration motor may be added to give hepatic feedback when there is an alarm. The circuitry 7400 optionally includes two processors 7404, 7406 that implement a method for warning the user when an alarm or alert is issued. A secondary battery or super cap 7412 may provide backup power when there is power failure. The circuit 7400 may be a pump module, e.g., a communications module, and/or a hub to attach to a cradle.

Figure 105:
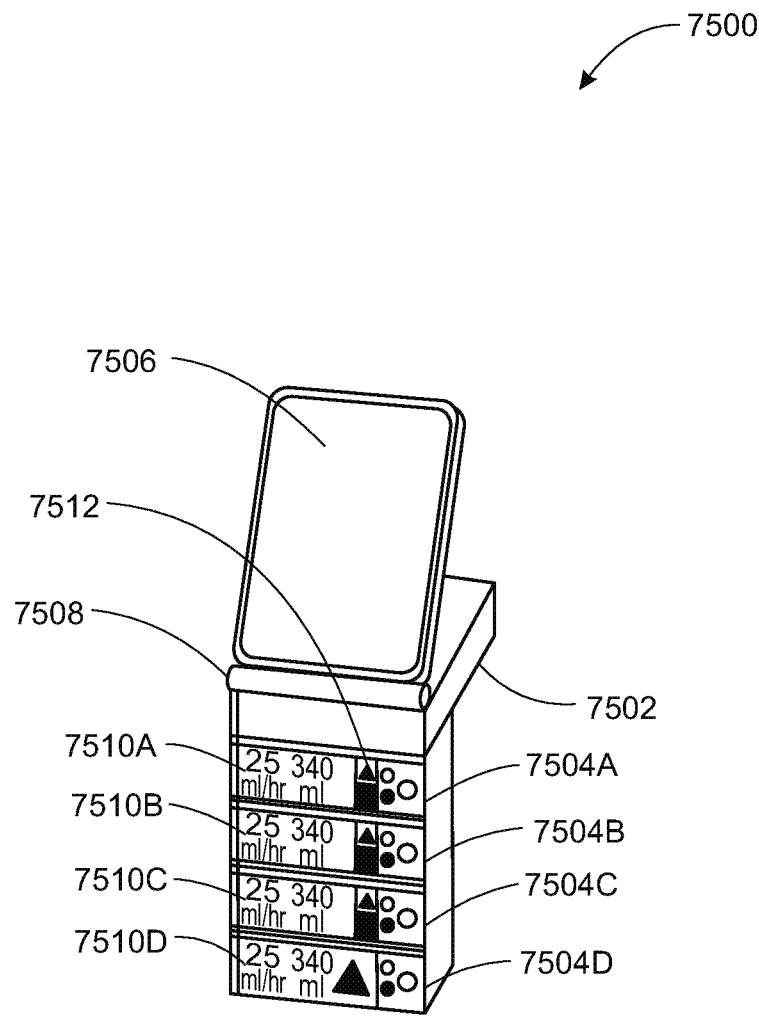
FIGS. 105-116 show several embodiments of attachable pumps attached to a monitoring client in accordance with additional embodiments of the present disclosure.

FIG. 105 shows a system 7500 for electronic patient care according to yet an additional embodiment of the present disclosure. System 7500 includes a monitoring client, more particularly, a stackable monitoring client 7502, and stackable patient-care devices, e.g., stackable infusion pumps 7504A-7504D. The stackable monitoring client 7502 includes a display 7506 that is pivots along a pivot 7508. The display 7506 may be a touchscreen. The stackable monitoring client 7502 may include a tilt sensor, e.g., an accelerometer, to orient the display 7506 such that it is always viewable to a user. Likewise, each of the stackable infusion pumps 7504A-7504D may include a respective display 7510A-7510D that orientates itself based upon the its tilt, e.g., the display may show letters in an upright position regardless whether the stackable infusion pumps 7504A-7504D are positioned in a horizontal orientation or a vertical orientation. Additionally or alternatively, each of the stackable infusion pumps 7504A-7504D may include a tilt sensor, e.g., an accelerometer.

Figure 106:
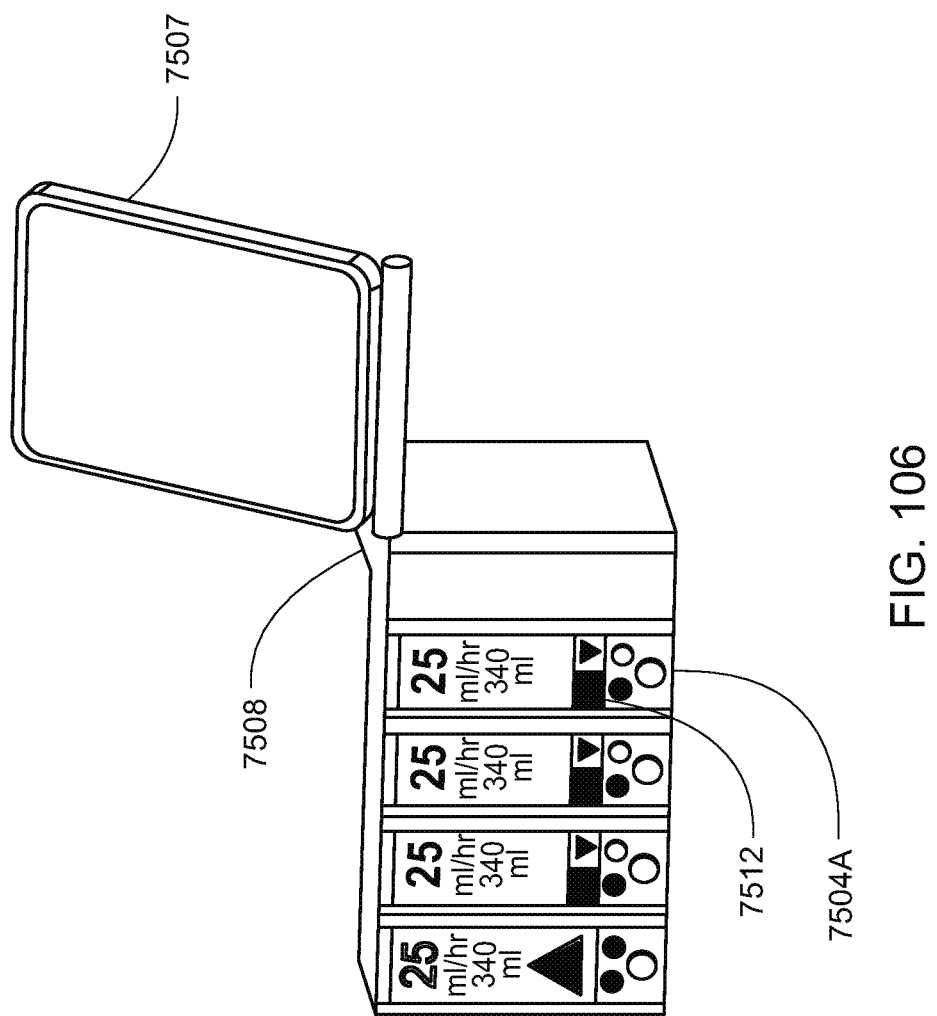
Figure 107:
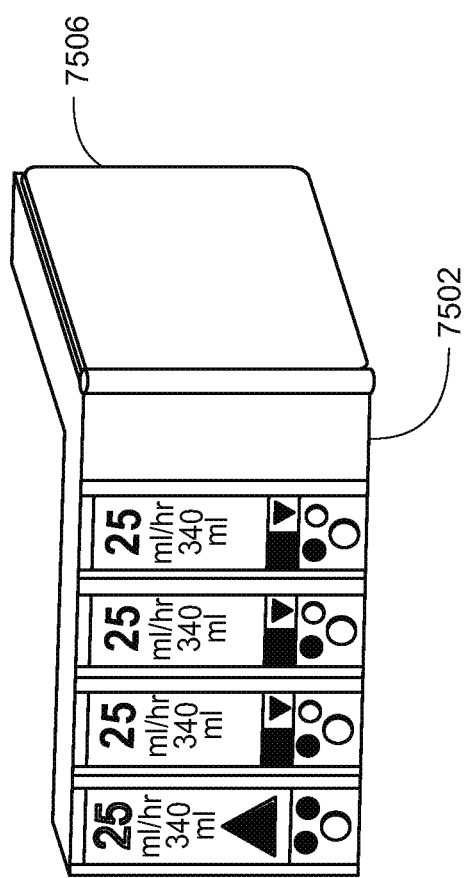
Figure 108:
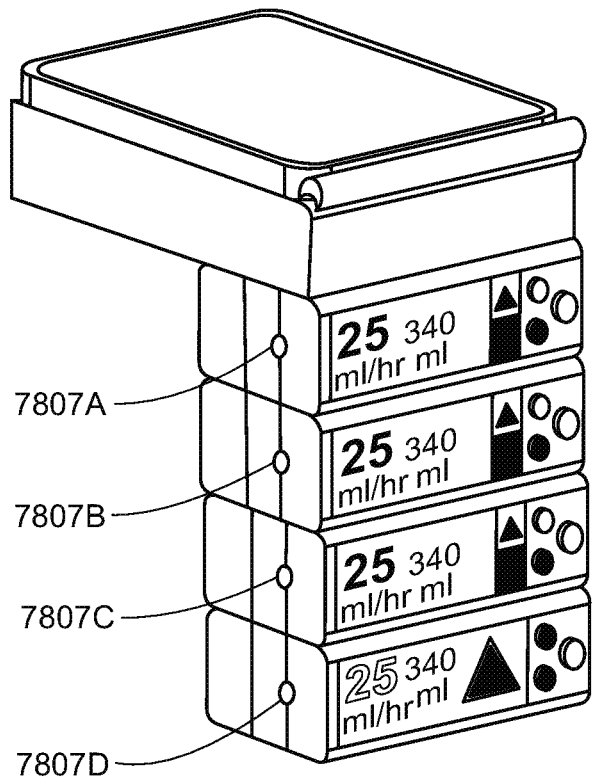
Figure 109:
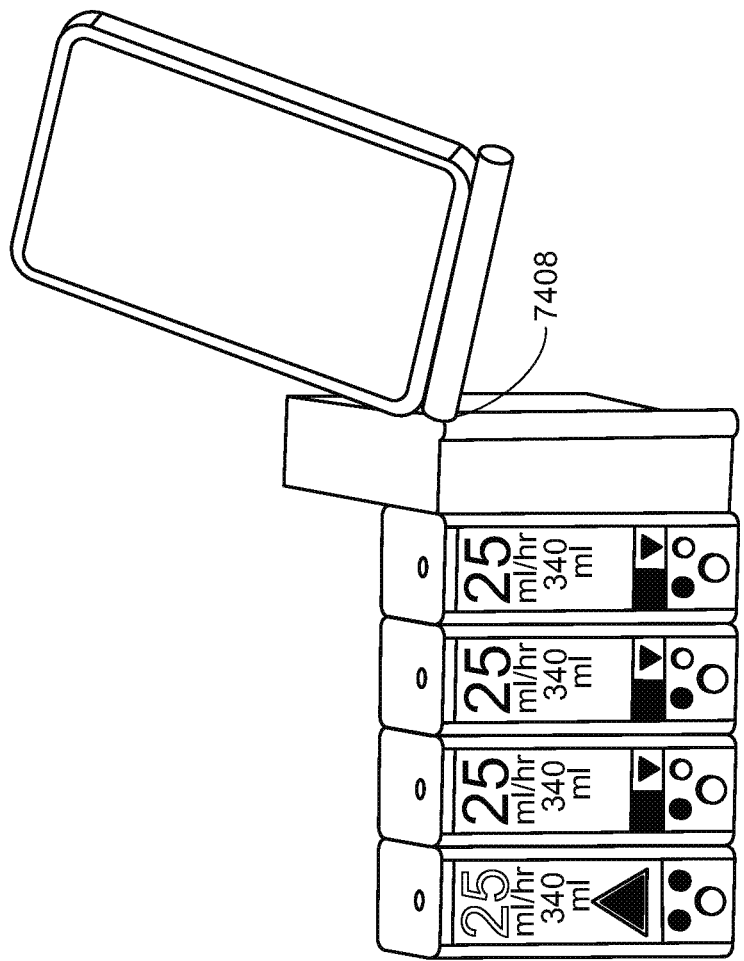

The displays 7510A-7510D may be touchscreen. Each display or the displays 7510A-7510D may include one or more buttons that orientates itself based upon the tilt as indicated by an internal tilt. For example, as shown in FIG. 105, a button 7512 is shown as being in an upright position relative to the elongated length of the stackable infusion pump 7504A. Referring to FIG. 106, the system 7500 is shown tilted such that the button 7512 is shows as being in an upright position relative to the length of the stackable infusion pump 7504A. Also note that the display 7507 is further pivoted along the pivot 7508. FIG. 107 shows the display 7506 pivoted against the monitoring client 7502. FIG. 108 shows the intravenous holes 7807A-7807D. FIG.

Figure 110:
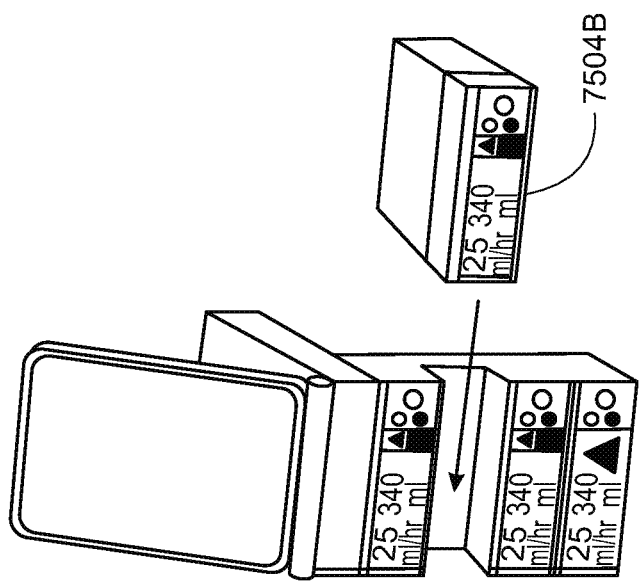

109 illustrates additional range of pivoting along the pivot 7408. FIG. 110 shows the infusion pump 7504B slidable into the stack.

Figure 111:
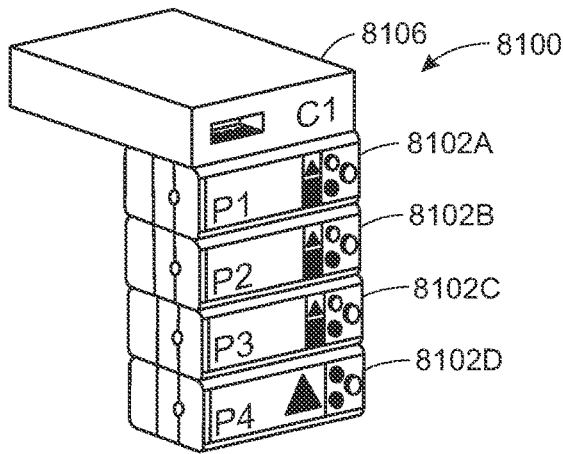
Figure 112:
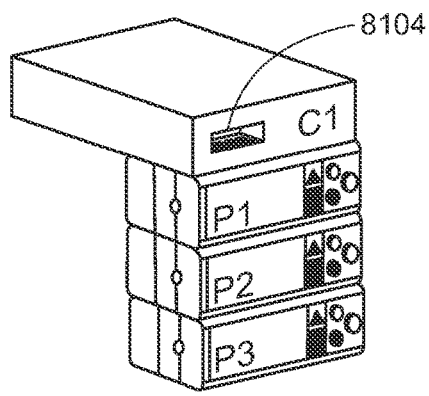

FIGS. 111-112 show an additional embodiment of a stackable electronic patient care system 8100 in which the stackable infusion pumps 8102A-8102D are connected together through respective top (e.g., connector 81004) and bottom connectors (not explicitly shown) such that the stackable infusion pumps 8102A-8102D are daisy chained together. FIG. 111 shows one configuration of the system 8100. FIG. 112 illustrates that the infusion pump 81002D is detachable from the system 8100. The infusion pump 8102D may include its own internal battery to continue operation, e.g., the infusion pump 8102D may have sufficient battery power to continue to pump infusion fluid into a patient for a predetermined amount of time.

Figure 113:
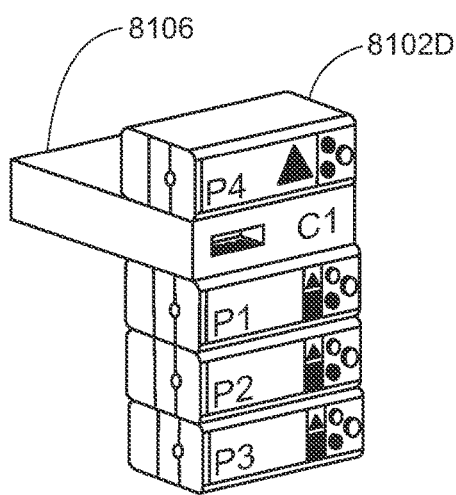
Figure 114:
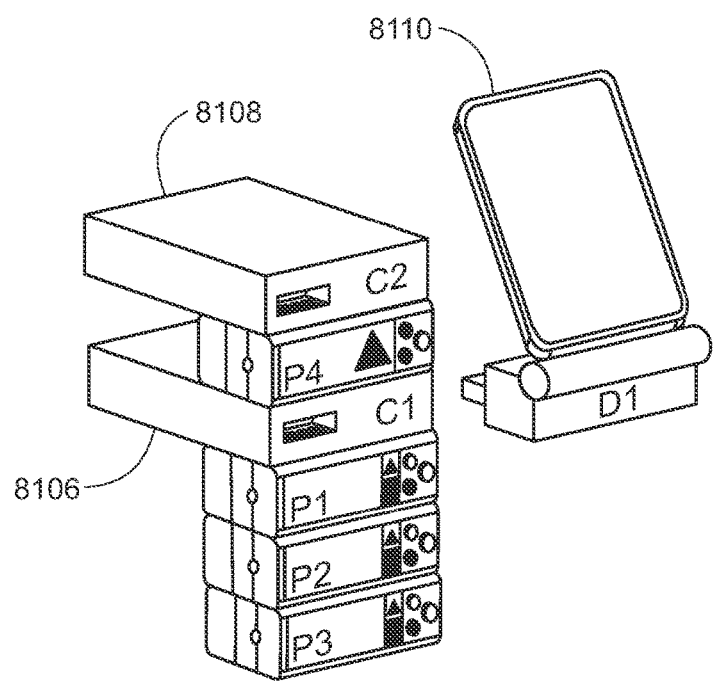

FIG. 113 illustrates that a monitoring client 8106 may include connectors to receive the infusion pump 8102D. The monitoring client 8106 may have an attachable/detachable display 8110. FIG. 114 illustrates that another monitoring client 8108 may be stacked onto the stackable infusion pump 8102D. The monitoring clients 8106, 8108 may coordinate their operation. For example, the monitoring clients 8106, 8108 may coordinate the supply of power to the infusion pumps such that both of the batteries of the infusion pumps 8106, 8106 supply power to the system 8000.

Figure 115:
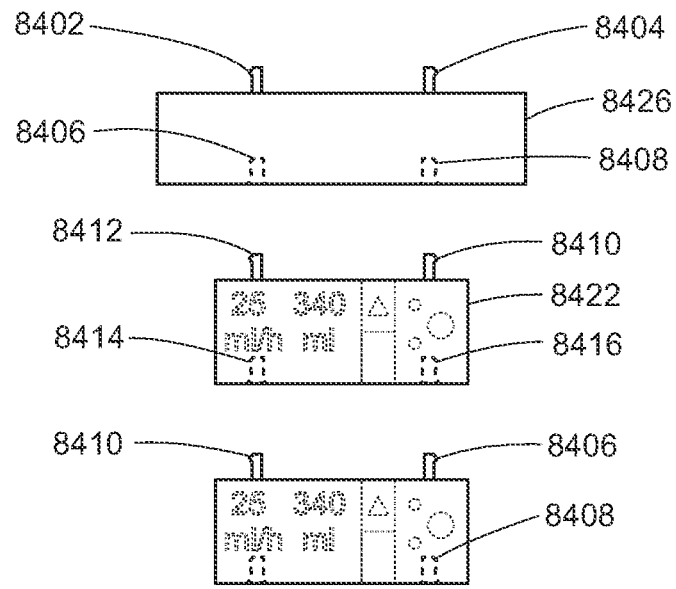
Figure 116:
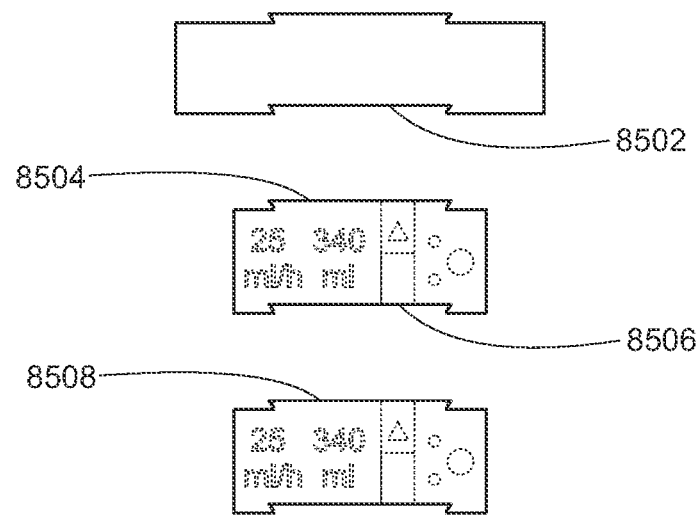

FIG. 115 shows the connections 8402-8420 enabling stackable infusion pumps 8422, 8424 and a monitoring client 8426 to be coupled together in a daisy chain configuration. FIG. 116 shows slideable connections 8502, 8504, 8506, 8508 such that the stackable infusion pumps 8422, 8424 and a monitoring client 8426 are daisy chained together. The slideable connections 8502, 8504, 8506, 8508 may include electrical connector enabling the stackable infusion pumps 8422, 8424 and a monitoring client 8426 to communicate with each other.

Figure 117:
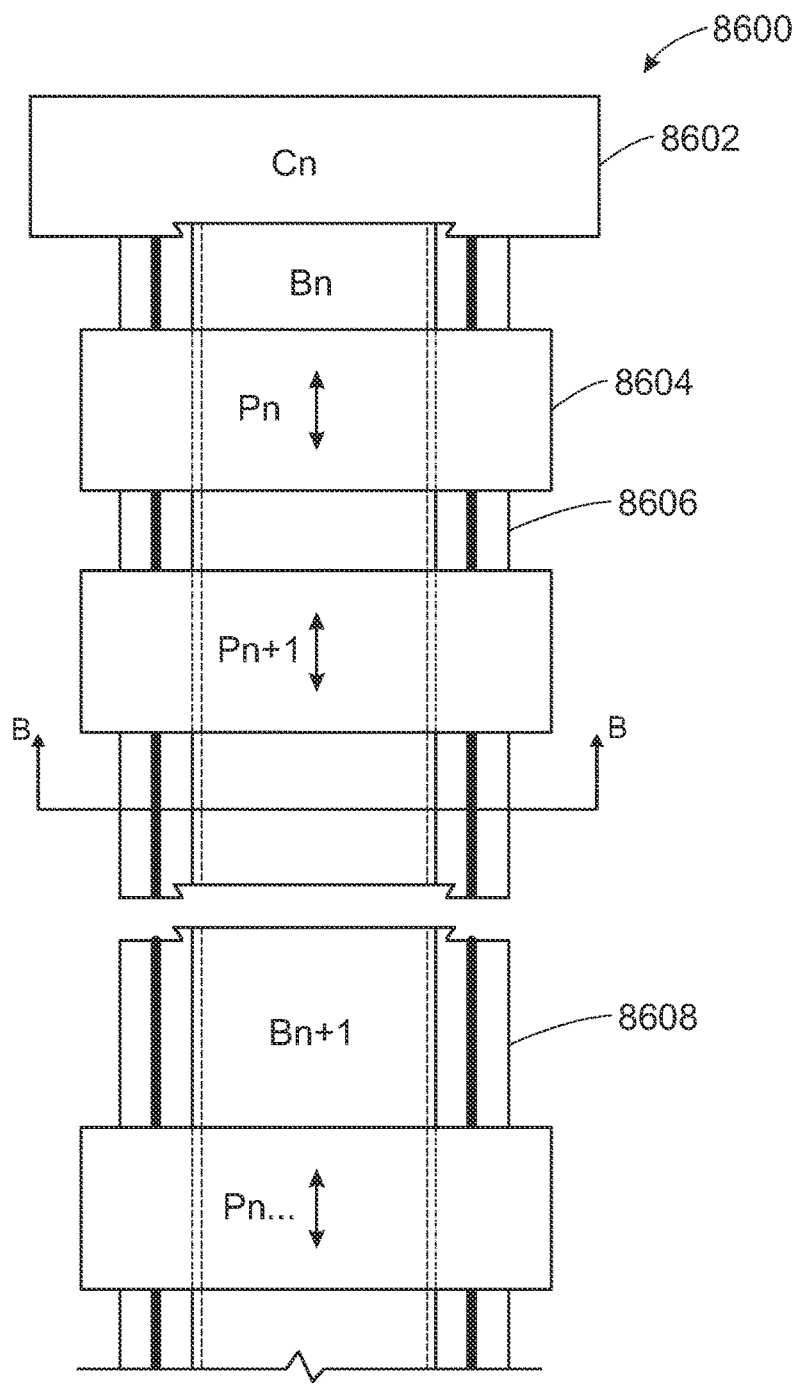
FIG. 117 shows a backplane for use with infusion pumps in accordance with an embodiment of the present disclosure.
Figure 118:
FIG. 118 shows a cross-sectional view of the backplane panel of FIG. 117 in accordance with an embodiment of the present disclosure.

FIG. 117 shows a system 8600 of a stackable monitoring client 8602 with a stackable infusion pump 8604 that connect together via a backplane panels 8606, 8608. The backplane panel 8606 includes a connector 8610 that matingly engages a connector 8612 of a backplane panel 8608. Additional backplane panels (not shown) may be added to example the backplane in accordance with the number of monitoring clients, 8602 or infusion pumps 8604 added thereto. FIG. 118 shows a cross-sectional view of the backplane panel 8608 of FIG. 117.

Figure 119:
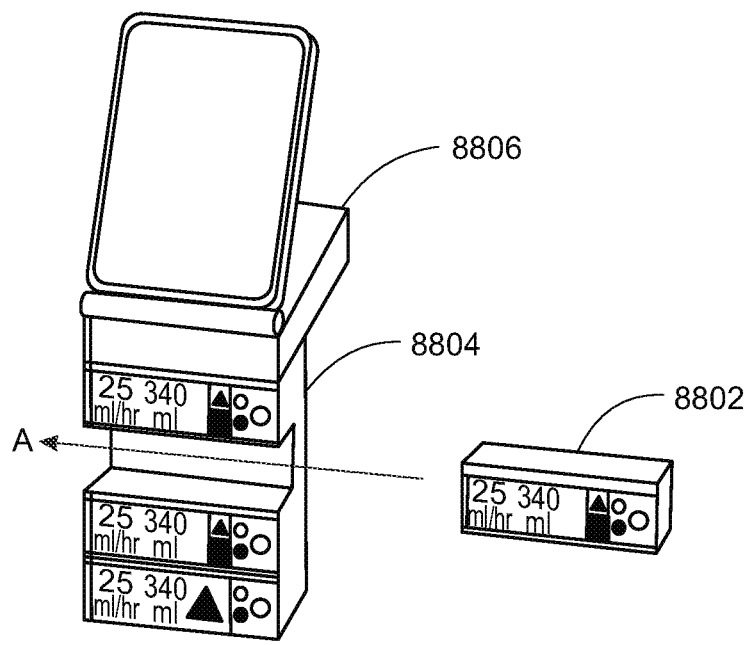
FIGS. 119-120 show several embodiments of attachable pumps attached to a monitoring client in accordance with additional embodiments of the present disclosure.

FIG. 119 shows a system 8800 that includes a monitoring client, more particularly, a stackable monitoring client 8806, and stackable patient-care devices, e.g., a stackable infusion pump 8802. The stackable infusion pump 8802 slides into a dock 8804 in a direction "A."

Figure 120:
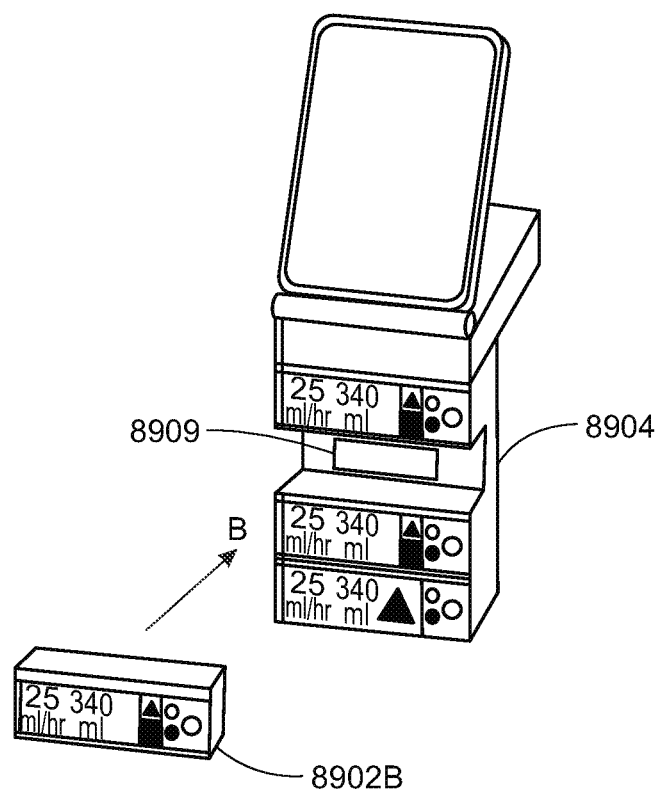

FIG. 120 shows a system 8900 where a stackable infusion pump 8902B engages a dock 8904 via a connector 8509 when moved in direction "B."

Figure 121:
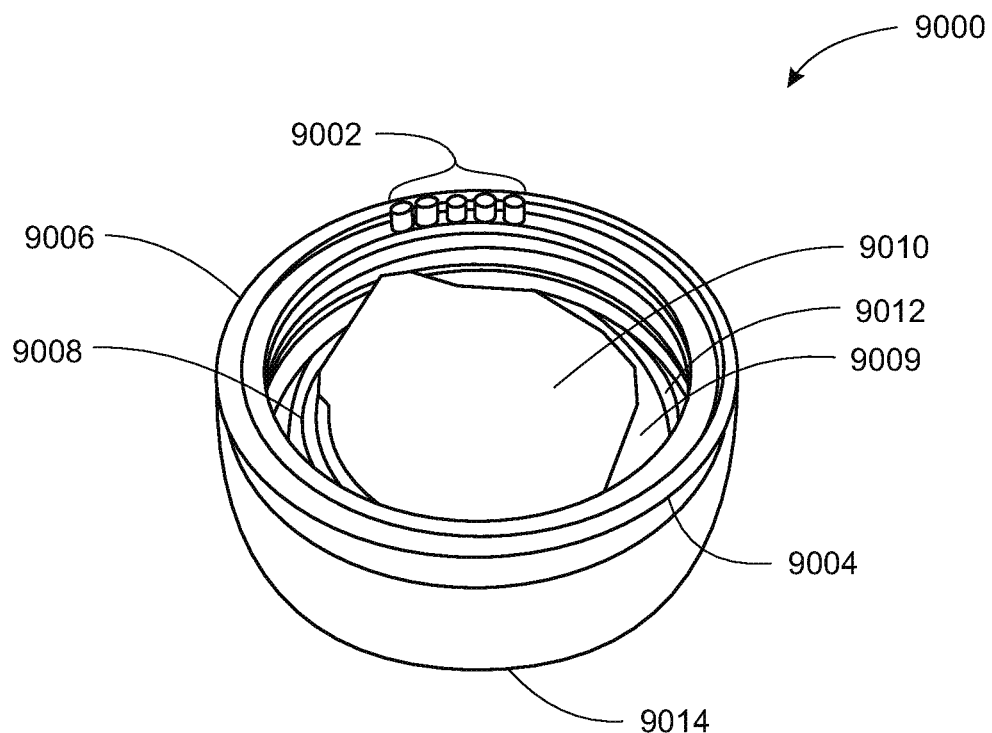
FIG. 121 shows a communication module in accordance with an embodiment of the present disclosure.
Figure 122:
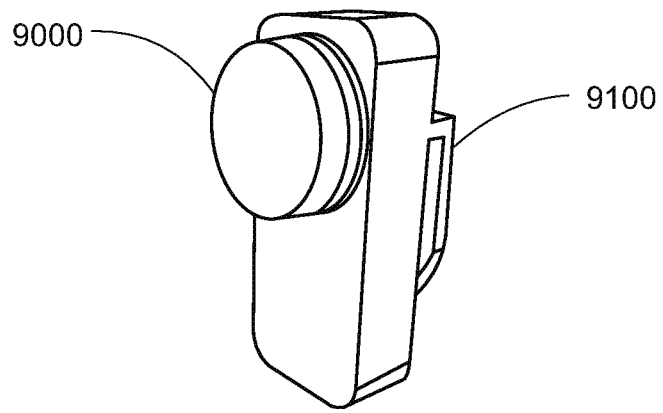
FIG. 122 shows a communication module attached to a patient-monitoring device in accordance with an embodiment of the present disclosure.
Figure 123:
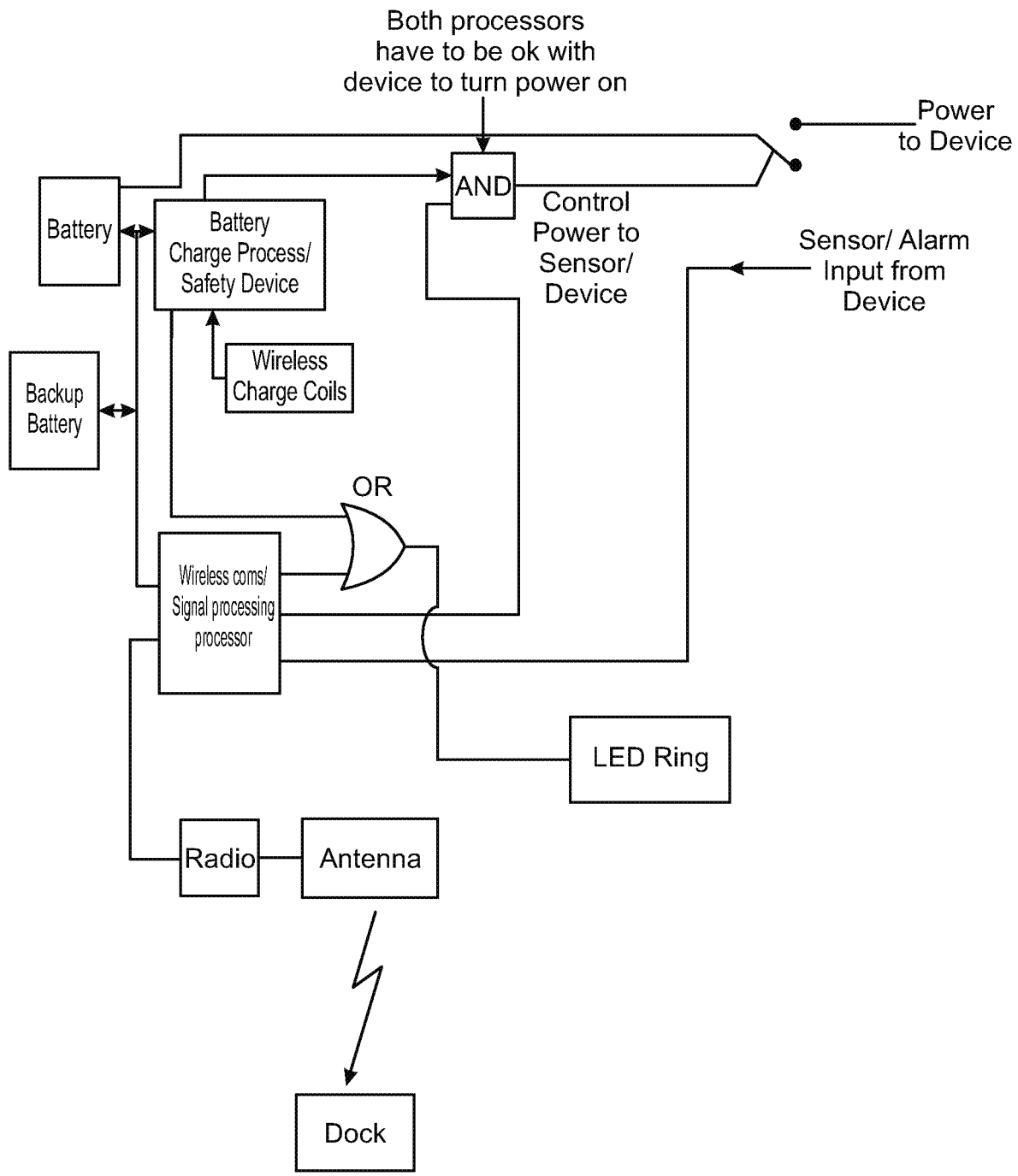
FIG. 123 shows a diagram of electronic circuitry of the communication module of FIG. 121 in accordance with an embodiment of the present disclosure.

FIG. 121 shows a communication module 9000 in accordance with an embodiment of the present disclosure. Communications modules 9000 include connectors 9002, a LED status ring 9004, a RF antenna 9004, a snap-on connector 9006, a wireless charging coil 9008, a battery charging and safety processor 9010, wireless communications and sensor processor 9012, and a battery 9014. The communications module 9000 of FIG. 121 may be a communications module 124A-124K of FIG. 1, 3, 5, 7, or 8. FIG. 122 shows the communications module 9000 coupled to a patient-care device 9100. FIG. 123 shows a diagram of electronic circuitry 9200 of the communications module 9000 of FIG. 121 in accordance with an embodiment of the present disclosure.

Figure 124:
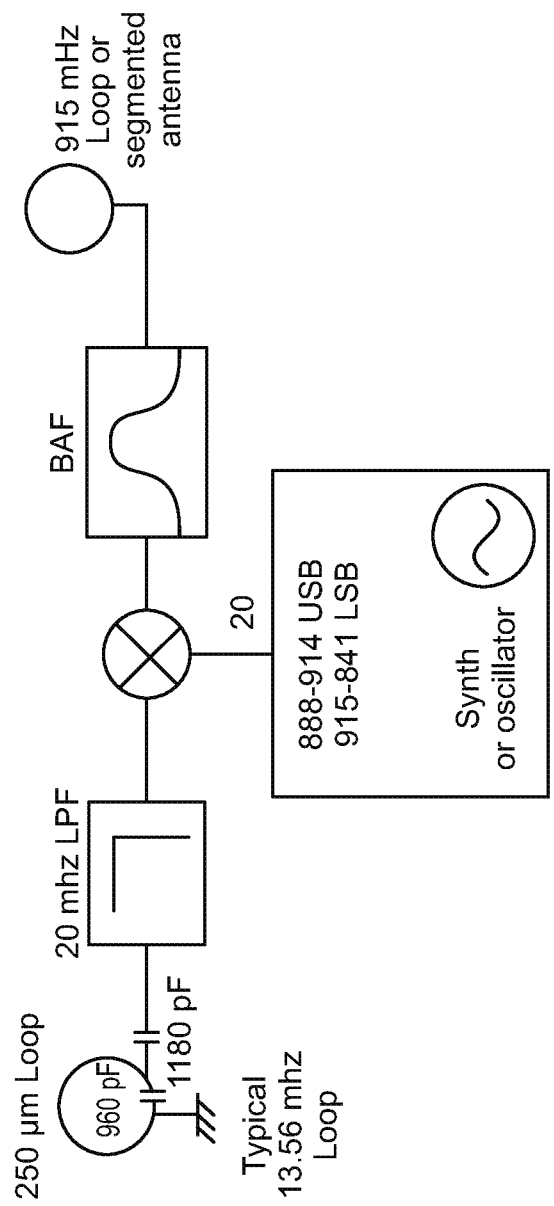
FIG. 124 shows a diagram of electronic circuitry to translate Near-Field Communications to UHF in accordance with an embodiment of the present disclosure.

FIG. 124 shows electronic circuitry 9300 for allowing a near field interrogator (e.g., one operating at about 13.56 MHz) to read a 900 MHz UHF RFID tag. The electronic circuitry 9300 includes a heterodyne transfer oscillator. The circuit 93000 translates near field interrogation signals to RFID interrogation signals. The electronic circuitry 9300 may be used by the communications module 9000 of FIG. 90 and/or a communications module 124A-124K of FIG. 1, 3, 5, 7, or 8 for enabling a near field communications circuit to interrogate an RFID tag. Each of the antennas may be replaced by an RF circuit to allow the circuit to be used on an interrogator or a receiver. Additionally or alternatively, in other embodiments, the electronic circuitry may be arranged such that the UHF RFID interrogator is used to communicate with a near field communications device.

Figure 125:
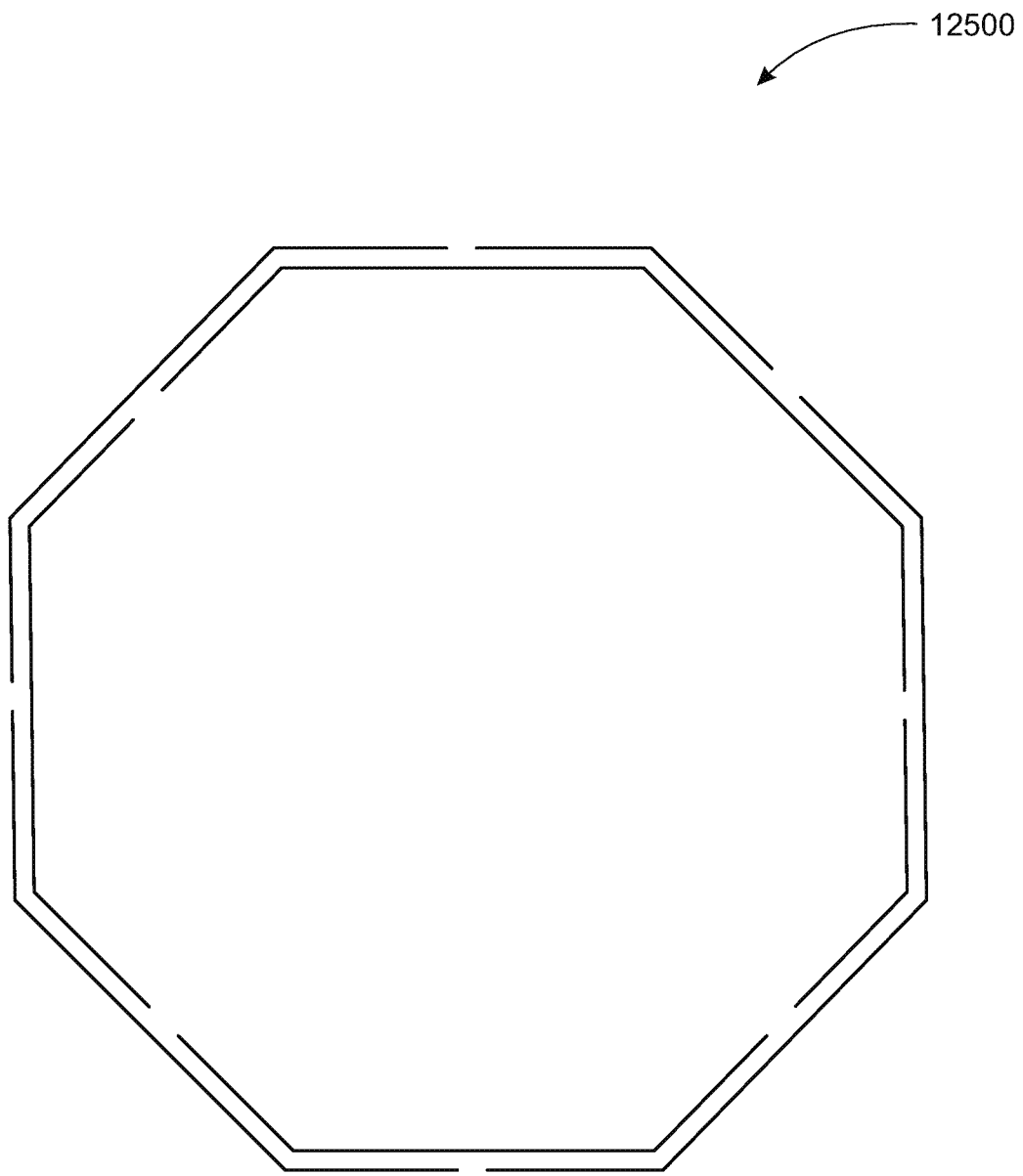
FIGS. 125-127 show several antennas in accordance with additional embodiments of the present disclosure.
Figure 126:
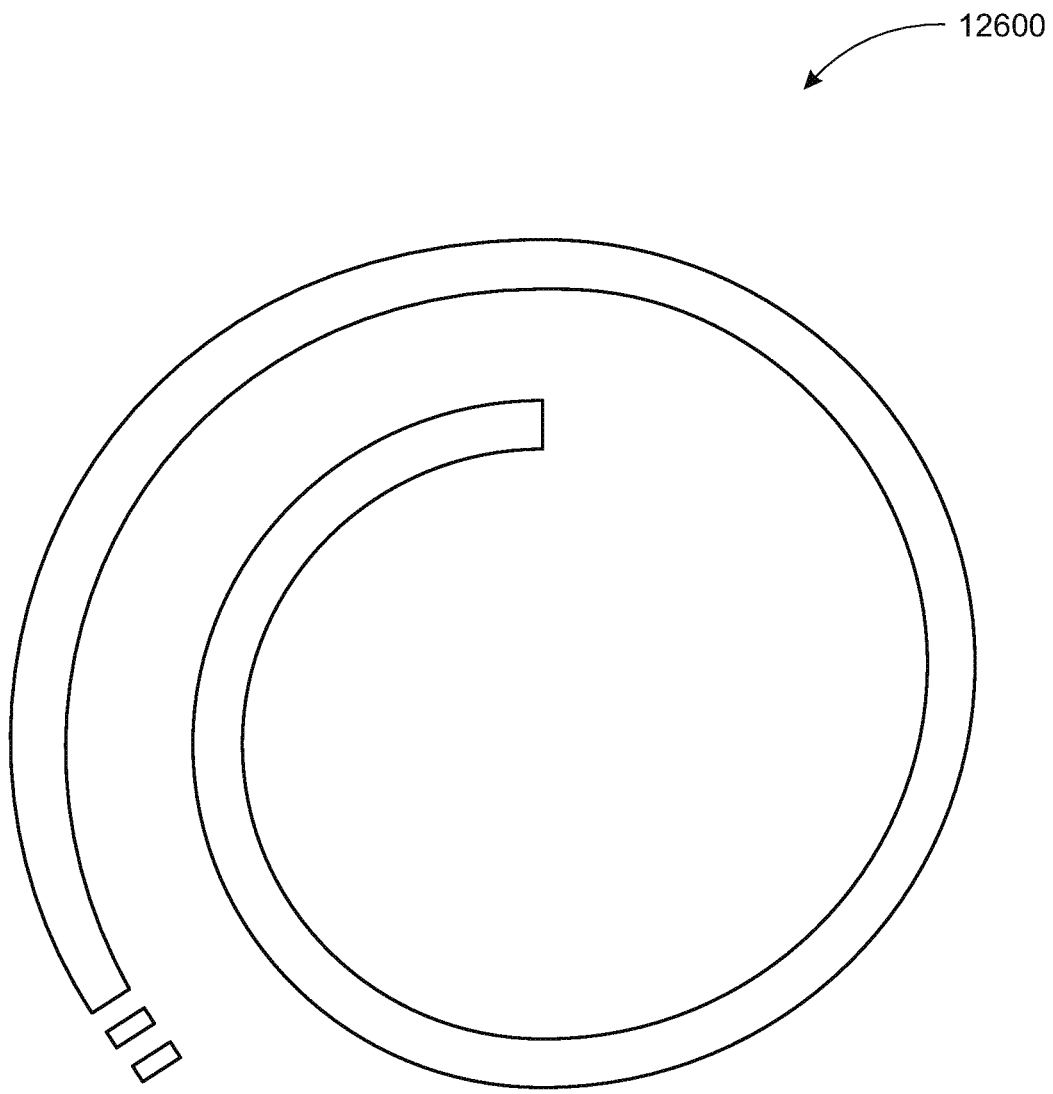
Figure 127:
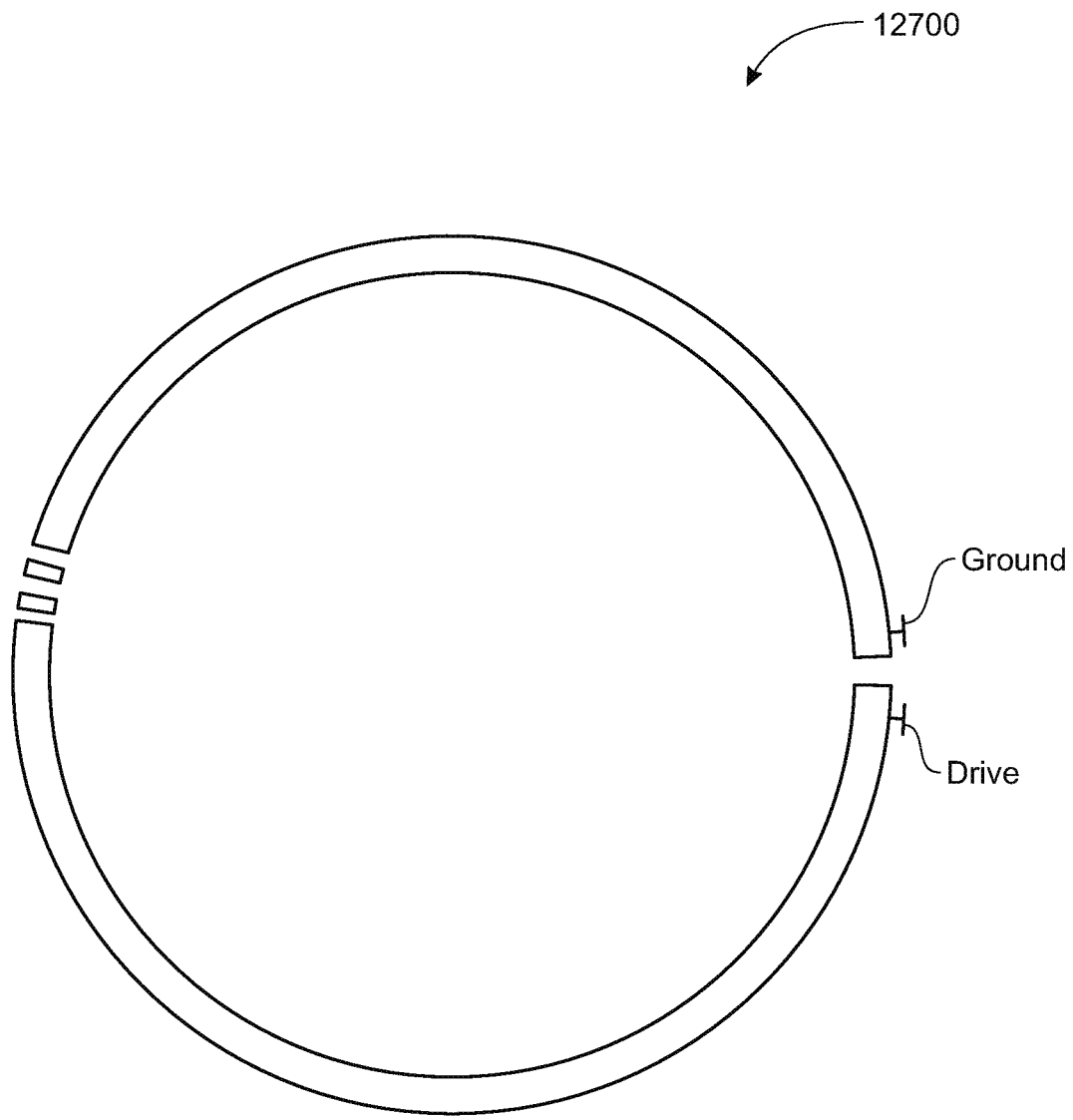

FIGS. 125-127 show several antennas in accordance with additional embodiments of the present disclosure. FIGS. 125 and 126 show two split-ring resonators 12500, 12600 that may be used with a scanner, e.g., placed in from of an RFID or near field interrogator and/or antenna (for sending or receiving). The resonators 12500, 12600 are made using 0.028 thick FR-4 single-sided board with 0.5 oz copper. Trimming may be used to tune the resonators (as shown).

FIG. 127 shows a near field antenna 12700 for a UHF reader (e.g., a 915 MHZ RFID reader), which focuses the near field pattern with a reader chip. Without a power amplifier, approximately 1.5 inches of read range is achieved. The antenna 12700 is made from a 0.028 thick FR-4, with a copper backing. Antenna 12700 may be used with a 10 pF shunt matching element.

Figure 128:
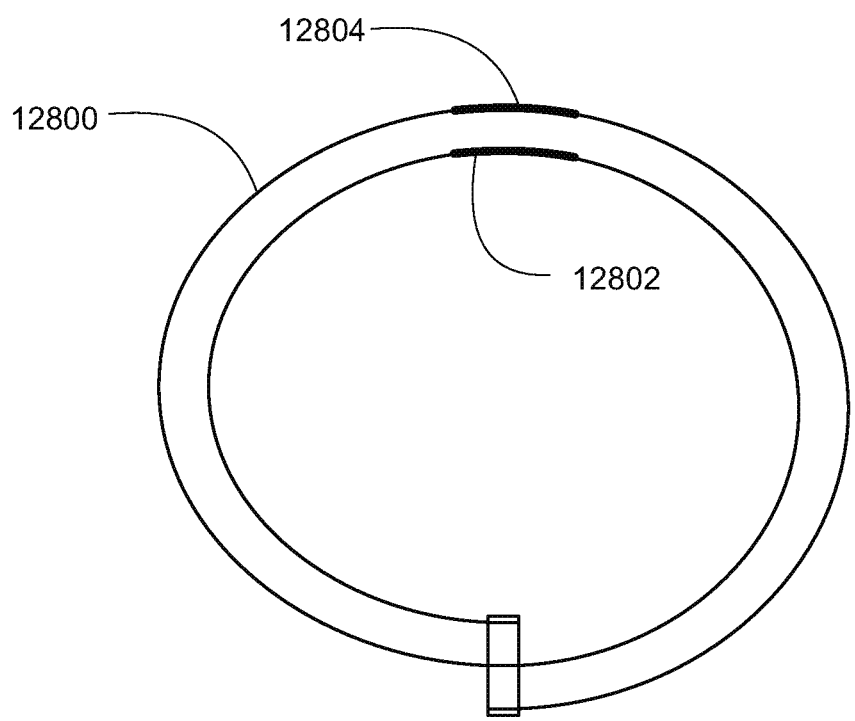
FIG. 128 shows a patient wristband with an RFID tag attached thereto in accordance with an embodiment of the present disclosure.
Figure 129:
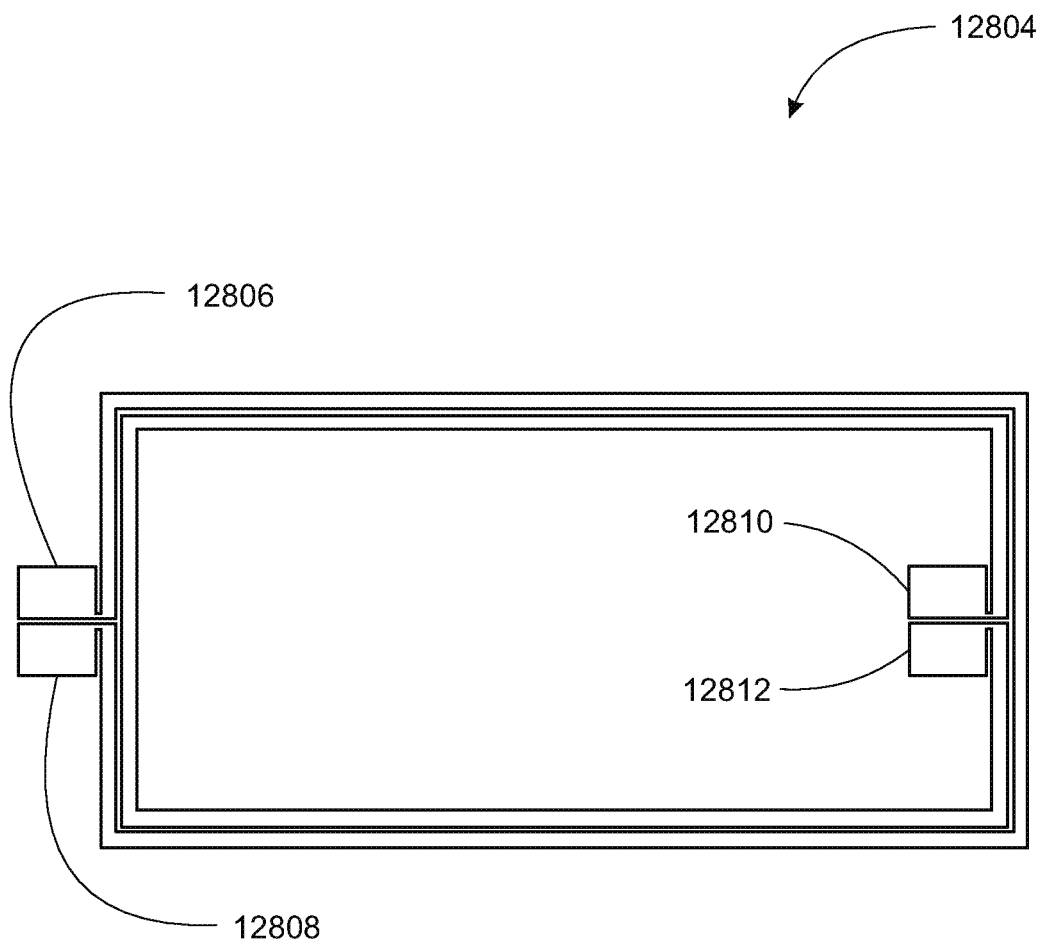
FIG. 129 shows split-ring resonator for use on the wristband of FIG. 128 in accordance with an embodiment of the present disclosure.

FIG. 128 shows a patient wristband 12800 with an RFID tag 12802 attached thereto in accordance with an embodiment of the present disclosure. Because capacitance is observed when an RFID tag 12802 is attached to a wristband of a patient, a split-ring resonator ("SRR") 12804 may be used such that it is 0.01 inches away from the patient. The dielectric loading from the capacitance of the patient knocks off the frequency of the RFID tag 12802; therefore, the SRR 12804 helps tune the RFID tag 12802 by coupling the RFID tag 12802 more closely to the antenna. The SRR 12804's resonant frequency should be slightly above the operating frequency of the RFID tag 12802. FIG. 129 shows a close-up view of the split-ring resonator 12804 for use on the wristband of FIG. 128.

The RFID tag 12802 of the patient's wristband 12800 may be writable. A hub, dock, patient-care device, and/or monitoring client may write data related to a patient into the RFID tag 12802, including: (1) treatment history such as flow rates, drug settings, vital signs, etc., (2) usage statistics (patient-care parameters, patient-treatment parameters, patient-care device operating parameters, diagnostic information from docks, hubs and monitoring clients, and the like); (3) a intravenous pump flow parameter, an ECG parameter, a blood pressure parameter, a pulse oximeter parameter, a CO2 capometer parameter, an intravenous bag parameter, and a drip-flow meter value; (4) patient parameter includes at least one of treatment progress of an infusion pump, an electrocardiographic signal, a blood pressure signal, a pulse oximeter signal, a CO2 capnometer signal, and a temperature signal; (5) patient-treatment parameters, such as infusion settings including an infusion rate or infusion pressure, and receive from it various operating parameters, such for example, the presence of air in the infusion line, the amount of solution remaining in an IV bag to which it is connected, or the pressure of fluid in the infusion line. In some embodiments, the RFID tag 12802 includes only a predetermined amount of passed time (i.e., a rolling history) in its memory, e.g., 6 hours or 14 hours of history on a 32 Kilobyte or 56 Kilobyte memory of the RFID tag 12802, in some specific embodiments. In yet additional embodiments, the RFID tag 12802 may include a patient ID and/or a Near-Field communications receiver to receive the data.

Figure 130:
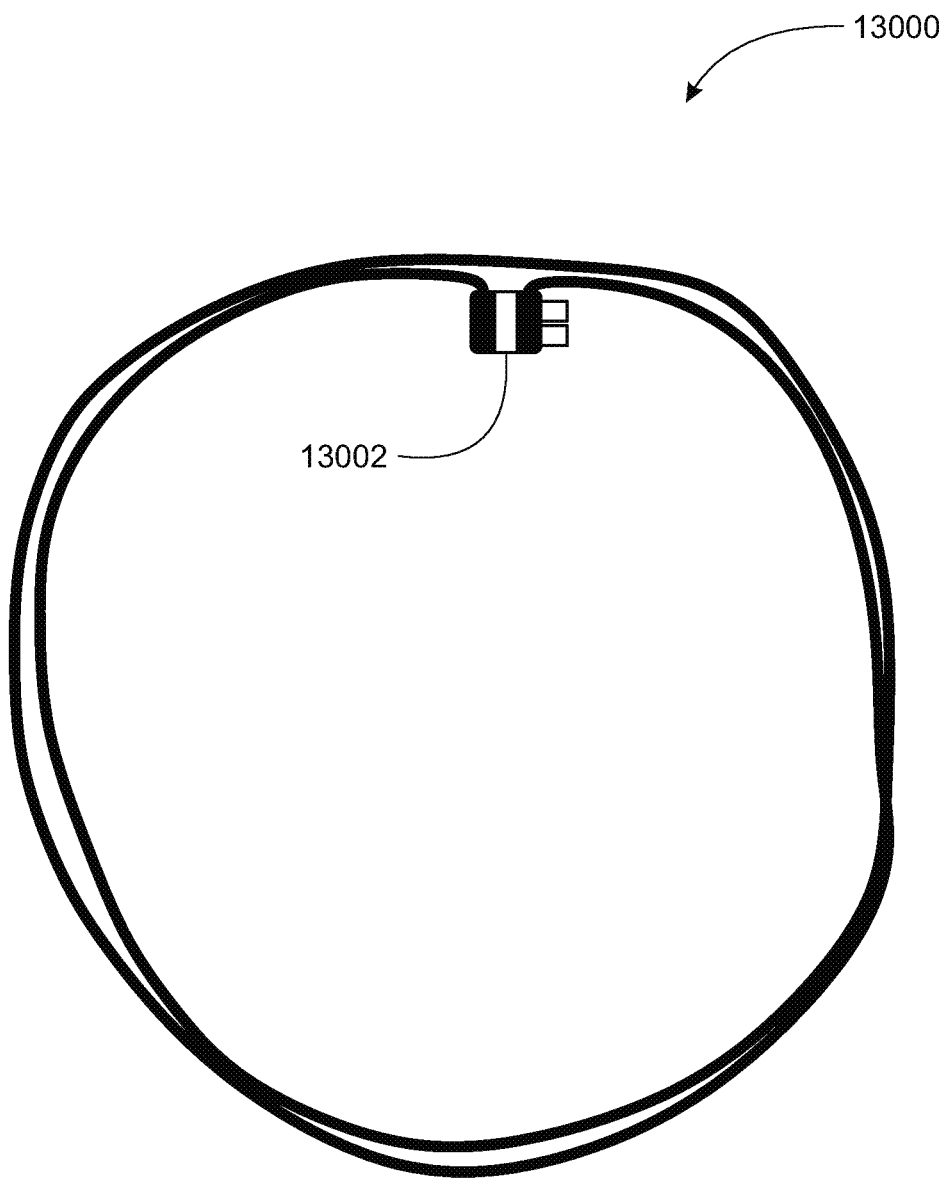
FIG. 130 shows a near-field antenna in accordance with an embodiment of the present disclosure.
Figure 131:
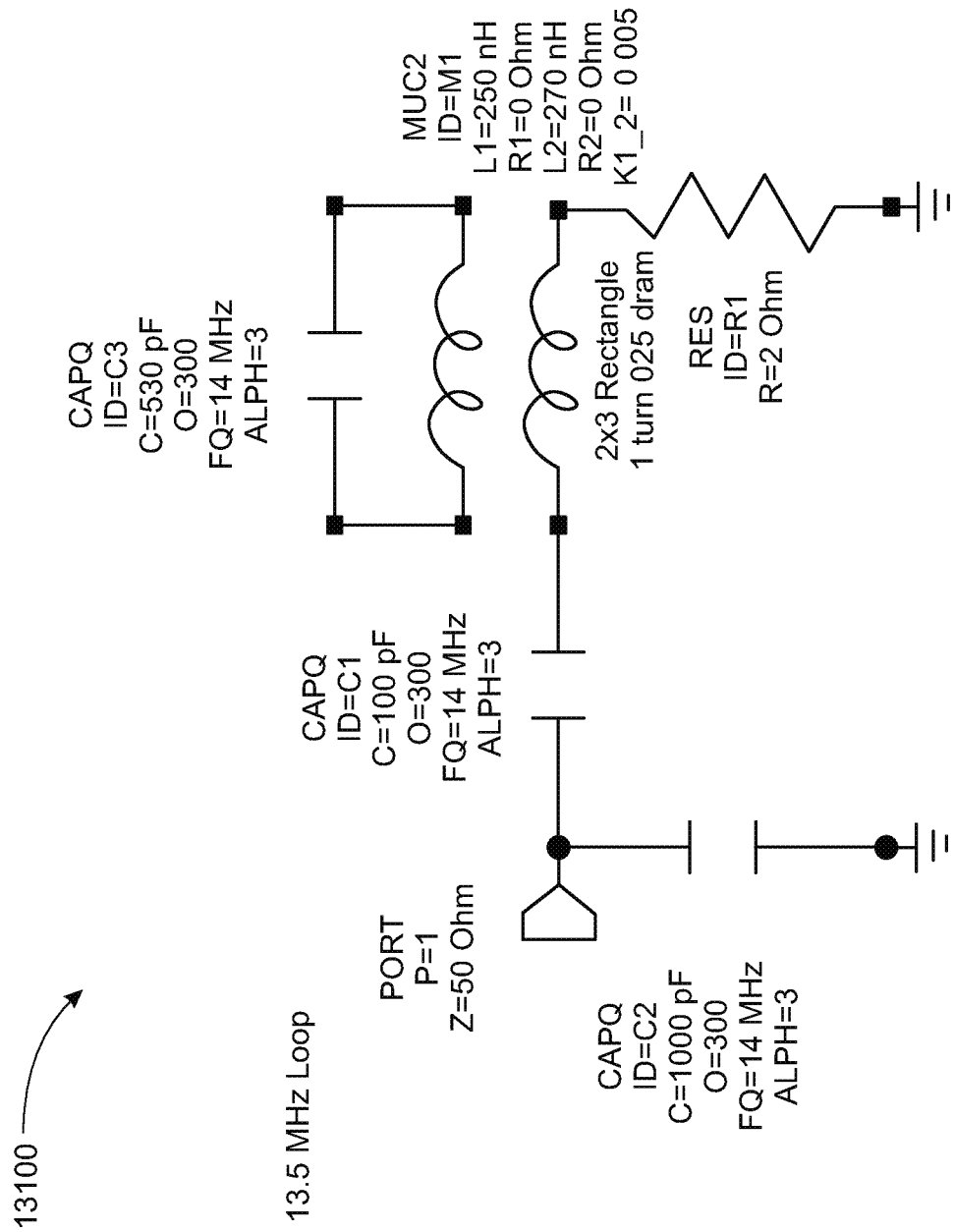
FIG. 131 shows an equivalent circuit for the split-ring resonator of FIG. 130 in accordance with an embodiment of the present disclosure.

FIG. 130 shows a split-ring resonator 13000 in accordance with an embodiment of the present disclosure. The high Q, split-ring resonator 13000 includes a capacitor 13002, which acts in the place of an air gap. The SRR 13000 may be placed approximately 8 inches away from a 13.56 MHZ NFC loop antenna to enhance the loop antenna by as much as 10 dB. The SRR 13000 may be designed to operate at 13.8 MHZ to reduce group-delay distortion to the 13.56 MHZ digitally modulated signal. FIG. 131 shows an equivalent circuit 13100 for the SRR 13000 of FIG. 130 in accordance with an embodiment of the present disclosure.

FIG. 132 shows a 5 R's checklist that may be displayed on any display disclosed herein. FIG. 133 shows an occlusion checklist that may be disclosed on any display disclosed herein. FIG. 134 shows a display in operative communication with several infusion pumps, e.g., a monitoring client 1 or 11 of FIG. 1, 3, 5, 7, 8, or 9.

Figure 136:
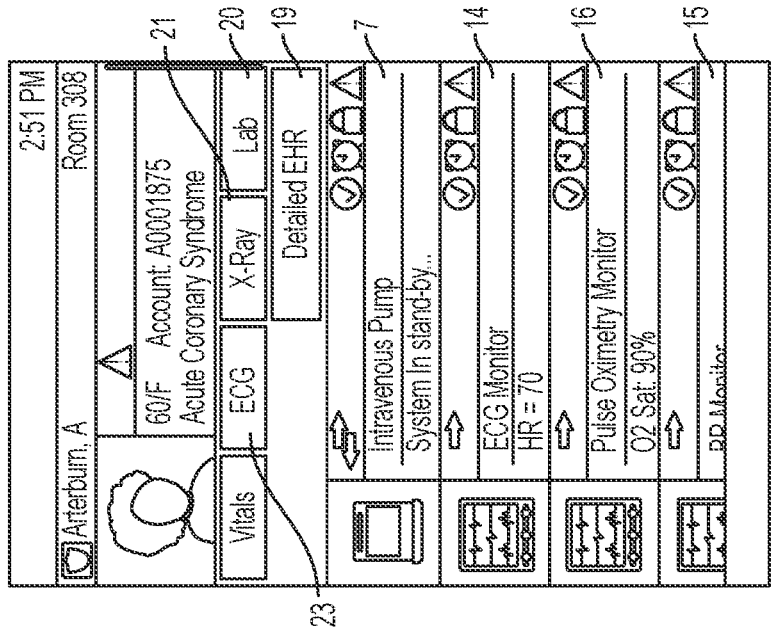
FIG. 136 is an illustration of a display on a health care provider's portable monitoring client, showing devices associated with a particular patient, with current data from the devices and one-touch access to some of the patient's medical information in accordance with an embodiment of the present disclosure.
Figure 135:
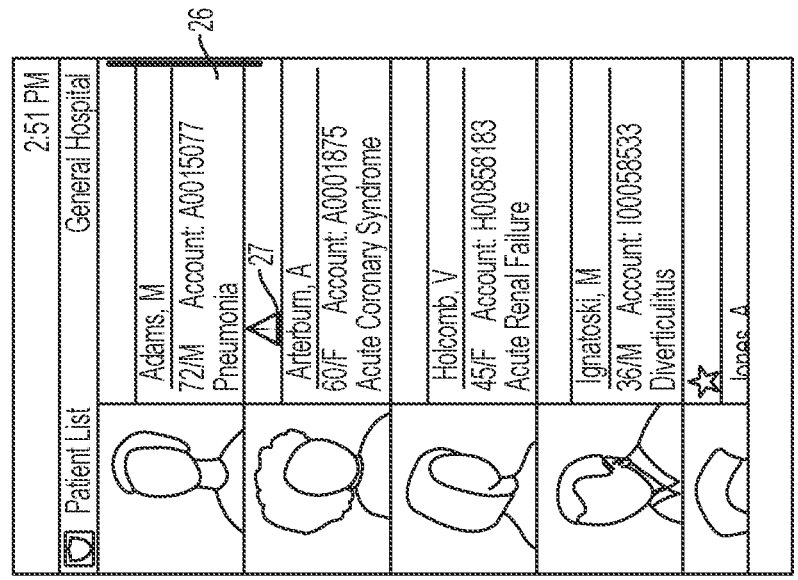
FIG. 135 is an illustration of a display on a health care provider's portable monitoring client, showing a list of patients whose information the provider can access in accordance with an embodiment of the present disclosure.
Figures 139, 140:
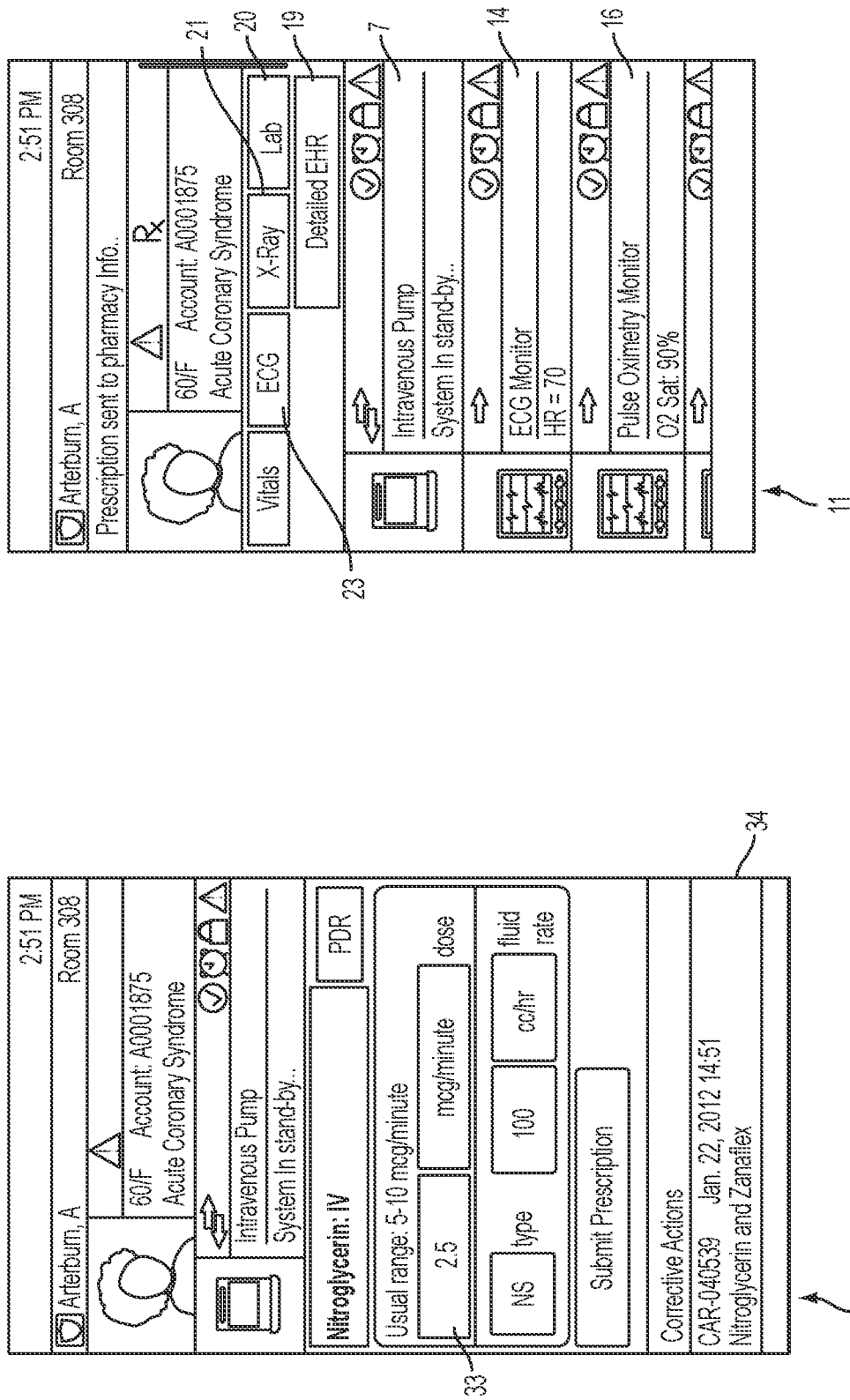
FIG. 139 is an illustration of a display on a health care provider's portable monitoring client, showing a medication prescription ready for submission by the ordering provider in accordance with an embodiment of the present disclosure.
FIG. 140 is an illustration of a display on a health care provider's portable monitoring client, showing how the monitoring system can display confirmation to the ordering provider that the prescription has been transmitted to the pharmacist in accordance with an embodiment of the present disclosure.

FIG. 135 is an illustration of a display on a health care provider's portable monitoring client, showing a list of patients whose information the provider can access in accordance with an embodiment of the present disclosure;

FIG. 136 is an illustration of a display on a health care provider's portable monitoring client, showing devices associated with a particular patient, with current data from the devices and one-touch access to some of the patient's medical information in accordance with an embodiment of the present disclosure. FIG. 137 is an illustration of a display on a health care provider's portable monitoring client, showing data entry fields for a prescription for a medication for use with an intravenous infusion pump in accordance with an embodiment of the present disclosure. FIG. 138 is an illustration of a display on a health care provider's portable monitoring client, showing a risk profile associated with an ordered medication, and a suggested course of action, as generated by the Monitoring in accordance with an embodiment of the present disclosure. FIG. 139 is an illustration of a display on a health care provider's portable monitoring client, showing a medication prescription ready for submission by the ordering provider in accordance with an embodiment of the present disclosure. FIG. 140 is an illustration of a display on a health care provider's portable monitoring client, showing how the Monitoring system can display confirmation to the ordering provider that the prescription has been transmitted to the pharmacist in accordance with an embodiment of the present disclosure.

Example of Monitoring-Assisted Order Entry

The functionality of the Patient Monitoring system can be illustrated by an example in which an ordering provider enters a new medication prescription for a patient. In this scenario, the physician may view his list of admitted patients on his hand-held device after entering the appropriate security pass code. In this example, the physician's patients can be listed as shown in FIG. 97, with limited and user-selectable information 26 on each patient, such as, for example, age, diagnosis, and medical record number. Alert symbols 27 may be transmitted by the monitoring client 1 to the physician's device 11 if, for example, orders for the patient 2 are incomplete, the nurse has flagged the patient for attention, or if the monitoring client 1 has received input from a database or a patient monitoring device 14-17 that has exceeded a predetermined threshold for physician notification.

After the physician selects a patient for further review, a display such as that shown in FIG. 135 may be transmitted to the physician's device 11. The physician can view user-selectable data originating from monitors 14-17 to which the patient is connected, and the physician may have one-touch access to a number of databases 19-21, 23 containing patient-specific information. In an embodiment, the monitoring client 1 may be connected or docked to an infusion pump 7 available for use with the patient 2. In a scenario illustrated in FIG. 136, the physician can press on the icon representing the infusion pump 7 to order an intravenous medication for the patient 2.

FIG. 137 shows one of a number of possible prescription ordering screens with which a physician can remotely order a medication. In the example illustrated, the physician enters the drug IV Nitroglycerin 28, which may be entered by typing or via a drop-down display populated by the hospital pharmacy's formulary 22, accessed by the monitoring client 1 via the Monitoring Server 3. The TDR' button 29 may represent the physician's one-touch access to an in-hospital 22 or proprietary drug database 9 for detailed drug information. The physician can order the dose of medication, either directly or by accepting a default standard starting dose 30 provided by the monitoring client 1 via the monitoring server 3. The physician may also specify the maximum fluid infusion rate 31 for the infusion pump 7, in order to assist the pharmacist in preparing the proper concentration of the drug in a bag for infusion.

FIG. 138 shows an example of how the Patient Monitoring system can detect a risk of an adverse reaction after the physician has entered the prescription. The monitoring client 1 can compare the new medication 28 to the patient's existing medications and drug allergy list downloaded from the EHR 19. The monitoring server 3 preferably will have populated the appropriate patient-specific data into the monitoring client 1, and the client 1 will be programmed to look up this information after the new medication order has been entered. The monitoring client 1 may be programmed to request a listing of significant adverse reactions and drug interactions associated with each of the patient's medications and the new medication 28 from the monitoring server 3. The server 3, in turn can access a pharmacy database 22 or external database 9 for this information. If a potential drug interaction or adverse reaction common to an existing medication and the new medication 28 are detected, the monitoring client 1 may issue a warning 32 and transmit it to the ordering physician, as shown in FIG. 138. If the potential adverse reaction is due to an effect common to both the new medication and an existing medication, the monitoring client 1 may categorize this as a potentially additive adverse effect and issue a recommendation 33 to reduce the initial drug dose, for example, by 50%.

As shown in FIG. 139, the ordering physician has the option either to accept the recommendation 33 or edit the recommended dose to another value. In any event, the monitoring client 1 may generate and log a report 34 of the warning 32 and any corrective action 33, if any, taken by the physician, with the option for the physician to further edit the report before logging and entry into the patient's EHR 19.

Once the medication dosing is finally determined, the monitoring client 1 can forward the order to the communication devices of both the hospital pharmacist 6 and the patient's nurse 5. A report of the accomplishment of this task may then be transmitted back to the ordering physician 11, as shown in FIG. 140. The pharmacist can use the information provided by the ordering physician to mix an appropriate concentration of the medication in a solution bag. Both the medication vial and the solution bag may have identification tags, such as, e.g., bar code identifiers, that can be read into the pharmacist's monitoring client 6, and which can be verified as correct by the monitoring client 1 (using the pharmacy database 22 as accessed by the monitoring server 3). The pharmacist may then generate a unique identification label, such as a bar code label, to be permanently affixed to the medication bag, the code now being linked uniquely to the patient 2 for whom the medication 28 has been prepared. The identifying code on the label may be transmitted to the monitoring client 1 for later reconciliation when the nurse is about to administer the medication 28.

After the prepared medication 28 arrives to the patient's floor, the nurse can then prepare to administer it to the patient 2. In this exemplary scenario, the monitoring client 1 may include an input device such as a bar code reader, which the nurse can use to verify that the identifying code on the medication bag matches the identity of the patient 2 for whom it has been prescribed. If the identification matches the information entered into the monitoring client 1 by the pharmacist, the nurse may be cleared by the device 1 to hang the medication bag and initiate the infusion via the infusion pump 7. In an embodiment, the monitoring client 1 displays to the nurse the prescription, including the dose, the maximum fluid rate for the patient, the concentration of the drug in the bag, and the infusion rate for the pump (which can optionally be calculated by a processor in the monitoring client 1. With this information, the nurse has the ability to manually calculate and verify that the infusion rate set by the monitoring client 1 for the pump 7 is correct.

Figure 141:
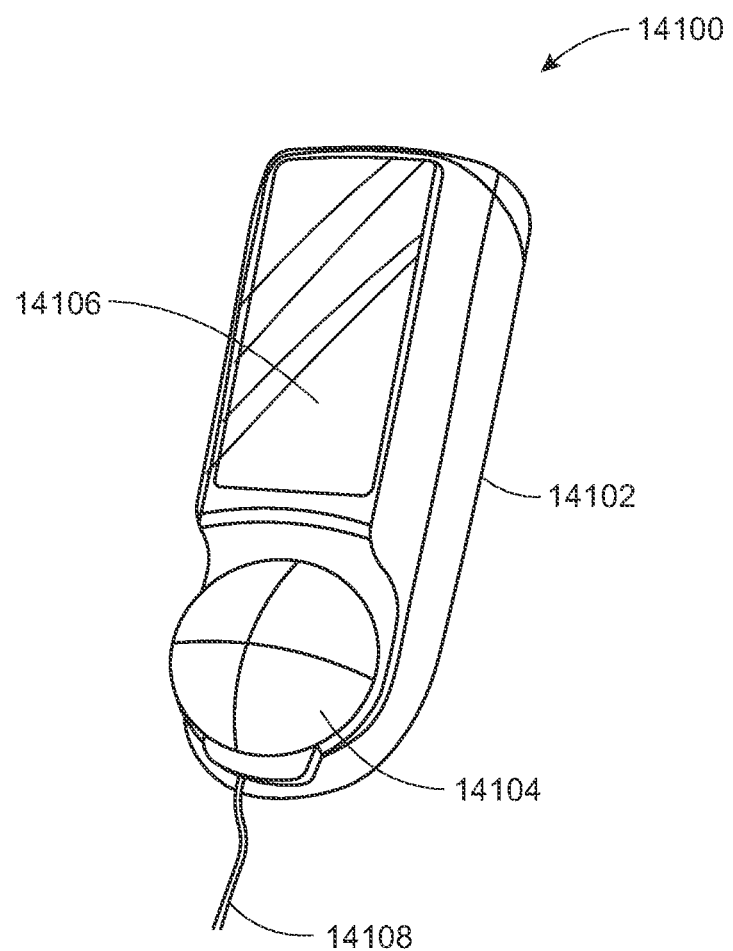
FIG. 141 shows a perspective-view of microinfusion pump coupled to an adapter in accordance with an embodiment of the present disclosure.

FIG. 141 shows an apparatus 14100 formed by a microinfusion pump 14104 coupled to an adapter 14102 in accordance with an embodiment of the present disclosure. The adapter 14102 includes a touchscreen 14106 that can be used to control the operation of the microinfusion pump 14104. The microinfusion pump 14104 pumps fluid out of a tube 14108.

The adapter 14102 may wirelessly communicate with a monitoring client 1 of FIGS. 3, 5, 7, 8, a monitoring client 902 of FIG. 9, a dock 102 or 104 of FIG. 1, a dock 102 or 104 of FIG. 3, a dock 502 of FIG. 5, a hub 802 of FIG. 8, a dock 804, 806 or 102 of FIG. 8, the dongle 133 of FIG. 1, 3, 5 or 7, or any patient-care device disclosed herein.

The adapter 14102 may include various electrical connectors such that the microinfusion pump 14104 may be docked to the adapter 4102. The adapter 14102 may include an electrical connector on a backside to interface with a patient-care device dock 104. For example, the adapter 14102 may include a connector such that the adapter 14102 docks to the The touchscreen 4106 may be used to set an infusion rate, a bolus amount, or an extended bolus setting, etc. Additionally or alternatively, the touchscreen 4106 may be used to estimate the amount of liquid medication left within the microinfusion pump 14104.

Figure 142:
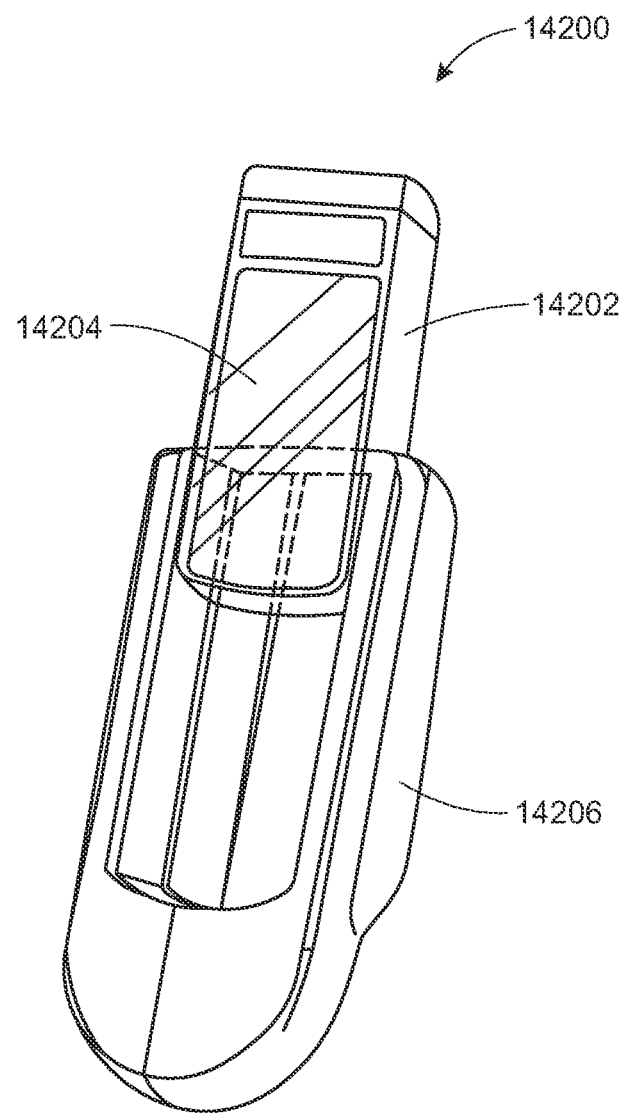
FIG. 142 shows a perspective-view of a wireless hub device that wirelessly relays data from a patient-care device to a monitoring client, another hub, or a dock in accordance with an embodiment of the present disclosure.

FIG. 142 shows a perspective-view of a wireless hub device 14200 that wirelessly relays data from a patient-care device to a monitoring client, another hub, or a dock in accordance with an embodiment of the present disclosure.

The wireless hub device 14200 includes a body 1402 coupled to a touchscreen 14204 and a holder 14206. The wirelessly hub device 1420 may communicate data from another patient-care device to a patient-care device to a monitoring client, another hub, a dock, etc. For example, the wireless hub device 14200 may communicate data with a patient-care device according to a first wireless protocol and relay the information via another wireless protocol to monitoring client, another hub, a dock, etc. For example, the wirelessly hub device 14200 may communicate with a patient-care device via Bluetooth and relays the data to a dock (e.g., dock 104 of FIG. 1) via near-field communications; In this specific embodiment, the holder 14206 may be shaped such that the holder 14206 may rest in a dock, e.g., the dock 104 of FIG. 1.

Figure 143:
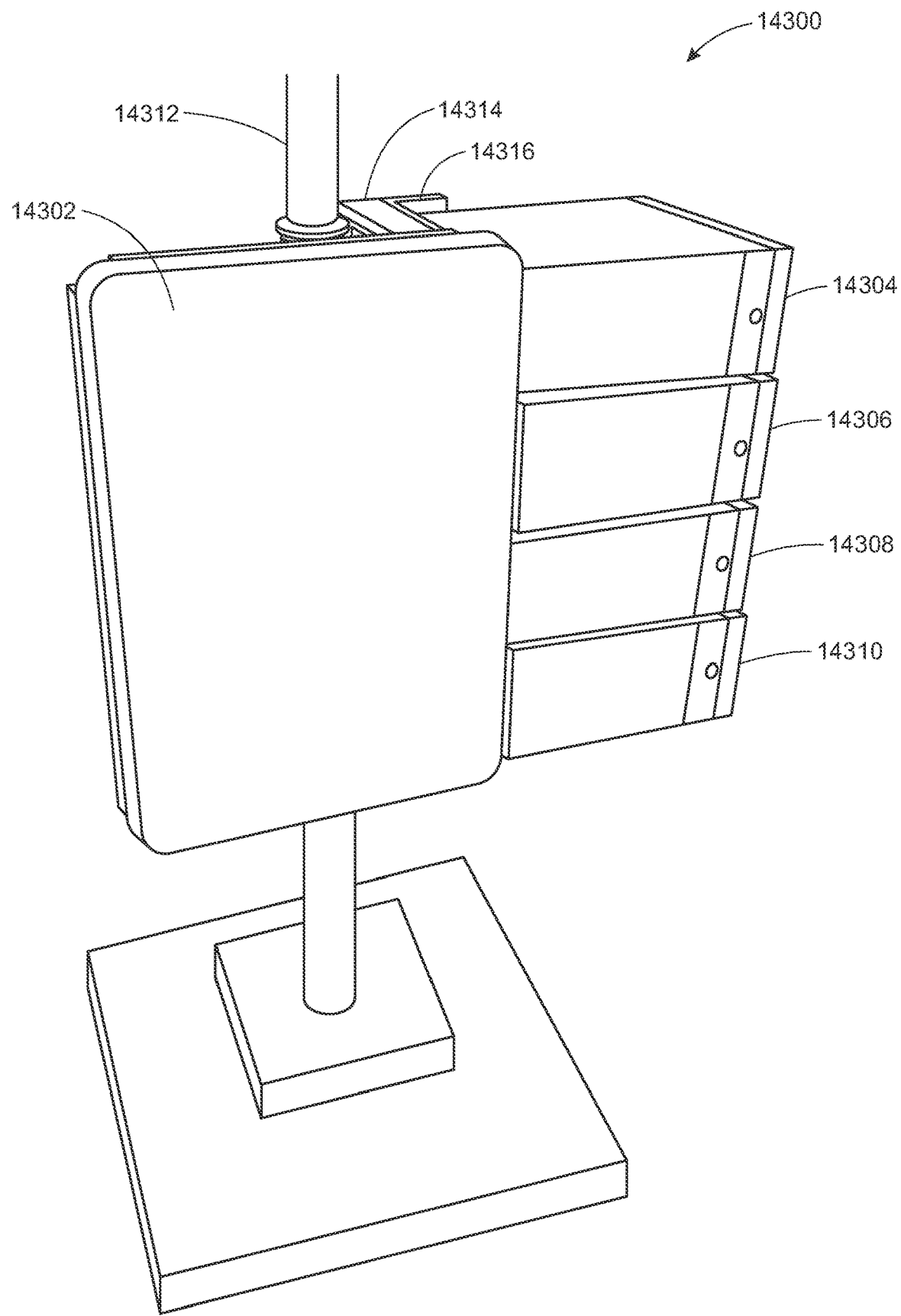
FIG. 143 shows a front, perspective-view of an electronic patient-care system having modular patient care devices coupled to a monitoring client via an adapter and a dock in accordance with an embodiment of the present disclosure.

FIG. 143 shows a front, perspective-view of an electronic patient-care system 14300 having modular patient-care devices 14304, 14306, 14308, and 14310 coupled a monitoring client 1430 via an adapter 14316 and a dock 14314 in accordance with an embodiment of the present disclosure. The dock 14314 is coupled to a pole 14312. The adapter 14316 provides an electrical connection between the dock 14314 and the patient care devices 14304, 14306, 14308, and 14310. That is, the adapter 14316 may be changed based upon the type of patient-care devices 14304, 14306, 14308, and 14310 used.

Figure 144:
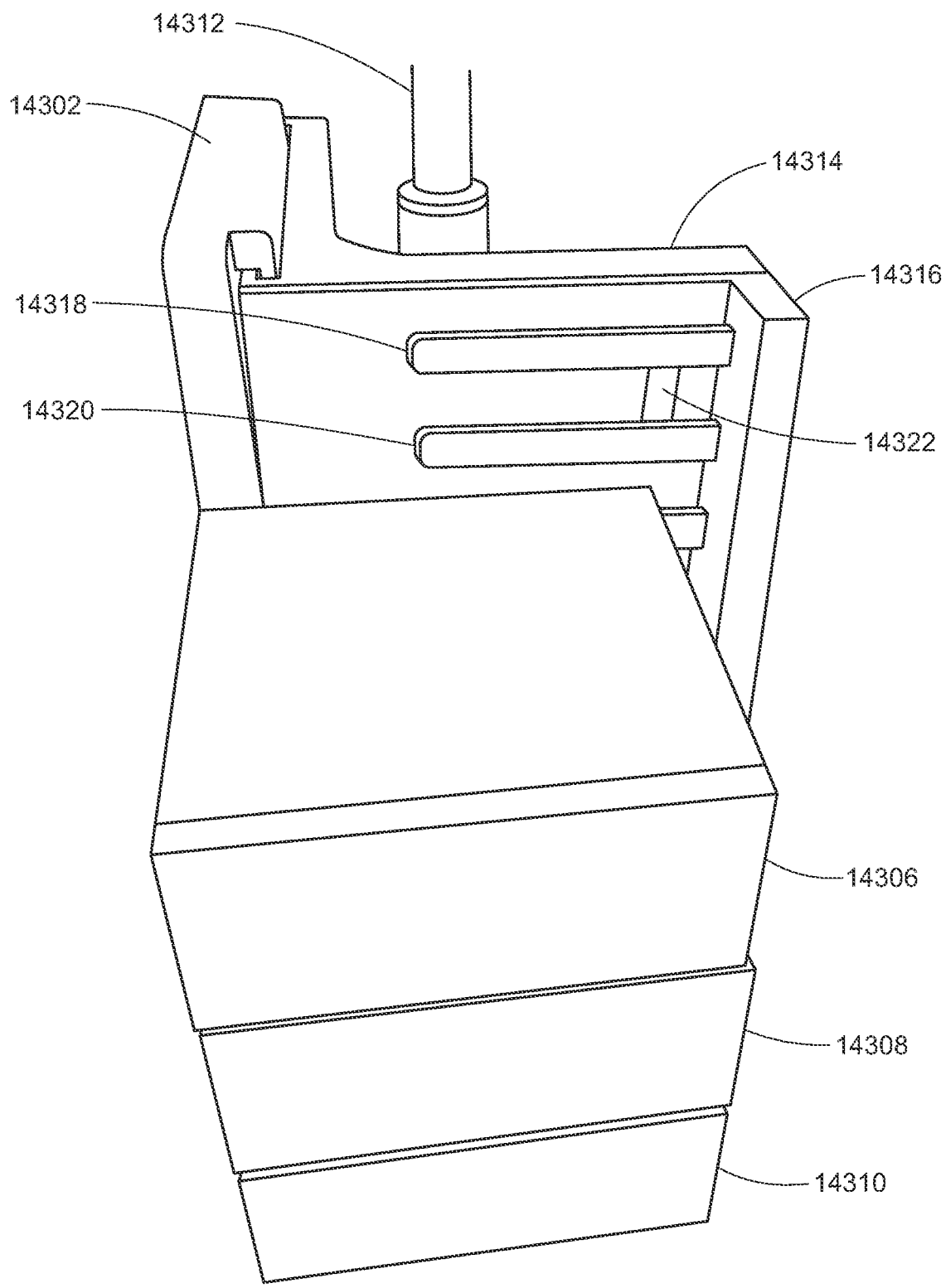
FIG. 144 shows a side, perspective-view of the electronic patient-care system of FIG. 143 in accordance with an embodiment of the present disclosure.

FIG. 144 shows a side, perspective-view of the electronic patient-care system of FIG. 143 in accordance with an embodiment of the present disclosure. Referring to FIGS. 143-144, the patient-care device 14306 slides onto the adapter 14316 via rails 14318 and 14320. The infusion pump 14304 may snap onto a spring-loaded flange 14322. A lever on the backside of the adapter 14316 may be pulled to pull away the flange from the infusion pump 14304.

Figure 145:
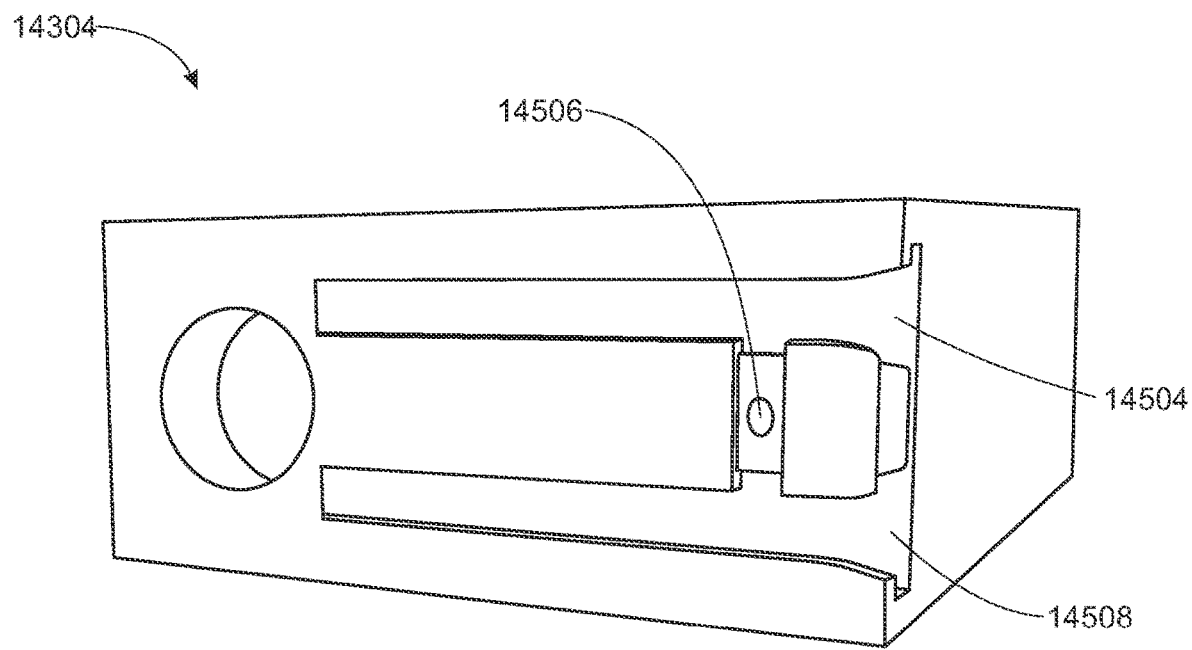
FIG. 145 shows a close-up, perspective view of the interface of one of the patient-care devices shown in FIG. 143 in accordance with an embodiment of the present disclosure.

FIG. 145 shows a close-up, perspective view of the interface of one of the patient-care devices shown in FIG. 143 in accordance with an embodiment of the present disclosure. Referring now to the FIGS. 144 and 145, the rail 14318 engage with the track 14502, and the rail 14320 engages with the rail 14504. A space 14506 receives the flange 14322 such that the infusion pump 14304 snaps into place in the adapter 14316.

Figure 146:
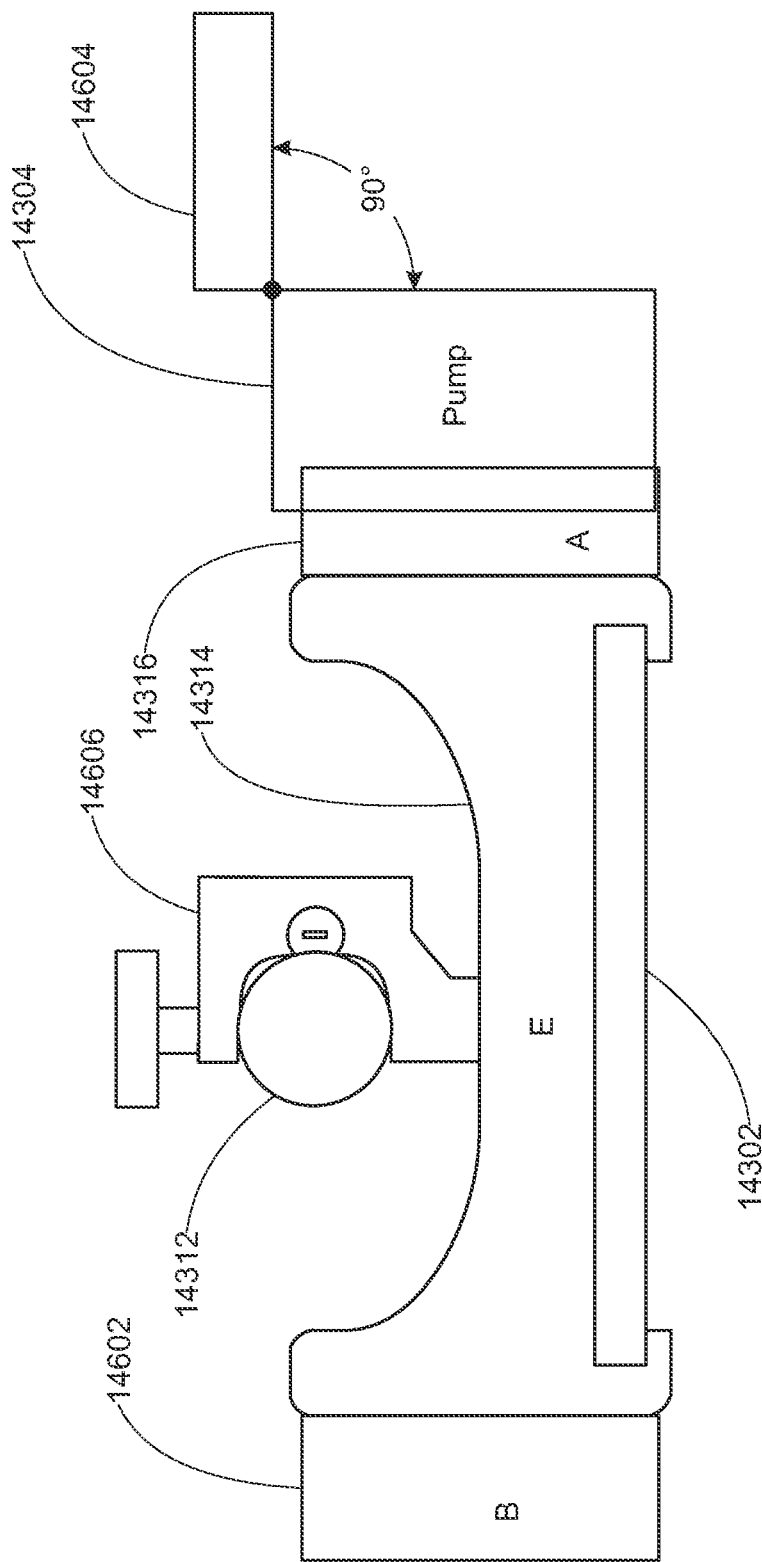
FIG. 146 shows a top view of the electronic patient-care system of FIG. 143 in accordance with an embodiment of the present disclosure.

FIG. 146 shows a top view of the electronic patient-care system 14300 of FIG. 143 in accordance with an embodiment of the present disclosure. The dock 14314 is coupled to two adapters 14602 and 14316. The dock 14314 is coupled to the pole 14312 via a clamp 14606. The pump 14304 is shown with the pump door 14604 opened.

Figure 147:
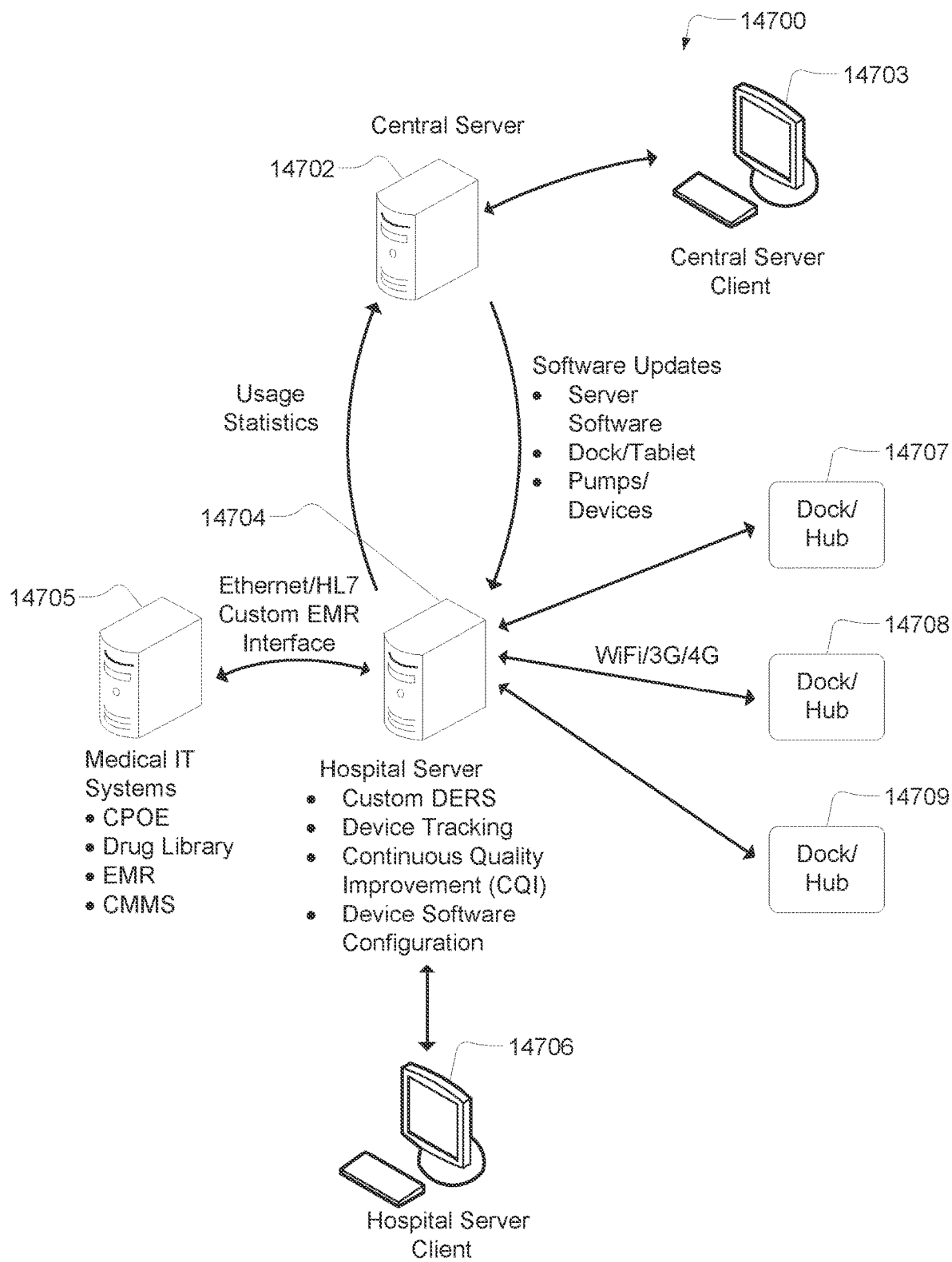
FIG. 147 shows an illustration of a system for electronic patient-care system in accordance with an embodiment of the present disclosure.

FIG. 147 shows an illustration of a system 14700 for electronic patient-care in accordance with an embodiment of the present disclosure. The system 14700 includes a central server 14702, a central server client 14703, a hospital server 14704, one or more medical IT systems 14705, docks/hubs 14707, 14708 and 14709, and a hospital server client 14706.

The central server 14702 may be an enterprise-level server, a hospital-level server, or a global server (e.g., a cloud server). The central server 14702 may provide software updates, firmware updates, and/or configuration files. For example, the central server 14702 may provide updates for the hospital server 14704, the docks/hubs 14707, 14708 and 14709, patient-care devices coupled to the docks/hubs 14707, 14708 and 14709, or monitoring clients in operative communication with the docks/hubs 14707, 14708 and 14709 based upon a device ID. Additionally or alternatively, the central server 14702 may provide software for download into a sandbox as described below (see FIG. 148). Additionally or alternatively, the central server 14702 can receive usage statistics (patient-care parameters, patient-treatment parameters, patient-care device operating parameters, diagnostic information from docks, hubs and monitoring clients, and the like). The central server 14702 may log the data in a database, e.g., an SQL database, an associative database, or the like.

The central server client 14703 can communicate with the central server 14702 to monitor the operation of the central server 14702, view the log files therein, or to view data relating to the efficacy of a drug as described above. In some embodiments of the present disclosure, the central server client 1403 is software at a nurse's station such that the nurse can monitor docks/hubs, patients, and/or patient-care devices.

The hospital server 14704 may be installed in a hospital, a care unit of a hospital (e.g., Neonatal Intensive Care Unit ("NICU"), Intensive Care Unit ("ICU"), etc.), a floor of a hospital, or for a group of hospitals (e.g., an administrative group of hospitals).

The hospital server 14704: (1) may include a custom set of DERS, may track patient-care devices, Docks/Hubs or monitoring clients; (2) may identify and log non-compliant patient-care devices, docks/hubs and/or monitoring clients; and/or (3) may configure or update docks/hubs, monitoring clients and/or patient-care devices (e.g., from updated software files, configuration files or firmware files from the central server 14702).

The one or more medical IT systems 14705 communicate with the hospital server 14704 to provide functionally thereto. The medical IT system 14705 may provide computerized provider order entry ("CPOE"), a drug library, electronic medical records ("EMR"), a computerized maintenance management system ("CMMS"), or other database or computerized system.

The docks/hubs 14707, 14708, and 14709 communicate with the hospital server 14704. There may be one or more of the docks/hubs 14707, 14708, and 14709 in a patient's room.

The hospital server client 14706 allows a user or technical to interface with the hospital server 14704 to facilitate the updating of software, to monitor the log files therein, or to help facilitate continuous quality improvement ("CQI").

Figure 148:
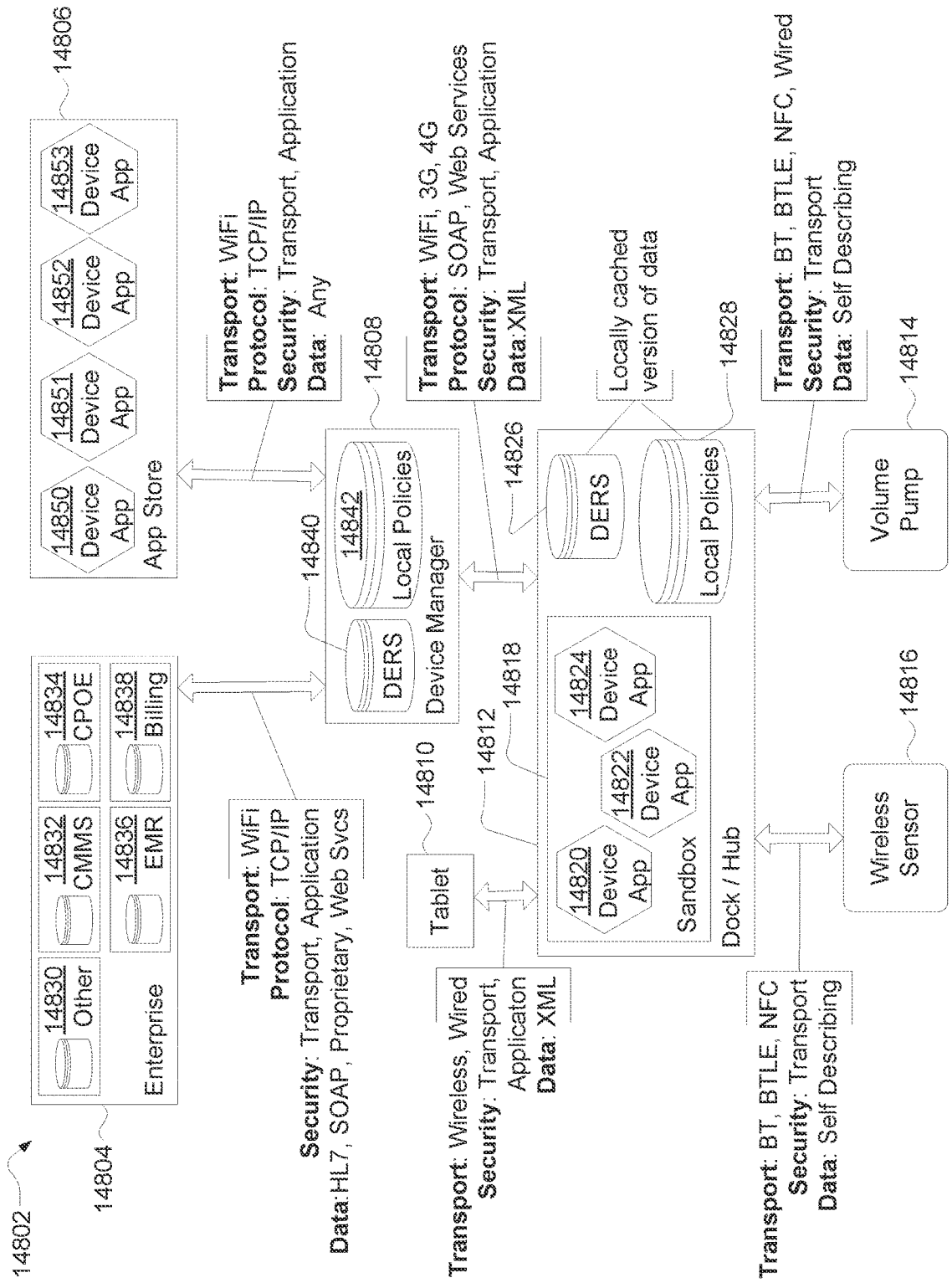
FIG. 148 shows a block diagram of an electronic patient-care system in accordance with an embodiment of the present disclosure.

FIG. 148 shows a block diagram of an electronic patient-care system 14802 in accordance with an embodiment of the present disclosure. The system 14802 includes an enterprise server system 14804, an application store 14806, a device manager 14808, one or more hubs 1426, one or more tablets 14810, one or more infusion pumps 14814, and one or more wireless sensors 14816. The communications between the tablet and the dock/hub 14812, between the dock/hub 14816 and the wireless sensor 14816, between the dock/hub 14812 and the infusion pump 14814, between the dock/hub 14812 and the device manager 14808, between the device manager 14808 and the application store 14806, and/or between the device manager 14840 and the enterprise server(s) 14804 may be made by using WiFi, Ethernet, Bluetooth, USB, 3G, 4G, HALO, SOAP, XML data, using self-describing data, HL7, TCP/IP, Bluetooth templates, a dedicated, and/or or non-dedicated communications link.

The enterprise server system 14804 may include, in some embodiments, a CMMS database 14832, a CPOE 14834, an EMR 14836, and/or a billing server 14838. The enterprise server system 14804 may receive equipment health information including calibration data, battery life, etc. with the CMMS 14832.

The application store 14806 may include one or more device applications (or programs) 14850, 14851, 14852 and/or 14853, which may control or program one or more patient-care devices, one or more sensors, one or more infusion pumps 14814, provide patient diagnostic functions, etc. The application store 14806 may provide encrypted communications to facilitate the downloading of one or more of the device applications 14850-14853.

The device manager 14808 may be a hospital-level server that provides global DERS 14840 and local policies 14842. The local policies 14842 may include additional hard or soft limits (e.g., on drugs) based upon, for example, the location of the particular dock/hub 14812 in the hospital (e.g., the ER, NICU, ICU, etc.).

The dock/hub 14812 may be coupled to one or more wired or wireless sensors 14816, one or more infusion pumps 14814, and/or may be connected to other patient-care devices. The dock/hub 14812 may communicate with the one or more wireless sensors 14816 using WiFi, Ethernet, Bluetooth, Bluetooth Low Energy, USB, 3G, 4G, HL7, TCP/IP, Bluetooth templates, or other protocol via a dedicated or non-dedicated communications link and may be using self-describing data. The wireless sensor may use one of the communication modules described above (e.g., the wireless sensor 14914 may be coupled to a communication module via a serial link such as SPI). The tablet 14810 may interface into the dock/hub 14812. The dock/hub 14812 may include a local copy of DERS 14826 that may be periodically updated by the DERS 14840 from the device manager 14808. Additionally or alternatively, the dock/hub may include a local copy of the local policies 14828 that may be periodically updated by the device manager 14808.

The tablet 14810 may provide care flow sheets that provide the caregiver or patient with a checklist of activities for their day and may record and log data from weight scales, vital monitors, data on bathing, dressing changes, dietary information from patient-care devices or may be manually entered into the tablet 14810, which can be updated and stored in the patient's EMR file within the EMR 14836. The tablet 14810 may provide tutorials to the home patient or caregiver to serve as a reminder for specific care operations such as how and when to change dressings, measure urine output, or take blood glucose readings. Additionally or alternatively, the tablet 14810 may instruct a caregiver, patient, or user how to resolve a source of a soft alarm and/or hard alarm.

A patient-care device, e.g., the infusion pump 14814, may include near-field communications ("NFC") which communicates with the dock/hub 14812 when the infusion pump 14814 is in close proximity with the dock/hub 14812 to, for example, pair the devices, to pass configuration data, or set the infusion pump 14814 parameters for the patient with which the dock/hub 14812 is associated with. After the NFC communications, the infusion pump 14814 may communicate with the dock/hub 14812 wirelessly or via a wireless link. For example, an infusion pump 14814 may be in close (or contacting) proximity with the dock/hub 14812 in which NFC communications are used to pair the infusion pump 14814 with the dock/hub 14812 using a Bluetooth communications link.

The dock/hub 14812 may execute a device application 14820-14824 with a sandbox 14814. The sandbox 14814 may require the application to be written with predetermined criteria. In some embodiments, the sandbox 14814 may include an API having a secure data class. In yet additional embodiments, the sandbox 14814 may reside on the monitoring client 14810. The sandbox 14814 may be a virtual machine, may be a program that controls the resources (e.g., hardware or software resources available via an API, for example) the device applications 14820-14824 may utilize, may have global variables accessible by the device applications 14820-14824, and may be interpreter based. That is, the sandbox 14812 is a protected area that allows the device applications 14820-14824 to execute in a controlled and limited resource environment. The sandbox 14812 may be downloaded from the device manager 14808 or the application store 14806. The sandbox 14812 may be preconfigured for the particular dock/hub type, e.g., based upon any single or combination of a version number, a serial number, a lot number, a hardware version number, a software version number, an operating system type, an operating system service pack, other identifier, etc.

For example, the dock/hub may identify the infusion pump 14814 by serial number and download from the app store a device application 14850 into the dock/hub 14812 (e.g., the device app 14820). The device apps 14820-14824 may control and/or communicate with the infusion pump 14814 to relay information about the infusion pump 14814 to the tablet 14810 for display (e.g., via XML, for example). Additionally or alternatively, the one or more of the device apps 14820-14824 can display data from devices, use complex heuristics to combine data from several sources, etc. The sandbox 14818 may also control the access to various resources, such as: memory, non-volatile memory, hard drives, network interfaces, input devices, output devices, a buzzer, etc. In some embodiments, the sandbox 14818 may limit or prohibit the device applications 14820-14824 from reading and/or writing to specific files, such as system files. The sandbox 14818 may provide temporary and/or protected resources to the device applications 14820-14824, such as: a "scratchpad" memory space and/or a scratchpad harddisk space.

Any attempts by the device app 14820 to violate the DERS 14826, the local policies 14828, or inhibit the dock/hub 14828 to perform its primary functions (e.g., designated, high-priority functions) will be prevented by other software running on the dock/hub 14812 (e.g., an operating system such as the android operating system, IOs, Linux, Windows, or Windows CE that controls the execution of the sandbox via one or more process control blocks or one or more threads from a thread pool).

The sandbox 14818 may control the launching of one or more of the device apps 14820-14824. For example, the sandbox 14818 may check rules or links (e.g., dynamically linked library calls) to ensure that a device app of the device apps 14820-14824 designated for execution does not have any broken links and conforms to predetermined criteria controlled by the sandbox 14818. For example, the sandbox 14818 may check that all of the references from a device application 14850 to shared libraries within the dock/hub's 14812 software exist within specific "safe" shared libraries, the particular function or variable within the library exists, and the variable and data type requested by the device applications 14820-14824 or communicated by the device applications 14820-14824 conforms to or exists within the library.

In some embodiments of the present disclosure, the sandbox 14818 prioritizes access to resources. For example, if multiple device applications 14820-14824 request access to an alarm device (e.g., a speaker) or variable that indicates an alarm condition, the sandbox 14812 may prioritize the sources of the requests and display the prioritized list of alarm causes on the tablet 14810 allowing a caregiver to disable certain alarm conditions, address multiple alarm sources and/or assess the condition of the patient.

In some embodiments of the present disclosure, the dock/hub 14812 includes a processor with two cores such that one of the cores executes the sandbox 14818 whilst another core executes an operating system which controls the allocation of the resources used by the sandbox 14818 via one of the device applications 14820-14824.

In some embodiments of the present disclosure, the dock/hub 14812 includes two processors such that one of the processors executes the sandbox 14818 whilst another processor executes an operating system which controls the allocation of resources used by the sandbox 14818 via one of the device applications 14820-14824.

In some embodiments of the present disclosure, the dock/hub 14812 includes two processors such that one of the processors executes the sandbox 14818 whilst another processor executes a watchdog function to ensure safe operation of resources used by the sandbox 14818 via one of the device applications 14820-14824.

In some embodiments of the present disclosure, the dock/hub 14812 includes two processors such that one of the processors executes a real-time safety processor whilst another processor executes the sandbox 14818 and an operating system which controls the allocation of resources used by the sandbox 14818 via one of the device applications 14820-14824.

In some embodiments of the present disclosure, the dock/hub 14812 includes one or more processors each with one or more cores such that at least one process control block executes the sandbox 14818 whilst at least another process control block executes an operating system which controls the allocations of resources used by the sandbox 14818 via one of the device applications 14820-14824.

The dock/hub 14812 may de-identify data from the patient-care devices and upload the data to the database 14830 (e.g., a cloud-based database); the data may be real-time data aggregated at the national level to facilitate epidemic detection, resource planning, and deployment planning within a hospital or hospital system.

Figure 149:
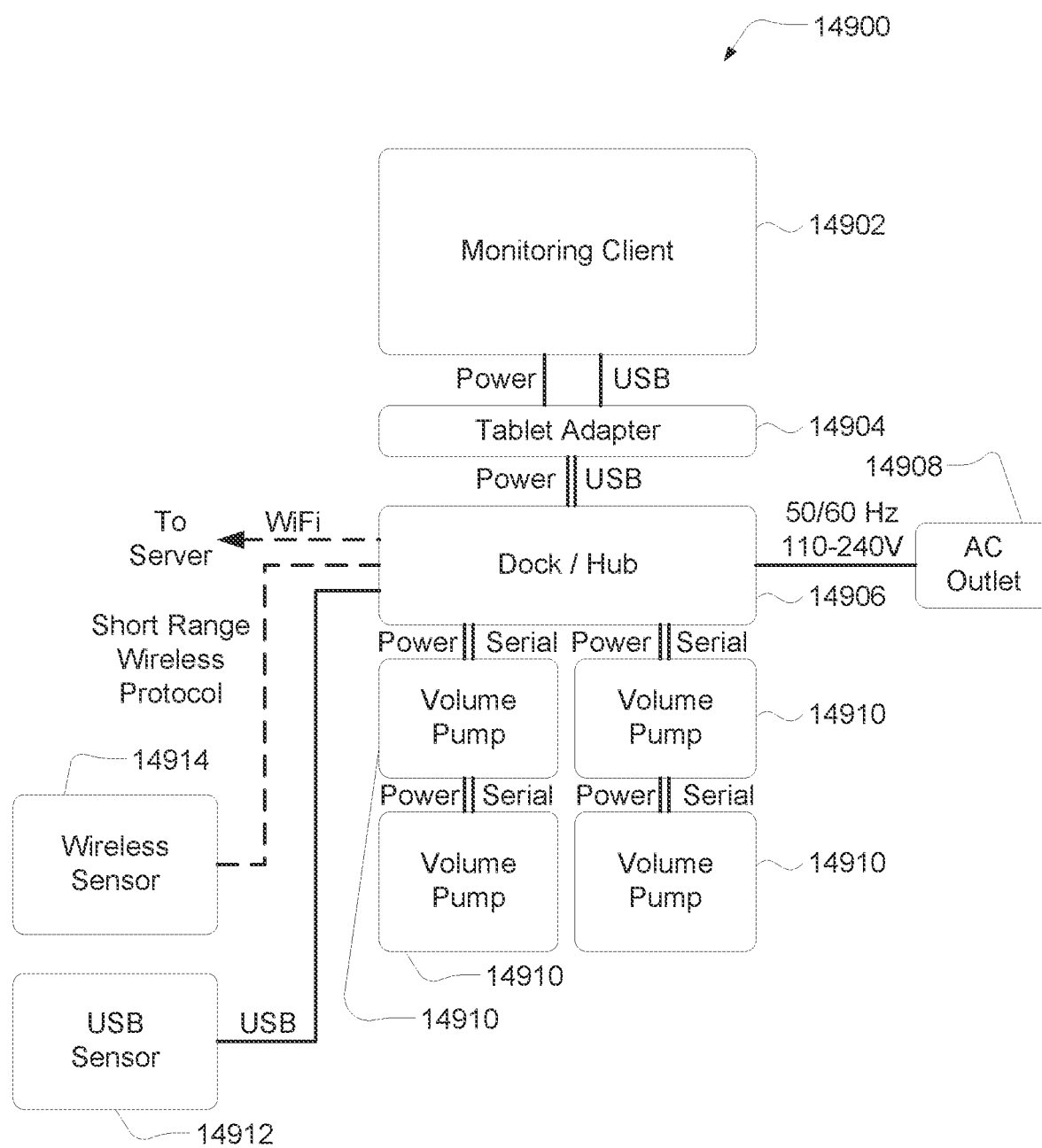
FIG. 149 shows a block diagram of a beside portion of the electronic patient-care system of FIG. 147 and/or FIG. 148 in accordance with an embodiment of the present disclosure.

FIG. 149 shows a block diagram 14900 of a beside portion of the electronic patient system of FIG. 147 and/or FIG. 148 in accordance with an embodiment of the present disclosure. The diagram 14900 includes a monitoring client 14902 (which may be the tablet 148120), a monitoring-client adapter 14904 such that the monitoring client 14902 can interface with the dock/hub 14906 (which may be the dock/hub 14812), and several infusion pumps 14910. The dock/hub 14906 may communicate with the infusion pumps 14910 via WiFi, Zigbee, Bluetooth, a mesh network, a point-to-point protocol (e.g., based upon WiFi), etc. The infusion pumps 14910 may be power directly via the AC outlet 14908 (not depicted) and/or from the dock/hub 14906 directly. The dock/hub 14906 is coupled to the wireless sensors 14814 (wirelessly or wired) and to USB sensors 14912 via a USB cable.

In some embodiments of the present disclosure, another in-room display may be present, e.g., a hub, monitoring client, computer, etc. that can communicate with the dock/hub 14812 and/or tablet 14810 via WiFi, Ethernet, Bluetooth, USB, or other protocol via a dedicated or non-dedicated communications link.

Figure 150:
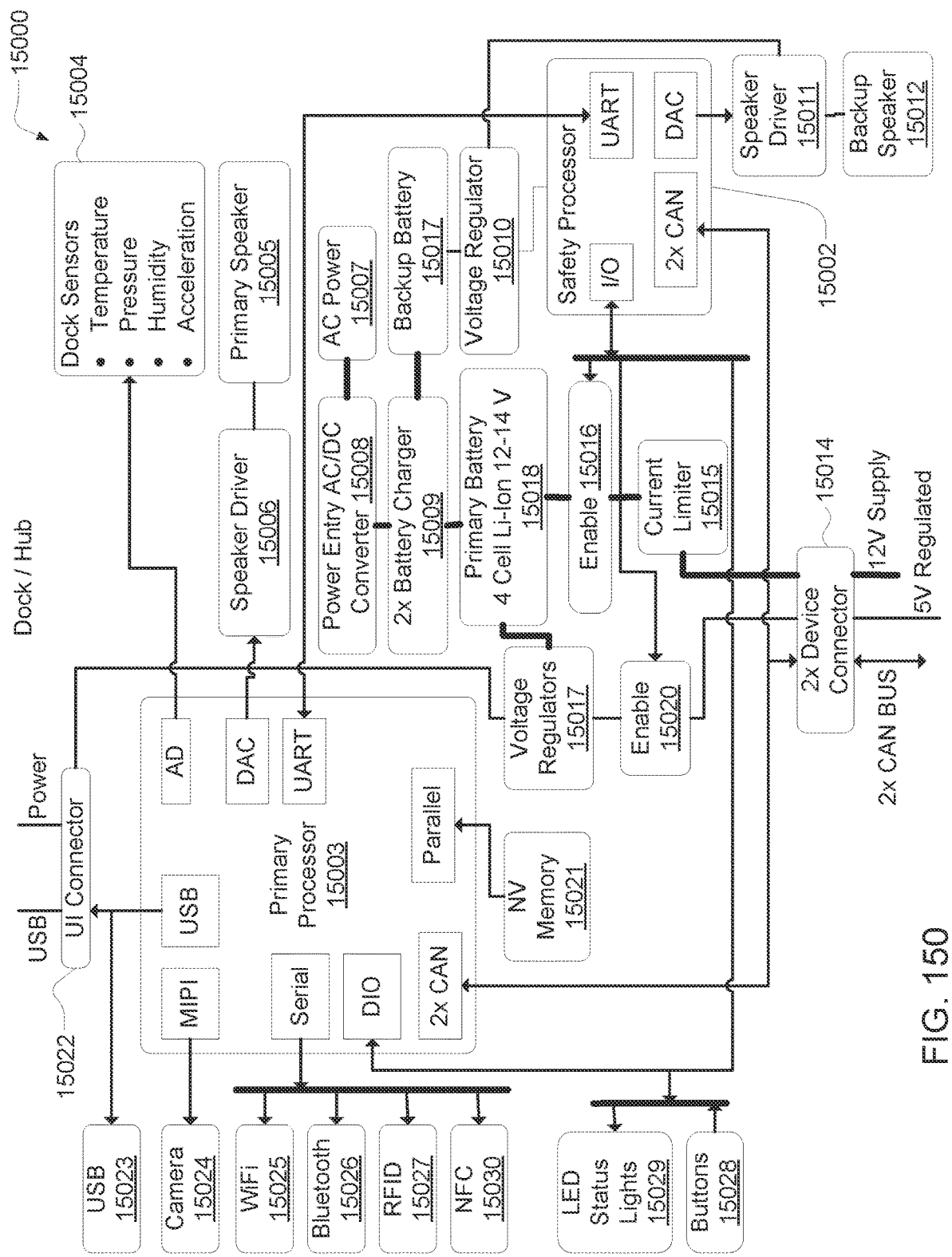
FIG. 150 shows a block diagram of the dock/hub of FIGS. 147, 148, and/or 149 in accordance with an embodiment of the present disclosure.

FIG. 150 shows a block diagram of the dock/hub 15000 of FIGS. 147, 148, and/or 149 in accordance with an embodiment of the present disclosure. The dock/hub 15000 includes a primary processor 15003 and a safety processor 15002 (which one or both may be a processor, a microprocessor, or a microcontroller, for example a Snapdragon processor).

The safety processor 15002 is coupled to a speaker driver 15011 which controls a backup speaker 15012. The safety processor 15002 is also coupled to a 2×CAN bus connected to a patient-care device via the device connector 15014. In some embodiments, the device connector 15014 communicates with a patient-care device via a Zigbee, Bluetooth, WiFi, CAN Bus, or SPI communications link.

The safety processor 15002 is coupled to a voltage regulator 15010 which receives power from a backup battery 15017 and/or from a battery charger 15009. The safety processor 15002 is coupled to an enable switch 15016 that can disable the power supply to a patient-care device coupled to the device connector 15014. The current limiter 15015 can also limit the current to a patient-care device coupled to the device connector 15014.

The safety processor 15002 is also coupled to an enable 15020 switch which enables/disables a 5 volt power supply to the patient-care device coupled via the device connector 15014. The 5V signal to the patient-care device is received from the voltage regulator 15010 which receives its power from a primary battery cell 15018 and/or the battery charger 15009. The battery charger receives power via an AC/DC converter 15008 coupled to an AC outlet 15007.

The primary processor 15003 is coupled to a camera 15024, a WiFi transceiver 15025, a Bluetooth 15026 transceiver, an RFID interrogator 15027, LED status lights 15029, buttons 15028, and a near-field communications transceiver 15030.

The primary processor 15003 is coupled to a USB cable that couples to a USB port 15023 and/or a monitoring client via a UI connector 15022. In some embodiments, the primary processor 15003 can communicate with a tablet via a WiFi or other wireless communications link. The primary processor 15003 can communicate with a patient-care device via the USB connection 15023 and/or the monitoring client via a USB port via the UI connector 15022. The primary processor 15003 communicates a signal to a speaker driver 15006 which drives a primary speaker 150005.

Figure 151:
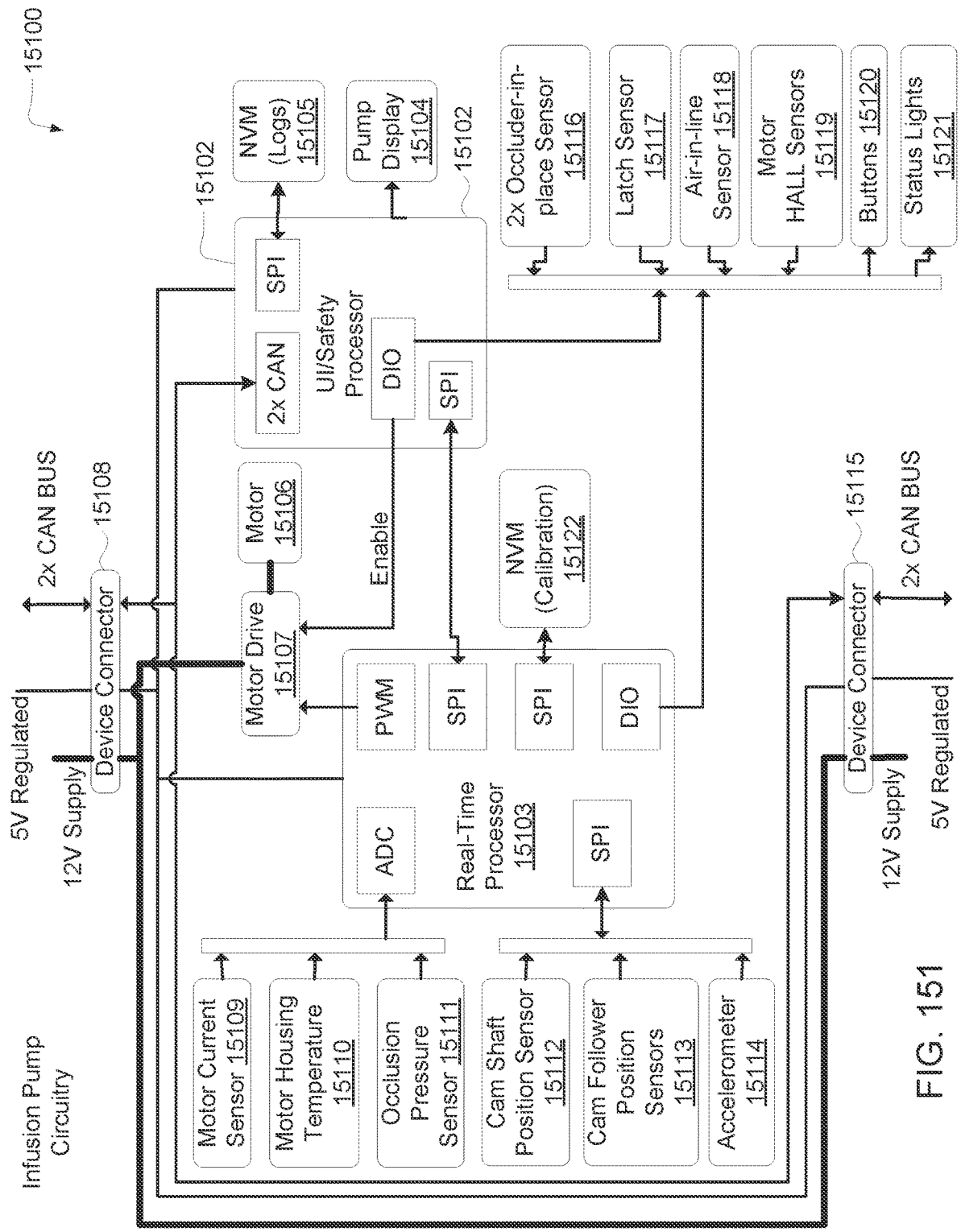
FIG. 151 is a block diagram illustrating the infusion pump circuitry of FIGS. 148 and/or 149 in accordance with an embodiment of the present disclosure.

FIG. 151 is a block diagram illustrating the infusion pump circuitry 15100 of FIGS. 148 and/or 149 in accordance with an embodiment of the present disclosure. The circuitry 151 includes a UI/safety processor 15102 that controls the pump display 15104 and logs data in non-volatile memory 15105. The UI/safety processor 15102 communicates with a hub/dock via a CAN bus coupled to the device connector 15108. In some embodiments the real-time processor 151102 and/or UI/safety processor 15102 communicates with a hub/dock via the device connector 15108 using a Bluetooth, a wireless, or a wired communications link. The UI/Safety processor 15102 may include an image processing library to processes imagery from a camera. Additionally or alternatively, the UI/Safety processor 15102 may include a library to display a GUI interface on the pump display 15104 (which may be a touchscreen).

The UI/safety processor 15102 is coupled to an occlude-in-place sensor 1516, a latch sensor 15117, an air-in-line sensor 1518, a motor hall sensors 15119, buttons 15120, and status lights 15112. The safety processor 15102 provides watchdog functionality to the real-time processor 15103 (which may be a processor, a microprocessor, or a microcontroller, for example a SnapDragon processor) and can enable the motor drive 15107.

The real-time processor 15103 (which one or both may be a processor, a microprocessor, or a microcontroller, for example a SnapDragon processor) controls the operation of the pump's motor 15106 via the motor drive 15107. The real-time processor 15103 communicates with the UI/Safety processor 15102 (e.g., to receive pump settings) via a serial interface. The real-time processor 15103 loads pump calibration data from a non-volatile memory 15122. The non-volatile memory 15122 and/or the non-volatile memory 15105 may be an SD card and/or an RFID tag.

The real-time processor 15103 receives data about the infusion pump from the motor current sensor 15109, the motor housing temperature 15110, the occlusion pressure sensor 15111, the cam shaft position sensor 15112, the cam follower position sensors 1513, and/or accelerometer 15114.

Figure 152:
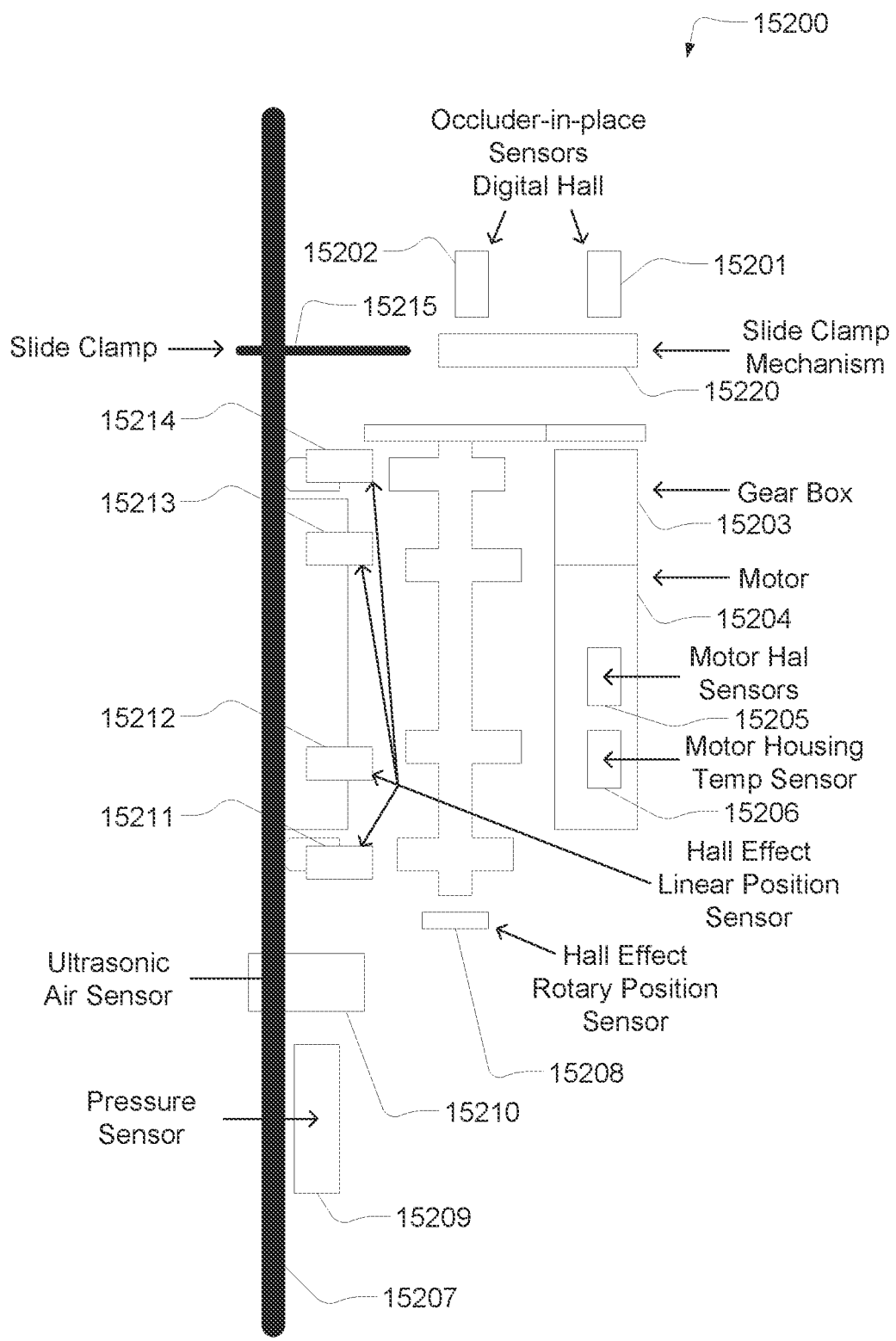
FIG. 152 is a block diagram illustrating the sensors coupled to the mechanics of an infusion pump in accordance with an embodiment of the present disclosure.

In FIGS. 151 and 152, the two processors may be used to confirm instruction(s), to perform safety checks, or other functionality (e.g., user confirmation of a patient-treatment parameter) in an identical and/or similar manner as disclosed in U.S. patent application Ser. No. 12/249,600, filed Oct. 10, 2008 and entitled Multi-Language/Multi-Processor Infusion Pump Assembly, now U.S. Publication No. US-2010-0094221, published Apr. 15, 2010, which is hereby incorporated by reference.

FIG. 152 is a block diagram 1500 illustrating the sensors coupled to the mechanics of an infusion pump for use with the infusion pump circuitry of FIG. 151 in accordance with an embodiment of the present disclosure. The infusion pumps fluid via a tube 15207. The motor 15204 includes motor hall-effect sensors 15205, a motor housing temperature sensor 15206, hall-effect sensors 15201 and 15202 to detect the movement of the slide-clamp mechanism 15220, a hall-effect sensor 15211 for an outlet valve, hall-effect sensors 15212 and 15213 for the plunger-position, a hall-effect sensor 15214 for an inlet valve, and a hall-effect rotary position sensor 15208.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present invention, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the invention described herein are capable of operation in other sequences and/or arrangements than are described or illustrated herein.

What is claimed is:

1. A system for electronic patient care wherein the system is configured to remotely identify a caregiver, the system comprising:
   a wearable system monitor; and
   a wearable dock configured to be worn by a patient and releasably couple to the wearable system monitor, wherein the wearable system monitor is configured to:
   start a timer when the wearable system monitor is uncoupled from the wearable dock,
   stop treatment by a first patient-care device separate from the wearable system monitor and wearable dock after a predetermined amount of time has elapsed after the timer is started,
   pair, upon a determination that the identified caregiver is an authorized caregiver,
   the wearable system monitor with a second patient-care device while uncoupled from the wearable dock,
   recouple with the wearable dock,
   identify and authenticate the wearable dock, and
   resume treatment of the first patient-care device after the wearable system monitor is recoupled to the wearable dock, the wearable dock is identified by the wearable system monitor, and the wearable dock is authenticated by the wearable system monitor.

2. The system according to claim 1, wherein the system is configured to identify the caregiver using voice recognition.

3. The system according to claim 1, wherein the system is configured to identify the caregiver using facial recognition.

4. The system according to claim 1, wherein the system is configured to identify the caregiver using an RFID tag.

5. The system according to claim 1, wherein the system is configured to identify the caregiver using near field communication.

6. The system according to claim 1, wherein the wearable dock is configured to the remotely identify the caregiver.

7. The system according to claim 1, wherein the wearable system monitor is configured to the remotely identify the caregiver.

8. The system according to claim 3 further comprising: a camera configured to record the image of the caregiver.

9. A system for electronic patient care wherein the system is configured to remotely identify a caregiver, the system comprising:
   a wearable system monitor; and
   a wearable dock configured to be worn by a patient and releasably couple to the wearable system monitor, wherein the wearable system monitor is configured to:
   start a timer when the wearable system monitor is uncoupled from the wearable dock,
   stop treatment by a first patient-care device separate from the wearable dock and wearable system monitor after a predetermined amount of time has elapsed after the timer is started,
   pair the wearable system monitor with a second patient-care device while uncoupled from the wearable dock,
   recouple with the wearable dock,
   identify and authenticate the wearable dock,
   resume treatment of the first patient-care device after the wearable system monitor is recoupled to the wearable dock, the wearable dock is identified by the wearable system monitor, and the wearable dock is authenticated by the wearable system monitor, and
   log the pairing of the wearable system monitor with the second patient-care device and include the caregiver identity in the log.

10. The system according to claim 9, wherein the system is configured to identify the caregiver using voice recognition.

11. The system according to claim 9, wherein the system is configured to identify the caregiver using facial recognition.

12. The system according to claim 9, wherein the system is configured to identify the caregiver using an RFID tag.

13. The system according to claim 9, wherein the system is configured to identify the caregiver using near field communication.

14. The system according to claim 9, wherein the wearable dock is configured to the remotely identify the caregiver.

15. The system according to claim 9, wherein the wearable system monitor is configured to the remotely identify the caregiver.

16. The system according to claim 11 further comprising: a camera configured to record the image of the caregiver.

17. A method for treating a patient, the method comprising:
   starting a timer when a wearable system monitor is uncoupled from a wearable dock;
   stopping treatment by a first patient-care device after a predetermined amount of time has elapsed after the timer is started;
   pairing, upon remote authentication of a caregiver, the wearable system monitor with a second patient-care device while uncoupled from the wearable dock;
   recoupling the wearable system monitor with the wearable dock;
   identifying the wearable dock;
   authenticating the wearable dock; and
   resuming treatment of the first patient-care device after the wearable system monitor is recoupled to the wearable dock, the wearable dock is identified by the wearable system monitor, and the wearable dock is authenticated by the wearable system monitor.

18. The method according to claim 17, further comprising identifying the caregiver using voice recognition.

19. The method according to claim 17, further comprising identifying the caregiver using facial recognition.

20. The method according to claim 17, identifying the caregiver using a near field communication.

21. The method according to claim 17, further comprising logging the pairing of the wearable system monitor with the second patient-care device.

22. The method according to claim 17, further comprising logging a caregiver identity.

23. The method according to claim 17, wherein the remote identification of the caregiver is performed by the wearable dock.

24. The method according to claim 17, wherein the remote identification of the caregiver is performed by the wearable system monitor.

25. An apparatus for electronic patient care wherein the apparatus is configured to remotely identify a caregiver, the apparatus comprising:

a wearable system monitor; and a wearable dock configured to be worn by a patient and releasably couple to the wearable system monitor, wherein the wearable dock is configured to identify a caregiver, wherein the wearable system monitor is configured to:

start a timer when the wearable system monitor is uncoupled from the wearable dock, stop treatment by a first patient-care device separate from the wearable system monitor and wearable dock after a predetermined amount of time has elapsed after the timer is started, pair, upon a determination that the identified caregiver is an authorized caregiver, the wearable system monitor with a second patient-care device while uncoupled from the wearable dock, recouple with the wearable dock, identify and authenticate the wearable dock, and resume treatment of the first patient-care device after the wearable system monitor is recoupled to the wearable dock, the wearable dock is identified by the wearable system monitor, and the wearable dock is authenticated by the wearable system monitor.

26. The apparatus according to claim 25, wherein the apparatus is configured to identify the caregiver using voice recognition.

27. The apparatus according to claim 25, wherein the apparatus is configured to identify the caregiver using facial recognition.

28. The apparatus according to claim 25, wherein the apparatus is configured to identify the caregiver using an RFID tag.

29. The apparatus according to claim 25, wherein the apparatus is configured to identify the caregiver using near field communication.

30. The apparatus according to claim 25, wherein the wearable dock is configured to the remotely identify the caregiver.

31. The apparatus according to claim 25, wherein the wearable system monitor is configured to the remotely identify the caregiver.

32. The apparatus according to claim 27 further comprising:

a camera configured to record the image of the caregiver.

* * * * *